United States Patent
Goldberg et al.

(10) Patent No.: US 11,987,641 B2
(45) Date of Patent: *May 21, 2024

(54) ANTI-PSMA ANTIBODIES AND USES THEREOF

(71) Applicant: Janssen Biotech, Inc., Horsham, PA (US)

(72) Inventors: Shalom Goldberg, Merion Station, PA (US); Donna Klein, Philadelphia, PA (US); Neeraj Kohli, North Wales, PA (US); Theresa Marie McDevitt, Warminster, PA (US); Steven J. Orcutt, Eagleville, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/895,295

(22) Filed: Aug. 25, 2022

(65) Prior Publication Data

US 2023/0131727 A1 Apr. 27, 2023

Related U.S. Application Data

(60) Provisional application No. 63/237,663, filed on Aug. 27, 2021.

(51) Int. Cl.
| | |
|---|---|
| C07K 16/00 | (2006.01) |
| A61K 47/68 | (2017.01) |
| A61P 35/04 | (2006.01) |
| C07K 16/30 | (2006.01) |

(52) U.S. Cl.
CPC ...... C07K 16/3069 (2013.01); A61K 47/6869 (2017.08); A61P 35/04 (2018.01); C07K 2317/51 (2013.01); C07K 2317/56 (2013.01); C07K 2317/72 (2013.01); C07K 2317/94 (2013.01)

(58) Field of Classification Search
CPC ............ C07K 16/3069; C07K 2317/51; C07K 2317/56; C07K 2317/72; A61K 47/6869; A61K 47/6803
See application file for complete search history.

(56) References Cited

U.S. PATENT DOCUMENTS

| | | |
|---|---|---|
| 541,606 A | 6/1895 | Fellows |
| 5,208,020 A | 5/1993 | Chari et al. |
| 5,225,539 A | 7/1993 | Winter |
| 5,545,807 A | 8/1996 | Surani et al. |
| 5,635,483 A | 6/1997 | Pettit et al. |
| 5,712,374 A | 1/1998 | Kuntsmann et al. |
| 5,714,586 A | 2/1998 | Kuntsmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,780,588 A | 7/1998 | Pettit et al. |
| 5,821,337 A | 10/1998 | Carter et al. |
| 5,877,296 A | 3/1999 | Hamann et al. |
| 6,150,584 A | 11/2000 | Kucherlapati et al. |
| 6,255,458 B1 | 7/2001 | Lonberg et al. |
| 6,630,579 B2 | 10/2003 | Chari et al. |
| 6,818,749 B1 | 11/2004 | Kashmiri et al. |
| 7,709,226 B2 | 5/2010 | Foote |
| 8,748,356 B2 | 6/2014 | Raghunathan |
| 10,639,373 B2 | 5/2020 | Dragovich et al. |
| 2010/0261620 A1 | 10/2010 | Almagro et al. |
| 2012/0058906 A1 | 3/2012 | Smider et al. |
| 2013/0266512 A1 | 10/2013 | Fox et al. |
| 2014/0161800 A1 | 6/2014 | Blankenship et al. |
| 2014/0302043 A1 | 10/2014 | Whittle et al. |
| 2016/0326232 A1 | 11/2016 | Rosa et al. |
| 2021/0085808 A1 | 3/2021 | Wilson et al. |

FOREIGN PATENT DOCUMENTS

| | | |
|---|---|---|
| EP | 0451216 B1 | 1/1996 |
| EP | 1391213 A1 | 2/2004 |
| WO | 90/04036 A1 | 4/1990 |
| WO | 90/07861 A1 | 7/1990 |
| WO | 92/22653 A1 | 12/1992 |
| WO | 99/45962 A1 | 9/1999 |
| WO | 02/43478 A2 | 6/2002 |
| WO | 02/66630 A1 | 8/2002 |
| WO | 2009/085462 A1 | 7/2009 |
| WO | 2010/054007 A1 | 5/2010 |
| WO | 2011/123708 A2 | 10/2011 |
| WO | 2013/020074 A2 | 2/2013 |
| WO | 2015/073746 A2 | 5/2015 |
| WO | 2018/183906 A1 | 10/2018 |
| WO | 2020/106886 A1 | 5/2020 |
| WO | 2020/229974 A1 | 11/2020 |

OTHER PUBLICATIONS

Rajasekaran et al Am J Physiol Cell Physiol 288:c975-c981, 2005 (Year: 2005).*
Henry et al, Cancer Res., 64 (21: 7995-8001, 2004 (Year: 2004).*
Agarwal et al., "Site-specific antibody-drug conjugates: the nexus of bioorthogonal chemistry, protein engineering, and drug development", Bioconjug Chem, 2015, vol. 26, No. 2, pp. 176-192.
Baert et al., "Influence of immunogenicity on the long-term efficacy of infliximab in Crohn's disease", N Engl J Med, 2003, vol. 348, pp. 601-608.
Ban et al., "Facile and Stabile Linkages through Tyrosine: Bioconjugation Strategies with the Tyrosine-Click Reaction", Bioconjugate Chemistry, 2013, vol. 24, 4, pp. 520-532.

(Continued)

*Primary Examiner* — Lei Yao
(74) *Attorney, Agent, or Firm* — BakerHostetler

(57) ABSTRACT

Disclosed herein are antibodies or antigen binding fragments thereof that bind prostate specific membrane antigen (PSMA), polynucleotides, vectors, host cells, radioconjugates, antibody drug conjugates and methods of treating cancer using the same.

27 Claims, No Drawings
Specification includes a Sequence Listing.

(56) References Cited

OTHER PUBLICATIONS

Bostwick et al., "Prostate Specific Membrane Antigen Expression inProstatic Intraepithelial Neoplasia and Adenocarcinoma", Cancer, 1998, vol. 82, No. 11, pp. 2256-2261.
Brinkley, "A brief survey of methods for preparing protein conjugates with dyes, haptens and crosslinking reagents", Bioconjugate Chem. 1992, vol. 3, No. 1, pp. 2-13.
Cruz et al., "Synthesis and Enhanced Cellular Uptake in Vitro of Anti-HER2 Multifunctional Gold Nanoparticles", Cancers 2019, vol. 11, No. 6,870, pp. 1-22.
Debets et al., "Bioconjugation with strained alkenes and alkynes", Ace Chem Res, 2011, vol. 44, No. 9, pp. 805-815.
Dubowchik et al., "Doxorubicin immunoconjugates containing bivalent, lysosomally-Cleavable dipeptide linkages", Bioorganic & Medicinal Chemistry Letters, vol. 12, Issue 11, Jun. 2002, pp. 1529-1532.
Gadi et al., "In vivo sensitization of ovarian tumors to chemotherapy by expression of E. coli purine nucleoside phosphorylase in a small fraction of cells", Gene Ther., 2000, vol. 7, pp. 1738-1743.
Gololobov et al., "Recent Advances in the Staudinger Reaction", Tetrahedron, 1992, vol. 48, pp. 1353-1406.
Hamblett et al., "Effects of drug loading on the antitumor activity of a monoclonal antibody drug conjugate", Clinical Cancer Research, 2004, vol. 10, pp. 7063-7070.
Hinman et al., "Preparation and characterization of monoclonal antibody conjugates of the calicheamicins: a novel and potent family of antitumor antibiotics", Cancer Res., 1993, vol. 53, pp. 3336-3342.
Hu et al., "Towards the next generation of biomedicines by site-selective conjugation", Chem Soc Rev., 2016, vol. 45, pp. 1691-1719.
Jeffrey et al., "Dipeptide-based highly potent doxorubicin antibody conjugates", Bioorganic & Medicinal Chemistry Letters, Jan. 2006, vol. 16, Issue 2, pp. 358-362.
Kantner et al., "In Situ Quenching of Trialkylphosphine Reducing Agents Using Water-Soluble PEG-Azides Improves Maleimide Conjugation to Proteins", ACS Omega, 2017, vol. 2, pp. 5785-5791.
Kawakami et al., "Enhanced Expression of Prostate-specific Membrane Antigen Gene in Prostate Cancer as Revealed by in Situ Hybridization", Cancer Res., 1997, vol. 57, No. 12, pp. 2321-2324.
King et al., "Monoclonal Antibody Conjugates of Doxorubicin Prepared with Branched Peptide Linkers: Inhibition of Aggregation by Methoxytriethyleneglycol Chains", J Med Chem, 2002, vol. 45, pp. 4336-4343.
Knappik et al., "Fully synthetic human combinatorial antibody libraries (HuCAL) based on modular consensus frameworks and CDRs randomized with trinucleotides", J Mol Biol, 2000, vol. 296, pp. 57-86.
Kratz et al., "Prodrugs of Anthracyclines in Cancer Chemotherapy", Current Med. Chem, 2006, vol. 13, No. 5, pp. 477-523.
Lin et al., "Redox-based reagents for chemoselective methionine bioconjugation", Science, 2017, vol. 355, pp. 597-602.
Liu et al., "Eradication of large colon tumor xenografts by targeted delivery of maytansinoids", Proc. Natl. Acad. Sci. USA, 1996, vol. 93, pp. 8618-8623.
Lode et al., "Targeted Therapy with a Novel Enediyene Antibiotic Calicheamicin ?I1 Effectively Suppresses Growth and Dissemination of Liver Metastases in a Syngeneic Model of Murine Neuroblastoma", Cancer Res., 1998, vol. 58, No. 2925-2928.
MacLennan et al., "Structure-function relationships in the Ca(2+)-binding and translocation domain of SERCA1: physiological correlates in Brody disease", Acta Physiol Scand Suppl., 1988, vol. 643, pp. 55-67.
Mandler et al., "Immunoconjugates of Geldanamycin and Anti-HER2 Monoclonal Antibodies: Antiproliferative Activity on Human Breast Carcinoma Cell Lines", Jour, of the Nat. Cancer Inst., 2000, vol. 92, No. 19, pp. 1573-1581.
Mandler et al., "Modifications in Synthesis Strategy Improve the Yield and Efficacy of Geldanamycin-Herceptin Immunoconjugates", 2000, Bioconjugate Chem. 2002, vol. 13, No. 4, pp. 786-791.
Mandler et al., "Synthesis and evaluation of antiproliferative activity of a geldanamycin-Herceptin™ immunoconjugate", Bioorganic & Med. Chem. Letters, 2000, vol. 10, pp. 1025-1028.
Mitsiades et al., "Molecular staging by RT-pCR analysis for PSA and PSMA in peripheral blood and bone marrow samples is an independent predictor of time to biochemical failure following radical prostatectomy for clinically localized prostate cancer", Clin Exp Metastasis, 2004, vol. 21, No. 6, pp. 495-505.
Nagy et al., "Stability of cytotoxic luteinizing hormone-releasing hormone conjugate (AN-152) containing doxorubicin 14-O-hemiglutarate in mouse and human serum in vitro: Implications for the design of preclinical studies", Proc Natl Acad Sci USA, 2000, vol. 97, pp. 829-834.
Padlan, "A possible procedure for reducing the immunogenicity of antibody variable domains while preserving their ligand-binding properties", Mol Immunol., 1991, vol. 28, No. 4/5, pp. 489-498.
Park et al., "Peptide-Directed Photo-Cross-Linking for Site-Specific Conjugation of IgG", Bioconjugate Chem, 2018, vol. 29, pp. 3240-3244.
Pham et al., "Tuning a Protein-Labeling Reaction to Achieve Highly Site Selective Lysine Conjugation", Chembiochem, 2018, vol. 18, pp. 799-804.
Rabuka, "Chemoenzymatic Methods for Site-Specific Protein Modification", Curr Opin Chem Biol., 2010, vol. 14, No. 6, pp. 790-796.
Roca-Sabio et al., "Macrocyclic Receptor Exhibiting Unprecedented Selectivity for Light Lanthanides" J. Am. Chem. Soc. 2009, vol. 131, No. 9, pp. 3331-3341.
Sasaki et al., "Structure-Mutation Analysis of the ATPase Site of Dictyostelium Discoideum Myosin II", Adv. Biophys., 1988, vol. 35, pp. 1-24.
Shi et al., "De novo selection of high-affinity antibodies from synthetic fab libraries displayed on phage as pIX fusion proteins", J Mol Biol, 2010, vol. 397, pp. 385-396.
Slichenmyer et al., "Camptothecin analogues: studies from The Johns Hopkins Oncology Center", Cancer Chemother Pharmacol, 1994, vol. 34, pp. S53-S57.
Stickler et al., "The human G1m1 allotype associates with CD4+ T-cell responsiveness to a highly conserved IgG1 constant region peptide and confers an asparaginyl endopeptidase cleavage site", Genes and Immunity, 2011, vol. 12, pp. 213-221.
Thiele et al., "An Eighteen-Membered Macrocyclic Ligand for Actinium-225 Targeted Alpha Therapy", Angew Chem Int Ed Engl., 2017, vol. 56, pp. 14712-14717.
Toda et al., "Rapid, Stable, Chemoselective Labeling of Thiols with Julia-Kocienski-like Reagents: A Serum-Stable Alternative to Maleimide-Based Protein Conjugation", Angew Chemie, 2013, vol. 52 Issue 48, pp. 12592-12596.
Torgov et al., "Generation of an Intensely Potent Anthracycline by a Monoclonal Antibody-13-Galactosidase Conjugate.", Bioconj Chem, 2005, vol. 16, pp. 717-721.
Wright et al., "Upregulation of prostate-specific membrane antigen after androgendeprivation therapy", Urology, 1996, vol. 48, No. 2, pp. 326-334.
Yamada et al., "AJICAP: Affinity Peptide Mediated Regiodivergent Functionalization of Native Antibodies", Angew Chem Int Ed Engl., Apr. 2019, vol. 58, No. 17, pp. 5592-5597.

* cited by examiner

ANTI-PSMA ANTIBODIES AND USES THEREOF

CROSS-REFERENCE TO RELATED APPLICATIONS

This application claims priority to U.S. Provisional Application No. 63/237,663 filed on Aug. 27, 2021, titled "ANTI-PSMA ANTIBODIES AND USES THEREOF", the disclosure of each of which is incorporated by reference herein in its entirety.

SEQUENCE LISTING

The instant application contains a Sequence Listing which has been submitted electronically in XML file format and is hereby incorporated by reference in its entirety. Said XML copy, created on Jul. 11, 2022, is named JBI6621USNP1_SL.xml and is 282,897 bytes in size.

TECHNICAL FIELD

Provided herein are antibodies or antigen binding fragments thereof that bind prostate specific membrane antigen (PSMA), polynucleotides, vectors, host cells, radioconjugates, antibody drug conjugates and methods of treating cancer using the same.

BACKGROUND

Prostate cancer is the second most common cancer in men worldwide, and the sixth leading cause of cancer-related death. Globally, there are approximately 1,100,000 new cases and 300,000 mortalities every year, comprising 4 percent of all cancer deaths. It is estimated that 1 in every 6 men will be diagnosed with the disease during his lifetime. In the U.S., more than 90% of prostate cancers are found in local or regional stages. At these early stages, the 5-year survival rate nears 100%. When the cancer has metastasized, however, the 5-year survival rate drops to 28%, and there remains a need for effective treatments for advanced-stage prostate cancer.

Prostate specific membrane antigen (PSMA), is a type II membrane protein that is highly expressed in prostatic intraepithelial neoplasia (PIN), a condition in which some prostate cells have begun to look and behave abnormally, and in primary and metastatic prostate cancers (Bostwick D G, et al, Prostate specific membrane antigen expression in prostatic intraepithelial neoplasia and adenocarcinoma: A study of 184 cases. Cancer 1998; 82 (11):2256-2261). Expression of PSMA in cancer tissues correlates with the stage of disease and Gleason score (Kawakami M, et al. Enhanced expression of prostate-specific membrane antigen gene in prostate cancer as revealed by in situ hybridization. Cancer Res 1997; 57(12):2321-2324). PSMA expression is also higher in prostate cancer cells from hormone-refractory patients (Wright G L et al., Upregulation of prostate-specific membrane antigen after androgen-deprivation therapy. Urology 1996; 48(2):326-334) and increased PSMA expression has been shown to be an independent marker of disease recurrence (Mitsiades C S, et al. Molecular staging by RT-pCR analysis for PSA and PSMA in peripheral blood and bone marrow samples is an independent predictor of time to biochemical failure following radical prostatectomy for clinically localized prostate cancer. Clin Exp Metastasis 2004; 21(6):495-505). High-level PSMA expression is correlated with early prostate-specific antigen (PSA) recurrence in surgically treated prostate cancer. PSMA expression levels correlate with the aggressiveness of the disease, and thereby strongly support PSMA as an excellent target for prostate cancer characterization and subsequent therapy.

Current treatments for prostate cancer include surgery, radiation and hormone therapies. When prostate cancers grow despite the lowering of testosterone levels by hormone therapy, treatment options are limited. This underscores the need for more improved treatment and effective therapies for PSMA-expressing advanced prostate cancer.

BRIEF SUMMARY

Provided herein is an isolated antibody or antigen binding fragment thereof that binds to PSMA comprising a heavy chain complementarity determining region 1 (HCDR1), a HCDR2, and a HCDR3, and a light chain complementarity determining region 1 (LCDR1), a LCDR2, and LCDR3, wherein the HCDR1, HCDR2, HCDR3, LCDR1, LCDR2 and LCDR3 comprise the amino acid sequences of:

a. RYGMH (SEQ ID NO: 4), LISYDGSNRYYADSVKG (SEQ ID NO: 5), ERESSGWFEGYFDY (SEQ ID NO: 6), GGNNIGSKSVH (SEQ ID NO: 7), DNSDRPS (SEQ ID NO: 8), and QVWDSSSDHVV (SEQ ID NO: 9), respectively;

b. SYYWN (SEQ ID NO: 10), RIYSSGNTDYNPSLKS (SEQ ID NO: 11), GRGANVGLFDY (SEQ ID NO: 12), TGSNSNIGANYDVH (SEQ ID NO: 13), GNINRPL (SEQ ID NO: 14), and QSYDFSLSGSV (SEQ ID NO: 15), respectively;

c. GYGMH (SEQ ID NO: 16), VISYDGSNRYYADSVKG (SEQ ID NO: 17), DGNWGSLDLYFDL (SEQ ID NO: 18), TGSSSNIGADYDVH (SEQ ID NO:19), VNNNRPS (SEQ ID NO: 20), and QSYDNTLSGVV (SEQ ID NO: 21), respectively;

d. SYGMH (SEQ ID NO: 22), VISYDGSNKYYADSVKG (SEQ ID NO: 23), EHYDSSGYYHGYYGMDV (SEQ ID NO: 24), SGSSSNIGSNYVY (SEQ ID NO: 25), SNNQRPS (SEQ ID NO: 26), AARDDSLSGYV (SEQ ID NO: 27), respectively;

e. SYDMH (SEQ ID NO: 28), VISFDGSNKYYVDSVKG (SEQ ID NO: 29), TYYDILTGYSHYSYGMDV (SEQ ID NO: 30), RASQGISNYLA (SEQ ID NO: 31), ATSTLQS (SEQ ID NO: 32), and QKYNSAPFT (SEQ ID NO: 33), respectively;

f. TYGMH (SEQ ID NO: 34), FISYDGSNKYYADSVKG (SEQ ID NO: 35), RDNLRFLEWFMDV (SEQ ID NO: 36), RASQSVRSNLA (SEQ ID NO: 37), GASTRAT (SEQ ID NO: 38), and HQYNDWPPYT (SEQ ID NO: 39), respectively;

g. IYSMN (SEQ ID NO: 40), SISSSSSYIFYADSVKG (SEQ ID NO: 41), SSYGADY (SEQ ID NO: 42), RASQDITNFLA (SEQ ID NO: 43), TASTLQS (SEQ ID NO: 44), and QKYNSAPLT (SEQ ID NO: 45), respectively;

h. SYSLN (SEQ ID NO: 46), SISSSSSYISYADAVKG (SEQ ID NO: 47), DRGFLEDYYYYYGMDV (SEQ ID NO: 48), RASQGISNWLA (SEQ ID NO: 49), VASSLQS (SEQ ID NO: 50), and QQAYSFPLT (SEQ ID NO: 51), respectively;

i. SYYWS (SEQ ID NO: 272), RIYSSGSTNYNPSLKS (SEQ ID NO: 273), VGVWPGAFDI (SEQ ID NO: 274), SGSSSNIGSNTVN (SEQ ID NO: 275), SSNQRPS (SEQ ID NO: 276) and AAWDDSLNGVV (SEQ ID NO: 277), respectively;

j. GFTLSRY (SEQ ID NO: 124), SYDGSN (SEQ ID NO:125), ERESSGWFEGYFDY (SEQ ID NO: 6), GGNNIGSKSVH (SEQ ID NO: 7), DNSDRPS (SEQ ID NO: 8) and QVWDSSSDHVV (SEQ ID NO: 9), respectively;

k. GGSISSY (SEQ ID NO: 130), YSSGN (SEQ ID NO:131), GRGANVGLFDY (SEQ ID NO: 12), TGSNSNIGANYDVH (SEQ ID NO: 13), GNINRPL (SEQ ID NO:14), and QSYDFSLSGSV (SEQ ID NO:15), respectively;

l. VRTFSGY (SEQ ID NO: 136), SYDGSN (SEQ ID NO:125), DGNWGSLDLYFDL (SEQ ID NO:18), TGSSSNIGADYDVH (SEQ ID NO:19), VNNNRPS (SEQ ID NO: 20), and QSYDNTLSGVV (SEQ ID NO: 21), respectively;

m. GFTFTSY (SEQ ID NO: 142), SYDGSN (SEQ ID NO: 125), EHYDSSGYYHGYYGMDV (SEQ ID NO: 24), SGSSSNIGSNYVY (SEQ ID NO:25), SNNQRPS (SEQ ID NO: 26), and AARDDSLSGYV (SEQ ID NO:27), respectively;

n. GFTFSSY (SEQ ID NO: 148), SFDGSN (SEQ ID NO:149), TYYDILTGYSHYSYGMDV (SEQ ID NO: 30), RASQGISNYLA (SEQ ID NO: 31), ATSTLQS (SEQ ID NO: 32), and QKYNSAPFT (SEQ ID NO: 33), respectively;

o. GFTFSTY (SEQ ID NO: 154), SYDGSN (SEQ ID NO: 125), RDNLRFLEWFMDV (SEQ ID NO:36), RASQSVRSNLA (SEQ ID NO:37), GASTRAT (SEQ ID NO:38), and HQYNDWPPYT (SEQ ID NO:39), respectively;

p. GFTLSIY (SEQ ID NO: 160), SSSSSY (SEQ ID NO:161), SSYGADY (SEQ ID NO:42), RASQDITNFLA (SEQ ID NO:43), TASTLQS (SEQ ID NO:44), and QKYNSAPLT (SEQ ID NO:45), respectively;

q. GFTFSSY (SEQ ID NO: 166), SSSSSY (SEQ ID NO: 167), DRGFLEDYYYYYGMDV (SEQ ID NO; 48), RASQGISNWLA (SEQ ID NO: 49), VASSLQS (SEQ ID NO:50), and QQAYSFPLT (SEQ ID NO: 51), respectively;

r. GGSIISY (SEQ ID NO: 290), YSSGS (SEQ ID NO:291), VGVWPGAFDI (SEQ ID NO: 274), SGSSSNIGSNTVN (SEQ ID NO:275), SSNQRPS (SEQ ID NO:276), and AAWDDSLNGVV (SEQ ID NO: 277), respectively;

s. GFTLSRYGMH (SEQ ID NO: 172), LISYDGSNRY (SEQ ID NO:173), ERESSGWFEGYFDY (SEQ ID NO:6), GGNNIGSKSVH (SEQ ID NO:7), DNSDRPS (SEQ ID NO: 8), and QVWDSSSDHVV (SEQ ID NO:9), respectively;

t. GGSISSYYWN (SEQ ID NO: 178), RIYSSGNTD (SEQ ID NO:179), GRGANVGLFDY (SEQ ID NO:12), TGSNSNIGANYDVH (SEQ ID NO:13), GNINRPL (SEQ ID NO:14), and QSYDFSLSGSV (SEQ ID NO:15), respectively;

u. VRTFSGYGMH (SEQ ID NO: 184), VISYDGSNRY (SEQ ID NO:185), DGNWGSLDLYFDL (SEQ ID NO: 18), TGSSSNIGADYDVH (SEQ ID NO:19), VNNNRPS (SEQ ID NO: 20), and QSYDNTLSGVV (SEQ ID NO:21), respectively;

v. GFTFTSYGMH (SEQ ID NO: 190), VISYDGSNKY (SEQ ID NO:191), EHYDSSGYYHGYYGMDV (SEQ ID NO:24), SGSSSNIGSNYVY (SEQ ID NO:25), SNNQRPS (SEQ ID NO:26), and AARDDSLSGYV (SEQ ID NO:27), respectively;

w. GFTFSSYDMH (SEQ ID NO: 196), VISFDGSNKY (SEQ ID NO: 197), TYYDILTGYSHYSYGMDV (SEQ ID NO: 30), RASQGISNYLA (SEQ ID NO:31), ATSTLQS (SEQ ID NO:32), and QKYNSAPFT (SEQ ID NO:33), respectively;

x. GFTFSTYGMH (SEQ ID NO: 202), FISYDGSNKY (SEQ ID NO:203), RDNLRFLEWFMDV (SEQ ID NO: 36), RASQSVRSNLA (SEQ ID NO:37), GASTRAT (SEQ ID NO:38), and HQYNDWPPYT (SEQ ID NO: 39), respectively;

y. GFTLSIYSMN (SEQ ID NO: 208), SISSSSSYIF (SEQ ID NO:209), SSYGADY (SEQ ID NO: 42), RASQDITNFLA, (SEQ ID NO: 43), TASTLQS (SEQ ID NO: 44), and QKYNSAPLT (SEQ ID NO:45), respectively;

z. GFTFSSYSLN (SEQ ID NO: 214), SISSSSSYIS (SEQ ID NO:215), DRGFLEDYYYYYGMDV (SEQ ID NO:48), RASQGISNWL (SEQ ID NO:49), VASSLQS (SEQ ID NO:50), and QQAYSF (SEQ ID NO:51), respectively;

aa. GGSIISYYWS (SEQ ID NO: 296), RIYSSGSTN (SEQ ID NO: 297), VGVWPGAFDI (SEQ ID NO:274), SGSSSNIGSNTVN (SEQ ID NO:275), SSNQRPS (SEQ ID NO:276), and AAWDDSLNGVV (SEQ ID NO:277), respectively;

bb. GFTLSRYG (SEQ ID NO: 220), ISYDGSNR (SEQ ID NO:221), ARERESSGWFEGYFDY (SEQ ID NO: 222), NIGSKS (SEQ ID NO:223), DNS, and QVWDSSSDHVV (SEQ ID NO:9), respectively;

cc. GGSISSYY (SEQ ID NO: 226), IYSSGNT (SEQ ID NO: 227), ARGRGANVGLFDY (SEQ ID NO:228), NSNIGANYD (SEQ ID NO:229), GNI, and QSYDFSLSGSV (SEQ ID NO:15), respectively;

dd. VRTFSGYG (SEQ ID NO: 232), ISYDGSNR (SEQ ID NO:233), ARDGNWGSLDLYFDL (SEQ ID NO:234), SSNIGADYD (SEQ ID NO:235), VNN, and QSYDNTLSGVV (SEQ ID NO:21), respectively;

ee. GFTFTSYG (SEQ ID NO: 238), ISYDGSNK (SEQ ID NO:239, AREHYDSSGYYHGYYGMDV (SEQ ID NO: 240), SSNIGSNY (SEQ ID NO:241), SNN, and AARDDSLSGYV (SEQ ID NO:27), respectively;

ff. GFTFSSYD (SEQ ID NO: 244), ISFDGSNK (SEQ ID NO:245), ARTYYDILTGYSHYSYGMDV (SEQ ID NO: 246), QGISNY (SEQ ID NO:247), ATS, and QKYNSAPFT (SEQ ID NO:33), respectively;

gg. GFTFSTYG (SEQ ID NO: 250), ISYDGSNK (SEQ ID NO:251), AGRDNLRFLEWFMDV (SEQ ID NO:252), QSVRSN (SEQ ID NO: 253), GAS, and HQYNDWPPYT (SEQ ID NO:39), respectively;

hh. GFTLSIYS (SEQ ID NO: 256), ISSSSSYI (SEQ ID NO:257), ARSSYGADY (SEQ ID NO:258), QDITNF (SEQ ID NO: 259), TAS, and QKYNSAPLT (SEQ ID NO:45), respectively;

ii. GFTFSSYS (SEQ ID NO: 262), ISSSSSYI (SEQ ID NO:263), ARDRGFLEDYYYYYGMDV (SEQ ID NO:264), QGISNW (SEQ ID NO:265), VAS, and QQAYSFPLT (SEQ ID NO:51), respectively; or jj. GGSIISYY (SEQ ID NO: 302), IYSSGST (SEQ ID NO:303), AKVGVWPGAFDI (SEQ ID NO:304), SSNIGSNT (SEQ ID NO:305), SSN, and AAWDDSLNGVV (SEQ ID NO: 277), respectively.

Also disclosed is an isolated antibody or antigen binding fragment thereof, comprising a heavy chain variable region (VH) and a light chain variable region (VL) of:

SEQ ID NOs: 52 and 53 respectively;
SEQ ID NOs: 54 and 55 respectively;
SEQ ID NOs: 56 and 57 respectively;
SEQ ID NOs: 58 and 59 respectively;
SEQ ID NOs: 60 and 61 respectively;

SEQ ID NOs: 62 and 63 respectively;
SEQ ID NOs: 64 and 65 respectively;
SEQ ID NOs: 66 and 67 respectively; or
SEQ ID NOs: 278 and 279 respectively, and wherein the antibody or antigen binding fragment thereof binds PSMA.

The disclosure also provides an isolated antibody or antigen binding fragment thereof, comprising a VH which is at least 80% (e.g. at least 85%, at least 90%, at least 95%, at least 99% or 100%) identical to the VH of SEQ ID NO: 52 and a VL which is at least 80% (e.g. at least 85%, at least 90%, at least 95%, at least 99% or 100%) identical to the VL of SEQ ID NO: 53.

The disclosure also provides an isolated antibody or antigen binding fragment thereof, comprising a VH which is at least 80%, at least 85%, at least 90%, at least 95%, at least 99% or 100% identical to the VH of SEQ ID NO: 54 and a VL which is at least 80%, at least 85%, at least 90%, at least 95%, at least 99% or 100% identical to the VL of SEQ ID NO: 55

The disclosure also provides an isolated antibody or antigen binding fragment thereof comprising an amino acid sequence selected from the group consisting of SEQ ID NOs: 84, 85, 86, 88, 89, 90, 92, 93, 94, 95, 96, 97, 98, 99, 100, 101, 102, 103, 268, 269, 282, 284, and 288.

The disclosure also provides an antibody or antigen binding fragment thereof comprising an amino acid sequence at least 80%, at least 85%, at least 90%, at least 95%, at least 99% or 100% identical to the amino acid sequence of SEQ ID NO: 84 or 85.

The disclosure also provides antibody or antigen binding fragment thereof comprising an amino acid sequence at least 80%, at least 85%, at least 90%, at least 95%, at least 99% or 100% identical to the amino acid sequence of SEQ ID NO: 86 or 85.

The disclosure also provides antibody or antigen binding fragment thereof comprising an amino acid sequence at least 80%. At least 85%, at least 90%, at least 95%, at least 99% or 100% identical to the amino acid sequence of SEQ ID NO: 88 or 89.

Also disclosed is an isolated antibody or antigen binding fragment thereof comprising:
a HCDR1, a HCDR2, a HCDR3, a LCDR1, a LCDR2 and a LCDR3 of SEQ ID NOs: 4, 5, 6, 7, 8, and 9, respectively;
a VH of SEQ ID NO: 52 and a VL of SEQ ID NO: 53; and/or
a HC of SEQ ID NO: 84 and a LC of SEQ ID NO: 85; and wherein the antibody or antigen binding fragment thereof binds PSMA.

Also disclosed is an isolated antibody or antigen binding fragment thereof comprising:
a HCDR1, a HCDR2, a HCDR3, a LCDR1, a LCDR2 and a LCDR3 of SEQ ID NOs: 4, 5, 6, 7, 8, and 9, respectively;
a VH of SEQ ID NO: 52 and a VL of SEQ ID NO: 53; and/or
a HC of SEQ ID NO: 86 and a LC of SEQ ID NO: 85; and wherein the antibody or antigen binding fragment thereof binds PSMA.

Also disclosed is an isolated antibody or antigen binding fragment thereof comprising:
a HCDR1, a HCDR2, a HCDR3, a LCDR1, a LCDR2 and a LCDR3 of SEQ ID NOs: 10, 11, 12, 13, 14 and 15, respectively;
a VH of SEQ ID NO: 54 and a VL of SEQ ID NO: 55; and/or
a HC of SEQ ID NO: 88 and a LC of SEQ ID NO: 89; and wherein the antibody or antigen binding fragment thereof binds PSMA.

Also disclosed is an isolated antibody or antigen binding fragment thereof comprising:
a HCDR1, a HCDR2, a HCDR3, a LCDR1, a LCDR2 and a LCDR3 of SEQ ID NOs: 10, 11, 12, 13, 14 and 15, respectively;
a VH of SEQ ID NO: 54 and a VL of SEQ ID NO: 55; and/or
a HC of SEQ ID NO: 90 and a LC of SEQ ID NO: 89; and wherein the antibody or antigen binding fragment thereof binds PSMA.

Also disclosed is an isolated antibody or antigen binding fragment thereof comprising:
a HCDR1, a HCDR2, a HCDR3, a LCDR1, a LCDR2 and a LCDR3 of SEQ ID NOs: 16, 17, 18, 19, 20 and 21, respectively;
a VH of SEQ ID NO: 56 and a VL of SEQ ID NO: 57; and/or
a HC of SEQ ID NO: 92 and a LC of SEQ ID NO: 93; and wherein the antibody or antigen binding fragment thereof binds PSMA.

Also disclosed is an isolated antibody or antigen binding fragment thereof comprising:
a HCDR1, a HCDR2, a HCDR3, a LCDR1, a LCDR2 and a LCDR3 of SEQ ID NOs: 22, 23, 24, 25, 26 and 27, respectively;
a VH of SEQ ID NO: 58 and a VL of SEQ ID NO: 59; and/or
a HC of SEQ ID NO: 94 and a LC of SEQ ID NO: 95; and wherein the antibody or antigen binding fragment thereof binds PSMA.

Also disclosed is an isolated antibody or antigen binding fragment thereof comprising:
a HCDR1, a HCDR2, a HCDR3, a LCDR1, a LCDR2 and a LCDR3 of SEQ ID NOs: 28, 29, 30, 31, 32, and 33, respectively;
a VH of SEQ ID NO: 60 and a VL of SEQ ID NO: 61; and/or
a HC of SEQ ID NO: 96 and a LC of SEQ ID NO: 97; and wherein the antibody or antigen binding fragment thereof binds PSMA.

Also disclosed is an isolated antibody or antigen binding fragment thereof comprising:
a HCDR1, a HCDR2, a HCDR3, a LCDR1, a LCDR2 and a LCDR3 of SEQ ID NOs: 34, 35, 36, 37, 38 and 39, respectively;
a VH of SEQ ID NO: 62 and a VL of SEQ ID NO: 63; and/or
a HC of SEQ ID NO: 98 and a LC of SEQ ID NO: 99; and wherein the antibody or antigen binding fragment thereof binds PSMA.

Also disclosed is an isolated antibody or antigen binding fragment thereof comprising:
a HCDR1, a HCDR2, a HCDR3, a LCDR1, a LCDR2 and a LCDR3 of SEQ ID NOs: 40, 41, 42, 43, 44 and 45, respectively;
a VH of SEQ ID NO: 64 and a VL of SEQ ID NO: 65; and/or
a HC of SEQ ID NO: 100 and a LC of SEQ ID NO: 101; and wherein the antibody or antigen binding fragment thereof binds PSMA.

Also disclosed is an isolated antibody or antigen binding fragment thereof comprising:
- a HCDR1, a HCDR2, a HCDR3, a LCDR1, a LCDR2 and a LCDR3 of SEQ ID NOs: 46, 47, 48, 49, 50 and 51, respectively;
- a VH of SEQ ID NO: 66 and a VL of SEQ ID NO: 67; and/or
- a HC of SEQ ID NO: 102 and a LC of SEQ ID NO: 103; and wherein the antibody or antigen binding fragment thereof binds PSMA.

The disclosure also provides an isolated antibody or antigen binding fragment thereof that binds PSMA, wherein the isolated antibody or antigen binding fragment thereof is a biparatopic antibody comprising two antigen-binding domains, wherein the first antigen binding domain binds to a first epitope of PSMA and the second binding domain binds to a second epitope on PSMA.

In some embodiments, the biparatopic antibody comprises two antigen-binding domains wherein:
- the first antigen binding domain is a Fab or a Fab fragment comprising a HCDR1 of SEQ ID NO: 4, a HCDR2 of SEQ ID NO: 5, a HCDR3 of SEQ ID NO: 6, a LCDR1 of SEQ ID NO: 7, a LCDR2 of SEQ ID NO: 8, a LCDR3 of SEQ ID NO: 9, a VH of SEQ ID NO: 52, a VL of SEQ ID NO: 53, a HC of SEQ ID NO: 268 and a LC of SEQ ID NO: 269; and the second antigen binding domain is in a scFv format comprising a HCDR1 of SEQ ID NO: 272, a HCDR2 of SEQ ID NO: 273, a HCDR3 of SEQ ID NO: 274 a LCDR1 of SEQ ID NO: 275, a LCDR2 of SEQ ID NO: 276, a LCDR3 of SEQ ID NO: 277, a VH of SEQ ID NO: 278, a VL of SEQ ID NO: 279, a HC of SEQ ID NO: 282; or
- the first antigen binding domain is a Fab or a Fab fragment comprising a HCDR1 of SEQ ID NO: 4, a HCDR2 of SEQ ID NO: 5, a HCDR3 of SEQ ID NO: 6, a LCDR1 of SEQ ID NO: 7, a LCDR2 of SEQ ID NO: 8, a LCDR3 of SEQ ID NO: 9, a VH of SEQ ID NO: 52, a VL of SEQ ID NO: 53, a HC of SEQ ID NO: 284 and a LC of SEQ ID NO: 269; and the second antigen binding domain is in a scFv format comprising a HCDR1 of SEQ ID NO: 272, a HCDR2 of SEQ ID NO: 273, a HCDR3 of SEQ ID NO: 274 a LCDR1 of SEQ ID NO: 275, a LCDR2 of SEQ ID NO: 276, a LCDR3 of SEQ ID NO: 277, a VH of SEQ ID NO: 278, a VL of SEQ ID NO: 279, a HC of SEQ ID NO: 288.

In some embodiments, the disclosed isolated antibody or antigen binding fragment thereof is of an IgG1, an IgG2, an IgG3 or an IgG4 isotype.

In some embodiments, the isolated antibody or antigen binding is an IgG1 isotype.

In some embodiments, the isolated antibody or antigen binding fragment thereof comprises an Ig constant region or the fragment of an Ig constant region, wherein the Ig constant region of the fragment or the constant region comprises at least one mutation that results in reduced binding of the antibody or antigen binding fragment thereof to a Fcγ receptor (FcγR).

In some embodiments, the at least one mutation that results in reduced binding of the protein to the FcγR is selected from the group consisting of F234A/L235A, L234A/L235A, L234A/L235A/D265S, V234A/G237A/P238S/H268A/V309L/A330S/P331S, F234A/L235A, S228P/F234A/L235A, N297A, V234A/G237A, K214T/E233P/L234V/L235A/G236-deleted/A327G/P331A/D365E/L358M, H268Q/V309L/A330S/P331S, S267E/L328F, L234F/L235E/D265A, L234A/L235A/G237A/P238S/H268A/A330S/P331S, S228P/F234A/L235A/G237A/P238S and S228P/F234A/L235A/G236-deleted/G237A/P238S, wherein residue numbering is according to the EU index.

In some embodiments, the mutations that results in reduced binding of the antibody or antigen binding fragment thereof to the FcγR are L234A_L235A_D265S.

In some embodiments, the FcγR is FcγRI, FcγRIIA, FcγRIIB or FcγRIII, or any combination thereof.

In some embodiments, the isolated antibody or antigen binding fragment thereof comprises an Ig constant region or the fragment of an Ig constant region, wherein the Ig constant region of the fragment or the constant region comprises at least one mutation that modulates the half-life of the antibody.

In some embodiments, the at least one mutation that modulates the half-life of the antibody is selected from the group consisting of H435A, P257I/N434H, D376V/N434H, M252Y/S254T/T256E, M252Y/S254T/T256E/H433K/N434F, T308P/N434A and H435R, wherein residue numbering is according to the EU index.

In some embodiments, the mutations that modulates the half-life of the antibody or antigen binding fragment thereof are M252Y/S254T/T256E mutations.

The disclosure also provides a polynucleotide encoding the isolated antibody or antigen binding fragment thereof of the disclosure.

Optionally, the polynucleotide encoding the isolated antibody or antigen binding fragment thereof that binds PSMA comprises a polynucleotide sequence of SEQ ID NOs: 68, 69, 70, 71, 72, 73, 74, 75, 76, 77, 78, 79, 80, 81, 82, 83, 104, 105, 106, 108, 109, 110, 112, 113, 114, 115, 116, 117, 118, 119, 120, 121, 122, 123, 134, 135, 270, 271, 280, 281, 283, 286 or 289.

Optionally, the polynucleotide encoding the isolated antibody or antigen binding fragment thereof that binds PSMA is at least 80% (e.g. at least 85%, at least 90%, at least 95%, at least 99% or 100%) identical to the polynucleotide sequence of SEQ ID NOs: 68, 69, 70, 71, 72, 73, 74, 75, 76, 77, 78, 79, 80, 81, 82, 83, 104, 105, 106, 108, 109, 110, 112, 113, 114, 115, 116, 117, 118, 119, 120, 121, 122, 123, 134, 135, 270, 271, 280, 281, 283, 286 or 289 The disclosure also provides a vector comprising the polynucleotide of the disclosure.

The disclosure also provides a host cell comprising the polynucleotide or vector of the disclosure.

The disclosure also provides a radioconjugate comprising at least one radiometal complex conjugated to an antibody, or an antigen binding fragment thereof, with binding specificity for PSMA, and wherein the radiometal complex comprises a radiometal ion.

The disclosure also provides a radioconjugate comprising at least one radiometal complex conjugated to any of the antibody, or an antigen binding fragment thereof of the disclosure and wherein the radiometal complex comprises a radiometal ion.

The disclosure also provides a radioconjugate, wherein the antibody, or an antigen binding fragment comprises a heavy chain variable domain comprising the HCDR1, HCDR2 and HCDR3 of SEQ ID NO: 4, 5, and 6, respectively, and a light chain variable region comprising the LCDR1, LCDR2 and LCDR3 of SEQ ID NO: 7, 8 and 9, respectively.

The disclosure also provides a radioconjugate wherein the antibody, or an antigen binding fragment comprises a heavy chain variable region (VH) having at least 80%, at least 85%, at least 90%, at least 95%, or at least 98% sequence identity to the amino acid sequence of SEQ ID NO: 52, and a light chain variable region (VL) having at least 80%, at least 85%, at least 90%, at least 95%, or at least 98% sequence identity to the amino acid sequence of SEQ ID NO: 53.

The disclosure also provides a radioconjugate wherein the antibody, or an antigen binding fragment comprises a heavy chain variable region (VH) comprising the amino acid sequence of SEQ ID NO: 52, and a light chain variable region (VL) comprises the amino acid sequence of SEQ ID NO: 53.

The disclosure also provides a radioconjugate wherein the antibody, or an antigen binding fragment comprises a HC of SEQ ID NO: 86 and a LC of SEQ ID NO: 85; and wherein the antibody or an antigen binding fragment thereof is an IgG1 comprising an Ig constant region or the fragment of an Ig constant region, and wherein the Ig constant region or the fragment of the constant region comprises at least one mutation that results in reduced binding of the antibody or antigen binding fragment thereof to a Fcγ receptor (FcγR).

In some embodiments, the at least one mutation that results in reduced binding of the protein to the FcγR is selected from the group consisting of F234A/L235A, L234A/L235A, L234A/L235A/D265S, V234A/G237A/P238S/H268A/V309L/A330S/P331S, F234A/L235A, S228P/F234A/L235A, N297A, V234A/G237A, K214T/E233P/L234V/L235A/G236-deleted/A327G/P331A/D365E/L358M, H268Q/V309L/A330S/P331S, S267E/L328F, L234F/L235E/D265A, L234A/L235A/G237A/P238S/H268A/A330S/P331S, S228P/F234A/L235A/G237A/P238S and S228P/F234A/L235A/G236-deleted/G237A/P238S, wherein residue numbering is according to the EU index.

In some embodiments, the mutations that results in reduced binding of the antibody or antigen binding fragment thereof to the FcγRare L234A_L235A_D265S.

The disclosure also provides a radioconjugate, wherein the antibody, or an antigen binding fragment comprises a HC of SEQ ID NO: 86 and a LC of SEQ ID NO: 85; and wherein the antibody or an antigen binding fragment thereof is an IgG1 comprising an Ig constant region or the fragment of an Ig constant region, and wherein the Ig constant region or the fragment of the constant region comprises at least one mutation that modulates a half-life of the antibody.

In some embodiments, the at least one mutation that modulates the half-life of the antibody is selected from the group consisting of H435A, P257I/N434H, D376V/N434H, M252Y/S254T/T256E, M252Y/S254T/T256E/H433K/N434F, T308P/N434A and H435R, wherein residue numbering is according to the EU index.

In some embodiments, the mutations that modulates the half-life of the antibody or antigen binding fragment thereof are M252Y/S254T/T256E mutations.

The disclosure also provides a radioconjugate comprising at least one radiometal complex conjugated to an antibody, or an antigen binding fragment thereof, wherein the radiometal complex comprises a chelator complexed with a radiometal ion selected from the group consisting of $^{225}$Ac, $^{111}$In, $^{177}$Lu, $^{32}$P, $^{47}$Sc, $^{67}$Cu, $^{77}$AS, $^{89}$Sr, $^{90}$Y, $^{99}$Tc, $^{105}$Rh, $^{109}$Pd, $^{111}$Ag, $^{131}$I, $^{134}$Ce, $^{149}$Tb, $^{152}$Tb, $^{155}$Tb, $^{153}$Sm, $^{159}$Gd, $^{165}$Dy, $^{166}$Ho, $^{169}$Er, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{255}$Fm, $^{227}$Th, $^{177}$Lu, $^{62}$Cu, 64Cu, $^{67}$Ga, $^{68}$Ga, $^{86}$Y, $^{89}$Zr, $^{111}$In and $^{34}$Xe.

In some embodiments, the radiometal ion is $^{225}$AC.
In some embodiments, the radiometal ion is $^{111}$In.
In some embodiments, the radiometal ion is $^{134}$Xe.

In some embodiments, the radiometal complex comprises a radiometal ion chelated to a compound of formula (I) or a pharmaceutical acceptable salt thereof.

In some embodiments, the radiometal complex comprises a radiometal ion chelated to a compound of formula (II) or a pharmaceutical acceptable salt thereof.

In some embodiments, the radiometal complex comprises a radiometal ion chelated to a compound of formula (III) or a pharmaceutical acceptable salt thereof.

The disclosure also provides a pharmaceutical composition comprising any of the disclosed antibody or antigen binding fragment thereof; or any of the disclosed radioconjugate, and a pharmaceutically acceptable carrier.

The disclosure also provides a method of treating a PSMA expressing cancer in a subject, comprising administering a therapeutically effective amount of any of the disclosed antibody or antigen fragment thereof, any of the disclosed radioconjugate, or any of the disclosed pharmaceutical compositions, to the subject for a time sufficient to treat the cancer.

In some embodiments, the subject has prostate cancer.
In some embodiments, the subject has renal cancer.

The disclosure also provides a method of detecting PSMA in a sample with a radioconjugate of the disclosure.

The disclosure also provides a kit comprising any of the antibody or antigen binding fragment thereof, any of the radioconjugate, or any of the pharmaceutical compositions of the disclosure.

DETAILED DESCRIPTION OF THE INVENTION

Various publications, articles and patents are cited or described in the background and throughout the specification; each of these references in herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

The disclosed isolated anti-PSMA antibody, antigen binding fragment thereof, radioconjugates, antibody-drug conjugates, polynucleotides, vectors, cells, compositions, kits, and methods may be understood more readily by reference to the following detailed description taken in connection with the accompanying figures, which form a part of this disclosure. It is to be understood that the disclosed antibodies, antigen binding domains, antibody fragments, radioconjugates, antibody-drug conjugates, polynucleotides, vectors, cells, compositions, kits, and methods are not limited to those specifically described and/or shown herein, and that the terminology used herein is for the purpose of describing particular embodiments by way of example only and is not intended to be limiting of the claimed antibody, antigen binding domains, antibody fragments, radioconjugates, antibody-drug conjugates, polynucleotides, vectors, cells, compositions, kits, and methods.

Unless specifically stated otherwise, any description as to a possible mechanism or mode of action or reason for improvement is meant to be illustrative only, and the disclosed antibodies, antigen binding fragments thereof, polynucleotides, vectors, cells, radioconjugates, antibody-drug conjugates, compositions, kits, and methods are not to be constrained by the correctness or incorrectness of any such suggested mechanism or mode of action or reason for improvement.

Throughout this text, the descriptions refer to antibodies, antigen binding fragments thereof, radioconjugates, antibody drug conjugates and methods of using said antibodies, antigen binding fragments thereof, radioconjugates, and antibody drug conjugates. Where the disclosure describes or claims a feature or embodiment associated with an antigen binding domain, radioconjugate, and antibody-drug conjugate such a feature or embodiment is equally applicable to the methods of using said antigen binding domains, radioconjugate, and antibody-drug conjugate. Likewise, where the disclosure describes or claims a feature or embodiment associated with a method of using an antigen binding domains, radioconjugate, and antibody-drug conjugate such a feature or embodiment is equally applicable to the antigen binding domain, radioconjugate, and antibody-drug conjugate. Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the invention which are, for clarity, described herein in the context of separate embodiments may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, although an embodiment may be described as part of a series of steps or part of a more general structure, each said step may also be considered an independent embodiment in itself, combinable with others.

Unless specifically stated otherwise, any description as to a possible mechanism or mode of action or reason for improvement is meant to be illustrative only, and the disclosed methods are not to be constrained by the correctness or incorrectness of any such suggested mechanism or mode of action or reason for improvement.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed disclosure. Embodiments described in terms of the phrase "comprising" (or its equivalents) also provide as embodiments those independently described in terms of "consisting of" and "consisting essentially of." Embodiments described in terms of the phrase "consisting essentially of" (or its equivalents) also provide as embodiments those independently described in terms of "consisting of."

As used in this specification and the appended claims, the phrase "and fragments thereof" when appended to a list includes fragments of one or more members of the associated list. The list may comprise a Markush group so that, as an example, the phrase "the group consisting of peptides A, B, and C, and fragments thereof" specifies or recites a Markush group including A, B, C, fragments of A, fragments of B, and/or fragments of C.

All publications, including but not limited to patents and patent applications, cited in this specification are herein incorporated by reference as though fully set forth.

Antibodies that Bind PSMA

The disclosure relates to isolated antibodies and antigen binding fragments thereof that specifically bind PSMA.

As used herein the term "Antibody" is meant in a broad sense and includes immunoglobulin molecules including monoclonal antibodies including murine, human, humanized and chimeric monoclonal antibodies, antigen binding fragments, multispecific antibodies, such as bispecific, trispecific, tetraspecific, dimeric, tetrameric, multimeric or biparatopic antibodies, single chain antibodies, domain antibodies and any other modified configuration of the immunoglobulin molecule that comprises an antigen binding site of the required specificity. The term antibody includes full length antibodies, whole antibodies, intact antibodies, antibody fragments, antigen binding fragment and antigen binding domains.

In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to some embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

"Complementarity determining regions" (CDR) are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) J Exp Med 132: 211-50; Kabat et al., Sequences of Proteins of Immunological Interest, 5th Ed. Public Health Service, National Institutes of Health, Bethesda, Md., 1991), Chothia (Chothia et al. (1987) J Mol Biol 196: 901-17), IMGT (Lefranc et al. (2003) Dev Comp Immunol 27: 55-77) and AbM (Martin and Thornton J Bmol Biol 263: 800-15, 1996). The correspondence between the various delineations and variable region numbering is described (see e.g., Lefranc et al. (2003) Dev Comp Immunol 27: 55-77; Honegger and Pluckthun (2001), J Mol Biol 309:657-70; International ImMunoGeneTics (IMGT) database; Web resources, www_imgt_org). Available programs such as abYsis by UCL Business PLC may be used to delineate CDRs. The terms "CDR", "HCDR1", "HCDR2", "HCDR3", "LCDR1", "LCDR2" and "LCDR3" as used herein include CDRs defined by any of the methods described supra, Kabat, Chothia, IMGT or AbM, unless otherwise explicitly stated in the specification. Correspondence between the numbering system, including, for example, the Kabat numbering and the IMGT unique numbering system, is well known to one skilled in the art (see, e.g., Kabat, supra; Chothia, supra; Martin, supra; Lefranc et al., supra).

TABLE 1

|  | IMGT | Kabat | AbM | Chothia |
|---|---|---|---|---|
| V$_H$ CDR1 | 27-38 | 31-35 | 26-35 | 26-32 |
| V$_H$ CDR2 | 56-65 | 50-65 | 50-58 | 53-55 |
| V$_H$ CDR3 | 105-117 | 95-102 | 95-102 | 96-101 |
| V$_L$ CDR1 | 27-38 | 24-34 | 24-34 | 26-32 |
| V$_L$ CDR2 | 56-65 | 50-56 | 50-56 | 50-52 |
| V$_L$ CDR3 | 105-117 | 89-97 | 89-97 | 91-96 |

The term "variable region" or "variable domain" refers to the heavy or light chain domain that is involved in the binding of the antibody to the antigen. The variable domains of the heavy or light chain (VH and VL, respectively) comprise four framework regions (FR) and three complementarity determining regions (CDRs).

As used herein, the term "isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

As used herein, the term an "isolated antibody" refers to an antibody which is substantially free of other antibodies having different antigenic specificities (e.g., an isolated antibody that specifically binds to PSMA is substantially free of antibodies that do not bind to PSMA). In addition, an isolated antibody is substantially free of other cellular material and/or chemicals. "Isolated antibody" encompasses antibodies that are isolated to a higher purity, such as antibodies that are 80%, 81%, 82%, 83%, 84%, 85%, 86%, 87%, 88%, 89%, 90%, 91%, 92%, 93%, 94%, 95%, 96%, 97%, 98%, 99% or 100% pure.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "prostate-specific membrane antigen" or "PSMA" refers to a type II membrane protein expressed on certain cells. The amino acid sequence of the human PSMA is encoded by the FOLH1 gene. Unless specified, as used herein, PSMA refers to human PSMA. The amino acid sequence of human PSMA is retrievable from Uniprot (Accession #Q04609). The amino acid sequence of full length human PSMA is shown in SEQ ID NO: 336. The extracellular domain spans residues—4-750, the transmembrane domain spans residues—0-43 and the cytoplasmic domain spans residues—1-19 of SEQ ID NO:336.

SEQ ID NO: 336 (full-length human PSMA) MWNLL-HETDSAVATARRPRWLCAGALVLAGGFFLLGFLFGW-FIKSSNEATNITPKHN MKAFLDELKAENIKKFLY-NFTQIPHLAGTEQNFQLAKQIQSQWKEFGLDSVELA-HYDV LLSYPNKTHPNYISIINEDGNEIFNTSLFEPPP-PGYENVSDIVPPFSAFSPQGMPEGDLVYV NYART-EDFFKLERDMKINCSGKIVIARYGKVFRGNKVK-NAQLAGAKGVILYSDPADYF APGVKSYPDGWNLP-GGGVQRGNILNLNGAGDPLTPGYPANEYAYRRGI-AEAVGLPSIP VHPIGYYDAQKLLEKMGGSAPPDSS-WRGSLKVPYNVGPGFTGNFSTQKVKMHIHSTNE VTRIYNVIGTLRGAVEPDRYVILGGHRDSWVFG-GIDPQSGAAVVHEIVRSFGTLKKEG WRPRRTILFAS-WDAEEFGLLGSTEWAEENSRLLQERGVAYI-NADSSIEGNYTLRVDCTP LMYSLVHNLTKELKSPDE-GFEGKSLYESWTKKSPSPEFSGMPRISKLGSGNDFE-VFFQR LGIASGRARYTKNWETNKFSGYPLYHSVY-ETYELVEKFYDPMFKYHLTVAQVRGGMV FELAN-SIVLPFDCRDYAVVLRKYADKIYSISMKHPQEMKTY-SVSFDSLFSAVKNFTEIAS KFSERLQDFDKSNPIV-LRMMNDQLMFLERAFIDPLGLPDRPFYRHVIYAP-SSHNKYAGE SFPGIYDALFDIESKVDPSKAWGEVK-RQIYVAAFTVQAAAETLSEVA The term "PSMA" includes any PSMA variant, isoform, and species homolog, which is naturally expressed by cells (including prostate cells) or can be expressed on cells transfected with genes or cDNA encoding the polypeptide. In specific embodiments, the PSMA is a human PSMA.

"Specifically binds," "specific binding," "specifically binding" or "binds" refer to a proteinaceous molecule binding to an antigen or an epitope within the antigen with greater affinity than for other antigens.

"Epitope" refers to a portion of an antigen to which an antibody specifically binds. Epitopes typically consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

Typically, the proteinaceous molecule binds to the antigen or the epitope within the antigen with an equilibrium dissociation constant ($K_D$) of about $1\times10^{-7}$ M or less, for example about $5\times10^{-8}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a non-specific antigen (e.g., BSA, casein).

The term "$K_D$" refers to the dissociation constant, which is obtained from the ratio of $K_D$ to Ka (i.e., Kd/Ka) and is expressed as a molar concentration (M). $K_D$ values for antibodies can be determined using methods in the art in view of the present disclosure. For example, the $K_D$ of an antibody can be determined by using surface plasmon resonance, such as by using a biosensor system, e.g., a Biacore® system, or by using bio-layer interferometry technology, such as an Octet RED96 system. The smaller the value of the $K_D$ of an antibody, the higher affinity that the antibody binds to a target antigen.

As used herein, an antibody that "binds to PSMA" or that "specifically binds to PSMA" refers to an antibody that binds to PSMA, preferably human PSMA, with a $K_D$ of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less.

The term "isolated antibody", "antigen binding fragment thereof" and "anti-PSMA antibody" and the like are used interchangeably and refer to an antibody that binds PSMA and that comprises at least one binding domain specifically binding PSMA.

The term "biparatopic antibody" as used herein, refers to an antibody that specifically binds to two different epitopes on the same target protein, e.g. PSMA.

In some embodiments, the anti-PSMA antibody or antigen binding fragment of the disclosure is a biparatopic antibody that binds to PSMA.

In some embodiments, the biparatopic antibody of the disclosure comprises at least one receptor binding domain for a first epitope on PSMA target protein and a second receptor binding domain for a second epitope on the same PSMA target protein. In some embodiments the $K_D$ for the first epitope and the $K_D$ for the second epitope are the same. In some embodiments the $K_D$ for the first epitope and the $K_D$ for the second epitope are the different. In some embodiments the $K_D$ for the first epitope and the $K_D$ for the second epitope are about $1\times10^{-7}$ M or less, preferably $1\times10^{-8}$ M or less, more preferably $5\times10^{-7}$ M or less, $1\times10^{-7}$ M or less, $5\times10^{-10}$ M or less, or $1\times10^{-10}$ M or less.

The anti-PSMA antibody of the disclosure include whole antibodies, antibody fragments that specifically bind to PSMA, and antigen binding fragments thereof that specifically binds to PSMA.

In some embodiments, the anti-PSMA antibody of the disclosure include whole antibodies or full-length antibodies, Fv fragments, single chain scFv fragments (scFv), Fab, F(ab)$_2$, or single chain antibodies. In some embodiments, the anti-PSMA antibody of the disclosure is a whole antibody or a full-length antibody.

In some embodiments, the anti-PSMA antibody of the disclosure is a full-length antibodies, whole antibodies and intact antibodies.

The terms "Full length antibodies", "whole antibodies" and "intact antibodies" are used herein interchangeably to refer to an antibody having a structure similar to a native antibody. "Intact antibodies" are comprised of two heavy chains (HC) and two light chains (LC) inter-connected by disulfide bonds as well as multimers thereof (e.g. IgM). Each heavy chain is comprised of a heavy chain variable region (VH) and a heavy chain constant region (comprised of domains CH1 hinge, CH2 and CH3). Each light chain is comprised of a light chain variable region (VL) and a light chain constant region (CL). The VH and the VL regions may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4. Immunoglobulins may be assigned to five major classes, IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species may be assigned to one of two clearly distinct types, namely kappa (x) and lambda (k), based on the amino acid sequences of their constant domains.

In some embodiments, the anti-PSMA antibody of the disclosure is an antibody fragment or an antigen binding domain that specifically binds to PSMA.

As used herein, the term "Antibody fragment", and "antigen binding fragment" refers to a molecule other than an intact antibody. Antigen binding fragments may be synthetic, enzymatically obtainable or genetically engineered polypeptides and include portions of an immunoglobulin that bind an antigen, such as a VH, a VL, a VH and aVL, a Fab, a Fab', a F(ab')$_2$, a Fd and a Fv fragments, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a domain antibody (dAb) consisting of one VH domain or one VL domain, a shark variable IgNAR domain, a camelized VH domain, a VHH domain, a minimal recognition unit consisting of the amino acid residues that mimic the CDRs of an antibody, such as a FR3-CDR3-FR4 portion, the HCDR1, the HCDR2 and/or the HCDR3 and the LCDR1, the LCDR2 and/or the LCDR3, an alternative scaffold that bind an antigen, a bivalent domain antibody, a multispecific protein comprising the antigen binding fragment or any other antibody fragment that binds to an antigen but does not comprise a complete antibody structure."

"dAb" or "dAb fragment" refers to an antibody fragment composed of a VH domain (Ward et al., Nature 341:544 546 (1989)).

"Fab" or "Fab fragment" refers to an antibody fragment composed of VH, CH1, VL and CL domains.

"F(ab')2" or "F(ab')2 fragment" refers to an antibody fragment containing two Fab fragments connected by a disulfide bridge in the hinge region.

"Fd" or "Fd fragment" refers to an antibody fragment composed of VH and CH1 domains.

"Fv" or "Fv fragment" refers to an antibody fragment composed of the VH and the VL domains from a single arm of the antibody. Fv fragments lack the constant regions of Fab (CH1 and CL) regions. The VH and VL in Fv fragments are held together by non-covalent interactions.

Antigen binding fragments (such as VH and VL) may be linked together via a synthetic linker to form various types of single antibody designs where the VH/VL domains may be paired intramolecularly, or intermolecularly to form a monovalent antigen binding domain, such as single chain Fv (scFv) or diabody. In recombinant expression systems, the linker is a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the VH and the VL in such a way that they form the correct conformation relative to one another so that they retain the desired activity, such as binding to PSMA. The linker may be about 5-50 amino acids long.

"Single chain Fv" or "scFv" are fusion proteins comprising at least one antibody fragment comprising a light chain variable region (VL) and at least one antibody fragment comprising a heavy chain variable region (VH), wherein the VL and the VH are contiguously linked via a polypeptide linker, and capable of being expressed as a single chain polypeptide. A scFv may have the VL and VH variable regions in either order, e.g., with respect to the N-terminal and C-terminal ends of the polypeptide, the scFv may comprise VL-linker-VH or may comprise VH-linker-VL.

In recombinant expression systems, the linker is a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the VH and the VL in such a way that they form the correct conformation relative to one another so that they retain the desired activity, such as binding to PSMA.

The linker may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. In some embodiments, the linker is 6 amino acids long. In some embodiments, the linker is 7 amino acids long. In some embodiments, the linker is 8 amino acids long. In some embodiments, the linker is 9 amino acids long. In some embodiments, the linker is 10 amino acids long. In some embodiments, the linker is 11 amino acids long. In some embodiments, the linker is 12 amino acids long. In some embodiments, the linker is 13 amino acids long. In some embodiments, the linker is 14 amino acids long. In some embodiments, the linker is 15 amino acids long. In some embodiments, the linker is 16 amino acids long. In some embodiments, the linker is 17 amino acids long. In some embodiments, the linker is 18 amino acids long. In some embodiments, the linker is 19 amino acids long. In some embodiments, the linker is 20 amino acids long. In some embodiments, the linker is 21 amino acids long. In some embodiments, the linker is 22 amino acids long. In some embodiments, the linker is 23 amino acids long. In some embodiments, the linker is 24 amino acids long. In some embodiments, the linker is 25 amino acids long. In some embodiments, the linker is 26 amino acids long. In some embodiments, the linker is 27 amino acids long. In some embodiments, the linker is 28 amino acids long. In some embodiments, the linker is 29 amino acids long. In some embodiments, the linker is 30 amino acids long. In some embodiments, the linker is 31 amino acids long. In some embodiments, the linker is 32 amino acids long. In some embodiments, the linker is 33 amino acids long. In some embodiments, the linker is 34 amino acids long. In some embodiments, the linker is 35 amino acids long. In some embodiments, the linker is 36 amino acids long. In some embodiments, the linker is 37 amino acids long. In some embodiments, the linker is 38 amino acids long. In some embodiments, the linker is 39 amino acids long. In some embodiments, the linker is 40 amino acids long. Exemplary linkers that may be used are Gly rich linkers, Gly and Ser containing linkers, Gly and Ala containing linkers, Ala and Ser containing linkers, and other flexible linkers.

Other linker sequences may include portions of immunoglobulin hinge area, CL or CH1 derived from any immunoglobulin heavy or light chain isotype. Alternatively, a variety of non-proteinaceous polymers, including polyethylene glycol (PEG), polypropylene glycol, polyoxyalkylenes, or copolymers of polyethylene glycol and polypropylene glycol, may find use as linkers. Exemplary linkers that may be used are shown in Table 2.

In some embodiments, the scFv comprises, from the N- to C-terminus, a VH, a first linker (L1) and a VL (VH-L1-VL).

In some embodiments, the scFv comprises, from the N- to C-terminus, the VL, the L1 and the VH (VL-L1-VH).

In some embodiments, the L1 comprises the amino acid sequence of SEQ ID NO: 308.

In some embodiments, the L1 comprises the amino acid sequence of SEQ ID NO: 309.

In some embodiments, the L1 comprises the amino acid sequence of SEQ ID NO: 310.

In some embodiments, the L1 comprises the amino acid sequence of SEQ ID NO: 311.

In some embodiments, the L1 comprises the amino acid sequence of SEQ ID NO: 312.

In some embodiments, the L1 comprises the amino acid sequence of SEQ ID NO: 313.

In some embodiments, the L1 comprises the amino acid sequence of SEQ ID NO: 314.

In some embodiments, the L1 comprises the amino acid sequence of SEQ ID NO: 315.

In some embodiments, the L1 comprises the amino acid sequence of SEQ ID NO: 316.

In some embodiments, the L1 comprises the amino acid sequence of SEQ ID NO: 317.

In some embodiments, the L1 comprises the amino acid sequence of SEQ ID NO: 318.

In some embodiments, the L1 comprises the amino acid sequence of SEQ ID NO: 319.

In some embodiments, the L1 comprises the amino acid sequence of SEQ ID NO: 320.

In some embodiments, the L1 comprises the amino acid sequence of SEQ ID NO: 321.

In some embodiments, the L1 comprises the amino acid sequence of SEQ ID NO: 322.

In some embodiments, the L1 comprises the amino acid sequence of SEQ ID NO: 323.

In some embodiments, the L1 comprises the amino acid sequence of SEQ ID NO: 324.

In some embodiments, the L1 comprises the amino acid sequence of SEQ ID NO: 325.

In some embodiments, the L1 comprises the amino acid sequence of SEQ ID NO: 326.

In some embodiments, the L1 comprises the amino acid sequence of SEQ ID NO: 327.

In some embodiments, the L1 comprises the amino acid sequence of SEQ ID NO: 328.

In some embodiments, the L1 comprises the amino acid sequence of SEQ ID NO: 329.

In some embodiments, the L1 comprises the amino acid sequence of SEQ ID NO: 330.

In some embodiments, the L1 comprises the amino acid sequence of SEQ ID NO: 331.

In some embodiments, the L1 comprises the amino acid sequence of SEQ ID NO: 332.

In some embodiments, the L1 comprises the amino acid sequence of SEQ ID NO: 333.

In some embodiments, the L1 comprises the amino acid sequence of SEQ ID NO: 334.

In some embodiments, the L1 comprises the amino acid sequence of SEQ ID NO: 335.

In some embodiments, the L1 comprises the amino acid sequence of SEQ ID NO: 87.

In some embodiments, the L1 comprises the amino acid sequence of SEQ ID NO: 107.

In some embodiments, the L1 comprises the amino acid sequence of SEQ ID NO: 91.

In some embodiments, the L1 comprises the amino acid sequence of SEQ ID NO: 111.

In some embodiments, the L1 comprises the amino acid sequence of SEQ ID NO: 285.

In some embodiments, the L1 comprises the amino acid sequence of SEQ ID NO: 287.

TABLE 2

The amino acid sequences of linkers.

| Linker name | Amino acid sequence | SEQ ID NO: |
|---|---|---|
| Linker 1 | GGSEGKSSGSGSESKSTGGS | 308 |
| Linker 2 | GGGSGGGS | 309 |
| Linker 3 | GGGSGGGSGGGS | 310 |
| Linker 4 | GGGSGGGSGGGSGGGS | 311 |
| Linker 5 | GGGSGGGSGGGSGGGSGGGS | 312 |
| Linker 6 | GGGGSGGGGSGGGGS | 313 |
| Linker 7 | GGGGSGGGGSGGGGSGGGGS | 314 |
| Linker 8 | GGGGSGGGGSGGGGSGGGGSGGGGS | 315 |
| Linker 9 | GSTSGSGKPGSGEGSTKG | 316 |
| Linker 10 | IRPRAIGGSKPRVA | 317 |
| Linker 11 | GKGGSGKGGSGKGGS | 318 |
| Linker 12 | GGKGSGGKGSGGKGS | 319 |
| Linker 13 | GGGKSGGGKSGGGKS | 320 |
| Linker 14 | GKGKSGKGKSGKGKS | 321 |
| Linker 15 | GGGKSGGKGSGKGGS | 322 |
| Linker 16 | GKPGSGKPGSGKPGS | 323 |
| Linker 17 | GKPGSGKPGSGKPGSGKPGS | 324 |
| Linker 18 | GKGKSGKGKSGKGKSGKGKS | 325 |
| Linker 19 | STAGDTHLGGEDFD | 326 |
| Linker 20 | GEGGSGEGGSGEGGS | 327 |
| Linker 21 | GGEGSGGEGSGGEGS | 328 |
| Linker 22 | GEGESGEGESGEGES | 329 |
| Linker 23 | GGGESGGGESGGGES | 330 |
| Linker 24 | GEGESGEGESGEGESGEGES | 331 |
| Linker 25 | GSTSGSGKPGSGEGSTKG | 332 |
| Linker 26 | PRGASKSGSASQTGSAPGS | 333 |
| Linker 27 | GTAAAGAGAAGGAAAGAAG | 334 |
| Linker 28 | GTSGSSGSGSGSGSGGGG | 335 |
| Linker 29 | GKPGSGKPGSGKPGSGKPGS | 87 |
| Linker 30 | GSGS | 107 |
| Linker 31 | APAPAPAP | 91 |
| Linker 32 | APAPAPAPAPAPAPAP | 111 |

TABLE 2-continued

The amino acid sequences of linkers.

| Linker name | Amino acid sequence | SEQ ID NO: |
|---|---|---|
| Linker 33 | AEAAAKEAAAKEAAAAKEAAAAKEAAAAKAAA | 285 |
| Linker 34 | GTEGKSSGSGSESKST | 287 |

Divalent or bivalent single chain variable fragments (di-scFv, bi-scFvs) can be engineered by linking two scFvs". (scFv)₂" or "tandem scFv" or "bis-scFv" fragments refers to a fusion protein comprising two light chain variable regions (VL) and two heavy chain variable regions (VH), wherein the two VL and the two VH regions are contiguously linked via polypeptide linkers, and capable of being expressed as a single chain polypeptide. The two VL and two VH regions fused by peptide linkers form a bivalent molecule $VL_A$-linker-$VH_A$-linker-$VL_B$-linker-$VH_B$ to form two binding sites, capable of binding two different antigens or epitopes concurrently. (ScFv)2 can be expressed as a single chain polypeptide.

Any of the VH and the VL domains identified herein that bind PSMA may be engineered into scFv format in either VH-linker-VL or VL-linker-VH orientation. Any of the VH and the VL domains identified herein may also be used to generate sc(Fv)₂ structures, such as VH-linker-VL-linker-VL-linker-VH, VH-linker-VL-linker-VH-linker-VL, VH-linker-VH-linker-VL-linker-VL, VL-linker-VH-linker-VH-linker-VL, VL-linker-VH-linker-VL-linker-VH or VL-linker-VL-linker-VH-linker-VH.

"Diabodies" are bivalent dimers formed from two chains, each containing a VH and a VL domain. The two domains within a chain are separated by a linker that is too short to facilitate intrachain dimerization leading to two chains dimerizing in a head-to-tail arrangement. The linker may be a pentameric glycine-rich linker (G4S (SEQ ID NO: 337)).

"VHH" refers to a single-domain antibody or nanobody, exclusively composed of the antigen binding domain of a heavy chain. A VHH single domain antibody lacks the light chain and the CH1 domain of the heavy chain of conventional Fab region. In some embodiments, the anti-PSMA antibodies of the disclosure include Fv fragments, single chain scFv fragments (scFv), (scFv)₂, Fab, F(ab)₂, diabodies, VHH, dAb, Fd, Fv, or other single chain antibodies.

The anti-PSMA antibody of the disclosure include chimeric, humanized or fully human antibodies that specifically bind to PSMA.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both.

Typically, a "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or a synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

Transgenic animals, such as mice, rat or chicken carrying human immunoglobulin (Ig) loci in their genome may be used to generate antigen binding fragments that bind PSMA, and are described in for example U.S. Pat. No. 6,150,584, Int. Patent Publ. No. WO1999/45962, Int. Patent Publ. Nos. WO2002/066630, WO2002/043478 and WO1990/04036. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (www_regeneron_com), Harbour Antibodies (www_harbourantibodies_com), Open Monoclonal Technology, Inc. (OMT) (www_omtinc_net), KyMab (www_kymab_com), Trianni (www_trianni_com) and Ablexis (www_ablexis_com) may be engaged to provide human antibodies directed against a selected antigen.

The antibody or antigen binding fragment thereof that bind PSMA generated by immunizing non-human animals may be humanized. Exemplary humanization techniques including selection of human acceptor frameworks include CDR grafting (U.S. Pat. No. 5,225,539), SDR grafting (U.S. Pat. No. 6,818,749), Resurfacing (Padlan, (1991) *Mol Immunol* 28:489-499), Specificity Determining Residues Resurfacing (U.S. Patent Publ. No. 2010/0261620), human framework adaptation (U.S. Pat. No. 8,748,356) or superhumanization (U.S. Pat. No. 7,709,226). In these methods, CDRs or a subset of CDR residues of parental antibodies are transferred onto human frameworks that may be selected based on their overall homology to the parental frameworks, based on similarity in CDR length, or canonical structure identity, or a combination thereof.

Humanized antigen binding domains may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antigen binding domain.

In some embodiments, the disclosure provides an isolated antibody or antigen binding fragment thereof that binds to PSMA comprising a heavy chain complementarity determining region 1 (HCDR1), a HCDR2, and a HCDR3, and a light chain complementarity determining region 1 (LCDR1), a LCDR2, and LCDR3, wherein the HCDR1, HCDR2, HCDR3, LCDR1, LCDR2 and LCDR3 comprise the amino acid sequences:

a. RYGMH (SEQ ID NO: 4), LISYDGSNRYYADSVKG (SEQ ID NO: 5), ERESSGWFEGYFDY (SEQ ID NO: 6), GGNNIGSKSVH (SEQ ID NO: 7), DNSDRPS (SEQ ID NO: 8), and QVWDSSSDHVV (SEQ ID NO: 9), respectively;

b. SYYWN (SEQ ID NO: 10), RIYSSGNTDYNPSLKS (SEQ ID NO: 11), GRGANVGLFDY (SEQ ID NO: 12), TGSNSNIGANYDVH (SEQ ID NO: 13), GNINRPL (SEQ ID NO: 14), and QSYDFSLSGSV (SEQ ID NO: 15), respectively;

c. GYGMH (SEQ ID NO: 16), VISYDGSNRYYADSVKG (SEQ ID NO: 17), DGNWGSLDLYFDL (SEQ ID NO: 18), TGSSSNIGADYDVH (SEQ ID NO:19), VNNNRPS (SEQ ID NO: 20), and QSYDNTLSGVV (SEQ ID NO: 21), respectively;

d. SYGMH (SEQ ID NO: 22), VISYDGSNKYYADSVKG (SEQ ID NO: 23), EHYDSSGYYHGYYGMDV (SEQ ID NO: 24), SGSSSNIGSNYVY (SEQ ID NO: 25), SNNQRPS (SEQ ID NO: 26), AARDDSLSGYV (SEQ ID NO: 27), respectively;

e. SYDMH (SEQ ID NO: 28), VISFDGSNKYYVDSVKG (SEQ ID NO: 29), TYYDILTGYSHYSYGMDV (SEQ ID NO: 30), RASQGISNYLA (SEQ ID NO: 31), ATSTLQS (SEQ ID NO: 32), and QKYNSAPFT (SEQ ID NO: 33), respectively;

f. TYGMH (SEQ ID NO: 34), FISYDGSNKYYADSVKG (SEQ ID NO: 35), RDNLRFLEWFMDV (SEQ ID NO: 36), RASQSVRSNLA (SEQ ID NO: 37), GASTRAT (SEQ ID NO: 38), and HQYNDWPPYT (SEQ ID NO: 39), respectively;

g. IYSMN (SEQ ID NO: 40), SISSSSSYIFYADSVKG (SEQ ID NO: 41), SSYGADY (SEQ ID NO: 42), RASQDITNFLA (SEQ ID NO: 43), TASTLQS (SEQ ID NO: 44), and QKYNSAPLT (SEQ ID NO: 45), respectively;

h. SYSLN (SEQ ID NO: 46), SISSSSSYISYADAVKG (SEQ ID NO: 47), DRGFLEDYYYYGMDV (SEQ ID NO: 48), RASQGISNWLA (SEQ ID NO: 49), VASSLQS (SEQ ID NO: 50), and QQAYSFPLT (SEQ ID NO: 51), respectively;

i. SYYWS (SEQ ID NO: 272), RIYSSGSTNYNPSLKS (SEQ ID NO: 273), VGVWPGAFDI (SEQ ID NO: 274), SGSSSNIGSNTVN (SEQ ID NO: 275), SSNQRPS (SEQ ID NO: 276) and AAWDDSLNGVV (SEQ ID NO: 277), respectively;

j. GFTLSRY (SEQ ID NO: 124), SYDGSN (SEQ ID NO:125), ERESSGWFEGYFDY (SEQ ID NO: 6), GGNNIGSKSVH (SEQ ID NO: 7), DNSDRPS (SEQ ID NO: 8) and QVWDSSSDHVV (SEQ ID NO: 9), respectively;

k. GGSISSY (SEQ ID NO: 130), YSSGN (SEQ ID NO: 131), GRGANVGLFDY (SEQ ID NO: 12), TGSNSNIGANYDVH (SEQ ID NO: 13), GNINRPL (SEQ ID NO:14), and QSYDFSLSGSV (SEQ ID NO:15), respectively;

l. VRTFSGY (SEQ ID NO: 136), SYDGSN (SEQ ID NO:125), DGNWGSLDLYFDL (SEQ ID NO:18), TGSSSNIGADYDVH (SEQ ID NO:19), VNNNRPS (SEQ ID NO: 20), and QSYDNTLSGVV (SEQ ID NO: 21), respectively;

m. GFTFTSY (SEQ ID NO: 142), SYDGSN (SEQ ID NO: 125), EHYDSSGYYHGYYGMDV (SEQ ID NO: 24), SGSSSNIGSNYVY (SEQ ID NO:25), SNNQRPS (SEQ ID NO: 26), and AARDDSLSGYV (SEQ ID NO:27), respectively;

n. GFTFSSY (SEQ ID NO: 148), SFDGSN (SEQ ID NO:149), TYYDILTGYSHYSYGMDV (SEQ ID NO: 30), RASQGISNYLA (SEQ ID NO: 31), ATSTLQS (SEQ ID NO: 32), and QKYNSAPFT (SEQ ID NO: 33), respectively;

o. GFTFSTY (SEQ ID NO: 154), SYDGSN (SEQ ID NO: 125), RDNLRFLEWFMDV (SEQ ID NO:36), RASQSVRSNLA (SEQ ID NO:37), GASTRAT (SEQ ID NO:38), and HQYNDWPPYT (SEQ ID NO:39), respectively;

p. GFTLSIY (SEQ ID NO: 160), SSSSSY (SEQ ID NO:161), SSYGADY (SEQ ID NO:42), RASQDITNFLA (SEQ ID NO:43), TASTLQS (SEQ ID NO:44), and QKYNSAPLT (SEQ ID NO:45), respectively;

q. GFTFSSY (SEQ ID NO: 166), SSSSSY (SEQ ID NO: 167), DRGFLEDYYYYYGMDV (SEQ ID NO; 48), RASQGISNWLA (SEQ ID NO: 49), VASSLQS (SEQ ID NO:50), and QQAYSFPLT (SEQ ID NO: 51), respectively;

r. GGSIISY (SEQ ID NO: 290), YSSGS (SEQ ID NO:291), VGVWPGAFDI (SEQ ID NO: 274), SGSSSNIGSNTVN (SEQ ID NO:275), SSNQRPS (SEQ ID NO:276), and AAWDDSLNGVV (SEQ ID NO: 277), respectively;

s. GFTLSRYGMH (SEQ ID NO: 172), LISYDGSNRY (SEQ ID NO:173), ERESSGWFEGYFDY (SEQ ID NO:6), GGNNIGSKSVH (SEQ ID NO:7), DNSDRPS (SEQ ID NO: 8), and QVWDSSSDHVV (SEQ ID NO:9), respectively;

t. GGSISSYYWN (SEQ ID NO: 178), RIYSSGNTD (SEQ ID NO:179), GRGANVGLFDY (SEQ ID NO:12), TGSNSNIGANYDVH (SEQ ID NO:13), GNINRPL (SEQ ID NO:14), and QSYDFSLSGSV (SEQ ID NO:15), respectively;

u. VRTFSGYGMH (SEQ ID NO: 184), VISYDGSNRY (SEQ ID NO:185), DGNWGSLDLYFDL (SEQ ID NO: 18), TGSSSNIGADYDVH (SEQ ID NO:19), VNNNRPS (SEQ ID NO: 20), and QSYDNTLSGVV (SEQ ID NO:21), respectively;

v. GFTFTSYGMH (SEQ ID NO: 190), VISYDGSNKY (SEQ ID NO:191), EHYDSSGYYHGYYGMDV (SEQ ID NO:24), SGSSSNIGSNYVY (SEQ ID NO:25), SNNQRPS (SEQ ID NO:26), and AARDDSLSGYV (SEQ ID NO:27), respectively;

w. GFTFSSYDMH (SEQ ID NO: 196), VISFDGSNKY (SEQ ID NO: 197), TYYDILTGYSHYSYGMDV (SEQ ID NO: 30), RASQGISNYLA (SEQ ID NO:31), ATSTLQS (SEQ ID NO:32), and QKYNSAPFT (SEQ ID NO:33), respectively;

x. GFTFSTYGMH (SEQ ID NO: 202), FISYDGSNKY (SEQ ID NO:203), RDNLRFLEWFMDV (SEQ ID NO: 36), RASQSVRSNLA (SEQ ID NO:37), GASTRAT (SEQ ID NO:38), and HQYNDWPPYT (SEQ ID NO: 39), respectively;

y. GFTLSIYSMN (SEQ ID NO: 208), SISSSSSYIF (SEQ ID NO:209), SSYGADY (SEQ ID NO: 42), RASQDITNFLA, (SEQ ID NO: 43), TASTLQS (SEQ ID NO: 44), and QKYNSAPLT (SEQ ID NO:45), respectively;

z. GFTFSSYSLN (SEQ ID NO: 214), SISSSSSYIS (SEQ ID NO:215), DRGFLEDYYYYYGMDV (SEQ ID NO:48), RASQGISNWL (SEQ ID NO:49), VASSLQS (SEQ ID NO:50), and QQAYSF (SEQ ID NO:51), respectively;

aa. GGSIISYYWS (SEQ ID NO: 296), RIYSSGSTN (SEQ ID NO: 297), VGVWPGAFDI (SEQ ID NO:274), SGSSSNIGSNTVN (SEQ ID NO:275), SSNQRPS (SEQ ID NO:276), and AAWDDSLNGVV (SEQ ID NO:277), respectively;

bb. GFTLSRYG (SEQ ID NO: 220), ISYDGSNR (SEQ ID NO:221), ARERESSGWFEGYFDY (SEQ ID NO: 222), NIGSKS (SEQ ID NO:223), DNS, and QVWDSSSDHVV (SEQ ID NO:9), respectively;

cc. GGSISSYY (SEQ ID NO: 226), IYSSGNT (SEQ ID NO: 227), ARGRGANVGLFDY (SEQ ID NO:228), NSNIGANYD (SEQ ID NO:229), GNI, and QSYDFSLSGSV (SEQ ID NO:15), respectively;

dd. VRTFSGYG (SEQ ID NO: 232), ISYDGSNR (SEQ ID NO:233), ARDGNWGSLDLYFDL (SEQ ID NO:234), SSNIGADYD (SEQ ID NO:235), VNN, and QSYDNTLSGVV (SEQ ID NO:21), respectively;

ee. GFTFTSYG (SEQ ID NO: 238), ISYDGSNK (SEQ ID NO:239, AREHYDSSGYYHGYYGMDV (SEQ ID NO: 240), SSNIGSNY (SEQ ID NO:241), SNN, and AARDDSLSGYV (SEQ ID NO:27), respectively;

ff. GFTFSSYD (SEQ ID NO: 244), ISFDGSNK (SEQ ID NO:245), ARTYYDILTGYSHYSYGMDV (SEQ ID NO: 246), QGISNY (SEQ ID NO:247), ATS, and QKYNSAPFT (SEQ ID NO:33), respectively;

gg. GFTFSTYG (SEQ ID NO: 250), ISYDGSNK (SEQ ID NO:251), AGRDNLRFLEWFMDV (SEQ ID NO:252), QSVRSN (SEQ ID NO: 253), GAS, and HQYNDWPPYT (SEQ ID NO:39), respectively;

hh. GFTLSIYS (SEQ ID NO: 256), ISSSSSYI (SEQ ID NO:257), ARSSYGADY (SEQ ID NO:258), QDITNF (SEQ ID NO: 259), TAS, and QKYNSAPLT (SEQ ID NO:45), respectively;

ii. GFTFSSYS (SEQ ID NO: 262), ISSSSSYI (SEQ ID NO:263), ARDRGFLEDYYYYYGMDV (SEQ ID NO:264), QGISNW (SEQ ID NO:265), VAS, and QQAYSFPLT (SEQ ID NO:51), respectively; or jj. GGSIISYY (SEQ ID NO: 302), IYSSGST (SEQ ID NO:303), AKVGVWPGAFDI (SEQ ID NO:304), SSNIGSNT (SEQ ID NO:305), SSN, and AAWDDSLNGVV (SEQ ID NO: 277), respectively.

In some embodiments, the antibody or antigen binding fragment thereof that binds PSMA comprises the HCDR1, the HCDR2, the HCDR3, the LCDR1, the LCDR2 and the LCDR3 of SEQ ID NO: 4, 5, 6, 7, 8, and 9, respectively.

In some embodiments, the antibody or antigen binding fragment thereof that binds PSMA comprises the HCDR1, the HCDR2, the HCDR3, the LCDR1, the LCDR2 and the LCDR3 of SEQ ID NO: 10, 11, 12, 13, 14, and 15, respectively.

In some embodiments, the antibody or antigen binding fragment thereof that binds PSMA comprises the HCDR1, the HCDR2, the HCDR3, the LCDR1, the LCDR2 and the LCDR3 of SEQ ID NO: 16, 17, 18, 29, 20 and 21, respectively.

In some embodiments, the antibody or antigen binding fragment thereof that binds PSMA comprises the HCDR1, the HCDR2, the HCDR3, the LCDR1, the LCDR2 and the LCDR3 of SEQ ID NO: 22, 23, 24, 25, 26 and 27, respectively.

In some embodiments, the disclosure provides an isolated antibody or antigen binding fragment thereof that binds PSMA comprising the HCDR1, the HCDR1, the HCDR3, the LCDR1, the LCDR2 and the LCDR3 of SEQ ID NOs: 28, 29, 30, 31, 32, and 33, respectively.

In some embodiments, the disclosure provides an isolated antibody or antigen binding fragment thereof that binds PSMA comprising the HCDR1, the HCDR1, the HCDR3, the LCDR1, the LCDR2 and the LCDR3 of SEQ ID NOs: 34, 35, 36, 37, 38 and 39, respectively.

In some embodiments, the disclosure provides an isolated antibody or antigen binding fragment thereof that binds PSMA comprising the HCDR1, the HCDR1, the HCDR3, the LCDR1, the LCDR2 and the LCDR3 of SEQ ID NOs: 40, 41, 42, 43, 44, and 45, respectively.

In some embodiments, the disclosure provides an isolated antibody or antigen binding fragment thereof that binds PSMA comprising the HCDR1, the HCDR1, the HCDR3, the LCDR1, the LCDR2 and the LCDR3 of SEQ ID NOs: 46, 47, 48, 49, 50, and 51, respectively.

In some embodiments, the disclosure provides an isolated antibody or antigen binding fragment thereof that binds PSMA comprising the HCDR1, the HCDR1, the HCDR3, the LCDR1, the LCDR2 and the LCDR3 of SEQ ID NOs: 272, 273, 274, 275, 276, and 277, respectively.

The disclosure also provides an isolated antibody or antigen binding fragment thereof comprising:
  a heavy chain complementarity determining region (HCDR) 1, a HCDR2 and a HCDR3 of a heavy chain variable region (VH) of SEQ ID NO: 52 and a light chain complementarity determining region (LCDR) 1, a LCDR2 and a LCDR3 of a light chain variable region (VL) of SEQ ID NO: 53; or
  the HCDR1, the HCDR2 and the HCDR3 of the VH of SEQ ID NO: 54 and the LCDR1, the LCDR2 and the LCDR3 of the VL of SEQ ID NO: 55; or the HCDR1, the HCDR2 and the HCDR3 of the VH of SEQ ID NO: 56 and the LCDR1, the LCDR2 and the LCDR3 of the VL of SEQ ID NO: 57; or
  the HCDR1, the HCDR2 and the HCDR3 of the VH of SEQ ID NO: 58 and the LCDR1, the LCDR2 and the LCDR3 of the VL of SEQ ID NO: 59; or
  the HCDR1, the HCDR2 and the HCDR3 of the VH of SEQ ID NO: 60 and the LCDR1, the LCDR2 and the LCDR3 of the VL of SEQ ID NO: 61; or
  the HCDR1, the HCDR2 and the HCDR3 of the VH of SEQ ID NO: 62 and the LCDR1, the LCDR2 and the LCDR3 of the VL of SEQ ID NO: 63; or
  the HCDR1, the HCDR2 and the HCDR3 of the VH of SEQ ID NO: 64 and the LCDR1, the LCDR2 and the LCDR3 of the VL of SEQ ID NO: 65; or
  the HCDR1, the HCDR2 and the HCDR3 of the VH of SEQ ID NO: 66 and the LCDR1, the LCDR2 and the LCDR3 of the VL of SEQ ID NO: 67; or
  the HCDR1, the HCDR2 and the HCDR3 of the VH of SEQ ID NO: 278 and the LCDR1, the LCDR2 and the LCDR3 of the VL of SEQ ID NO: 279.

In some embodiments, the isolated protein comprising an antigen binding domain, comprises the HCDR1, the HCDR2 and the HCDR3 of the VH of SEQ ID NO: 52 and the LCDR1, the LCDR2 and the LCDR3 of the VL of SEQ ID NO: 53 and wherein the antibody or antigen binding fragment thereof binds PSMA.

In some embodiments, the isolated protein comprising an antigen binding domain, comprises the HCDR1, the HCDR2 and the HCDR3 of the VH of SEQ ID NO: 54 and the LCDR1, the LCDR2 and the LCDR3 of the VL of SEQ ID NO: 55 and wherein the antibody or antigen binding fragment thereof binds PSMA.

In some embodiments, the disclosure provides an isolated antibody or antigen binding fragment thereof comprising:
  the VH of SEQ ID NO: 52 and the VL of SEQ ID NO: 53; or
  the VH of SEQ ID NO: 54 and the VL of SEQ ID NO: 55; or
  the VH of SEQ ID NO: 56 and the VL of SEQ ID NO: 57; or
  the VH of SEQ ID NO: 58 and the VL of SEQ ID NO: 59; or
  the VH of SEQ ID NO: 60 and the VL of SEQ ID NO: 61; or
  the VH of SEQ ID NO: 62 and the VL of SEQ ID NO: 63; or
  the VH of SEQ ID NO: 64 and the VL of SEQ ID NO: 65; or
  the VH of SEQ ID NO: 66 and the VL of SEQ ID NO: 67; or
  the VH of SEQ ID NO: 278 and the VL of SEQ ID NO: 279; and wherein the antibody or antigen binding fragment thereof binds PSMA.

In some embodiments, the antibody or antigen binding fragment thereof that binds PSMA comprises the VH of SEQ ID NO: 52 and the VL of SEQ ID NO: 53.

In some embodiments, the antibody or antigen binding fragment thereof that binds PSMA comprises the VH of SEQ ID NO: 54 and the VL of SEQ ID NO: 55.

In some embodiments, the antibody or antigen binding fragment thereof that binds PSMA comprises the VH of SEQ ID NO: 56 and the VL of SEQ ID NO: 57.

In some embodiments, the antibody or antigen binding fragment thereof that binds PSMA comprises the VH of SEQ ID NO: 58 and the VL of SEQ ID NO: 59.

In some embodiments, the antibody or antigen binding fragment thereof that binds PSMA comprises the VH of SEQ ID NO: 60 and the VL of SEQ ID NO: 61.

In some embodiments, the antibody or antigen binding fragment thereof that binds PSMA comprises the VH of SEQ ID NO: 62 and the VL of SEQ ID NO: 63.

In some embodiments, the antibody or antigen binding fragment thereof that binds PSMA comprises the VH of SEQ ID NO: 64 and the VL of SEQ ID NO: 65.

In some embodiments, the antibody or antigen binding fragment thereof that binds PSMA comprises the VH of SEQ ID NO: 66 and the VL of SEQ ID NO: 67.

In some embodiments, the antibody or antigen binding fragment thereof that binds PSMA comprises the VH of SEQ ID NO: 278 and the VL of SEQ ID NO: 279.

In some embodiment, the disclosure also provides an isolated antibody or antigen binding fragment thereof comprising an amino acid sequence selected from the group consisting of SEQ ID NOs: 84, 85, 86, 88, 89, 90, 92, 93, 94, 95, 96, 97, 98, 99, 100, 101, 102, 103, 268, 269, 282, 284, and 288.

In some embodiments, the disclosure provides an isolated antibody or antigen binding fragment thereof comprising an amino acid sequence of SEQ ID NO: 84.

In some embodiments, the disclosure also provides an isolated antibody or antigen binding fragment thereof comprising an amino acid sequence of SEQ ID NO: 85.

In some embodiments, the disclosure provides an isolated antibody or antigen binding fragment thereof comprising an amino acid sequence of SEQ ID NO: 86.

In some embodiments, the disclosure provides an isolated antibody or antigen binding fragment thereof comprising an amino acid sequence of SEQ ID NO: 88.

In some embodiments, the disclosure provides an isolated antibody or antigen binding fragment thereof comprising an amino acid sequence of SEQ ID NO: 89.

In some embodiments, the disclosure provides an isolated antibody or antigen binding fragment thereof comprising an amino acid sequence of SEQ ID NO: 90.

In some embodiments, the antibody or antigen binding fragment thereof that binds PSMA comprises the heavy chain of SEQ ID NO: 84 and the light chain of SEQ ID NO: 85.

In some embodiments, the antibody or antigen binding fragment thereof that binds PSMA comprises the heavy chain of SEQ ID NO: 86 and the light chain of SEQ ID NO: 85.

In some embodiments, the antibody or antigen binding fragment thereof that binds PSMA comprises the heavy chain of SEQ ID NO: 88 and the light chain of SEQ ID NO: 89.

In some embodiments, the antibody or antigen binding fragment thereof that binds PSMA comprises the heavy chain of SEQ ID NO: 90 and the light chain of SEQ ID NO: 89.

In some embodiments, the antibody or antigen binding fragment thereof that binds PSMA comprises the heavy chain of SEQ ID NO: 92 and the light chain of SEQ ID NO: 93.

In some embodiments, the antibody or antigen binding fragment thereof that binds PSMA comprises the heavy chain of SEQ ID NO: 94 and the light chain of SEQ ID NO: 95.

In some embodiments, the antibody or antigen binding fragment thereof that binds PSMA comprises the heavy chain of SEQ ID NO: 96 and the light chain of SEQ ID NO: 97.

In some embodiments, the antibody or antigen binding fragment thereof that binds PSMA comprises the heavy chain of SEQ ID NO: 98 and the light chain of SEQ ID NO: 99.

In some embodiments, the antibody or antigen binding fragment thereof that binds PSMA comprises the heavy chain of SEQ ID NO: 100 and the light chain of SEQ ID NO: 101.

In some embodiments, the antibody or antigen binding fragment thereof that binds PSMA comprises the heavy chain of SEQ ID NO: 102 and the light chain of SEQ ID NO: 103.

In some embodiments, the antibody or antigen binding fragment thereof that binds PSMA comprises a first heavy chain of SEQ ID NO: 268, a second heavy chain of SEQ ID NO: 282 and the light chain of SEQ ID NO: 269.

In some embodiments, the antibody or antigen binding fragment thereof that binds PSMA comprises a first heavy chain of SEQ ID NO: 284, a second heavy chain of SEQ ID NO: 288 and the light chain of SEQ ID NO: 269.

In some embodiments, the disclosure provides an isolated antibody or antigen binding fragment thereof comprising:
  a HCDR1, a HCDR2, a HCDR3, a LCDR1, a LCDR2 and a LCDR3 of SEQ ID NOs: 4, 5, 6, 7, 8, and 9, respectively;
  a VH of SEQ ID NO: 52 and a VL of SEQ ID NO: 53; and/or
  a HC of SEQ ID NO: 84 and a LC of SEQ ID NO: 85; and wherein the antibody or antigen binding fragment thereof binds PSMA.

In some embodiments, the disclosure provides an isolated antibody or antigen binding fragment thereof comprising:
  a HCDR1, a HCDR2, a HCDR3, a LCDR1, a LCDR2 and a LCDR3 of SEQ ID NOs: 4, 5, 6, 7, 8, and 9, respectively;
  a VH of SEQ ID NO: 52 and a VL of SEQ ID NO: 53; and/or
  a HC of SEQ ID NO: 86 and a LC of SEQ ID NO: 85; and wherein the antibody or antigen binding fragment thereof binds PSMA.

In some embodiments, the disclosure provides an isolated antibody or antigen binding fragment thereof comprising:
  a HCDR1, a HCDR2, a HCDR3, a LCDR1, a LCDR2 and a LCDR3 of SEQ ID NOs: 10, 11, 12, 13, 14 and 15, respectively;
  a VH of SEQ ID NO: 54 and a VL of SEQ ID NO: 55; and/or
  a HC of SEQ ID NO: 88 and a LC of SEQ ID NO: 89; and wherein the antibody or antigen binding fragment thereof binds PSMA.

In some embodiments, the disclosure provides an isolated antibody or antigen binding fragment thereof comprising:
  a HCDR1, a HCDR2, a HCDR3, a LCDR1, a LCDR2 and a LCDR3 of SEQ ID NOs: 10, 11, 12, 13, 14 and 15, respectively;
  a VH of SEQ ID NO: 54 and a VL of SEQ ID NO: 55; and/or
  a HC of SEQ ID NO: 90 and a LC of SEQ ID NO: 89; and wherein the antibody or antigen binding fragment thereof binds PSMA.

In some embodiments, the disclosure provides an isolated antibody or antigen binding fragment thereof comprising:
  a HCDR1, a HCDR2, a HCDR3, a LCDR1, a LCDR2 and a LCDR3 of SEQ ID NOs: 16, 17, 18, 19, 20, and 21, respectively;
  a VH of SEQ ID NO: 56 and a VL of SEQ ID NO: 57; and/or
  a HC of SEQ ID NO: 92 and a LC of SEQ ID NO: 93; and wherein the antibody or antigen binding fragment thereof binds PSMA.

In some embodiments, the disclosure provides an isolated antibody or antigen binding fragment thereof comprising:
  a HCDR1, a HCDR2, a HCDR3, a LCDR1, a LCDR2 and a LCDR3 of SEQ ID NOs: 22, 23, 24, 25, 26, and 27, respectively;
  a VH of SEQ ID NO: 58 and a VL of SEQ ID NO: 59; and/or
  a HC of SEQ ID NO: 94 and a LC of SEQ ID NO: 95; and wherein the antibody or antigen binding fragment thereof binds PSMA.

In some embodiments, the disclosure provides an isolated antibody or antigen binding fragment thereof comprising:
  a HCDR1, a HCDR2, a HCDR3, a LCDR1, a LCDR2 and a LCDR3 of SEQ ID NOs: 28, 29, 30, 31, 32, and 33, respectively;
  a VH of SEQ ID NO: 60 and a VL of SEQ ID NO: 61; and/or
  a HC of SEQ ID NO: 96 and a LC of SEQ ID NO: 97; and wherein the antibody or antigen binding fragment thereof binds PSMA.

In some embodiments, the disclosure provides an isolated antibody or antigen binding fragment thereof comprising
  a HCDR1, a HCDR2, a HCDR3, a LCDR1, a LCDR2 and a LCDR3 of SEQ ID NOs: 34, 35, 36, 37, 38, and 39, respectively;
  a VH of SEQ ID NO: 62 and a VL of SEQ ID NO: 63; and/or
  a HC of SEQ ID NO: 98 and a LC of SEQ ID NO: 99; and wherein the antibody or antigen binding fragment thereof binds PSMA.

In some embodiments, the disclosure provides an isolated antibody or antigen binding fragment thereof comprising:

a HCDR1, a HCDR2, a HCDR3, a LCDR1, a LCDR2 and a LCDR3 of SEQ ID NOs: 40, 41, 42, 43, 44, and 45, respectively;
a VH of SEQ ID NO: 64 and a VL of SEQ ID NO: 65; and/or
a HC of SEQ ID NO: 100 and a LC of SEQ ID NO: 101; and wherein the antibody or antigen binding fragment thereof binds PSMA.

In some embodiments, the disclosure provides an isolated antibody or antigen binding fragment thereof comprising:
a HCDR1, a HCDR2, a HCDR3, a LCDR1, a LCDR2 and a LCDR3 of SEQ ID NOs: 46, 47, 48, 49, 50, and 51, respectively;
a VH of SEQ ID NO: 66 and a VL of SEQ ID NO: 67; and/or
a HC of SEQ ID NO: 102 and a LC of SEQ ID NO: 103; and wherein the antibody or antigen binding fragment thereof binds PSMA.

The disclosure also provides an isolated antibody or antigen binding fragment thereof comprising two antigen-binding domains, wherein the first antigen binding domain binds to an epitope of PSMA and the second binding domain binds to a different epitope on PSMA.

The disclosure also provides an isolated antibody or antigen binding fragment thereof comprising a heavy chain variable region comprising a CDR1 sequence having an amino acid sequence of SEQ ID NO: 4, a CDR2 sequence having an amino acid sequence of SEQ ID NO: 5, a CDR3 sequences having an amino acid sequence of SEQ ID NO: 6; a light chain a light chain variable region comprising a CDR1 sequence having an amino acid sequence of SEQ ID NO: 7, a CDR2 sequence having an amino acid sequence of SEQ ID NO: 8, a CDR3 sequence having an amino acid sequence of SEQ ID NO: 9; combined with a heavy chain variable region comprising a CDR1 sequence having an amino acid sequence of SEQ ID NO: 272, a CDR2 sequence having an amino acid sequence of SEQ ID NO: 273, a CDR3 sequence having an amino acid sequence of SEQ ID NO: 274; a light chain a light chain variable region comprising a CDR1 sequence having an amino acid sequence of SEQ ID NO: 275, a CDR2 sequence having an amino acid sequence of SEQ ID NO 276, a CDR3 sequence having an amino acid sequence of SEQ ID NO: 277; and wherein the antibody or antigen binding fragment thereof binds to PSMA, optionally to two different epitopes on PSMA.

In some embodiments, the disclosure provides an isolated antibody or antigen binding fragment thereof comprising two antigen-binding domains, wherein the first antigen binding domain binds to an epitope of PSMA and the second binding domain binds to a different epitope on PSMA and wherein:
the first antigen binding domain is a Fab or a Fab fragment comprising a HCDR1 of SEQ ID NO: 4, a HCDR2 of SEQ ID NO: 5, a HCDR3 of SEQ ID NO: 6, a LCDR1 of SEQ ID NO: 7, a LCDR2 of SEQ ID NO: 8, a LCDR3 of SEQ ID NO: 9, a VH of SEQ ID NO: 52, a VL of SEQ ID NO: 53, a HC of SEQ ID NO: 268 and a LC of SEQ ID NO: 269; and
the second antigen binding domain is in a scFv format comprising a HCDR1 of SEQ ID NO: 272, a HCDR2 of SEQ ID NO: 273, a HCDR3 of SEQ ID NO: 274 a LCDR1 of SEQ ID NO: 275, a LCDR2 of SEQ ID NO: 276, a LCDR3 of SEQ ID NO: 277, a VH of SEQ ID NO: 278, a VL of SEQ ID NO: 279, a HC of SEQ ID NO: 282.

In some embodiments the disclosure provides an isolated antibody or antigen binding fragment thereof comprising two antigen-binding domains, wherein the first antigen binding domain binds to an epitope of PSMA and the second binding domain binds to a different epitope on PSMA and wherein:
the first antigen binding domain is a Fab or a Fab fragment comprising a HCDR1 of SEQ ID NO: 4, a HCDR2 of SEQ ID NO: 5, a HCDR3 of SEQ ID NO: 6, a LCDR1 of SEQ ID NO: 7, a LCDR2 of SEQ ID NO: 8, a LCDR3 of SEQ ID NO: 9, a VH of SEQ ID NO: 52, a VL of SEQ ID NO: 53, a HC of SEQ ID NO: 284 and a LC of SEQ ID NO: 269; and
the second antigen binding domain is in a scFv format comprising a HCDR1 of SEQ ID NO: 272, a HCDR2 of SEQ ID NO: 273, a HCDR3 of SEQ ID NO: 274 a LCDR1 of SEQ ID NO: 275, a LCDR2 of SEQ ID NO: 276, a LCDR3 of SEQ ID NO: 277, a VH of SEQ ID NO: 278, a VL of SEQ ID NO: 279, a HC of SEQ ID NO: 288.

In some embodiments the disclosure provides an isolated antibody or antigen binding fragment thereof comprising two antigen-binding domains, wherein the first antigen binding domain binds to an epitope of PSMA and comprises a heavy chain of SEQ ID NO: 268 and a light chain of SEQ ID NO: 269 and the second binding domain binds to a different epitope on PSMA and comprises a heavy chain of SEQ ID NO 282.

In some embodiments the disclosure provides an isolated antibody or antigen binding fragment thereof comprising two antigen-binding domains, wherein the first antigen binding domain binds to an epitope of PSMA and comprises a heavy chain of SEQ ID NO: 284 and a light chain of SEQ ID NO: 269 and the second binding domain binds to a different epitope on PSMA and comprises a heavy chain of SEQ ID NO 288.

In some embodiments, the disclosure provides an isolated antibody or antigen binding fragment thereof comprising:
a first binding domain that binds to a first epitope on PSMA and wherein the first binding domain comprises
a HCDR1, a HCDR2, a HCDR3, a LCDR1, a LCDR2 and a LCDR3 of SEQ ID NOs: 4, 5, 6, 7, 8, and 9, respectively;
a VH of SEQ ID NO: 52 and a VL of SEQ ID NO: 53; and/or
a HC of SEQ ID NO: 268 and a LC of SEQ ID NO: 269;
a second binding domain that binds to a second epitope on PSMA and wherein the second binding domain comprises
a HCDR1, a HCDR2, a HCDR3, a LCDR1, a LCDR2 and a LCDR3 of SEQ ID NOs: 272, 273, 274, 275, 276 and 277, respectively;
a VH of SEQ ID NO: 278 and a VL of SEQ ID NO: 279; and/or
a HC of SEQ ID NO: 282.

In some embodiments, the disclosure provides an isolated antibody or antigen binding fragment thereof comprising:
a first binding domain that binds to a first epitope on PSMA and wherein the first binding domain comprises
a HCDR1, a HCDR2, a HCDR3, a LCDR1, a LCDR2 and a LCDR3 of SEQ ID NOs: 4, 5, 6, 7, 8, and 9, respectively;
a VH of SEQ ID NO: 52 and a VL of SEQ ID NO: 53; and/or
a HC of SEQ ID NO: 284 and a LC of SEQ ID NO: 269;
a second binding domain that binds to a second epitope on PSMA and wherein the second binding domain comprises a HCDR1, a HCDR2, a HCDR3, a LCDR1, a LCDR2 and a LCDR3 of SEQ ID NOs: 272, 273, 274, 275, 276 and 277, respectively;

a VH of SEQ ID NO: 278 and a VL of SEQ ID NO: 279; and/or a HC of SEQ ID NO: 288.

Homologous Antibodies and Antigen Binding Fragment Thereof

Derivatives, homologous antigen binding domains, functional equivalents or variants of said antibody or antigen binding fragment thereof are also object of the disclosure. The antibodies of the present disclosure include homologous antibodies, homologous antigen binding domains, functional equivalents or variants of the disclosed antibody or antigen binding fragment thereof that bind PSMA, that include polypeptides with amino acid sequences substantially identical to the amino acid sequence of the variable domain or hypervariable domain of the antibodies of the present disclosure or polypeptides with conservative substitutions. The homologous antibodies and antigen binding domain, functional equivalents or variants of the disclosure have sufficient homology with the sequences of said antibody or antigen binding fragment thereof that binds PSMA and are functionally similar to the unmodified anti-PSMA antibody to retain binding to PSMA or retain at least one of the activities of the unmodified antibody.

The term "antibody derivative", "homologous antigen binding domain", "functional equivalents" or "variants" refer to antibodies comprising one or more mutations, substitutions, deletions and/or additions of one or more amino acid residues. Such an addition, substitution or deletion can be located at any position in the molecule. In the case where several amino acids have been added, substituted or deleted, any combination of addition, substitution or deletion can be considered, on condition that the resulting antibody still has at least the advantageous properties of the antibody of the disclosure.

In some embodiments, the disclosure provides amino acid sequence modification(s) of the antibodies or antigen binding fragment thereof described herein. For example, it may be desirable to improve the binding affinity and/or other biological properties of the antibody, including but not limited to specificity, thermostability, expression level, effector functions, glycosylation (e.g., fucosylation), reduced immunogenicity, or solubility. Thus, in addition to the antibodies and antigen binding fragment described herein, antibody variants can be prepared by introducing appropriate nucleotide changes into the encoding DNA, and/or by adding mutations, substitutions, deletions and/or additions of one or more amino acid residues to the antibodies and antigen binding fragment described herein.

In some embodiments, the antibodies and antigen binding fragments thereof provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

Variations may also include a substitution, deletion, or insertion of one or more codons encoding the antibody or polypeptide that results in a change in the amino acid sequence as compared with the native sequence antibody or polypeptide. Amino acid substitutions can be the result of replacing one amino acid with another amino acid having similar structural and/or chemical properties.

Sequences of the disclosure may comprise amino acid sequences with at least 80% identity or homology to the sequences of the antibody or antigen binding fragment thereof, described above. In some embodiments, the sequence identity may be about 80%, 81%, 82%, 83%, 84%, 85%, 86%, 87%, 88%, 89%, 90%, 91%, 92%, 93%, 94%, 95%, 96%, 97%, 98% or 99% to the antigen binding domains that bind PSMA of the disclosure. Variants of the antigen binding domains that bind PSMA comprising 1, 2, 3, 4, 5, 6, 7, 8, 9, 10, 11, 12, 13, 14, 15, 16, 17, 18, 19, 20, 21, 22, 23, 24, 25, 26, 27, 28 or 29 amino acid substitutions in the antigen binding domain that bind PSMA are within the scope of the disclosure, as long as they retain or have improved functional properties when compared to the parent antigen binding domains. Functional equivalents or variants of the antigen binding domains that bind PSMA include one or more deletions and/or additions of one or more amino acid residues. Such an addition, substitution or deletion can be located at any position in the molecule. In the case where several amino acids have been added, substituted or deleted, any combination of addition, substitution or deletion can be considered, on condition that the resulting antibody still has at least the advantageous properties of the antibody of the disclosure.

The terms "identical" or percent "identity" in the context of two or more nucleic acids or polypeptide sequences (e.g., anti-PSMA antibodies and polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection. The percent (%) amino acid sequence identity with respect to a reference polypeptide is defined as the percentage of amino acid residues in a given sequence that are identical to the amino acid residues in the reference polypeptide sequence. The percent (%) identity between the two sequences is a function of the number of identical positions shared by the sequences (i.e., % identity=number of identical positions/total number of positions×100), taking into account the number of gaps, and the length of each gap, which need to be introduced for optimal alignment of the two sequences. The percent identity between two amino acid sequences may be determined using various the algorithms that are within the skill in the art, using publicly available software such as BLAS, BLAST-2, ALIGN. Megalin (DNASTAR) or the GAP program available in the GCG software package.

A polypeptide is typically substantially identical to a second polypeptide, for example, where the two peptides differ only by conservative substitutions. The antibodies of the present disclosure also include those for which binding characteristics, functional or physical properties have been improved by direct mutations. In some embodiments, variant antigen binding domains that bind PSMA comprise one or two conservative substitutions in any of the CDR regions, while retaining desired functional properties of the parent antigen binding fragments that bind PSMA.

In a specific embodiment, the substitution is a conservative amino acid substitution made at one or more predicted non-essential amino acid residues. "Conservative modifications" or "conservative substitution" refer to amino acid modifications that do not significantly affect or alter the binding characteristics of the antibody containing the amino acid modifications. Conservative modifications include amino acid substitutions, additions and deletions. Conservative amino acid substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., (1988) *Acta Physiol Scand Suppl* 643:55-67; Sasaki et al., (1988) *Adv Biophys* 35:1-24).

Standard techniques known to those of skill in the art can be used to introduce mutations in the nucleotide sequence encoding a molecule provided herein, including, for example, site-directed mutagenesis and PCR-mediated mutagenesis which results in amino acid substitutions.

Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for antibody-directed enzyme prodrug therapy) or a polypeptide which increases the serum half-life of the antibody.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 52 and a VL of at least 80% (e.g. at least 85%, at least 90%, at least 95%, or at least 99%) identical to the VL of SEQ ID NO: 53.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 54 and a VL of at least 80% (e.g. at least 85%, at least 90%, at least 95%, or at least 99%) identical to the VL of SEQ ID NO: 55.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 56 and a VL of at least 80% (e.g. at least 85%, at least 90%, at least 95%, or at least 99%) identical to the VL of SEQ ID NO: 57.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 58 and a VL of at least 80% (e.g. at least 85%, at least 90%, at least 95%, or at least 99%) identical to the VL of SEQ ID NO: 59.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 60 and a VL of at least 80% (e.g. at least 85%, at least 90%, at least 95%, or at least 99%) identical to the VL of SEQ ID NO: 61.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 62 and a VL of at least 80% (e.g. at least 85%, at least 90%, at least 95%, or at least 99%) identical to the VL of SEQ ID NO: 63.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 64 and a VL of at least 80% (e.g. at least 85%, at least 90%, at least 95%, or at least 99%) identical to the VL of SEQ ID NO: 65.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 66 and a VL of at least 80% (e.g. at least 85%, at least 90%, at least 95%, or at least 99%) identical to the VL of SEQ ID NO: 67.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 278 and a VL of at least 80% (e.g. at least 85%, at least 90%, at least 95%, or at least 99%) identical to the VL of SEQ ID NO: 279.

In some embodiments, the antibody or antigen binding fragment thereof that binds PSMA comprises a VH which is at least 80% (e.g. at least 85%, at least 90%, at least 95% or at least 99%) identical to the VH of SEQ ID NO: 52 and a VL of SEQ ID NO: 53.

In some embodiments, the antibody or antigen binding fragment thereof that binds PSMA comprises a VH of SEQ ID NO: 52 and a VL which is at least 80% (e.g. at least 85%, at least 90%, at least 95% or at least 99%) identical to the VL of SEQ ID NO: 53.

In some embodiments, the antibody or antigen binding fragment thereof that binds PSMA comprises a VH which is at least 95% identical to the VH of SEQ ID NO: 52 and a VL which is at least 95% identical to the VL of SEQ ID NO: 53.

In some embodiments, the antibody or antigen binding fragment thereof that binds PSMA comprises a VH which is at least 95% identical to the VH of SEQ ID NO: 52 and a VL of SEQ ID NO: 53.

In some embodiments, the antibody or antigen binding fragment thereof that binds PSMA comprises a VH of SEQ ID NO: 52 and a VL which is at least 95% identical to the VL of SEQ ID NO: 53.

In some embodiments, the antibody or antigen binding fragment thereof that binds PSMA comprises a VH which is at least 95% identical to the VH of SEQ ID NO: 52 and a VL which is at least 99% identical to the VL of SEQ ID NO: 53.

In some embodiments, the antibody or antigen binding fragment thereof that binds PSMA comprises a VH which is at least 99% identical to the VH of SEQ ID NO: 52 and a VL which is at least 99% identical to the VL of SEQ ID NO: 53.

In some embodiments, the antibody or antigen binding fragment thereof that binds PSMA comprises a VH which is at least 99% identical to the VH of SEQ ID NO: 52 and a VL which is at least 95% identical to the VL of SEQ ID NO: 53.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 52 and a VL of at least 80% (e.g. at least 85%, at least 90%, at least 95%, or at least 99%) identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs 4, 5, 6, 7, 8, and 9, respectively.

In some embodiments, the antibody or antigen binding fragment thereof that binds PSMA comprises a VH which is at least 80% (e.g. at least 85%, at least 90%, at least 95% or at least 99%) identical to the VH of SEQ ID NO: 52 and a VL of SEQ ID NO: 53, wherein the antibody or antigen binding fragment comprises a HCDR1, a HCDR2, a HCDR3, a LCDR1, a LCDR2 and a LCDR3 of SEQ ID NOs 4, 5, 6, 7, 8, and 9, respectively.

In some embodiments, the antibody or antigen binding fragment thereof that binds PSMA comprises a VH of SEQ ID NO: 52 and a VL which is at least 80% (e.g. at least 85%, at least 90%, at least 95% or at least 99%) identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs 4, 5, 6, 7, 8, and 9, respectively.

In some embodiments, the antibody or antigen binding fragment thereof that binds PSMA comprises a VH which is at least 95% identical to the VH of SEQ ID NO: 52 and a VL which is at least 95% identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs 4, 5, 6, 7, 8, and 9, respectively.

In some embodiments, the antibody or antigen binding fragment thereof that binds PSMA comprises a VH which is at least 95% identical to the VH of SEQ ID NO: 52 and a VL of SEQ ID NO: 53, wherein the antibody or antigen binding fragment comprises a HCDR1, a HCDR2, a HCDR3, a LCDR1, a LCDR2 and a LCDR3 of SEQ ID NOs 4, 5, 6, 7, 8, and 9, respectively.

In some embodiments, the antibody or antigen binding fragment thereof that binds PSMA comprises a VH of SEQ ID NO: 52 and a VL which is at least 95% identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs 4, 5, 6, 7, 8, and 9, respectively.

In some embodiments, the antibody or antigen binding fragment thereof that binds PSMA comprises a VH which is at least 95% identical to the VH of SEQ ID NO: 52 and a VL which is at least 99% identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs 4, 5, 6, 7, 8, and 9, respectively.

In some embodiments, the antibody or antigen binding fragment thereof that binds PSMA comprises a VH which is at least 99% identical to the VH of SEQ ID NO: 52 and a VL which is at least 99% identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs 4, 5, 6, 7, 8, and 9, respectively.

In some embodiments, the antibody or antigen binding fragment thereof that binds PSMA comprises a VH which is at least 99% identical to the VH of SEQ ID NO: 52 and a VL which is at least 95% identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs 4, 5, 6, 7, 8, and 9, respectively.

In some embodiment, the disclosure also provides an isolated antibody or antigen binding fragment thereof comprising an amino acid sequence at least 80% (e.g. at least 85%, at least 90%, at least 95%, at least 99% or 100%) identical to the amino acid sequence of SEQ ID NO: 84 and wherein the antibody or antigen binding fragment thereof binds PSMA.

In some embodiments, the disclosure also provides an isolated antibody or antigen binding fragment thereof comprising an amino acid sequence at least 80% (e.g. at least 85%, at least 90%, at least 95%, at least 99% or 100%) identical to the amino acid sequence of SEQ ID NO: 85; and wherein the antibody or antigen binding fragment thereof binds PSMA.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 84 and a LC which is at least 80% (e.g. at least 85%, at least 90%, at least 95%, at least 99% or 100%) identical to the LC of SEQ ID NO: 85; and wherein the antibody or antigen binding fragment thereof binds PSMA.

In some embodiments, the antibody or antigen binding fragment thereof that binds PSMA comprises a HC which is at least 80% (e.g. at least 85%, at least 90%, at least 95% or at least 99%) identical to the HC of SEQ ID NO: 84 and a LC of SEQ ID NO: 85.

In some embodiments, the antibody or antigen binding fragment thereof that binds PSMA comprises a HC of SEQ ID NO: 84 and a LC which is at least 80% (e.g. at least 85%, at least 90%, at least 95% or at least 99%) identical to the LC of SEQ ID NO: 85.

In some embodiments, the antibody or antigen binding fragment thereof that binds PSMA comprises a HC which is at least 95% identical to the HC of SEQ ID NO: 84 and a LC which is at least 95% identical to the LC of SEQ ID NO: 85.

In some embodiments, the antibody or antigen binding fragment thereof that binds PSMA comprises a HC which is at least 95% identical to the HC of SEQ ID NO: 84 and a LC which is at least 99% identical to the LC of SEQ ID NO: 85.

In some embodiments, the antibody or antigen binding fragment thereof that binds PSMA comprises a HC which is at least 99% identical to the HC of SEQ ID NO: 84 and a LC which is at least 99% identical to the LC of SEQ ID NO: 85.

In some embodiments, the antibody or antigen binding fragment thereof that binds PSMA comprises a HC which is at least 99% identical to the HC of SEQ ID NO: 84 and a LC which is at least 95% identical to the LC of SEQ ID NO: 85.

In some embodiment, the disclosure also provides an isolated antibody or antigen binding fragment thereof comprising an amino acid sequence at least 80% (e.g. at least 85%, at least 90%, at least 95%, at least 99% or 100%) identical to the amino acid sequence of SEQ ID NO: 86 and wherein the antibody or antigen binding fragment thereof binds PSMA.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 86 and a LC which is at least 80% (e.g. at least 85%, at least 90%, at least 95%, at least 99% or 100%) identical to the LC of SEQ ID NO: 85; and wherein the antibody or antigen binding fragment thereof binds PSMA.

In some embodiments, the antibody or antigen binding fragment thereof that binds PSMA comprises a HC which is at least 80% (e.g. at least 85%, at least 90%, at least 95% or at least 99%) identical to the HC of SEQ ID NO: 86 and a LC of SEQ ID NO: 85.

In some embodiments, the antibody or antigen binding fragment thereof that binds PSMA comprises a HC of SEQ ID NO: 86 and a LC which is at least 80% (e.g. at least 85%, at least 90%, at least 95% or at least 99%) identical to the LC of SEQ ID NO: 85.

In some embodiments, the antibody or antigen binding fragment thereof that binds PSMA comprises a HC which is at least 95% identical to the HC of SEQ ID NO: 86 and a LC which is at least 95% identical to the LC of SEQ ID NO: 85.

In some embodiments, the antibody or antigen binding fragment thereof that binds PSMA comprises a HC which is at least 95% identical to the HC of SEQ ID NO: 86 and a LC which is at least 99% identical to the LC of SEQ ID NO: 85.

In some embodiments, the antibody or antigen binding fragment thereof that binds PSMA comprises a HC which is at least 99% identical to the HC of SEQ ID NO: 86 and a LC which is at least 99% identical to the LC of SEQ ID NO: 85.

In some embodiments, the antibody or antigen binding fragment thereof that binds PSMA comprises a HC which is at least 99% identical to the HC of SEQ ID NO: 86 and a LC which is at least 95% identical to the LC of SEQ ID NO: 85.

In some embodiment, the disclosure also provides an isolated antibody or antigen binding fragment thereof comprising an amino acid sequence at least 80% (e.g. at least 85%, at least 90%, at least 95%, at least 99% or 100%) identical to the amino acid sequence of SEQ ID NO: 88 and wherein the antibody or antigen binding fragment thereof binds PSMA.

In some embodiment, the disclosure also provides an isolated antibody or antigen binding fragment thereof comprising an amino acid sequence at least 80% (e.g. at least 85%, at least 90%, at least 95%, at least 99% or 100%) identical to the amino acid sequence of SEQ ID NO: 89 and wherein the antibody or antigen binding fragment thereof binds PSMA.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 88 and a LC which is at least 80% (e.g. at least 85%, at least 90%, at least 95%, at least 99% or 100%) identical to the LC of SEQ ID NO: 89; and wherein the antibody or antigen binding fragment thereof binds PSMA.

In some embodiments, the antibody or antigen binding fragment thereof that binds PSMA comprises a HC which is at least 80% (e.g. at least 85%, at least 90%, at least 95% or at least 99%) identical to the HC of SEQ ID NO: 88 and a LC of SEQ ID NO: 89.

In some embodiments, the antibody or antigen binding fragment thereof that binds PSMA comprises a HC of SEQ ID NO: 88 and a LC which is at least 80% (e.g. at least 85%, at least 90%, at least 95% or at least 99%) identical to the LC of SEQ ID NO: 89.

In some embodiments, the antibody or antigen binding fragment thereof that binds PSMA comprises a HC which is at least 95% identical to the HC of SEQ ID NO: 88 and a LC which is at least 95% identical to the LC of SEQ ID NO: 89.

In some embodiments, the antibody or antigen binding fragment thereof that binds PSMA comprises a HC which is at least 95% identical to the HC of SEQ ID NO: 88 and a LC which is at least 99% identical to the LC of SEQ ID NO: 89.

In some embodiments, the antibody or antigen binding fragment thereof that binds PSMA comprises a HC which is at least 99% identical to the HC of SEQ ID NO: 88 and a LC which is at least 99% identical to the LC of SEQ ID NO: 89.

In some embodiments, the antibody or antigen binding fragment thereof that binds PSMA comprises a HC which is at least 99% identical to the HC of SEQ ID NO: 88 and a LC which is at least 95% identical to the LC of SEQ ID NO: 89.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 84 and a LC which is at least 80% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 80% (e.g. at least 85%, at least 90%, at least 95% or at least 99%) identical to the HC of SEQ ID NO: 84 and a LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC of SEQ ID NO: 84 and a LC which is at least 80% (e.g. at least 85%, at least 90%, at least 95% or at least 99%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 95% identical to the HC of SEQ ID NO: 84 and a LC which is at least 95% identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 95% identical to the HC of SEQ ID NO: 84 and a LC which is at least 99% identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 99% identical to the HC of SEQ ID NO: 84 and a LC which is at least 99% identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 99% identical to the HC of SEQ ID NO: 84 and a LC which is at least 95% identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 86 and a LC which is at least 80% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 80% (e.g. at least 85%, at least 90%, at least 95% or at least 99%) identical to the HC of SEQ ID NO: 86 and a LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC of SEQ ID NO: 86 and a LC which is at least 80% (e.g. at least 85%, at least 90%, at least 95% or at least 99%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 95% identical to the HC of SEQ ID NO: 86 and a LC which is at least 95% identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 95% identical to the HC of SEQ ID NO: 86 and a LC which is at least 99% identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 99% identical to the HC of SEQ ID NO: 86 and a LC which is at least 99% identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 99% identical to the HC of SEQ ID NO: 86 and a LC which is at least 95% identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 88 and a LC which is at least 80% (e.g. at least 85%, at least 90%, at least 95%, at least 99% or 100%) identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 80% (e.g. at least 85%, at least 90%, at least 95% or at least 99%) identical to the HC of SEQ ID NO: 88 and a LC of SEQ ID NO: 89, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC of SEQ ID NO: 88 and a LC which is at least 80% (e.g. at least 85%, at least 90%, at least 95% or at least 99%) identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 95% identical to the HC of SEQ ID NO: 88 and a LC which is at least 95% identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 95% identical to the HC of SEQ ID NO: 88 and a LC which is at least 99% identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 99% identical to the HC of SEQ ID NO: 88 and a LC which is at least 99% identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

In some embodiments, the antibody or antigen binding fragment thereof that binds PSMA comprises a HC which is at least 99% identical to the HC of SEQ ID NO: 88 and a LC which is at least 95% identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively.

The disclosure also provides an isolated antibody comprising a HC which is at least 80% (e.g. at least 85%, at least 90%, at least 95%, at least 99% or 100%) identical to the HC of SEQ ID NO: 84 and a LC which is at least 80% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53.

In some embodiments, the antibody that binds PSMA comprises a HC which is at least 80% (e.g. at least 85%, at least 90%, at least 95% or at least 99%) identical to the HC of SEQ ID NO: 84 and a LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC of SEQ ID NO: 84 and a LC which is at least 80% (e.g. at least 85%, at least 90%, at least 95% or at least 99%) identical to the LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC which is at least 95% identical to the HC of SEQ ID NO: 84 and a LC which is at least 95% identical to the LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC which is at least 95% identical to the HC of SEQ ID NO: 84 and a LC which is at least 99% identical to the LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC which is at least 99% identical to the HC of SEQ ID NO: 84 and a LC which is at least 99% identical to the LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC which is at least 99% identical to the HC of SEQ ID NO: 84 and a LC which is at least 95% identical to the LC of SEQ ID NO: 85, wherein the antibody or antigen binding fragment comprises a VH of SEQ ID NO: 52 and a VL of SEQ ID NO: 53.

The disclosure also provides an isolated antibody comprising a HC which is at least 80% (e.g. at least 85%, at least 90%, at least 95%, at least 99% or 100%) identical to the HC of SEQ ID NO: 86 and a LC which is at least 80% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53.

In some embodiments, the antibody that binds PSMA comprises a HC which is at least 80% (e.g. at least 85%, at least 90%, at least 95% or at least 99%) identical to the HC of SEQ ID NO: 86 and a LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC of SEQ ID NO: 86 and a LC which is at least 80% (e.g. at least 85%, at least 90%, at least 95% or at least 99%) identical to the LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC which is at least 95% identical to the HC of SEQ ID NO: 86 and a LC which is at least 95% identical to the LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC which is at least 95% identical to the HC of SEQ ID NO: 86 and a LC which is at least 99% identical to the LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC which is at least 99% identical to the HC of SEQ ID NO: 86 and a LC which is at least 99% identical to the LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a HC which is at least 99% identical to the HC of SEQ ID NO: 86 and a LC which is at least 95% identical to the LC of SEQ ID NO: 85, wherein the antibody or antigen binding fragment comprises a VH of SEQ ID NO: 52 and a VL of SEQ ID NO: 53.

In some embodiments, the antibody or antigen binding fragment thereof that binds PSMA comprises a VH which is at least 80% (e.g. at least 85%, at least 90%, at least 95% or at least 99%) identical to the VH of SEQ ID NO: 54 and a VL of SEQ ID NO: 55.

In some embodiments, the antibody or antigen binding fragment thereof that binds PSMA comprises a VH of SEQ ID NO: 54 and a VL which is at least 80% (e.g. at least 85%, at least 90%, at least 95% or at least 99%) identical to the VL of SEQ ID NO: 55.

In some embodiments, the antibody or antigen binding fragment thereof that binds PSMA comprises a VH which is at least 95% identical to the VH of SEQ ID NO: 54 and a VL which is at least 95% identical to the VL of SEQ ID NO: 55.

In some embodiments, the antibody or antigen binding fragment thereof that binds PSMA comprises a VH which is at least 95% identical to the VH of SEQ ID NO: 54 and a VL of SEQ ID NO: 55.

In some embodiments, the antibody or antigen binding fragment thereof that binds PSMA comprises a VH of SEQ ID NO: 54 and a VL which is at least 95% identical to the VL of SEQ ID NO: 55.

In some embodiments, the antibody or antigen binding fragment thereof that binds PSMA comprises a VH which is at least 95% identical to the VH of SEQ ID NO: 54 and a VL which is at least 99% identical to the VL of SEQ ID NO: 55.

In some embodiments, the antibody or antigen binding fragment thereof that binds PSMA comprises a VH which is at least 99% identical to the VH of SEQ ID NO: 54 and a VL which is at least 99% identical to the VL of SEQ ID NO: 55.

In some embodiments, the antibody or antigen binding fragment thereof that binds PSMA comprises a VH which is at least 99% identical to the VH of SEQ ID NO: 54 and a VL which is at least 95% identical to the VL of SEQ ID NO: 55.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 54 and a VL of at least 80% (e.g. at least 85%, at least 90%, at least 95%, or at least 99%) identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs 10, 11, 12, 13, 14 and 15, respectively.

In some embodiments, the antibody or antigen binding fragment thereof that binds PSMA comprises a VH which is at least 80% (e.g. at least 85%, at least 90%, at least 95% or at least 99%) identical to the VH of SEQ ID NO: 54 and a VL of SEQ ID NO: 55, wherein the antibody or antigen binding fragment comprises a HCDR1, a HCDR2, a HCDR3, a LCDR1, a LCDR2 and a LCDR3 of SEQ ID NOs 10, 11, 12, 13, 14 and 15, respectively.

In some embodiments, the antibody or antigen binding fragment thereof that binds PSMA comprises a VH of SEQ ID NO: 54 and a VL which is at least 80% (e.g. at least 85%, at least 90%, at least 95% or at least 99%) identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs 10, 11, 12, 13, 14 and 15, respectively.

In some embodiments, the antibody or antigen binding fragment thereof that binds PSMA comprises a VH which is at least 95% identical to the VH of SEQ ID NO: 54 and a VL which is at least 95% identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs 10, 11, 12, 13, 14 and 15, respectively.

In some embodiments, the antibody or antigen binding fragment thereof that binds PSMA comprises a VH which is at least 95% identical to the VH of SEQ ID NO: 54 and a VL of SEQ ID NO: 55, wherein the antibody or antigen binding fragment comprises a HCDR1, a HCDR2, a HCDR3, a LCDR1, a LCDR2 and a LCDR3 of SEQ ID NOs 10, 11, 12, 13, 14 and 15, respectively.

In some embodiments, the antibody or antigen binding fragment thereof that binds PSMA comprises a VH of SEQ ID NO: 54 and a VL which is at least 95% identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs 10, 11, 12, 13, 14 and 15, respectively.

In some embodiments, the antibody or antigen binding fragment thereof that binds PSMA comprises a VH which is at least 95% identical to the VH of SEQ ID NO: 54 and a VL which is at least 99% identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs 10, 11, 12, 13, 14 and 15, respectively.

In some embodiments, the antibody or antigen binding fragment thereof that binds PSMA comprises a VH which is at least 99% identical to the VH of SEQ ID NO: 54 and a VL which is at least 99% identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs 10, 11, 12, 13, 14 and 15, respectively.

In some embodiments, the antibody or antigen binding fragment thereof that binds PSMA comprises a VH which is at least 99% identical to the VH of SEQ ID NO: 54 and a VL which is at least 95% identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs 10, 11, 12, 13, 14 and 15, respectively.

The disclosure also provides an isolated antibody comprising a HC which is at least 80% (e.g. at least 85%, at least 90%, at least 95%, at least 99% or 100%) identical to the HC of SEQ ID NO: 88 and a LC which is at least 80% (e.g. at least 85%, at least 90%, at least 95%, at least 99% or 100%) identical to the LC of SEQ ID NO: 89, wherein the antibody or antigen binding fragment comprises a VH of SEQ ID NO: 54 and a VL of SEQ ID NO: 55.

In some embodiments, the antibody that binds PSMA comprises a HC which is at least 80% (e.g. at least 85%, at least 90%, at least 95% or at least 99%) identical to the HC of SEQ ID NO: 88 and a LC of SEQ ID NO: 89, wherein the antibody or antigen binding fragment comprises a VH of SEQ ID NO: 54 and a VL of SEQ ID NO: 55.

In some embodiments, the antibody or antigen binding fragment thereof that binds PSMA comprises a HC of SEQ ID NO: 88 and a LC which is at least 80% (e.g. at least 85%, at least 90%, at least 95% or at least 99%) identical to the LC of SEQ ID NO: 89, wherein the antibody or antigen binding fragment comprises a VH of SEQ ID NO: 54 and a VL of SEQ ID NO: 55.

In some embodiments, the antibody or antigen binding fragment thereof that binds PSMA comprises a HC which is at least 95% identical to the HC of SEQ ID NO: 88 and a LC which is at least 95% identical to the LC of SEQ ID NO: 89, wherein the antibody or antigen binding fragment comprises a VH of SEQ ID NO: 54 and a VL of SEQ ID NO: 55.

In some embodiments, the antibody or antigen binding fragment thereof that binds PSMA comprises a HC which is at least 95% identical to the HC of SEQ ID NO: 88 and a LC which is at least 99% identical to the LC of SEQ ID NO: 89, wherein the antibody or antigen binding fragment comprises a VH of SEQ ID NO: 54 and a VL of SEQ ID NO: 55.

In some embodiments, the antibody or antigen binding fragment thereof that binds PSMA comprises a HC which is at least 99% identical to the HC of SEQ ID NO: 88 and a LC which is at least 99% identical to the LC of SEQ ID NO: 89, wherein the antibody or antigen binding fragment comprises a VH of SEQ ID NO: 54 and a VL of SEQ ID NO: 55.

In some embodiments, the antibody or antigen binding fragment thereof that binds PSMA comprises a HC which is at least 99% identical to the HC of SEQ ID NO: 88 and a LC which is at least 95% identical to the LC of SEQ ID NO: 89, wherein the antibody or antigen binding fragment comprises a VH of SEQ ID NO: 54 and a VL of SEQ ID NO: 55.

In some embodiments, the antibody or antigen binding fragment thereof that binds PSMA comprises comprising two antigen-binding domains, wherein the first antigen binding domain binds to an epitope of PSMA and the second binding domain binds to a different epitope on PSMA and wherein:
 the first antigen binding domain comprises a VH which is at least 80% (e.g. at least 85%, at least 90%, at least 95%, or at least 99%) identical to the VH of SEQ ID NO: 52 and a VL of at least 80% (e.g. at least 85%, at least 90%, at least 95%, or at least 99%) identical to the VL of SEQ ID NO: 53; and
 the second antigen binding domain comprises a VH which is at least 80% (e.g. at least 85%, at least 90%, at least 95%, or at least 99%) identical to the VH of SEQ ID NO: 278 and a VL of at least 80% (e.g. at least 85%, at least 90%, at least 95%, or at least 99%) identical to the VL of SEQ ID NO: 279.

In some embodiments, the antibody or antigen binding fragment thereof that binds PSMA comprises comprising two antigen-binding domains, wherein the first antigen binding domain binds to an epitope of PSMA and the second binding domain binds to a different epitope on PSMA and wherein:
 the first antigen binding domain comprises a heavy chain which is at least 80% (e.g. at least 85%, at least 90%, at least 95%, or at least 99%) identical to SEQ ID NO: 268 and a light chain which is at least 80% (e.g. at least 85%, at least 90%, at least 95%, or at least 99%) identical to SEQ ID NO: 269; and
 the second antigen binding domain comprises a heavy chain which is at least 80% (e.g. at least 85%, at least 90%, at least 95%, or at least 99%) identical to SEQ ID NO: 282.

In some embodiments, the antibody or antigen binding fragment thereof that binds PSMA comprises comprising two antigen-binding domains, wherein the first antigen binding domain binds to an epitope of PSMA and the second binding domain binds to a different epitope on PSMA and wherein:
 the first antigen binding domain comprises a heavy chain which is at least 80% (e.g. at least 85%, at least 90%, at least 95%, or at least 99%) identical to SEQ ID NO: 284 and a light chain which is at least 80% (e.g. at least 85%, at least 90%, at least 95%, or at least 99%) identical to SEQ ID NO: 269; and
 the second antigen binding domain comprises a heavy chain which is at least 80% (e.g. at least 85%, at least 90%, at least 95%, or at least 99%) identical to SEQ ID NO: 288.

Half-Life Extension Moiety and Fc Engineering

In addition to the modification set forth above, the anti-PSMA antibody or antigen binding fragment thereof of the present disclosure and their functional equivalents may be conjugated to other antibodies, proteins, antigen binding fragments or alternative scaffolds that may be used to adjust, alter, improve or moderate antibody characteristics as desired.

For example, antibodies with increased in vivo half-lives can be generated by attaching half-life extending moiety such as albumin, albumin variants, albumin-binding proteins and/or domains, transferrin and fragments and analogues thereof, immunoglobulins (Ig) or fragments thereof, such as Fc regions to the antibody, antigen binding fragment of the disclosure. Additional half-life extending moieties include polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the antibody or antigen binding fragment of the disclosure and may be generated by standard cloning and expression techniques.

Half-life extending moieties can be attached to antibodies or antibody fragments or derivatives with or without a multifunctional linker either through conjugation to the N- or C-terminus of said antibodies or antibody fragments or via epsilon-amino groups present on lysine residues. Alternatively, well known chemical coupling methods may be used to attach the moieties to the recombinantly produced antibody or antigen binding fragment of the disclosure.

A pegyl moiety may for example be conjugated to the antibody or antigen binding fragment thereof that bind PSMA by incorporating a cysteine residue to the C-terminus of the antibody or antigen binding fragment that bind PSMA or engineering cysteines into residue positions that face away from the PSMA binding site and attaching a pegyl group to the cysteine using well known methods.

In some embodiments, the half-life extending moiety is albumin.

In some embodiments, the half-life extending moiety is the albumin binding domain.

In some embodiments, the half-life extending moiety is transferrin.

In some embodiments, the half-life extending moiety is polyethylene glycol.

In some embodiments, the half-life extending moiety is an Ig constant region or a fragment of the Ig constant region.

In some embodiments, the half-life extending moiety is an Ig.

In some embodiments, the half-life extending moiety is a fragment of the Ig.

In some embodiments, the half-life extending moiety is the Ig constant region.

In some embodiments, the half-life extending moiety is the fragment of the Ig constant region.

In some embodiments, the half-life extending moiety is the Fc region.

The Ig constant region or the fragment of the Ig constant region, such as the Fc region present in the antibody or antigen binding fragment thereof of the disclosure may be of any allotype or isotype, i.e., IgG1, IgG2, IgG3, IgG4, IgM, IgA and IgE.

In some embodiments, the Ig constant region or the fragment of the Ig constant region is an IgG1 isotype.

In some embodiments, the Ig constant region or the fragment of the Ig constant region is an IgG2 isotype.

In some embodiments, the Ig constant region or the fragment of the Ig constant region is an IgG3 isotype.

In some embodiments, the Ig constant region or the fragment of the Ig constant region is an IgG4 isotype.

It is expected that allotype has no influence on properties of the Ig constant region, such as binding or Fc-mediated effector functions. Immunogenicity of therapeutic proteins comprising Ig constant regions of fragments thereof is associated with increased risk of infusion reactions and decreased duration of therapeutic response (Baert et al., (2003) N Engl J Med 348:602-08). The extent to which therapeutic proteins comprising Ig constant regions of fragments thereof induce an immune response in the host may be determined in part by the allotype of the Ig constant region (Stickler et al., (2011) Genes and Immunity 12:213-21). Ig constant region allotype is related to amino acid sequence variations at specific locations in the constant region sequences of the antibody.

The antibody or antigen binding fragment thereof of the present disclosure and their functional equivalents may be conjugated to an Ig constant region or to the fragment of an Ig constant region to modulate the antibody or antigen binding fragment effector functions such as ADCC, ADCP and/or ADCP and/or pharmacokinetic properties. This may be achieved by introducing mutation(s) into the Fc that modulate binding of the mutated Fc to activating FcγRs (FcγRI, FcγRIIa, FcγRIII), inhibitory FcγRIIb and/or to FcRn.

In some embodiments, the antibody or antigen binding fragment thereof that binds PSMA is conjugated to an Ig constant region or the fragment of the Ig constant region comprising at least one mutation in the Ig constant region or in the fragment of the Ig constant region.

In some embodiments, the at least one mutation is in the Fc region.

In some embodiments, the antibody or antigen binding fragment thereof that binds PSMA is conjugated to an Ig constant region or to the fragment of the Ig constant region comprises at least one, two, three, four, five, six, seven, eight, nine, ten, eleven, twelve, thirteen, fourteen or fifteen mutations in the Fc region.

The neonatal Fc receptor (FcRn) plays a central role in the cellular trafficking and serum half-life of IgGs. In some embodiments, the antibody or antigen binding fragment thereof that binds PSMA is conjugated to an Ig constant region or to the fragment of the Ig constant region comprising at least one mutation in the Fc region that modulates binding of the antibody or antigen binding fragment to FcRn and modulates the half-life of the antibody or antigen binding fragment.

In some embodiments, the Ig constant region or the fragment of the first Ig constant region comprises at least one mutation that modulates a half-life of the isolated antibody or antigen binding fragment thereof.

Fc positions that may be mutated to modulate half-life (e.g. binding to FcRn) include positions 250, 252, 253, 254, 256, 257, 307, 376, 380, 428, 434 and 435. Exemplary mutations that may be made singularly or in combination are mutations T250Q, M252Y, I253A, S254T, T256E, P257I, T307A, D376V, E380A, M428L, H433K, N434S, N434A, N434H, N434F, H435A and H435R. Exemplary singular or combination mutations that may be made to increase the half-life are mutations M428L/N434S, M252Y/S254T/T256E, T250Q/M428L, N434A and T307A/E380A/N434A.

In some embodiments, the at least one mutation that modulates the half-life of the antibody or antigen binding fragment thereof of the disclosure and their functional equivalents is selected from the group consisting of H435A, P257I/N434H, D376V/N434H, M252Y/S254T/T256E/H433K/N434F, T308P/N434A and H435R, wherein residue numbering is according to the EU index In some embodiments, the antibody or antigen binding fragment thereof that binds PSMA is conjugated to the Ig constant region or to the fragment of the Ig constant region comprising M252Y/S254T/T256E mutation.

In some embodiments, the antibody or antigen binding fragment of the disclosure and their function equivalents is conjugated to an Ig constant region or to the fragment of the Ig constant region comprising at least one mutation in the Fc region that reduces binding of the protein to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Fc positions that may be mutated to reduce binding of the protein to the activating FcγR and subsequently to reduce effector function include positions 214, 233, 234, 235, 236, 237, 238, 265, 267, 268, 270, 295, 297, 309, 327, 328, 329, 330, 331 and 365. Exemplary mutations that may be made singularly or in combination are mutations K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S in IgG1, IgG2, IgG3 or IgG4. Exemplary combination mutations that result in proteins with reduced ADCC are mutations L234A/L235A on IgG1, L234A/L235A/D265S on IgG1, V234A/G237A/P238S/H268A/V309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4. Hybrid IgG2/4 Fc domains may also be used, such as Fc with residues 117-260 from IgG2 and residues 261-447 from IgG4.

In some embodiments, the antibody or antigen binding fragment thereof that binds PSMA is conjugated to an IgG1 heavy chain constant region or a fragment of the IgG1 heavy chain constant region. In some embodiments, the IgG1 heavy chain constant region comprises at least one mutation that results in reduced binding of the antibody to a FcγR. In some embodiments, the at least one mutation that results in reduced binding of the antibody to the FcγR is selected from the group consisting of F234A/L235A, L234A/L235A, L234A/L235A/D265S, V234A/G237A/P238S/H268A/V309L/A330S/P331S, F234A/L235A, S228P/F234A/L235A, N297A, V234A/G237A, K214T/E233P/L234V/L235A/G236-deleted/A327G/P331A/D365E/L358M, H268Q/V309L/A330S/P331S, S267E/L328F, L234F/L235E/D265A, L234A/L235A/G237A/P238S/H268A/A330S/P331S, S228P/F234A/L235A/G237A/P238S and S228P/F234A/L235A/G236-deleted/G237A/P238S, wherein residue numbering is according to the EU index.

In some embodiments, the first Ig constant region or the fragment of the first Ig constant region and/or the second Ig constant region or the fragment of the second Ig constant region comprise the following mutations: L234A_L235A_D265S.

In some embodiments, the FcγR is FcγRI, FcγRIIA, FcγRIIB or FcγRIII, or any combination thereof.

In some embodiments, the antibody or antigen binding fragment of the disclosure and their function equivalents is conjugated to an Ig constant region or to a fragment of an Ig constant region comprising at least one mutation in the Fc region that enhances binding of the protein to an Fcγ receptor (FcγR) and/or enhances Fc effector functions such as C1q binding, complement dependent cytotoxicity (CDC), antibody-dependent cell-mediated cytotoxicity (ADCC) and/or phagocytosis (ADCP).

Fc positions that may be mutated to increase binding of the protein to the activating FcγR and/or enhance Fc effector functions include positions 236, 239, 243, 256, 290, 292, 298, 300, 305, 312, 326, 330, 332, 333, 334, 345, 360, 339, 378, 396 or 430 (residue numbering according to the EU index). Exemplary mutations that may be made singularly or in combination are G236A, S239D, F243L, T256A, K290A, R292P, S298A, Y300L, V305L, K326A, A330K, I332E, E333A, K334A, A339T and P396L. Exemplary combination mutations that result in proteins with increased ADCC or ADCP are a S239D/I332E, S298A/E333A/K334A, F243L/R292P/Y300L, F243L/R292P/Y300L/P396L, F243L/R292P/Y300L/V305I/P396L and G236A/5239D/I332E.

Fc positions that may be mutated to enhance CDC include positions 267, 268, 324, 326, 333, 345 and 430. Exemplary mutations that may be made singularly or in combination are S267E, F1268F, S324T, K326A, K326W, E333A, E345K, E345Q, E345R, E345Y, E430S, E430F and E430T. Exemplary combination mutations that result in proteins with increased CDC are K326A/E333A, K326W/E333A, H268F/S324T, S267E/H268F, S267E/S324T and S267E/H268F/S324T.

In some embodiments, the disclosure provides an isolated antibody or antigen binding fragment thereof comprising a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or M252Y/S254T/T256E mutations, such as wherein the first Ig constant region or the fragment of the first Ig constant region and the second Ig constant region or the fragment of the second Ig constant region comprise the L234A_L235A_D265S and/or M252Y/S254T/T256E mutations.

In some embodiments, the disclosure provides an isolated antibody or antigen binding fragment thereof comprising a VH of SEQ ID NO: 52 and a VL of SEQ ID NO: 53 and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 52 and a VL of at least 80% (e.g. at least 85%, at least 90%, at least 95%, or at least 99%) identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 80% (e.g. at least 85%, at least 90%, at least 95% or at least 99%) identical to the VH of SEQ ID NO: 52 and a VL of SEQ ID NO: 53, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH of SEQ ID NO: 52 and a VL which is at least 80% (e.g. at least 85%, at least 90%, at least 95% or at least 99%) identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 95% identical to the VH of SEQ ID NO: 52 and a VL which is at least 95% identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 95% identical to the VH of SEQ ID NO: 52 and a VL which is at least 99% identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 99% identical to the VH of SEQ ID NO: 52 and a VL which is at least 99% identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 99% identical to the VH of SEQ ID NO: 52 and a VL which is at least 95% identical to the VL of SEQ ID NO: 53, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the disclosure provides an isolated antibody or antigen binding fragment thereof comprising a HCDR1, a HCDR2, a HCDR3, a LCDR1, a LCDR2 and a LCDR3 of SEQ ID NOs: 10, 11, 12, 13, 14, and 15 respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or M252Y/S254T/T256E mutations, such as wherein the first Ig constant region or the fragment of the first Ig constant region and the second Ig constant region or the fragment of the second Ig constant region comprise the L234A_L235A_D265S and/or M252Y/S254T/T256E mutations.

In some embodiments, the disclosure provides an isolated antibody or antigen binding fragment thereof comprising a VH of SEQ ID NO: 54 and a VL of SEQ ID NO: 55 and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 80% (e.g. at least 85%, at least 90%, at least 95%, or at least 99%) identical to the VH of SEQ ID NO: 54 and a VL of at least 80% (e.g. at least 85%, at least 90%, at least 95%, or at least 99%) identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 80% (e.g. at least 85%, at least 90%, at least 95% or at least 99%) identical to the VH of SEQ ID NO: 54 and a VL of SEQ ID NO: 55, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH of SEQ ID NO: 54 and a VL which is at least 80% (e.g. at least 85%, at least 90%, at least 95% or at least 99%) identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs: 10, 11, 12, 13, 14, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 95% identical to the VH of SEQ ID NO: 54 and a VL which is at least 95% identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 95% identical to the VH of SEQ ID NO: 54 and a VL which is at least 99% identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 99% identical to the VH of SEQ ID NO: 54 and a VL which is at least 99% identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a VH which is at least 99% identical to the VH of SEQ ID NO: 54 and a VL which is at least 95% identical to the VL of SEQ ID NO: 55, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiment, the disclosure also provides an isolated antibody or antigen binding fragment thereof comprising an amino acid sequence at least 80% (e.g. at least 85%, at least 90%, at least 95%, at least 99% or 100%) identical to the amino acid sequence of SEQ ID NO: 84 and wherein the antibody or antigen binding fragment thereof binds PSMA, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the disclosure also provides an isolated antibody or antigen binding fragment thereof comprising an amino acid sequence at least 80% (e.g. at least 85%, at least 90%, at least 95%, at least 99% or 100%) identical to the amino acid sequence of SEQ ID NO: 85; and wherein the antibody or antigen binding fragment thereof binds PSMA, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 84 and a LC which is at least 80% (e.g. at least 85%, at least 90%, at least 95%, at least 99% or 100%) identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 80% (e.g. at least 85%, at least 90%, at least 95% or at least 99%) identical to the HC of SEQ ID NO: 84 and a LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC of SEQ ID NO: 84 and a LC which is at least 80% (e.g. at least 85%, at least 90%, at least 95% or at least 99%) identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 95% identical to the HC of SEQ ID NO: 84 and a LC which is at least 95% identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 95% identical to the HC of SEQ ID NO: 84 and a LC which is at least 99% identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 99% identical to the HC of SEQ ID NO: 84 and a LC which is at least 99% identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 99% identical to the HC of SEQ ID NO: 84 and a LC which is at least 95% identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the following L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiment, the disclosure also provides an isolated antibody or antigen binding fragment thereof comprising an amino acid sequence at least 80% (e.g. at least 85%, at least 90%, at least 95%, at least 99% or 100%) identical to the amino acid sequence of SEQ ID NO: 86 and wherein the antibody or antigen binding fragment thereof binds PSMA, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the disclosure also provides an isolated antibody or antigen binding fragment thereof comprising an amino acid sequence at least 80% (e.g. at least 85%, at least 90%, at least 95%, at least 99% or 100%) identical to the amino acid sequence of SEQ ID NO: 85; and wherein the antibody or antigen binding fragment thereof binds PSMA, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 86 and a LC which is at least 80% (e.g. at least 85%, at least 90%, at least 95%, at least 99% or 100%) identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 80% (e.g. at least 85%, at least 90%, at least 95% or at least 99%) identical to the HC of SEQ ID NO: 86 and a LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC of SEQ ID NO: 86 and a LC which is at least 80% (e.g. at least 85%, at least 90%, at least 95% or at least 99%) identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 95% identical to the HC of SEQ ID NO: 86 and a LC which is at least 95% identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 95% identical to the HC of SEQ ID NO: 86 and a LC which is at least 99% identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 99% identical to the HC of SEQ ID NO: 86 and a LC which is at least 99% identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 99% identical to the HC of SEQ ID NO: 86 and a LC which is at least 95% identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the following L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 88 and a LC which is at least 80% (e.g. at least 85%, at least 90%, at least 95%, at least 99% or 100%) identical to the LC of SEQ ID NO: 89, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 80% (e.g. at least 85%, at least 90%, at least 95% or at least 99%) identical to the HC of SEQ ID NO: 88 and a LC of SEQ ID NO: 89, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC of SEQ ID NO: 88 and a LC which is at least 80% (e.g. at least 85%, at least 90%, at least 95% or at least 99%) identical to the LC of SEQ ID NO: 89, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 95% identical to the HC of SEQ ID NO: 88 and a LC which is at least 95% identical to the LC of SEQ ID NO: 89, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 95% identical to the HC of SEQ ID NO: 88 and a LC which is at least 99% identical to the LC of SEQ ID NO: 89, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 99% identical to the HC of SEQ ID NO: 88 and a LC which is at least 99% identical to the LC of SEQ ID NO: 89, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC which is at least 99% identical to the HC of SEQ ID NO: 86 and a LC which is at least 95% identical to the LC of SEQ ID NO: 85, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the following L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO:

84 and a LC which is at least 80% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 84 and a LC which is at least 100% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 100% (e.g. at least 85%, at least 90%, at least 95%, at least 99% or 100%) identical to the HC of SEQ ID NO: 84 and a LC which is at least 80% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 84 and a LC which is at least 95% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 84 and a LC which is at least 99% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 84 and a LC which is at least 99% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 84 and a LC which is at least 95% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 86 and a LC which is at least 80% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 86 and a LC which is at least 100% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 100% (e.g. at least 85%, at least 90%, at least 95%, at least 99% or 100%) identical to the HC of SEQ ID NO: 86 and a LC which is at least 80% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 86 and a LC which is at least 95% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 86 and a LC which is at least 99% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 86 and a LC which is at least 99% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 86 and a LC which is at least 95% (e.g. at least 85%, at least 90%, at least 95%, at least 99% or 100%) identical to the LC of SEQ ID NO: 85, wherein the antibody or antigen binding fragment comprises a HCDR1, a HCDR2, a HCDR3, a LCDR1, a LCDR2 and a LCDR3 of SEQ ID NOs: 4, 5, 6, 7, 8, and 9, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 88 and a LC which is at least 80% (e.g. at least 85%, at least 90%, at least 95%, at least 99% or 100%) identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 88 and a LC which is at least 100% (e.g. at least 85%, at least 90%, at least 95%, at least 99% or 100%) identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 100% (e.g. at least 85%, at least 90%, at least 95%, at least 99% or 100%) identical to the HC of SEQ ID NO: 88 and a LC which is at least 80% (e.g. at least 85%, at least 90%, at least 95%, at least 99% or 100%) identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 88 and a LC which is at least 95% (e.g. at least 85%, at least 90%, at least 95%, at least 99% or 100%) identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 88 and a LC which is at least 99% (e.g. at least 85%, at least 90%, at least 95%, at least 99% or 100%) identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 88 and a LC which is at least 99% (e.g. at least 85%, at least 90%, at least 95%, at least 99% or 100%) identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 88 and a LC which is at least 95% (e.g. at least 85%, at least 90%, at least 95%, at least 99% or 100%) identical to the LC of SEQ ID NO: 89, wherein the antibody or antigen binding fragment comprises a HCDR1, a HCDR2, a HCDR3, a LCDR1, a LCDR2 and a LCDR3 of SEQ ID NOs: 10, 11, 12, 13, 14, and 15, respectively, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 84 and a LC which is at least 80% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 84 and a LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC of SEQ ID NO: 84 and a LC which is at least 80% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 84 and a LC which is at least 95% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 84 and a LC which is at least 99% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 84 and a LC which is at least 99% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 84 and a LC which is at least 95% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 86 and a LC which is at least 80% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 86 and a LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC of SEQ ID NO: 86 and a LC which is at least 80% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 86 and a LC which is at least 95% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 86 and a LC which is at least 99% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 86 and a LC which is at least 99% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 86 and a LC which is at least 95% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 86 and a LC which is at least 80% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 86 and a LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC of SEQ ID NO: 86 and a LC which is at least 80% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 86 and a LC which is at least 95% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 86 and a LC which is at least 99% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 86 and a LC which is at least 99% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 86 and a LC which is at least 95% (e.g. at least 85%, at least 90%, at least 95%, at least 99% or 100%) identical to the LC of SEQ ID NO: 85, wherein the antibody or antigen binding fragment comprises a VH of SEQ ID NO: 52 and a VL of SEQ ID NO: 53, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 88 and a LC which is at least 80% (e.g. at least 85%, at least 90%, at least 95%, at least 99% or 100%) identical to the LC of SEQ ID NO: 89, wherein the antibody or antigen binding fragment comprises a VH of SEQ ID NO: 54 and a VL of SEQ ID NO: 55, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 80% (e.g. at least 85%, at least 90%, at least 95%, at least 99% or 100%) identical to the HC of SEQ ID NO: 88 and a LC of SEQ ID NO: 89, wherein the antibody or antigen binding fragment comprises a VH of SEQ ID NO: 54 and a VL of SEQ ID NO: 55, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

In some embodiments, the antibody or antigen binding fragment thereof that binds PSMA comprises a HC of SEQ ID NO: 88 and a LC which is at least 80% (e.g. at least 85%, at least 90%, at least 95%, at least 99% or 100%) identical to the LC of SEQ ID NO: 89, wherein the antibody or antigen binding fragment comprises a VH of SEQ ID NO: 54 and a VL of SEQ ID NO: 55, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 88 and a LC which is at least 95% (e.g. at least 85%, at least 90%, at least 95%, at least 99% or 100%) identical to the LC of SEQ ID NO: 89, wherein the antibody or antigen binding fragment comprises a VH of SEQ ID NO: 54 and a VL of SEQ ID NO: 55, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 95% (e.g. at least 85%, at least 90%, at least 95%, at least 99% or 100%) identical to the HC of SEQ ID NO: 85 and a LC which is at least 99% (e.g. at least 85%, at least 90%, at least 95%, at least 99% or 100%) identical to the LC of SEQ ID NO: 89, wherein the antibody or antigen binding fragment comprises a VH of SEQ ID NO: 54 and a VL of SEQ ID NO: 55, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 88 and a LC which is at least 99% (e.g. at least 85%, at least 90%, at least 95%, at least 99% or 100%) identical to the LC of SEQ ID NO: 89, wherein the antibody or antigen binding fragment comprises a VH of SEQ ID NO: 54 and a VL of SEQ ID NO: 55, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

The disclosure also provides an isolated antibody or antigen binding fragment thereof comprising a HC which is at least 99% (e.g. at least 85%, at least 90%, at least 95%, at least 99% or 100%) identical to the HC of SEQ ID NO: 88 and a LC which is at least 95% (e.g. at least 85%, at least 90%, at least 95%, at least 99% or 100%) identical to the LC of SEQ ID NO: 89, wherein the antibody or antigen binding fragment comprises a VH of SEQ ID NO: 54 and a VL of SEQ ID NO: 55, and wherein the antibody or antigen binding fragment is IgG1 (e.g. IgG1λ), optionally wherein the first Ig constant region or the fragment of the first Ig constant region and/or the second Ig constant region or the fragment of the second Ig constant region comprise the L234A_L235A_D265S and/or the M252Y/S254T/T256E mutations, such as wherein the first Ig constant region or the fragment of the first Ig constant region and the second Ig constant region or the fragment of the second Ig constant region comprise the L234A_L235A_D265S and/or the M252Y/S254T/T256E mutations.

Polynucleotides

Polynucleotides encoding the anti-PSMA antibody or antigen binding fragment of the disclosure and their functional equivalents are also provided. The disclosure provides an isolated polynucleotide encoding any of the anti-PSMA antibody or antigen binding fragment thereof of the disclosure.

In some embodiment, the disclosure provides an isolated polynucleotide encoding the VH of SEQ ID NO: 52.

In some embodiment, the disclosure provides an isolated polynucleotide encoding the VH of SEQ ID NO: 54.

In some embodiment, the disclosure provides an isolated polynucleotide encoding the VH of SEQ ID NO: 56.

In some embodiment, the disclosure provides an isolated polynucleotide encoding the VH of SEQ ID NO: 58.

In some embodiment, the disclosure provides an isolated polynucleotide encoding the VH of SEQ ID NO: 60.

In some embodiment, the disclosure provides an isolated polynucleotide encoding the VH of SEQ ID NO: 62.

In some embodiment, the disclosure provides an isolated polynucleotide encoding the VH of SEQ ID NO: 64.

In some embodiment, the disclosure provides an isolated polynucleotide encoding the VH of SEQ ID NO: 66.

In some embodiment, the disclosure provides an isolated polynucleotide encoding the VH of SEQ ID NO: 278.

In some embodiment, the disclosure provides an isolated polynucleotide encoding the VL of SEQ ID NO: 53.

In some embodiment, the disclosure provides an isolated polynucleotide encoding the VL of SEQ ID NO: 55.

In some embodiment, the disclosure provides an isolated polynucleotide encoding the VL of SEQ ID NO: 57.

In some embodiment, the disclosure provides an isolated polynucleotide encoding the VL of SEQ ID NO: 59.

In some embodiment, the disclosure provides an isolated polynucleotide encoding the VL of SEQ ID NO: 61.

In some embodiment, the disclosure provides an isolated polynucleotide encoding the VL of SEQ ID NO: 63.

In some embodiment, the disclosure provides an isolated polynucleotide encoding the VL of SEQ ID NO: 65.

In some embodiment, the disclosure provides an isolated polynucleotide encoding the VL of SEQ ID NO: 67.

In some embodiment, the disclosure provides an isolated polynucleotide encoding the VL of SEQ ID NO: 279.

In some embodiment, the disclosure provides an isolated polynucleotide encoding the heavy chain of SEQ ID NO: 84.

In some embodiment, the disclosure provides an isolated polynucleotide encoding the heavy chain of SEQ ID NO: 86.

In some embodiment, the disclosure provides an isolated polynucleotide encoding the heavy chain of SEQ ID NO: 88.

In some embodiment, the disclosure provides an isolated polynucleotide encoding the heavy chain of SEQ ID NO: 90.

In some embodiment, the disclosure provides an isolated polynucleotide encoding the heavy chain of SEQ ID NO: 92.

In some embodiment, the disclosure provides an isolated polynucleotide encoding the heavy chain of SEQ ID NO: 94.

In some embodiment, the disclosure provides an isolated polynucleotide encoding the heavy chain of SEQ ID NO: 96.

In some embodiment, the disclosure provides an isolated polynucleotide encoding the heavy chain of SEQ ID NO: 98.

In some embodiment, the disclosure provides an isolated polynucleotide encoding the heavy chain of SEQ ID NO: 100.

In some embodiment, the disclosure provides an isolated polynucleotide encoding the heavy chain of SEQ ID NO: 102.

In some embodiment, the disclosure provides an isolated polynucleotide encoding the heavy chain of SEQ ID NO: 268.

In some embodiment, the disclosure provides an isolated polynucleotide encoding the heavy chain of SEQ ID NO: 282.

In some embodiment, the disclosure provides an isolated polynucleotide encoding the heavy chain of SEQ ID NO: 284.

In some embodiment, the disclosure provides an isolated polynucleotide encoding the heavy chain of SEQ ID NO: 288.

In some embodiment, the disclosure provides an isolated polynucleotide encoding the light chain of SEQ ID NO: 85.

In some embodiment, the disclosure provides an isolated polynucleotide encoding the light chain of SEQ ID NO: 89.

In some embodiment, the disclosure provides an isolated polynucleotide encoding the light chain of SEQ ID NO: 93.

In some embodiment, the disclosure provides an isolated polynucleotide encoding the light chain of SEQ ID NO: 95.

In some embodiment, the disclosure provides an isolated polynucleotide encoding the light chain of SEQ ID NO: 97.

In some embodiment, the disclosure provides an isolated polynucleotide encoding the light chain of SEQ ID NO: 99.

In some embodiment, the disclosure provides an isolated polynucleotide encoding the light chain of SEQ ID NO: 101.

In some embodiment, the disclosure provides an isolated polynucleotide encoding the light chain of SEQ ID NO: 103.

In some embodiment, the disclosure provides an isolated polynucleotide encoding the light chain of SEQ ID NO: 269.

In some embodiments, the disclosure provides isolated polynucleotide sequences encoding polypeptide sequences of SEQ ID NOs: 52 and 53.

In some embodiments, the disclosure provides isolated polynucleotide sequences encoding polypeptide sequences of SEQ ID NOs: 84 and 85.

In some embodiments, the disclosure provides isolated polynucleotide sequences encoding polypeptide sequences of SEQ ID NOs: 86 and 85.

In some embodiments, the disclosure provides isolated polynucleotide sequences encoding polypeptide sequences of SEQ ID NOs: 54 and 55.

In some embodiments, the disclosure provides isolated polynucleotide sequences encoding polypeptide sequences of SEQ ID NOs: 88 and 89.

In some embodiments, the disclosure provides isolated polynucleotide sequences encoding polypeptide sequences of SEQ ID NOs: 52, 53, 278 and 279.

In some embodiments, the disclosure provides isolated polynucleotide sequences encoding polypeptide sequences of SEQ ID NOs: 268, 269 and 282.

In some embodiments, the disclosure provides isolated polynucleotide sequences encoding polypeptide sequences of SEQ ID NOs: 284, 269 and 288.

In some embodiments, the disclosure provides an isolated polynucleotide of SEQ ID NO: 68, 69, 70, 71, 72, 73, 74, 75, 76, 77, 78, 79, 80, 81, 82, 83, 104, 105, 106, 108, 109, 110, 112, 113, 114, 115, 116, 117, 118, 119, 120, 121, 122, 123, 134, 135, 270, 271, 280, 281, 283, 286 or 289.

Polynucleotides encoding the anti-PSMA antibody or antigen binding fragment of the disclosure include polynucleotides with nucleic acid sequences that are substantially the same as the nucleic acid sequences of the polynucleotide of the disclosure. "Substantially the same" nucleic acid sequence is defined herein as a sequence with at least 80% identity to another nucleic acid sequence when the two sequences are aligned. Two nucleic acid sequences are substantially identical if the polypeptide encoded by the first nucleic acid is immunologically cross reactive with the polypeptide encoded by the second nucleic acid. Another indication that two nucleic acid sequences are substantially identical is that the two molecules hybridize to each other under stringent conditions.

Modified nucleotides may be used to generate the polynucleotides of the disclosure. Exemplary modified nucleotides are 5-fluorouracil, 5-bromouracil, 5-chlorouracil, 5-iodouracil, hypoxanthine, xanthine, 4-acetylcytosine, 5-(carboxyhydroxymethyl) uracil, carboxymethylaminomethyl-2-thiouridine, 5-carboxymethylaminomethyluracil, dihydrouracil, $N^6$-substituted adenine, 7-methylguanine, 5-methylaminomethyluracil, 5-methoxyaminomethyl-2-thiouracil, beta-D-mannosylqueosine, 5"-methoxycarboxymethyluracil, 5-methoxyuracil, 2-methylthio-$N^6$-isopentenyladenine, uracil-5-oxyacetic acid (v), wybutoxosine, pseudouracil, queuosine, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine.

Vectors Comprising Polynucleotides Encoding for the Anti-PSMA Antibodies

Vectors comprising DNA encoding the anti-PSMA antibody or antigen binding fragment of the disclosure are also provided. The disclosed vectors can be used, for example, to generate any of the above disclosed anti-PSMA antibody, or antigen binding fragment thereof. Polynucleotides encoding any of the anti-PSMA antibody or antigen binding fragment thereof of the disclosure may be incorporated into vectors using standard molecular biology methods.

In some embodiments, the disclosure provides an expression vector comprising the polynucleotide of the invention. Such vectors may be plasmid vectors, viral vectors, vectors for baculovirus expression, transposon-based vectors or any other vector suitable for introduction of the synthetic polynucleotide of the invention into a given organism or genetic background by any means. The vector of the disclosure may be an expression vector for the efficient synthesis of PSMA antibody polypeptide and expression of the PSMA antibody polypeptide of the disclosure in prokaryotic and eukaryotic systems, including but not limited to yeast and mammalian cell culture.

Exemplary vectors that may be used are Bacterial: pBs, phagescript, PsiX174, pBluescript SK, pBs KS, pNH8a, pNH16a, pNH18a, pNH46a (Stratagene, La Jolla, Calif, USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia), pEE6.4 (Lonza) and pEE12.4 (Lonza). Additional vectors include the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif). Bacteriophage vectors, such as λGT10, λGT11, λEMBL4, and λNM1149, λZapII (Stratagene) can be used. Exemplary plant expression vectors include pBI01, pBI01.2, pBI121, pBI101.3, and pBIN19 (Clontech). Exemplary animal expression vectors include pEUK-Cl, pMAM, and pMAMneo (Clontech). The expression vector may be a viral vector, e.g., a retroviral vector, e.g., a gamma retroviral vector.

The vector of the disclosure may contain a promoter and an enhancer sequence. Polynucleotides encoding the PSMA binding proteins of the disclosure may be operably linked to control sequences in the expression vector(s) that ensure the expression of the PSMA binding proteins. Such regulatory elements may include a transcriptional promoter, sequences encoding suitable mRNA ribosomal binding sites, and sequences that control the termination of transcription and translation. Expression vectors may also include one or more non-transcribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

Vectors of the disclosure may also contain one or more Internal Ribosome Entry Site(s) (IRES). Inclusion of an IRES sequence into fusion vectors may be beneficial for enhancing expression of some proteins. In some embodiments, the vector system will include one or more polyadenylation sites (e.g., SV40), which may be upstream or downstream of any of the aforementioned nucleic acid sequences. Vector components may be contiguously linked or arranged in a manner that provides optimal spacing for expressing the gene products (i.e., by the introduction of "spacer" nucleotides between the ORFs) or positioned in another way. Regulatory elements, such as the IRES motif, may also be arranged to provide optimal spacing for expression.

Vectors of the disclosure may be circular or linear. They may be prepared to contain a replication system functional in a prokaryotic or eukaryotic host cell. Replication systems can be derived, e.g., from ColE1, SV40, 2μ plasmid, λ, bovine papilloma virus, and the like.

The recombinant expression vectors can be designed for either transient expression, for stable expression, or for both. Also, the recombinant expression vectors can be made for constitutive expression or for inducible expression.

The vectors may also comprise selection markers, which are well known in the art. Selection markers include positive and negative selection marker. Marker genes include biocide resistance, e.g., resistance to antibiotics, heavy metals, etc., complementation in an auxotrophic host to provide prototrophy, and the like. Exemplary marker genes include antibiotic resistance genes (e.g., neomycin resistance gene, a hygromycin resistance gene, a kanamycin resistance gene, a tetracycline resistance gene, a penicillin resistance gene, histidinol resistance gene, histidinol x resistance gene), glutamine synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

Host Cells

The disclosure also provides for a host cell comprising any of the vectors of the disclosure. "Host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell but are still included within the scope of the term "host cell" as used herein. Such host cells may be eukaryotic cells, prokaryotic cells, plant cells or archeal cells. *Escherichia*

*coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (e.g., *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, VA, CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, MD), CHO-K1 (ATCC CRL-61) or DG44.

The disclosure provides recombinant host cells containing any of the expression vectors of the disclosure. Nucleic acids encoding any of the PSMA binding proteins or fragments thereof can be used for transformation of a suitable mammalian host cell. Host cell transformation, culture, antibody expression and purification are done using well known methods.

Cell lines may be selected based on high level of expression of the PSMA antibody of interest and minimal contamination from host cell proteins. Mammalian cell lines available as host cells for expression are well known in the art and include, but are not limited to from Chinese Hamster Ovary (CHO) cells such as CHO-K1 SV (Lonza Biologics, Walkersville, MD), CHO-K1 (ATCC CRL-61), or CHO DG44, and Baby Hamster Kidney (BHK) cells. These cell lines can be used to produce any of the anti-PSMA antibody or antibody fragment of the disclosure by culturing the cells under conditions suitable for expression of the antibody and purifying the antibody from the host cell or medium surrounding the host cell.

The disclosure also provides a method of producing the anti-PSMA binding protein of the disclosure comprising culturing the host cell of the disclosure in conditions that the anti-PSMA binding protein is expressed, and recovering the anti-PSMA antibody binding protein produced by the host cell using well known methods in the art. A subject protein may be substantially pure, e.g., at least about 80% to 85% pure, at least about 85% to 90% pure, at least about 90% to 95% pure, or at least about 98% to 99%, or more, pure, e.g., free from contaminants such as cell debris, macromolecules, etc. other than the subject protein.

Radioconjugates and Antibody Drug Conjugates

The disclosure also provides antibody drug conjugates (ADCs) and radioconjugates comprising the anti-PSMA antibodies of the disclosure. In certain embodiments, the antibodies or antigen binding fragment thereof of the disclosure may be conjugated with pharmaceutically active moieties or diagnostic moieties to form an "antibody drug conjugate" (ADC), or a "radioconjugate". The ADCs or radioconjugates of the disclosure may be used to deliver cytotoxins or other payloads to the target location.

As used herein, the term "antibody drug conjugate" is used broadly and refers to an antibody, or antigen binding fragments thereof, conjugated to (e.g., covalently associated) a second molecule such as any pharmaceutically active moiety, a therapeutic moiety, a toxin, or a drug.

As used herein, the term "targeting ligand" refers to any molecule that provides an enhanced affinity for a selected target, e.g., an antigen, a cell, cell type, tissue, organ, region of the body, or a compartment (e.g., a cellular, tissue or organ compartment). Targeting ligands include, but are not limited to, antibodies or antigen binding fragments thereof, aptamers, polypeptides, and scaffold proteins. In some embodiments, a targeting ligand is a polypeptide. In some embodiments, the targeting ligand is an antibody or antigen binding fragment thereof, engineered domain, or scaffold protein. The targeting ligand may serve as a shuttle to deliver a payload to a specific site, which is defined by the target recognized by said targeting ligand. A targeting ligand, for instance, targeting a receptor, delivers its payload to a site which is characterized by abundance of said receptor. In the present disclosure, the targeting ligand is an anti-PSMA antibody or fragment thereof conjugated to pharmaceutical active moiety and capable of delivering a payload to a site which is characterized by the abundance of PSMA.

The term "payload", as used herein, represents any naturally occurring or synthetically generated molecule, including small-molecular weight molecules or chemical entities that can chemically be synthesized, and larger molecules or biological entities that need to be produced by fermentation of host cells and that confer a novel functionality to a targeting ligand specific for binding to targets or antigens. Examples of payload include but are not limited to drugs, toxins, cytokines, markers, oligonucleotides, antisense, small interfering RNAs oligonucleotides (siRNAs), or the like, for the generation of site-specifically conjugated antibody drug conjugates (ADCs). The payload may also be a radiometal complex or a radio metal ion as described below.

As used herein the terms "drug" or "warhead" may be used interchangeably and will mean a biologically active or detectable molecule or compound, including anti-cancer agents as described below. A "payload" may comprise a drug or warhead in combination with an optional linker compound. The warhead on the conjugate may comprise peptides, proteins, prodrugs which are metabolized to an active agent in vivo, polymers, nucleic acid molecules, small molecules, binding agents, mimetic agents, synthetic drugs, inorganic molecules, organic molecules and radioisotopes. In some embodiments, the disclosed ADCs or radioconjugates will direct the bound payload to the target site in a relatively unreactive, non-toxic state before releasing and activating the payload. This targeted release of the payload is preferably achieved through stable conjugation of the payloads via residue-specific or site-specific conjugation as describe below, and the relatively homogeneous composition of the ADC or radioconjugate preparations which minimize over-conjugated toxic species.

In some embodiments the disclosure comprises payloads of therapeutic moieties (e.g., cytotoxins), or other payloads such as diagnostic agents. The selected payload may be covalently or non-covalently linked to the antibody and exhibit various stoichiometric molar ratios depending, at least in part, on the method used to affect the conjugation.

The conjugates of the disclosure may be represented by the formula:

Ab-[L-D]n or a pharmaceutically acceptable salt thereof
    wherein
    a) Ab comprises an anti-PSMA antibody or antigen binding fragment thereof disclosed herein;
    b) L comprises an optional linker;
    c) D comprises a drug moiety or chelator; and
    d) n is an integer from about 1 to about 20.

Those of skill in the art will appreciate that conjugates according to the aforementioned formula may be fabricated using a number of different linkers and drugs and that conjugation methodology will vary depending on the selection of components.

In preferred embodiments compatible linkers will confer stability on the ADCs or radioconjugate in the extracellular environment, prevent aggregation of the ADC molecules or radioconjugate and keep the ADC and radioconjugate freely soluble in aqueous media and in a monomeric state. Before transport or delivery into a cell, the ADC or radioconjugate is preferably stable and remains intact, i.e. the antibody remains linked to the drug moiety. While the linkers are stable outside the target cell they are designed to be cleaved or degraded at some efficacious rate inside the cell. Accordingly, an effective linker will: (i) maintain the specific binding properties of the antibody; (ii) allow intracellular delivery of the conjugate or drug moiety; (iii) remain stable and intact, i.e. not cleaved or degraded, until the conjugate has been delivered or transported to its targeted site; and (iv) maintain a cytotoxic, cell-killing effect or a cytostatic effect of the drug moiety.

The stability of the ADC or radioconjugate may be measured by standard analytical techniques such as mass spectroscopy, hydrophobic interaction chromatography (HIC), HPLC, and the separation/analysis technique LC/MS.

Cytotoxic Agents and Drugs

In some embodiments, the anti-PSMA antibody or antigen binding fragment thereof of the disclosure is conjugated to one or more therapeutic moiety or a drug such as an anti-cancer agent including, but not limited to, cytotoxic agents, cytostatic agents, anti-angiogenic agents, debulking agents, chemotherapeutic agents, radiotherapeutic agents, targeted anti-cancer agents, biological response modifiers, cancer vaccines, cytokines, hormone therapies, oligonucleotides, antisense, siRNAs, anti-metastatic agents and immunotherapeutic agents.

In some embodiments, the anti-PSMA antibody or antigen binding fragment thereof of the disclosure is conjugated to one or more cytotoxic agents. Exemplary cytotoxic agents include chemotherapeutic agents or drugs, growth inhibitory agents, toxins (e.g., protein toxins, enzymatically active toxins of bacterial, fungal, plant, or animal origin, or fragments thereof), and radioactive isotopes. Exemplary toxins include, but are not limited to, bacterial toxins such as diphtheria toxin, plant toxins such as ricin, small molecule toxins such as geldanamycin (Mandler et al (2000) Jour, of the Nat. Cancer Inst. 92(19): 1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may achieve their cytotoxic and cytostatic effects by mechanisms including tubulin binding, DNA binding, or topoisomerase inhibition. Some cytotoxic drugs tend to be inactive or less active. Enzymatically active toxins and fragments thereof that can be used include diphtheria A chain, nonbinding active fragments of diphtheria toxin, exotoxin A chain (from *Pseudomonas aeruginosa*}, ricin A chain, abrin A chain, modeccinAchain, alpha-sarcin, Aleuritesfordii proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the anti-PSMA antibody or antigen binding fragment thereof provided herein is conjugated to one or more drugs. Exemplary drugs include a maytansinoid (see, e.g., U.S. Pat. Nos. 5,208,020, 5,416,06); an auristatin such as monomethyl auristatin drug moieties DE and DF (MMAE and MMAF) (see, e.g., U.S. Pat. Nos. 5,635,483 and 5,780,588, and 7,498,298), a dolastatin, a calicheamicin or derivative thereof (see, e.g., U.S. Pat. Nos. 5,712,374, 5,714,586, 5,739, 116, 5,767,285, 5,770,701, 5,770,710, 5,773,001, and 5,877,296; Hinman et al., (1993) Cancer Res 53:3336-3342; and Lode et al., (1998) Cancer Res 58:2925-2928); an anthracycline such as daunomycin or doxorubicin (see, e.g., Kratz et al., (2006) Current Med. Chem 13:477-523; Jeffrey et al., (2006) Bioorganic & Med Chem Letters 16:358-362; Torgov et al., (2005) Bioconj Chem 16:717-721; Nagy et al., (2000) Proc Natl Acad Sci USA 97:829-834; Dubowchik et al, Bioorg. & Med. Chem. Letters 12: 1529-1532 (2002); King et al., (2002) J Med Chem 45:4336-4343; and U.S. Pat. No. 6,630,579), methotrexate, vindesine, a taxane such as docetaxel, paclitaxel, larotaxel, tesetaxel, and ortataxel, a camptothecin (CPT) analogue such as topotecan and irinotecan (see, e.g., Slichenmyer et al, (1994) Cancer Chemother Pharmacol, 34 (Suppl): S 53-S 570), a pyrrolobenzodiazepine (PBD) derivative (U.S. Pat. No. 10,639,373), an amatoxin derivative such as, α-amanitin and β-amanitin, or a duocarmycin analogs.

Radioconjugates

In some embodiments, the anti-PSMA antibodies or antigen binding fragments thereof of the disclosure is conjugated to a radiometal ion to form radioconjugates.

A "radioconjugate" (also referred to herein as a "radioimmunoconjugate" or "immunoconjugate") is an immunoconjugate in which an antibody or antigen binding fragment thereof is labeled with a radiometal or conjugated to a radiometal complex. A "radioconjugate" in particular, refers to an antibody or an antigen binding domain, that is conjugated (joined, e.g., bound via a covalent bond) to at least one radiometal complex. Stated another way, a radioconjugate refers to at least one radiometal complex joined, e.g., bound via a covalent bond, to an antibody or antigen binding domain. A radioconjugate may comprise at least one radiometal complex that comprises a linker, wherein the radiometal complex is joined to the antibody or antigen binding domain via the linker. A "radiometal complex" as used herein refers to a complex comprising a radiometal ion associated with a chelator. Typically, a radiometal ion is bound to or coordinated to a chelator via coordinate bonding. In some embodiments, the chelator is a macrocycle compound. Heteroatoms of the macrocyclic ring can participate in coordinate bonding of a radiometal ion to a chelator. A chelator can be substituted with one or more substituent groups, and the one or more substituent groups can also participate in coordinate bonding of a radiometal ion to a chelator in addition to, or alternatively to the heteroatoms of the macrocyclic ring.

As used herein, the term "radiometal ion" or "radioactive metal ion" refers to one or more isotopes of the elements that emit particles and/or photons. Any radiometal ion known to those skilled in the art in view of the present disclosure can be used in the invention. Exemplary radioactive isotopes may be γ-emitting, Auger-emitting, β-emitting, alpha-emitting or positron-emitting radioactive isotope. Exemplary radioactive isotopes include $^{3}H$, $^{11}C$, $^{13}C$, $^{15}N$, $^{18}F$, $^{19}F$, $^{55}Co$, $^{57}Co$, $^{60}Co$, $^{61}Cu$, $^{62}Cu$, $^{64}Cu$, $^{67}Cu$, $^{68}Ga$, $^{72}As$, $^{75}Br$, $^{86}Y$, $^{89}Zr$, $^{90}Sr$, $^{94m}Tc$, $^{99m}Tc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{134}Ce$, $^{225}Ac$ and $^{227}Ac$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, *neptunium* atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the radiometal ion is a "therapeutic emitter," meaning a radiometal ion that is useful in therapeutic applications such as to damage cells, such as cancer cells. A suitable radiometal for use as a therapeutic agent is one that is capable of reducing or inhibiting the growth of, or in particular killing, a cancer cell, such as a prostate cancer cell. High energy radiometal selected to target cancer cells, preferably acts over a short range so that the cytotoxic effects are localized to the targeted cells. In certain embodiments, the radioconjugates of the disclosure can deliver a cytotoxic payload with the ability to emit alpha and/or beta particles in the vicinity of a tumor by binding onto cancer cells' surface antigens and initiating cell death. Radiotherapy is thus delivered in a more localized fashion to decrease damage to non-cancerous cells.

Examples of radiometal ions suitable for use to generate the radioconjugates of the disclosure include, but are not limited to, $^{47}$Sc, $^{62}$Cu, $^{64}$Cu, $^{67}$Cu, $^{67}$Ga, $^{68}$Ga, $^{86}$Y, $^{89}$Zr, $^{89}$Sr, $^{90}$Y, $^{99}$Tc, $^{105}$Rh, $^{109}$Pd, $^{111}$Ag, $^{111}$In, $^{117}$Sn, $^{149}$Tb, $^{152}$Tb, $^{155}$Tb, $^{153}$Sm, $^{159}$Gd, $^{165}$Dy, $^{166}$Ho, $^{169}$Er, $^{177}$Lu, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{225}$Ac, $^{227}$Th, and $^{255}$FM. Preferably, the radiometal ion is a "therapeutic emitter," meaning a radiometal ion that is useful in therapeutic applications. Examples of therapeutic emitters include, but are not limited to, beta or alpha emitters, such as, $^{132}$La, $^{135}$La, $^{134}$Ce, $^{144}$Nd, $^{149}$Tb, $^{152}$Tb, $^{155}$Tb, $^{153}$Sm, $^{159}$Gd, $^{165}$Dy, $^{166}$Ho, $^{169}$Er, $^{177}$Ln, $^{186}$Re, $^{188}$Re, $^{194}$Ir, $^{198}$Au, $^{199}$Au, $^{211}$At, $^{212}$Pb, $^{212}$Bi, $^{213}$Bi, $^{223}$Ra, $^{225}$Ac, $^{255}$Fm and $^{227}$Th, $^{226}$Th, $^{230}$U.

In some embodiments, the radiometal ion used as a therapeutic agent is an alpha-emitting radiometal ion, such as actinium-225 ($^{255}$Ac) The 10-day half-life of $^{225}$Ac is long enough to facilitate radio-conjugate production, but short enough to match the circulation pharmacokinetics of delivery vehicles such as antibodies. As such, $^{225}$AC radioimmunoconjugates are of particular interest. Additionally, $^{225}$AC decays in a series of steps that ultimately emits 4 alpha particles before reaching a stable isotope, In some embodiments the radiometals may be used as an imaging agents or detectable label. Radionuclides used to radiolabel include, but are not limited to, carbon-11, nitrogen-13, oxygen-15, fluorine-18, copper-67, gallium-67, gallium-68, krypton-81m, rubidium-82, technetium-99, indium-111, iodine-123, iodine-124, iodine-125, iodine-131, xenon-133, thallium-201, zirconium-89, copper-64, yttrium-90, technetium-99m, iodine-123, iodine-124, and iodine-125, lutetium-177, At-211, lead-212, bismuth-212, bismuth-213, cerium-134 and actinium-225. These radionuclides, as well as their characteristics (e.g., half-life, emission, etc) are well known in the art, as are methods of making them and labeling proteins with them. In some embodiments the radiometal used as an imaging agents or detectable label is Cerium 134 ($^{134}$Ce).

In some embodiments the radiometal used as an imaging agents or detectable label is Indium 111 ($^{111}$In) or Xenon 134 ($^{134}$Xe).

In some embodiments, the radiometal ion is conjugated to the isolated antibody or the antigen binding fragment thereof of the disclosure using known methods.

In some embodiments, the radiometal ion is conjugated to the antibody or antigen binding fragment of the disclosure with a linker.

In some embodiments, the radiometal ion is complexed with a chelating agent or a chelator.

In some embodiments, the anti-PSMA antibodies or antigen binding fragments thereof of the disclosure is conjugated to (i.e., covalently linked to) chelators and radiometal complexes to produce radioimmunoconjugates that are suitable, for example, for medicinal applications in subjects, e.g., humans, such as targeted radiotherapy. In some embodiments, the anti-PSMA antibodies or antigen binding fragments thereof of the disclosure is conjugated to (i.e., covalently linked to) chelators and radiometal complexes to produce radioimmunoconjugates that are suitable for detection.

As used herein, the term "chelator" or "chelant" refers to a chemical compound to which a radionuclide or radiometal, can be chelated via coordinate bonding to form a radiometal complex. In some embodiments, the chelator is a macrocyclic ring containing one or more heteroatoms, e.g., oxygen and/or nitrogen as ring atoms.

In some embodiments, the chelator comprises a macrocyclic chelating moiety. Examples of macrocyclic chelating moieties include, without limitation, 1,4,7,10-tetraazacyclododecane-1,4,7,10,tetraacetic acid (DOTA), S-2-(4-isothiocyanatobenzyl)-1,4,7-triazacyclononane-1,4,7-triacetic acid (NOTA), 1,4,8,11-tetraazacyclodocedan-1,4,8,11-tetraacetic acid (TETA), 3,6,9,15-tetraazabicyclo[9.3.1]-pentadeca-1(15),11,13-triene-4-(S)-(4-isothiocyanatobenzyl)-3,6,9-triacetic acid (PCTA), 5-S-(4-aminobenzyl)-1-oxa-4,7,10-triazacyclododecane-4,7,10-tris(acetic acid) (DO3A), or a derivative thereof. In some aspects, the chelator is 1,4,7,10-tetraazacyclododecane-1,4,7,10,tetraacetic acid (DOTA). In other aspects, the chelator is S-2-(4-isothiocyanatobenzyl)-1,4,7-triazacyclononane-1,4,7-triacetic acid (NOTA). In further aspects, the chelator is 1,4,8,11-tetraazacyclodocedan-1,4,8,11-tetraacetic acid (TETA). In yet other aspects, the chelator is 3,6,9,15-tetraazabicyclo[9.3.1]-pentadeca-1(15),11,13-triene-4-(S)-(4-isothiocyanatobenzyl)-3,6,9-triacetic acid (PCTA). In still further aspects, the chelator is 5-S-(4-aminobenzyl)-1-oxa-4,7,10-triazacyclododecane-4,7,10-tris (acetic acid) (DO3A). In other aspects, the chelator is DOTA, DFO, DTPA, NOTA, TETA, DTPA, or HOPO.

In some embodiments, the chelator is DOTA (1,4,7,10-Tetraazacyclododecane-1,4,7,10-tetraacetic acid; tetraxaten).

In some embodiments, the chelator is H$_2$bp18c6 (N,N'-bis[(6-carboxy-2-pyridil)methyl]-4,13-diaza-18-crown-6) or a H$_2$bp18c6 derivative as described in Thiele et al. "An Eighteen-Membered Macrocyclic Ligand for Actinium-225 Targeted Alpha Therapy" *Angew. Chem. Int. Ed.* (2017) 56, 14712-14717, and Roca-Sabio et al. "Macrocyclic Receptor Exhibiting Unprecedented Selectivity for Light Lanthanides" *J. Am. Chem. Soc.* (2009) 131, 3331-3341.

Additional chelators suitable for use in accordance with the present invention are described in WO2018/183906 and WO2020/106886, which are incorporated by reference herein. In some embodiments, the radioconjugate of the present disclosure comprises a radiometal ion chelated to a chelator described in WO2020/229974 which is incorporated herein by reference in its entirety. In some embodiments, the chelator has the structure of formula (I)

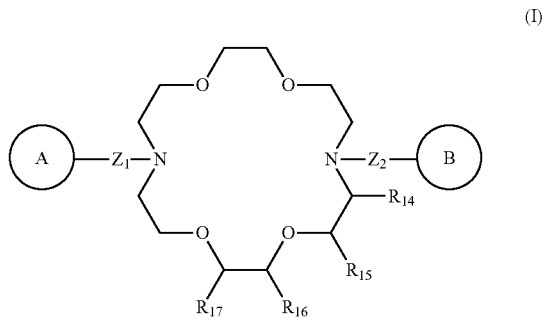

(I)

or a pharmaceutically acceptable salt thereof, wherein:
  each of ring A and ring B is independently a 6-10 membered aryl or a 5-10 membered heteroaryl
  each of $Z_1$ and $Z_2$ is independently —$(C(R_{12})_2)_m$— or —$(CH_2)_n$—$C(R_{12})(X)$—$(CH_2)_n$—;
  each of $R_{14}$, $R_{15}$, $R_{16}$, and $R_{17}$ is independently hydrogen, alkyl, or X, or alternatively $R_{14}$ and $R_{15}$ and/or $R_{16}$ and $R_{17}$ are taken together with the carbon atoms to which they are attached to form a 5- or 6-membered cycloalkyl ring optionally substituted with X;
  each X is independently -$L_1$-$R_4$;
  $R_4$ is a nucleophilic moiety or an electrophilic moiety, or $R_4$ comprises a targeting ligand; and $L_1$ is absent or a linker.

In some embodiments, the radioconjugate of the disclosure comprises a radiometal ion chelated to a compound of formula (II)

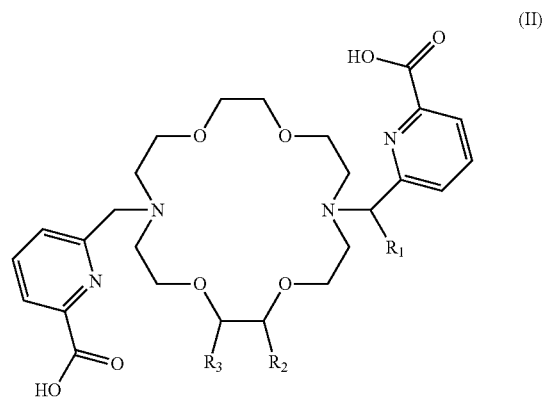

(II)

or a pharmaceutically acceptable salt thereof, wherein:
  $R_1$ is hydrogen and $R_2$ is -$L_1$-$R_4$;
  alternatively, $R_1$ is -$L_1$-$R_4$ and $R_2$ is hydrogen;
  $R_3$ is hydrogen;
  alternatively, $R_2$ and $R_3$ are taken together with the carbon atoms to which they are attached to form a 5- or 6-membered cycloalkyl, wherein the 5- or 6-membered cycloalkyl is optionally substituted with -$L_1$-$R_4$,
  $L_1$ is absent or a linker; and
  $R_4$ is a nucleophilic moiety, an electrophilic moiety, or a targeting ligand.

In some embodiments, $L_1$ is absent. When $L_1$ is absent, $R_4$ is directly bound (e.g., via covalent linkage) to the compound.

In some embodiments, the radioconjugate comprises a radiometal ion chelated to a compound of formula (III)

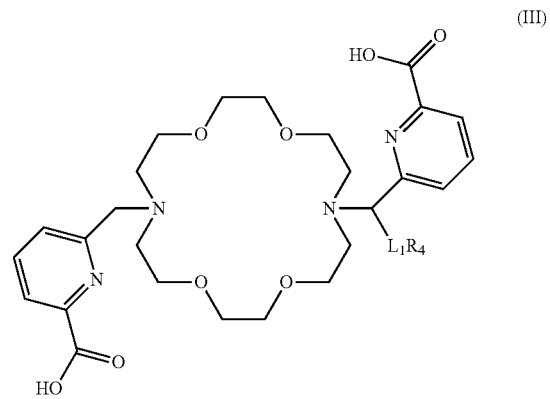

(III)

or a pharmaceutically acceptable salt thereof, wherein:
  $L_1$ is absent or a linker; and
  $R_4$ is a nucleophilic moiety, an electrophilic moiety, or a targeting ligand.

Chelators of the disclosure can be produced by any method known in the art in view of the present disclosure. For example, the pendant aromatic/heteroaromatic groups can be attached to the macrocyclic ring portion by methods known in the art, such as those exemplified and described below.

In some embodiments, the disclosure also provides a chelator, preferably a chelator to which radiometal ions can be chelated via coordinate bonding.

As used herein, an "antibody-chelator complex" or "conjugate intermediate" refers to a precursor of a radioconjugate, which comprises an antibody, or antigen binding domain, that is conjugated (joined, e.g., bound via a covalent bond) to a chelator that does not comprise a radiometal. A conjugate intermediate may comprise a linker, wherein the chelator is joined to the antibody or antigen binding domain via the linker. After a radiometal is chelated to the chelator of a conjugate intermediate, it becomes a radioconjugate. For example, "DOTA-mAb" refers to a conjugate intermediate comprising a DOTA conjugated to an antibody.

Any of the chelators described herein can comprise a radiometal ion. In some embodiments the radiometal ion is an alpha-emitting radiometal ion. In some embodiments, the radiometal is $^{225}$Ac. In some embodiments the radiometal ion is a gamma-emitting radiometal ion. In some embodiments, the radiometal is $^{111}$In. In some embodiments, the radiometal is $^{134}$Ce. Chelators of the disclosure can robustly chelate radiometal ions, particularly $^{225}$Ac at any specific activity irrespective of metal impurities, thus forming a radiometal complex having high chelation stability in vivo and in vitro and which is stable.

Radiometal complexes can be produced by any method known in the art in view of the present disclosure. For example, a chelator of the invention can be mixed with a radiometal ion and the mixture incubated to allow for formation of the radiometal complex. In an exemplary embodiment, a chelator is mixed with a solution of $^{225}$Ac (NO3)$_3$ to form a radiocomplex comprising $^{225}$Ac bound to the chelator via coordinate bonding. Chelators of in the invention efficiently chelate radiometals, particularly $^{225}$Ac. Thus, in particular embodiments, a chelator of the invention is mixed with a solution of $^{225}$Ac ion at a ratio by concentration of chelator to $^{225}$Ac ion of 1:1000, 1:500, 1:400, 1:300, 1:200, 1:100, 1:50, 1:10, or 1:5, preferably 1:5 to 1:200, more preferably 1:5 to 1:100. The radiocomplex can be characterized by instant thin layer chromatography (e.g., iTLC-SG), HPLC, LC-MS, etc.

Linker

In some embodiments, the (ADCs) of the disclosure comprise a linker that links the anti-PSMA antibodies and antigen binding fragment thereof of the disclosure to a drug moiety or a chelator.

Numerous linker compounds can be used to conjugate the antibodies of the disclosure to the relevant drug or chelator. Preferably linkers will covalently bind with the reactive residue (preferably a cysteine or lysine) and the selected drug compound. Accordingly, any linker that reacts with the selected antibody residue and may be used to provide the relatively stable conjugates (site-specific or otherwise) of the instant invention is compatible with the teachings herein.

As used herein, the term "linker" refers to a chemical moiety that joins a chelator or a drug to an antibody or antigen binding domain. Any suitable linker known to those skilled in the art in view of the present disclosure can be used to conjugate the antibodies of the disclosure to the relevant drug. Preferably, linkers will covalently bind with a reactive residue of the antibody. Accordingly, any linker that reacts with a selected antibody residue and may be used to provide the relatively stable conjugates (site-specific or otherwise) of the instant disclosure is compatible with the teachings herein. Ideally, linkers are designed to largely release the drug once it has been delivered to the tumor site, substantially reducing undesirable non-specific toxicity by minimizing exposure of non-targeted cells and tissue to the cytotoxic drug, thereby providing an enhanced therapeutic index.

The linkers can contain, for example, a substituted or unsubstituted alkyl, a substituted or unsubstituted heteroalkyl moiety, a substituted or unsubstituted aryl or heteroaryl, a polyethylene glycol (PEG) linker, a peptide linker, a sugar-based linker, or a cleavable linker, such as a disulfide linkage or a protease cleavage site such as valine-citrullinep-aminobenzyl (PAB).

The linker may be composed of one or more linker components. Exemplary linker components include 6-maleimidocaproyl ("MC"), maleimidopropanoyl ("MP"), valine-citrulline ("val-cit"), alanine-phenylalanine ("alaphe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC"), and N-Succinimidyl (4-iodo-acetyl) aminobenzoate ("STAB"). In on embodiment, the linker is valinecitrullin-p-aminobenzyloxycaronyl ("vc-PAB"). In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

According to some embodiments, a chelator or chelator-linker comprises a nucleophilic moiety or an electrophilic moiety. Reaction of the nucleophilic group or electrophilic group of a chelator or chelator-linker with an antibody or antigen binding domain comprising the corresponding reaction partner allows for covalent linkage of the antibody or antigen binding domain to the chelator-linker.

Numerous compatible linkers can advantageously bind to reduced cysteines and lysines, which are nucleophilic. Conjugation reactions involving reduced cysteines and lysines include, but are not limited to, thiol-maleimide, thiol-halogeno (acyl halide), thiol-ene, thiol-yne, thiol-vinylsulfone, thiol-bisulfone, thiol-thiosulfonate, thiol-pyridyl disulfide and thiol-parafluoro reactions.

Exemplary linker structures suitable for use in the disclosure also include, but are not limited to:

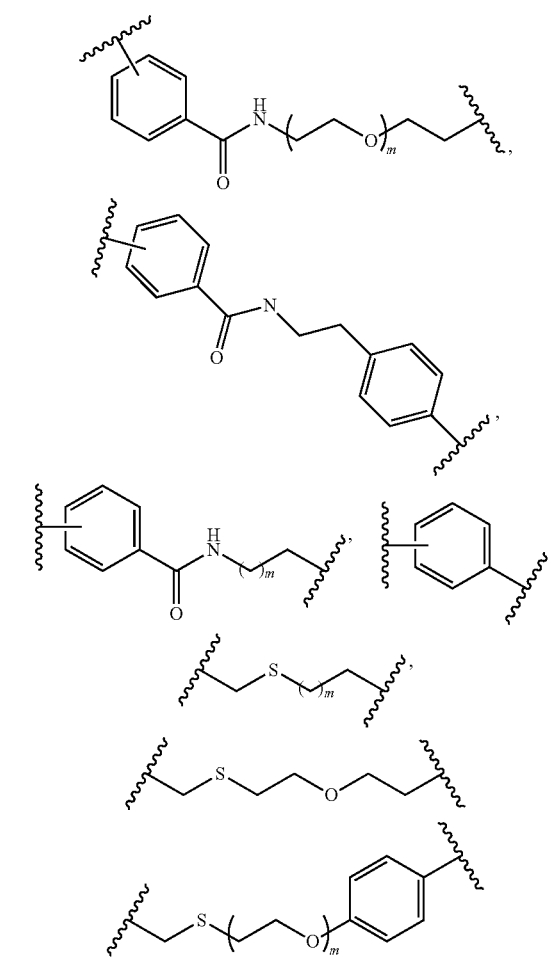

and wherein m is an integer of 0 to 12.

In preferred embodiments compatible linkers will confer stability on the ADCs in the extracellular environment, prevent aggregation of the ADC molecules and keep the ADC freely soluble in aqueous media and in a monomeric state. Before transport or delivery into a cell, the ADC is preferably stable and remains intact, i.e. the antibody remains linked to the drug moiety. While the linkers are stable outside the target cell they are designed to be cleaved or degraded at some efficacious rate inside the cell. Accordingly an effective linker will: (i) maintain the specific binding properties of the antibody; (ii) allow intracellular delivery of the conjugate or drug moiety; (iii) remain stable and intact, i.e. not cleaved or degraded, until the conjugate has been delivered or transported to its targeted site; and (iv) maintain a cytotoxic, cell-killing effect or a cytostatic effect of the drug moiety. The stability of the ADC may be measured by standard analytical techniques such as mass spectroscopy, hydrophobic interaction chromatography (HIC), HPLC, and the separation/analysis technique LC/MS.

Conjugation

It will be appreciated that a number of well-known different reactions may be used to attach the drug moiety, chelator and/or linker to the selected antibody.

According to certain embodiments, a drug moiety, chelator or chelator-linker comprises a nucleophilic moiety or an electrophilic moiety. Reaction of the nucleophilic group or electrophilic group of a chelator or chelator-linker with an antibody or antigen binding domain comprising the corresponding reaction partner allows for covalent linkage of the antibody or antigen binding domain to the drug moiety, chelator, or chelator-linker. Examples of nucleophilic groups include, but are not limited to, azides, amines, and thiols. Examples of electrophilic groups include, but are not limited to amine-reactive groups, thiol-reactive groups, alkynyls and cycloalkynyls. An amine-reactive group preferably reacts with primary amines, including primary amines that exist at the N-terminus of each polypeptide chain and in the side-chain of lysine residues. Examples of amine-reactive groups include, but are not limited to, N-hydroxy succinimide (NHS), substituted NHS (such as sulfo-NHS), isothiocyanate (—NCS), isocyanate (—NCO), esters, carboxylic acid, acyl halides, amides, alkylamides, and tetra- and per-fluoro phenyl ester. A thiol-reactive group reacts with thiols, or sulfhydryls, preferably thiols present in the side-chain of cysteine residues of polypeptides. Examples of thiol-reactive groups include, but are not limited to, Michael acceptors (e.g., maleimide), haloacetyl, acyl halides, activated disulfides, and phenyloxadiazole sulfone.

Residue Specific Conjugation

In some embodiments the conjugation of drug moiety, chelator and/or linker to the antibody or antigen binding fragment thereof of the disclosure may be achieved through residue-specific methods (random conjugation) such as acylation of amines on lysine residues and alkylation of thiols on cysteine residues. Examples of residue specific methods for conjugation that can be used include, but are not limited to, conjugation of a drug moiety, chelator, linker and/or radiometal complex to lysine residues of the antibody using a drug moiety, chelator, linker, or radiometal complex comprising, e.g., an activated ester or isothiocyanate group; conjugation of a drug moiety, chelator, linker and/or radiometal complex to cysteine residues of the antibody using a drug moiety, chelator, linker, or radiometal complex comprising, e.g., a maleimide, haloacetyl derivative, acyl halide, activated disulfide group, or methylsulfonyl phenyloxadiazole group; conjugation of a drug moiety, chelator, linker and/or radiometal complex to tyrosine resides of the antibody using a drug moiety, chelator, linker, or radiometal complex comprising, e.g., 4-phenyl-3H-1,2,4-triazoline-3,5 (4H)-diones (PTADs); and conjugation of a drug moiety, chelator, linker and/or radiometal complex to methionine residues of the antibody using a drug moiety, chelator, linker, or radiometal complex comprising, e.g., an oxaziridine derivative.

Residue-specific methods for conjugation to proteins are well established and most commonly involve either lysine side chains, using an activated ester or isothiocyanate, or cysteine side chains with a maleimide, haloacetyl derivative or activated disulfide (Brinkley Bioconjugate Chem 1992:2). Since most proteins have multiple lysine and cysteine residues, heterogeneous mixtures of product with different numbers of conjugated molecules at a variety of amino acid positions are typically obtained using such methods. Additional methods have been established including tyrosine-specific conjugation (Ban et al. *Bioconjugate Chemistry* 2013:520), methionine-specific methods (Lin et al. Science 2017 (355) 597), additional cysteine-focused approaches (Toda et al. *Angew Chemie* 2013:12592), and others.

In some embodiments, the PSMA antibody or antibody fragment thereof of the disclosure can be conjugated to any of the radiometal complexes described herein through one or more Lysine residues of the antibody.

In some embodiments, the ADCs or radioconjugates of the disclosure may be generated through conjugation of a drug moiety, chelator, linker, or radiometal complex to solvent-exposed amino groups of lysine residues present in the selected antibody. Conjugation reactions involving lysines include, but are not limited to, isothiocyanate, NETS-ester, sulfonyl fluorides, fluorosulfates, dichlorotriazines, activated esters, activated sulfonamides, vinyl sulfonamides, imidoesters, isothiocyanates, salicylaldehydes, iminoboronates and α,β-unsaturated carbonyls In some embodiments, the ADCs or radioconjugates of the disclosure may be generated through reactions exploiting sulfhydryl groups of cysteines residues present in the selected antibody. Particularly preferred embodiments will comprise conjugation of antibodies comprising one or more free cysteines. Conjugation reactions involving reduced cysteines include, but are not limited to, thiol-maleimide, thiol-halogeno (acyl halide), thiol-ene, thiol-yne, thiol-vinylsulfone, thiol-bisulfone, thiol-thiosulfonate, thiol-pyridyl disulfide and thiol-parafluoro reactions.

In some embodiments, prior to conjugation, antibodies may be made reactive for conjugation with linker reagents by treatment with a reducing agent such as dithiothreitol (DTT) or (tris(2-carboxyethyl)phosphine (TCEP). In some embodiments reactive thiol groups may be introduced into the selected antibody (or fragment thereof) by introducing one, two, three, four, or more free cysteine residues. In some embodiments, conjugation methodology may include full or partial reduction of each of the intrachain or interchain antibody disulfide bonds to provide conjugation sites. In some embodiments, free cysteines may be made reactive for conjugation with linker reagents by treatment with a reducing agent such as dithiothreitol (DTT) or (tris (2-carboxyethyl)phosphine (TCEP). Each free cysteine will thus present, theoretically, a reactive thiol nucleophile.

Since most proteins have multiple lysine, threonine, methionine and cysteine residues, heterogeneous mixtures of product with different numbers of conjugated molecules at a variety of amino acid positions are typically obtained using residue-specific conjugations methods.

Site Specific Conjugation

More recently, site-selective and site-specific conjugation methods have been established for monoclonal antibodies and other proteins (Agarwal, P. and C. R. Bertozzi, Bioconjug Chem, 2015. 26(2): p. 176-92; Rabuka et al. Curr Opin Chem Biol 2010:790). These include incorporation of unnatural amino acids; fusion of the protein of interest to a 'self-labeling tag' such as SNAP or DHFR or a tag that is recognized and modified specifically by another enzyme such as sortase A, lipoic acid ligase and formylglycine-generating enzyme; enzymatic modification of the glycan to allow conjugation of payloads of interest (Hu et al. Chem Soc Rev 2016:1691); use of microbial transglutaminase to selectively recognize defined positions on the antibody; and additional methods using molecular recognition and/or chemical approaches to affect selective conjugation (Yamada et al. 2019:5592; Park et al. Bioconjugate Chem 2018:3240; Pham et al. Chembiochem 2018:799). Efficacy and safety of immunoconjugates can be increased with site-specific methods as compared to random conjugation.

In some embodiments the conjugation of drug moiety, chelator and/or linker to the antibody or antigen binding fragment of the disclosure may be achieved through site-specific conjugation.

In some embodiment, transglutaminase may be used to attach the drug moiety, chelator and/or linker to the antibody or antigen binding fragment of the disclosure. Transglutaminases are enzymes that catalyzes the formation of an isopeptide bond between a free amine group on a payload and the acyl group on the side chain of a glutamine residue in an antibody or antigen binding fragment thereof. Transglutaminases are protein-glutamine γ-glutamyltransferases (EC 2.3.2.13), which typically catalyze pH-dependent transamidation of glutamine residues with lysine residues. Examples of transglutaminases include, but are not limited to, microbial transglutaminase (mTG), human transglutaminase, tissue transglutaminase (tTG), and Factor XIII Examples of human transglutaminases include, but are not limited to, keratinocyte transglutaminase (Uniprot P22735), tissue transglutaminase (UniProt P21980), epidermal transglutaminase and prostate transglutaminase. These enzymes can be from either natural or recombinant sources. Glutamine and lysine amino acids in a peptide or polypeptide can be substrates for transglutaminase crosslinking. For example, the payload can be linked to a linker comprising a lysine.

The transglutaminase can be any transglutaminase deemed suitable by those of skill in the art. The transglutaminase can be obtained or made from a variety of sources. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, MO) and MP Biomedicals (Irvine, CA)).

In some embodiments, the transglutaminase is derived from a fungal protein (e.g., Oomycetes, Actinomycetes, *Saccharomyces, Candida, Cryptococcus*, Monascus, or *Rhizopus* transglutaminases). In some embodiments, the transglutaminase polypeptide is derived from Myxomycetes (e.g., *Physarum polycephalum* transglutaminase). In some embodiments, the mTGase polypeptide is derived from a bacterial protein, such as transglutaminase from, but not limited to, *Streptoverticillium mobarensis, Streptoverticillium griseocameum, Streptoverticillium ladakanum, Streptomyces mobarensis, Streptomyces viridis, Streptomyces ladakanum, Streptomyces caniferus, Streptomyces platensis, Streptomyces hygroscopius, Streptomyces netropsis, Streptomyces fradiae, Streptomyces roseovertivillatus, Streptomyces cinnamaoneous, Streptomyces griseocameum, Streptomyces lavendulae, Streptomyces lividans, Streptomyces lydicus, Streptomyces sioyansis, Actinomadura* sp., *Bacillus* (e.g., *Bacillus circulans, Bacillus subtilis*, etc.), *Corynebacterium ammonia* genes, *Corynebacterium glutamicum, Clostridium, Enterobacter* sp., *Micrococcus, Providencia* sp., or isolates thereof. In some embodiments, the transglutaminase polypeptide is derived from *S. mobarensis*.

Commercially available calcium independent transglutaminase such as ACTIVA (Ajinomoto, Japan) is also suitable for the present invention. In some embodiments, the transglutaminase can also be a recombinant protein produced using recombinant techniques known to persons skilled in the art. In some embodiments, the transglutaminase used in the invention described herein can be a purified protein.

In some embodiments, the antibody or antigen binding fragment of the disclosure is conjugated at Gln295, in the CH2 domain, using transglutaminase to generate the ADC, immunoconjugate or radioimmunoconjugate of the disclosure.

In some embodiments, the antibody or antigen binding fragment of the disclosure is modified before conjugation with transglutaminase. In some embodiments, the antibody or antigen binding fragment of the disclosure used to produce the ADC, immunoconjugate or radioimmunoconjugate of the disclosure comprises a substitution at position 302 of the heavy chain. Such substitution can be, for example, V302S, V302A, V302I, V302L, V302M, V302T, V302F, and V302Y, preferably the amino acid substitutions V302A and V302S, wherein the amino acid numbering is according to the EU Index of Kabat.

In some embodiments, the antibody or antigen binding fragment of the disclosure used to produce the ADC, immunoconjugate or radioimmunoconjugate of the disclosure comprises the amino acid substitution V302A or V302S, optionally Y300L, and further comprises a glutamine substitution at heavy chain position 286, 287, 288, 289, 290, 293 or 294, preferably the amino acid substitution N286Q, A287Q, K288Q, T289Q, K290Q, E293Q or E294Q, wherein the amino acid numbering is according to the EU Index of Kabat.

In some embodiments, the antibody or antigen binding fragment of the disclosure used to produce the ADC, immunoconjugate or radioimmunoconjugate of the disclosure comprises the amino acid substitution V302A or V302S and at least one of the amino acid substitutions E293Q and E294Q, wherein the amino acid numbering is according to the EU Index of Kabat.

In some embodiments, the antibody or antigen binding fragment of the disclosure used to produce the ADC, immunoconjugate or radioimmunoconjugate of the disclosure comprises the amino acid substitution V302A or V302S and further comprises a glutamine substitution at heavy chain position 286, 287, 288, 289, 290, 293 or 294, such as the amino acid substitution N286Q, A287Q, K288Q, T289Q, K290Q, E293Q or E294Q, and/or an alanine substitution at heavy chain position 241, 243, 294 or 301, such as F241A, F243A, E294A or R301A.

In some embodiments, the antibody or antigen binding fragment of the disclosure conjugated with transglutaminase to produce the ADC, immunoconjugate or radioimmunoconjugate of the disclosure is glycosylated or is a glycan intact antibody or its glycan content is unchanged compared to the native antibody. In some embodiments, the antibody or antigen binding fragment of the disclosure conjugated with transglutaminase to produce the ADC, immunoconjugate or radioimmunoconjugate of the disclosure is glycosylated at position N297 or the glycan content of the antibody or antigen binding fragment thereof at position N297 is unchanged compared to the native antibody.

In some embodiments, the method of producing the ADC, or radioconjugate of the disclosure comprises reacting a glycosylated or glycan intact antibody or antigen binding fragment of the disclosure with an amine compound in the presence of transglutaminase in low-ionic strength conditions. Low-ionic strength conditions include, but are not limited to, solutions comprising a salt concentration of about 25 mM or less, of about 20 mM or less, of about 15 mM or less, of about 10 mM or less.

In some embodiments, the antibody or antigen binding fragment of the disclosure used to produce the ADC, immunoconjugate or radioimmunoconjugate of the disclosure is modified by trimming the antibody or antigen binding fragment thereof with a bacterial endoglycosidase specific for the β-1,4 linkage between a core GlcNac residue in an Fc-glycosylation site of the antibody, such as GlycINATOR (Genovis), which leaves the inner most GlcNAc intact on the Fc, allowing for the site-specific incorporation of azido sugars at that site. The trimmed antibody or antigen binding fragment thereof can then be reacted with an azide-labeled sugar, such as UDP-N-azidoacetylgalactosamine (UDP-Gal-NAz) or UDP-6-azido 6-deoxy GalNAc, in the presence of a sugar transferase, such as GalT galactosyltransferase or GalNAc transferase, to thereby obtain the modified antibody or antigen binding fragment thereof.

In other embodiments, the antibody or antigen binding fragment thereof of the disclosure used for producing the immunoconjugate or radioimmunoconjugate of the disclosure is modified by deglycosylating the antibody or antigen binding fragment thereof with an amidase.

Click Chemistry

In some embodiment, click chemistry may be used to attach the drug moiety, chelator and/or linker to the selected antibody of the disclosure. As used herein, the term "click chemistry" refers to a chemical philosophy introduced by Sharpless, describing chemistry tailored to generate covalent bonds quickly and reliably by joining small units comprising reactive groups together (see Kolb, et al., Angewandte ChemieInternational Edition (2001) 40: 2004-2021). Click chemistry does not refer to a specific reaction, but to a concept including, but not limited to, reactions that mimic reactions found in nature. In some embodiments, click chemistry reactions are modular, wide in scope, give high chemical yields, generate inert byproducts, are stereospecific, exhibit a large thermodynamic driving force to favor a reaction with a single reaction product, and/or can be carried out under physiological conditions. In some embodiments, a click chemistry reaction can be carried out under simple reaction conditions, uses readily available starting materials and reagents, uses non-toxic solvents or uses a solvent that is benign or easily removed, such as water, and/or provides simple product isolation by non-chromatographic methods, such as crystallization or distillation.

Click chemistry reactions utilize reactive groups that are rarely found in naturally-occurring biomolecules and are chemically inert towards biomolecules, but when the click chemistry partners are reacted together, the reaction can take place efficiently under biologically relevant conditions, for example in cell culture conditions, such as in the absence of excess heat and/or harsh reagents. In general, click chemistry reactions require at least two molecules comprising click reaction partners that can react with each other. Such click reaction partners that are reactive with each other are sometimes referred to herein as click chemistry handle pairs, or click chemistry pairs. In some embodiments, the click reaction partners are an azide and a strained alkyne, e.g. cycloalkyne such as a cyclooctyne or cyclooctyne derivative, or any other alkyne. In other embodiments, the click reaction partners are reactive dienes and suitable tetrazine dienophiles. For example, trans-cyclooctene, norbornene, or biscyclononene can bepaired with a suitable tetrazine dienophile as a click reaction pair.

In yet other embodiments, tetrazoles can act as latent sources of nitrile imines, which can pair with unactivated alkenes in the presence of ultraviolet light to create a click reaction pair, termed a "photo-click" reaction pair.

In other embodiments, the click reaction partners are a cysteine and a maleimide. For example the cysteine from a peptide (e.g., GGGC (SEQ ID NO: 338)) can be reacted with a maleimide that is associated with a chelating agent (e.g., NOTA). Other suitable click chemistry handles are known to those of skill in the art (see, e.g., Spicer et al., Selective chemical protein modification. Nature Communications. 2014; 5: p. 4740). In other embodiments, the click reaction partners are Staudinger ligation components, such as phosphine and azide. In other embodiments, the click reaction partners are Diels-Alder reaction components, such as dienes (e.g., tetrazine) and alkenes (e.g., trans-cyclooctene (TCO) or norbornene). Exemplary click reaction partners are described in US20130266512 and in WO2015073746, the relevant description on click reaction partners in both of which are incorporated by reference herein.

According to preferred embodiments, a click chemistry reaction utilizes an azide group and an alkyne group, more preferably a strained alkyne group, e.g., cycloalkyne such as a cyclooctyne or cyclooctyne derivative, as the click chemistry pair or reaction partners. In such embodiments, the click chemistry reaction is a Huisgen cycloaddition or 1,3-dipolar cycloaddition between the azide ($-N_3$) and alkyne moiety to form a 1,2,3-triazole linker. Click chemistry reactions between alkynes and azides typically require the addition of a copper catalyst to promote the 1,3-cycloaddition reaction, and are known as copper-catalyzed azide-alkyne cycloaddition (CuAAC) reactions. However, click chemistry reactions between cyclooctyne or cyclooctyne derivatives and azides typically do not require the addition of a copper catalyst, and instead proceed via strain-promoted azide-alkyne cycloaddition (SPAAC) (Debets, M. F., et al., Bioconjugation with strained alkenes and alkynes. *Acc Chem Res,* 2011. 44(9): p. 805-15). A radioimmunoconjugate can be produced by first preparing an immunoconjugate of the invention by covalently linking a chelator of the invention to an antibody or antigen-binding fragment thereof by, for example, a click chemistry reaction; the immunoconjugate can subsequently be labeled with a radiometal ion to produce a radioimmunoconjugate.

Radioimmunoconjugates produced by the methods described herein can be analyzed using methods known to those skilled in the art in view of the present disclosure. For example, LC/MS analysis can be used to determine the ratio of the chelator to the labeled polypeptide, e.g., antibody or antigen binding fragment thereof; analytical size-exclusion chromatography can be used to determine the oligomeric state of the polypeptides and polypeptide conjugates, e.g., antibody and antibody conjugates; radiochemical yield can be determined by instant thin layer chromatography (e.g., iTLC-SG), and radiochemical purity can be determined by size-exclusion HPLC.

DAR Distribution

The term "drug-to-antibody ratio (DAR)" or "chelator antibody ratio (CAR)" refers, to the number of drug-linker molecules per antibody molecule or the number of chelator molecules per antibody. The DAR can be measured by intact mass analysis using RP-HPLC with online mass analysis. According to certain embodiments, the average DAR of a conjugate intermediate of the disclosure is from about 1 to about 10, or from 1 to about 9, or from 1 to about 8, of from about 1 to about 7, or from about 1 to about 6, or from about 1 to about 5, or from about 1 to about 4, or from about 1 to about 3, or from about 2 to about 4, or from about 2 to about 3.

In some embodiments a conjugate preparation may be substantially homogeneous with respect to its DAR distribution, meaning that within the preparation is a predominant species of site-specific ADC with a particular DAR that is also uniform with respect to the site of loading (i.e., on the free cysteines). In certain embodiments it is possible to achieve the desired homogeneity through the use of site-specific antibodies or selective combination. In other embodiments the desired homogeneity may be achieved through the use of site-specific constructs in combination with selective reduction. In yet other embodiments, the preparations may be further purified using analytical or preparative chromatography techniques. In each of these embodiments the homogeneity of the ADC sample can be analyzed using various techniques known in the art including but not limited to SDS-PAGE, HPLC (e.g. size exclusion HPLC, RP-HPLC, HIC-HPLC etc.) or capillary electrophoresis.

In some embodiments, the anti-PSMA antibody or antigen binding fragment thereof is conjugated to a radiometal complex with a DAR of 4. In some embodiments, the anti-PSMA antibody or antigen binding fragment thereof if conjugated to a radiometal complex with a DAR of 8.

Radioconjugates and ADCs of the Disclosure

Any of the anti-PSMA antibodies, antigen binding fragment thereof, chelators or radiometal complexes of the disclosure such as those described herein, can be used to produce the radioimmunoconjugates or ADCs of the disclosure.

In some embodiments, the radioconjugate or ADC comprises an antibody, or an antigen binding domain, which specifically binds to PSMA.

In some embodiments, the radioconjugate or ADC comprises an antibody, or an antigen binding domain, that specifically binds to PSMA and which comprises (a) a heavy chain variable region (VH) comprising a VH CDR1 having an amino acid sequence of SEQ ID NO:4, a VH CDR2 having an amino acid sequence of and SEQ ID NO:5 and a VH CDR3 having an amino acid sequence of SEQ ID NO:6; and (b) a light chain variable region (VL) comprising a VL CDR1 having an amino acid sequence of SEQ ID NO:7, a VL CDR2 having an amino acid sequence of and SEQ ID NO:8 and a VL CDR3 having an amino acid sequence of SEQ ID NO:9.

In some embodiments, the radioconjugate or ADC comprises an antibody, or an antigen binding domain, that specifically binds to PSMA and which comprises a heavy chain variable region (VH) having at least 80%, at least 85%, at least 90%, at least 95%, or at least 98% sequence identity to the amino acid sequence of SEQ ID NO: 52, and/or a light chain variable region (VL) having at least 80%, at least 85%, at least 90%, at least 95%, or at least 98% sequence identity to the amino acid sequence of SEQ ID NO: 53.

In some embodiments, the radioconjugate or ADC comprises an antibody, or an antigen binding domain, that specifically binds to PSMA and which comprises a heavy chain variable region (VH) comprising the amino acid sequence of SEQ ID NO: 52, and/or a light chain variable region (VL) comprising the amino acid sequence of SEQ ID NO: 53.

In some embodiments, the radioconjugate or ADC comprises an antibody, or an antigen binding domain, that specifically binds to PSMA and which comprises a heavy chain constant region having at least 80%, at least 85%, at least 90%, at least 95%, or at least 98% sequence identity to the amino acid sequence of SEQ ID NO: 84, and/or a light chain constant region having at least 80%, at least 85%, at least 90%, at least 95%, or at least 98% sequence identity to the amino acid sequence of SEQ ID NO: 85.

In some embodiments, the radioconjugate or ADC comprises an antibody, or an antigen binding domain, that specifically binds to PSMA and which comprises a heavy chain constant region comprising the amino acid sequence of SEQ ID NO: 84, and/or a light chain constant region comprising the amino acid sequence of SEQ ID NO: 85.

In some embodiments, the radioconjugate or ADC comprises an antibody, or an antigen binding domain, that specifically binds to PSMA and which comprises a heavy chain constant region having at least 80%, at least 85%, at least 90%, at least 95%, or at least 98% sequence identity to the amino acid sequence of SEQ ID NO: 86, and/or a light chain constant region having at least 80%, at least 85%, at least 90%, at least 95%, or at least 98% sequence identity to the amino acid sequence of SEQ ID NO: 85.

In some embodiments, the radioconjugate or ADC comprises an antibody, or an antigen binding domain, that specifically binds to PSMA and which comprises a heavy chain constant region comprising the amino acid sequence of SEQ ID NO: 86, and/or a light chain constant region comprising the amino acid sequence of SEQ ID NO: 85.

In some embodiments, the radioconjugate or ADC comprises an antibody, or an antigen binding domain, that specifically binds to PSMA and which comprises (a) a heavy chain variable region (VH) comprising a VH CDR1 having an amino acid sequence of SEQ ID NO:10, a VH CDR2 having an amino acid sequence of and SEQ ID NO:11 and a VH CDR3 having an amino acid sequence of SEQ ID NO:12; and (b) a light chain variable region (VL) comprising a VL CDR1 having an amino acid sequence of SEQ ID NO:13, a VL CDR2 having an amino acid sequence of and SEQ ID NO:14 and a VL CDR3 having an amino acid sequence of SEQ ID NO:15.

In some embodiments, the radioconjugate or ADC comprises an antibody, or an antigen binding domain, that specifically binds to PSMA and which comprises a heavy chain variable region (VH) having at least 80%, at least 85%, at least 90%, at least 95%, or at least 98% sequence identity to the amino acid sequence of SEQ ID NO: 54, and/or a light chain variable region (VL) having at least 80%, at least 85%, at least 90%, at least 95%, or at least 98% sequence identity to the amino acid sequence of SEQ ID NO: 55.

In some embodiments, the radioconjugate or ADC comprises an antibody, or an antigen binding domain, that specifically binds to PSMA and which comprises a heavy chain variable region (VH) comprising the amino acid sequence of SEQ ID NO: 54, and/or a light chain variable region (VL) comprising the amino acid sequence of SEQ ID NO: 55.

In some embodiments, the radioconjugate or ADC comprises an antibody, or an antigen binding domain, that specifically binds to PSMA and which comprises a heavy chain constant region having at least 80%, at least 85%, at least 90%, at least 95%, or at least 98% sequence identity to the amino acid sequence of SEQ ID NO: 88, and/or a light chain constant region having at least 80%, at least 85%, at least 90%, at least 95%, or at least 98% sequence identity to the amino acid sequence of SEQ ID NO: 89.

In some embodiments, the radioconjugate or ADC comprises an antibody, or an antigen binding domain, that specifically binds to PSMA and which comprises a heavy chain constant region comprising the amino acid sequence of SEQ ID NO: 88, and/or a light chain constant region comprising the amino acid sequence of SEQ ID NO: 89.

In some embodiments, the radioconjugate or ADC comprises an antibody, or an antigen binding domain, that specifically binds to PSMA and which comprises a heavy chain constant region having at least 80%, at least 85%, at least 90%, at least 95%, or at least 98% sequence identity to the amino acid sequence of SEQ ID NO: 90, and/or a light chain constant region having at least 80%, at least 85%, at least 90%, at least 95%, or at least 98% sequence identity to the amino acid sequence of SEQ ID NO: 89.

In some embodiments, the radioconjugate or ADC comprises an antibody, or an antigen binding domain, that specifically binds to PSMA and which comprises a heavy chain constant region comprising the amino acid sequence of SEQ ID NO: 90, and/or a light chain constant region comprising the amino acid sequence of SEQ ID NO: 89.

In some embodiments, the radioconjugate comprises an antibody, such as the PSMA antibody or antigen binding fragment thereof of the disclosure, conjugated to a radiometal complex comprising a chelator and a radiometal. In some embodiments, the PSMA antibody or antigen binding fragment thereof is covalently bound to the chelator. In some embodiments, the radiometal complex comprises a linker.

In some embodiments the radiometal ion is actinium-225 ($^{225}$Ac).

In some embodiments the radiometal ion is Cerium 134 (134 Ce).

In some embodiments the radiometal ion is Indium 111 ($^{111}$In).

In some embodiments, the radioconjugate of the disclosure comprises an anti-PSMA antibody or antigen binding fragment thereof which comprises:
  (a) a heavy chain variable region (VH) comprising a VH CDR1 having an amino acid sequence of SEQ ID NO:4, a VH CDR2 having an amino acid sequence of and SEQ ID NO:5 and a VH CDR3 having an amino acid sequence of SEQ ID NO:6;
  (b) a light chain variable region (VL) comprising a VL CDR1 having an amino acid sequence of SEQ ID NO:7, a VL CDR2 having an amino acid sequence of and SEQ ID NO:8 and a VL CDR3 having an amino acid sequence of SEQ ID NO:9; and
  (c) an alpha-emitting radiometal ion coordinated to a chelator moiety, wherein the alpha-emitting radiometal ion is $^{225}$AC.

In some embodiments, the radioconjugate of the disclosure comprises an anti-PSMA antibody which comprises a heavy chain variable region (VH) having at least 80%, at least 85%, at least 90%, at least 95%, or at least 98% sequence identity to the amino acid sequence of SEQ ID NO: 52, a light chain variable region (VL) having at least 80%, at least 85%, at least 90%, at least 95%, or at least 98% sequence identity to the amino acid sequence of SEQ ID NO: 53; and
  an alpha-emitting radiometal ion coordinated to a chelator moiety, wherein the alpha-emitting radiometal ion is $^{225}$AC.

In some embodiments, the radioconjugate of the disclosure comprises an anti-PSMA antibody which comprises a heavy chain variable region (VH) comprising the amino acid sequence of SEQ ID NO: 52, a light chain variable region (VL) comprising the amino acid sequence of SEQ ID NO: 53; and an alpha-emitting radiometal ion coordinated to a chelator moiety, wherein the alpha-emitting radiometal ion is $^{225}$Ac.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 84, a light chain constant region having at least 80%, at least 85%, at least 90%, at least 95%, or at least 98% sequence identity to the amino acid sequence of SEQ ID NO: 85; and
  an alpha-emitting radiometal ion coordinated to a chelator moiety, wherein the alpha-emitting radiometal ion is $^{225}$AC.

In some embodiments, the radioconjugate of the disclosure comprises an anti-PSMA antibody which comprises a heavy chain constant region comprising the amino acid sequence of SEQ ID NO: 84, a light chain constant region comprising the amino acid sequence of SEQ ID NO: 85; and an alpha-emitting radiometal ion coordinated to a chelator moiety, wherein the alpha-emitting radiometal ion is $^{225}$AC.

In some embodiments, the radioconjugate of the disclosure comprises an anti-PSMA antibody or antigen binding fragment thereof which comprises:
  (a) a heavy chain variable region (VH) comprising a VH CDR1 having an amino acid sequence of SEQ ID NO:10, a VH CDR2 having an amino acid sequence of and SEQ ID NO:11 and a VH CDR3 having an amino acid sequence of SEQ ID NO:12;
  (b) a light chain variable region (VL) comprising a VL CDR1 having an amino acid sequence of SEQ ID NO:13, a VL CDR2 having an amino acid sequence of and SEQ ID NO:14 and a VL CDR3 having an amino acid sequence of SEQ ID NO:15; and
  (c) an alpha-emitting radiometal ion coordinated to a chelator moiety, wherein the alpha-emitting radiometal ion is $^{225}$AC.

In some embodiments, the radioconjugate of the disclosure comprises an anti-PSMA antibody which comprises a heavy chain variable region (VH) having at least 80%, at least 85%, at least 90%, at least 95%, or at least 98% sequence identity to the amino acid sequence of SEQ ID NO: 54, a light chain variable region (VL) having at least 80%, at least 85%, at least 90%, at least 95%, or at least 98% sequence identity to the amino acid sequence of SEQ ID NO: 55; and
  an alpha-emitting radiometal ion coordinated to a chelator moiety, wherein the alpha-emitting radiometal ion is $^{225}$AC.

In some embodiments, the radioconjugate of the disclosure comprises an anti-PSMA antibody which comprises a heavy chain variable region (VH) comprising the amino acid sequence of SEQ ID NO: 54, a light chain variable region (VL) comprising the amino acid sequence of SEQ ID NO: 55; and an alpha-emitting radiometal ion coordinated to a chelator moiety, wherein the alpha-emitting radiometal ion is $^{225}$Ac.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 88, a light chain constant region having at least 80%, at least 85%, at least 90%, at least 95%, or at least 98% sequence identity to the amino acid sequence of SEQ ID NO: 89; and an alpha-emitting radiometal ion coordinated to a chelator moiety, wherein the alpha-emitting radiometal ion is $^{225}$AC.

In some embodiments, the radioconjugate of the disclosure comprises an anti-PSMA antibody which comprises a heavy chain constant region comprising the amino acid sequence of SEQ ID NO: 88, a light chain constant region comprising the amino acid sequence of SEQ ID NO: 89; and an alpha-emitting radiometal ion coordinated to a chelator moiety, wherein the alpha-emitting radiometal ion is $^{225}$AC.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 86, a light chain constant region having at least 80%, at least 85%, at least 90%, at least 95%, or at least 98% sequence identity to the amino acid sequence of SEQ ID NO: 85; and an alpha-emitting radiometal ion coordinated to a chelator moiety, wherein the alpha-emitting radiometal ion is $^{225}$AC.

In some embodiments, the radioconjugate of the disclosure comprises an anti-PSMA antibody which comprises a heavy chain constant region comprising the amino acid sequence of SEQ ID NO: 86, a light chain constant region comprising the amino acid sequence of SEQ ID NO: 85; and an alpha-emitting radiometal ion coordinated to a chelator moiety, wherein the alpha-emitting radiometal ion is 225Ac.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 90, a light chain constant region having at least 80%, at least 85%, at least 90%, at least 95%, or at least 98% sequence identity to the amino acid sequence of SEQ ID NO: 89; and an alpha-emitting radiometal ion coordinated to a chelator moiety, wherein the alpha-emitting radiometal ion is $^{225}$AC.

In some embodiments, the radioconjugate of the disclosure comprises an anti-PSMA antibody which comprises a heavy chain constant region comprising the amino acid sequence of SEQ ID NO: 90, a light chain constant region comprising the amino acid sequence of SEQ ID NO: 89; and an alpha-emitting radiometal ion coordinated to a chelator moiety, wherein the alpha-emitting radiometal ion is $^{225}$AC.

In some embodiments, the radioconjugate of the disclosure comprises an anti-PSMA antibody or antigen binding fragment thereof which comprises
  (a) a heavy chain variable region (VH) comprising a VH CDR1 having an amino acid sequence of SEQ ID NO:4, a VH CDR2 having an amino acid sequence of and SEQ ID NO:5 and a VH CDR3 having an amino acid sequence of SEQ ID NO:6;
  (b) a light chain variable region (VL) comprising a VL CDR1 having an amino acid sequence of SEQ ID NO:7, a VL CDR2 having an amino acid sequence of and SEQ ID NO:8 and a VL CDR3 having an amino acid sequence of SEQ ID NO:9; and
  (c) a radiometal ion coordinated to a chelator moiety, wherein radiometal ion is $^{111}$In.

In some embodiments, the radioconjugate of the disclosure comprises an anti-PSMA antibody which comprises a heavy chain variable region (VH) having at least 80%, at least 85%, at least 90%, at least 95%, or at least 98% sequence identity to the amino acid sequence of SEQ ID NO: 52, a light chain variable region (VL) having at least 80%, at least 85%, at least 90%, at least 95%, or at least 98% sequence identity to the amino acid sequence of SEQ ID NO: 53 and a radiometal ion coordinated to a chelator moiety, wherein radiometal ion is $^{111}$In.

In some embodiments, the radioconjugate of the disclosure comprises an anti-PSMA antibody which comprises a heavy chain variable region (VH) comprising the amino acid sequence of SEQ ID NO: 52, a light chain variable region (VL) comprising the amino acid sequence of SEQ ID NO: 53 and a radiometal ion coordinated to a chelator moiety, wherein radiometal ion is $^{111}$In.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 84, a light chain constant region having at least 80%, at least 85%, at least 90%, at least 95%, or at least 98% sequence identity to the amino acid sequence of SEQ ID NO: 85 and a radiometal ion coordinated to a chelator moiety, wherein radiometal ion is $^{111}$In.

In some embodiments, the radioconjugate of the disclosure comprises an anti-PSMA antibody which comprises a heavy chain constant region comprising the amino acid sequence of SEQ ID NO: 84, a light chain constant region comprising the amino acid sequence of SEQ ID NO: 85 and a radiometal ion coordinated to a chelator moiety, wherein radiometal ion is $^{111}$In.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 86, a light chain constant region having at least 80%, at least 85%, at least 90%, at least 95%, or at least 98% sequence identity to the amino acid sequence of SEQ ID NO: 85 and a radiometal ion coordinated to a chelator moiety, wherein radiometal ion is $^{111}$In.

In some embodiments, the radioconjugate of the disclosure comprises an anti-PSMA antibody which comprises a heavy chain constant region comprising the amino acid sequence of SEQ ID NO: 86, a light chain constant region comprising the amino acid sequence of SEQ ID NO: 85 and a radiometal ion coordinated to a chelator moiety, wherein radiometal ion is $^{111}$In.

In some embodiments, the radioconjugate of the disclosure comprises an anti-PSMA antibody or antigen binding fragment thereof which comprises
  (a) a heavy chain variable region (VH) comprising a VH CDR1 having an amino acid sequence of SEQ ID NO:10, a VH CDR2 having an amino acid sequence of and SEQ ID NO:11 and a VH CDR3 having an amino acid sequence of SEQ ID NO:12;
  (b) a light chain variable region (VL) comprising a VL CDR1 having an amino acid sequence of SEQ ID NO:13, a VL CDR2 having an amino acid sequence of and SEQ ID NO:14 and a VL CDR3 having an amino acid sequence of SEQ ID NO:15; and
  (c) a radiometal ion coordinated to a chelator moiety, wherein radiometal ion is $^{111}$In.

In some embodiments, the radioconjugate of the disclosure comprises an anti-PSMA antibody which comprises a heavy chain variable region (VH) having at least 80%, at least 85%, at least 90%, at least 95%, or at least 98% sequence identity to the amino acid sequence of SEQ ID NO: 54, a light chain variable region (VL) having at least 80%, at least 85%, at least 90%, at least 95%, or at least 98% sequence identity to the amino acid sequence of SEQ ID NO: 55 and
  a radiometal ion coordinated to a chelator moiety, wherein radiometal ion is $^{111}$In.

In some embodiments, the radioconjugate of the disclosure comprises an anti-PSMA antibody which comprises a heavy chain variable region (VH) comprising the amino acid sequence of SEQ ID NO: 54, a light chain variable region (VL) comprising the amino acid sequence of SEQ ID NO: 55 and a radiometal ion coordinated to a chelator moiety, wherein radiometal ion is $^{111}$In.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 88, a light chain constant region having at least 80%, at least 85%, at least 90%, at least 95%, or at least 98% sequence identity to the amino acid sequence of SEQ ID NO: 89 and a radiometal ion coordinated to a chelator moiety, wherein radiometal ion is $^{111}$In.

In some embodiments, the radioconjugate of the disclosure comprises an anti-PSMA antibody which comprises a heavy chain constant region comprising the amino acid sequence of SEQ ID NO: 88, a light chain constant region comprising the amino acid sequence of SEQ ID NO: 89 and a radiometal ion coordinated to a chelator moiety, wherein radiometal ion is $^{111}$In.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 90, a light chain constant region having at least 80%, at least 85%, at least 90%, at least 95%, or at least 98% sequence identity to the amino acid sequence of SEQ ID NO: 89 and a radiometal ion coordinated to a chelator moiety, wherein radiometal ion is $^{111}$In.

In some embodiments, the radioconjugate of the disclosure comprises an anti-PSMA antibody which comprises a heavy chain constant region comprising the amino acid sequence of SEQ ID NO: 90, a light chain constant region comprising the amino acid sequence of SEQ ID NO: 89 and a radiometal ion coordinated to a chelator moiety, wherein radiometal ion is $^{111}$In.

In some embodiments, the radioconjugate of the disclosure comprises an anti-PSMA antibody or antigen binding fragment thereof which comprises
  (a) a heavy chain variable region (VH) comprising a VH CDR1 having an amino acid sequence of SEQ ID NO:4, a VH CDR2 having an amino acid sequence of and SEQ ID NO:5 and a VH CDR3 having an amino acid sequence of SEQ ID NO:6;
  (b) a light chain variable region (VL) comprising a VL CDR1 having an amino acid sequence of SEQ ID NO:7, a VL CDR2 having an amino acid sequence of and SEQ ID NO:8 and a VL CDR3 having an amino acid sequence of SEQ ID NO:9; and
  (c) a radiometal ion coordinated to a chelator moiety, wherein radiometal ion is 134 Ce.

In some embodiments, the radioconjugate of the disclosure comprises an anti-PSMA antibody which comprises a heavy chain variable region (VH) having at least 80%, at least 85%, at least 90%, at least 95%, or at least 98% sequence identity to the amino acid sequence of SEQ ID NO: 52, a light chain variable region (VL) having at least 80%, at least 85%, at least 90%, at least 95%, or at least 98% sequence identity to the amino acid sequence of SEQ ID NO: 53 and
  a radiometal ion coordinated to a chelator moiety, wherein radiometal ion is 134 Ce.

In some embodiments, the radioconjugate of the disclosure comprises an anti-PSMA antibody which comprises a heavy chain variable region (VH) comprising the amino acid sequence of SEQ ID NO: 52, a light chain variable region (VL) comprising the amino acid sequence of SEQ ID NO: 53 and a radiometal ion coordinated to a chelator moiety, wherein radiometal ion is $^{134}$Ce.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 84, a light chain constant region having at least 80%, at least 85%, at least 90%, at least 95%, or at least 98% sequence identity to the amino acid sequence of SEQ ID NO: 85 and a radiometal ion coordinated to a chelator moiety, wherein radiometal ion is $^{134}$Ce.

In some embodiments, the radioconjugate of the disclosure comprises an anti-PSMA antibody which comprises a heavy chain constant region comprising the amino acid sequence of SEQ ID NO: 84, a light chain constant region comprising the amino acid sequence of SEQ ID NO: 85 and a radiometal ion coordinated to a chelator moiety, wherein radiometal ion is $^{134}$Ce.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 86, a light chain constant region having at least 80%, at least 85%, at least 90%, at least 95%, or at least 98% sequence identity to the amino acid sequence of SEQ ID NO: 85 and a radiometal ion coordinated to a chelator moiety, wherein radiometal ion is $^{134}$Ce.

In some embodiments, the radioconjugate of the disclosure comprises an anti-PSMA antibody which comprises a heavy chain constant region comprising the amino acid sequence of SEQ ID NO: 86, a light chain constant region comprising the amino acid sequence of SEQ ID NO: 85 and a radiometal ion coordinated to a chelator moiety, wherein radiometal ion is $^{134}$Ce.

In some embodiments, the radioconjugate of the disclosure comprises an anti-PSMA antibody which comprises a heavy chain constant region having at least 80%, at least 85%, at least 90%, at least 95%, or at least 98% sequence identity to the amino acid sequence of SEQ ID NO: 90, a light chain constant region having at least 80%, at least 85%, at least 90%, at least 95%, or at least 98% sequence identity to the amino acid sequence of SEQ ID NO: 89 and a radiometal ion coordinated to a chelator moiety, wherein radiometal ion is $^{134}$Ce.

In some embodiments, the radioconjugate of the disclosure comprises an anti-PSMA antibody which comprises a heavy chain constant region comprising the amino acid sequence of SEQ ID NO: 90, a light chain constant region comprising the amino acid sequence of SEQ ID NO: 89 and a radiometal ion coordinated to a chelator moiety, wherein radiometal ion is $^{134}$Ce.

In some embodiments, the chelator is any of the chelator of the disclosure.

Pharmaceutical Composition

Also provided is the use of any of the disclosed antibodies, antigen binding fragments thereof, radioconjugates or ADCs of the disclosure for the preparation of a medicament for treating a PSMA positive cancer.

Also provided is a pharmaceutical composition comprising the antibody, antigen binding fragment thereof radioconjugates or ADCs of the disclosure and a pharmaceutically acceptable carrier.

For therapeutic use, the anti-PSMA antibody, antigen binding fragment thereof, radioconjugates or ADCs of the disclosure may be prepared as pharmaceutical compositions containing an effective amount of the antibody as an active ingredient in a pharmaceutically acceptable carrier.

"Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies, antigen binding fragments thereof, radioconjugates or ADCs of the disclosure in such pharmaceutical formulation may vary from less than about 0.5%, usually to at least about 1% to as much as 15 or 20% by weight and may be selected primarily based on required dose, fluid volumes, viscosities, etc., according to the mode of administration selected. Suitable vehicles and formulations, inclusive of other human proteins, e.g., human serum albumin, are described, for example, in e.g., Remington: The Science and Practice of Pharmacy, 21st Edition, Troy, D. B. ed., Lipincott Williams and Wilkins, Philadelphia, P A 2006, Part 5, Pharmaceutical Manufacturing pp 691-1092, See especially pp. 958-989.

A pharmaceutically acceptable carrier can include a buffer, excipient, stabilizer, or preservative. The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/or in humans.

Examples of pharmaceutically acceptable carriers are solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, or combinations thereof. The amounts of pharmaceutically acceptable carrier(s) in the pharmaceutical compositions may be determined experimentally based on the activities of the carrier(s) and the desired characteristics of the formulation, such as stability and/or minimal oxidation.

Pharmaceutical compositions may comprise buffers such as acetic acid, citric acid, formic acid, succinic acid, phosphoric acid, carbonic acid, malic acid, aspartic acid, histidine, boric acid, Tris buffers, HEPPSO, HEPES, neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); antibacterial and antifungal agents; and preservatives.

Pharmaceutical compositions of the present disclosure can be formulated for a variety of means of parenteral or non-parenteral administration. In one embodiment, the compositions can be formulated for infusion or intravenous administration. Pharmaceutical compositions disclosed herein can be provided, for example, as sterile liquid preparations, e.g., isotonic aqueous solutions, emulsions, suspensions, dispersions, or viscous compositions, which may be buffered to a desirable pH. Formulations suitable for oral administration can include liquid solutions, capsules, sachets, tablets, lozenges, and troches, powders liquid suspensions in an appropriate liquid and emulsions.

Method of Treatment and Uses

Also provided is the use of any of the disclosed antibody, antigen binding fragment thereof, radioconjugates, ADCs or pharmaceutical composition for the treatment of cancer.

In some embodiments, the disclosure provides methods of treating a PSMA expressing cancer in a subject with any of the antibody, antigen binding fragment thereof or pharmaceutical composition of the disclosure.

In some embodiments, the disclosure provides methods of treating a PSMA expressing cancer in a subject with any of the antibody drug conjugate of the disclosure.

In some embodiments, the disclosure provides methods of treating a PSMA expressing cancer in a subject with any of the radioimmunoconjugate of the disclosure.

"Treat," "treating," or "treatment" of a disease or disorder such as cancer refers to accomplishing one or more of the following: reducing the severity and/or duration of the disorder, delaying the progression of the disorder, slowing the progression of the disorder, inhibiting worsening of symptoms characteristic of the disorder being treated, limiting or preventing recurrence of the disorder in subjects that have previously had the disorder, or limiting or preventing recurrence of symptoms in subjects that were previously symptomatic for the disorder. As used herein, the terms "delaying the progression of" or "slowing the progression of" shall include (a) delaying or slowing the development of one or more symptoms or complications of the disease, condition or disorder; (b) delaying or slowing the development of one or more new/additional symptoms or complications of the disease, condition or disorder; and/or (c) delaying or slowing the progression of the disease, condition or disorder to a later stage or more serious form of said disease, condition or disorder.

"Subject" includes any human or nonhuman animal. "Nonhuman animal" includes all vertebrates, e.g., mammals and non-mammals. The term "mammal" as used herein, encompasses any mammal. Examples of mammals include, but are not limited to, non-human primates, cows, horses, sheep, pigs, cats, dogs, mice, rats, rabbits, guinea pigs, monkeys, humans, etc. The terms "subject" and "patient" can be used interchangeably herein. In some embodiments, the subject or patient is human.

A "therapeutically effective amount" refers to an amount effective, at doses and for periods of time necessary, to achieve a desired therapeutic result. A therapeutically effective amount may vary depending on factors such as the disease state, age, sex, and weight of the individual.

In some embodiments, the medical condition is a PSMA expressing cancer.

In some embodiments, the medical condition is a disease or disorder of the prostate. In some embodiments, the disease or disorder is a prostate-related disease or disorder. In some embodiments, the disease or disorder is prostate cancer. In some embodiments, the prostate cancer is a primary prostate cancer. In some embodiments, the prostate cancer is a metastatic prostate cancer. In another embodiment, the prostate cancer is a castration-resistant cancer. In another embodiment, the prostate cancer is a metastatic castration-resistant cancer (mCRPC). In one embodiment, the disease or disorder of the prostate is a prostate intraepithelial neoplasia. In some embodiments, the disease or disorder of the prostate is a prostate tumor. In some embodiments, the prostate tumor is a solid tumor.

In certain embodiments, the disease or disorder is a clear cell renal carcinoma. In certain embodiments, the disease or disorder is a renal cell carcinoma (RCC). In some embodiments, the RCC is a kidney clear cell carcinoma. In some embodiments, the RCC is a kidney papillary cell carcinoma. In certain embodiments, the disease or disorder is a metastatic lesion of a RCC. In certain embodiments, the disease or disorder is a bladder cancer. In certain embodiments, the disease or disorder is a breast cancer. In certain embodiments, the disease or disorder is a kidney cancer. In certain embodiments, the disease or disorder is a neovascular disorder. In certain embodiments, the disease or disorder is a cancer characterized by solid tumor growth. In some embodiments, the neovascular disorder is a clear cell renal carcinoma. In certain embodiments, the disease or disorder is a colorectal cancer. In certain embodiments, the disease or disorder is a breast cancer. In certain embodiments, the disease or disorder is a bladder cancer. In certain embodiments, the disease or disorder is a lung cancer. In certain embodiments, the disease or disorder is a pancreatic cancer. In certain embodiments, the disease or disorder is a non-prostate cancers. In certain embodiments, the disease or disorder is a renal cancer. In certain embodiments, the disease or disorder is a urothelial cancer. In certain embodiments, the disease or disorder is a lung cancer. In certain embodiments, the disease or disorder is a colon cancer. In certain embodiments, the disease or disorder is a breast cancer. In certain embodiments, the disease or disorder is a liver adenocarinaoma.

The cancer can be a hyperproliferative condition or disorder, a solid tumor, a neovasculature, a soft tissue tumor, or a metastatic lesion. "Cancer" is meant to include all types of cancerous growths or oncogenic processes, metastatic tissues or malignantly transformed cells, tissues, or organs, irrespective of histopathology type or stage of invasiveness. Examples of cancers include solid tumors, hematological malignancies, soft tissue tumors, and metastatic lesions. Exemplary solid tumors include malignancies, e.g., sarcomas, and carcinomas (including adenocarcinomas and squamous cell carcinomas) of the various organ systems, such as those affecting prostate, liver, lung, breast, lymphoid, gastrointestinal (e.g., colon), genitourinary tract (e.g., renal, urothelial cells), prostate and pharynx. Adenocarcinomas include malignancies such as most colon cancers, a rectal cancer, a renal-cell carcinoma, a liver cancer, a non-small cell carcinoma of the lung, a cancer of the small intestine and a cancer of the esophagus. Squamous cell carcinomas include malignancies, e.g., in the lung, esophagus, skin, head and neck region, oral cavity, anus, and cervix.

In some embodiments, the disclosure provides methods of treating a PSMA expressing cancer in a subject with any of the antibody, antigen binding fragment thereof or pharmaceutical composition of the disclosure.

In some embodiments, the disclosure provides methods of treating a PSMA expressing cancer in a subject with any of the antibody drug conjugate of the disclosure.

In some embodiments, the disclosure provides methods of treating a PSMA expressing cancer in a subject comprising administering to the subject an antibody, or an antigen binding domain that specifically binds to PSMA wherein the antibody, or an antigen binding domain that binds PSMA comprises a heavy chain variable region (VH) comprising a VH CDR1 having an amino acid sequence of SEQ ID NO:4, a VH CDR2 having an amino acid sequence of and SEQ ID NO:5 and a VH CDR3 having an amino acid sequence of SEQ ID NO:6; and a light chain variable region (VL) comprising a VL CDR1 having an amino acid sequence of SEQ ID NO:7, a VL CDR2 having an amino acid sequence of and SEQ ID NO:8 and a VL CDR3 having an amino acid sequence of SEQ ID NO:9; or a heavy chain variable region (VH) having at least 80%, at least 85%, at least 90%, at least 95%, or at least 98% sequence identity to the amino acid sequence of SEQ ID NO: 52, and/or a light chain variable region (VL) having at least 80%, at least 85%, at least 90%, at least 95%, or at least 98% sequence identity to the amino acid sequence of SEQ ID NO: 53.

In some embodiments, the disclosure provides methods of treating PSMA expressing cancer comprising administering to the subject an antibody, or an antigen binding domain that specifically binds to PSMA wherein the antibody, or an antigen binding domain that binds PSMA comprises a heavy chain variable region (VH) comprising a VH CDR1 having an amino acid sequence of SEQ ID NO:10, a VH CDR2 having an amino acid sequence of and SEQ ID NO:11 and a VH CDR3 having an amino acid sequence of SEQ ID NO:12; and a light chain variable region (VL) comprising a VL CDR1 having an amino acid sequence of SEQ ID NO:13, a VL CDR2 having an amino acid sequence of and SEQ ID NO:14 and a VL CDR3 having an amino acid sequence of SEQ ID NO:15; or a heavy chain variable region (VH) having at least 80%, at least 85%, at least 90%, at least 95%, or at least 98% sequence identity to the amino acid sequence of SEQ ID NO: 54, and/or a light chain variable region (VL) having at least 80%, at least 85%, at least 90%, at least 95%, or at least 98% sequence identity to the amino acid sequence of SEQ ID NO: 55.

In some embodiments, the PSMA expressing cancer is prostate cancer.

In some embodiments, the PSMA expressing cancer is renal cancer.

Also provided are methods of detecting PSMA in a sample comprising obtaining the sample, contacting the sample with the anti-PSMA antibody, the antigen binding fragment thereof or the radioconjugate of the disclosure, and detecting the antibody or radioconjugate bound to PSMA in the sample.

The disclosure provides a method of detecting PSMA in a sample, comprising obtaining the sample, contacting the sample with the anti-PSMA antibody, antigen binding fragment thereof or the radioconjugate comprising the anti-PSMA antibody or antigen binding fragment and detecting the antibody bound to PSMA in the sample.

In some embodiments, the sample may be derived from urine, blood, serum, plasma, saliva, ascites, circulating cells, circulating tumor cells, cells that are not tissue associated (i.e., free cells), tissues (e.g., surgically resected tumor tissue, biopsies, including fine needle aspiration), histological preparations, and the like.

The antibodies and radioconjugates of the disclosure may be used in a variety of assays to detect PSMA in the sample. Exemplary assays are western blot analysis, radioimmunoassay, surface plasmon resonance, immunoprecipitation, equilibrium dialysis, immunodiffusion, electrochemiluminescence (ECL) immunoassay, immunohistochemistry, fluorescence-activated cell sorting (FACS) or ELISA assay.

Kits

Described herein are kits comprising the antibody, antigen binding fragment, radioconjugates, ADCs composition, or the pharmaceutical composition of the disclosure.

The terms "kit" and "article of manufacture" are used as synonyms.

In some embodiments, the disclosure provides a kit comprising the antibody or antigen binding fragment thereof that binds PSMA.

In some embodiments, the disclosure provides a kit comprising the radioconjugates, ADCs or pharmaceutical composition.

The kit may be used for therapeutic uses and as diagnostic kits.

The kit may be used to detect the presence of PSMA in a sample.

In some embodiments, the kit comprises the anti-PSMA antibody or antigen binding fragment of the disclosure and reagents for detecting the PSMA binding protein. In some embodiments, the kit comprises the radioconjugates of the disclosure and reagents for detecting the PSMA binding protein. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

In some embodiments, the kit comprises the disclosed antibody, antigen binding fragment thereof radioconjugates, ADCs or pharmaceutical composition in a container and instructions for use of the kit.

In some embodiments, the antibody or antigen binding fragment thereof that binds PSMA in the kit is labeled.

In some embodiments, the kit comprises the disclosed antibody, antigen binding fragment thereof, radioconjugates, ADCs or pharmaceutical composition a container and instructions for use of the kit.

In some embodiments, the kit comprises an antibody, antigen binding fragment thereof that binds PSMA, wherein the antibody or antigen binding fragment comprises:
the VH of SEQ ID NO: 52 and the VL of SEQ ID NO: 53;
the VH of SEQ ID NO: 54 and the VL of SEQ ID NO: 55;
the VH of SEQ ID NO: 56 and the VL of SEQ ID NO: 57;
the VH of SEQ ID NO: 58 and the VL of SEQ ID NO: 59;
the VH of SEQ ID NO: 60 and the VL of SEQ ID NO: 61;
the VH of SEQ ID NO: 62 and the VL of SEQ ID NO: 63;
the VH of SEQ ID NO: 64 and the VL of SEQ ID NO: 65;
the VH of SEQ ID NO: 66 and the VL of SEQ ID NO: 67; or
the VH of SEQ ID NO: 278 and the VL of SEQ ID NO: 279.

In some embodiments, the kit comprises the antibody or antigen binding fragment thereof that binds PSMA comprising a VH of SEQ ID NO: 52 and a VL of SEQ ID NO: 53.

In some embodiments, the kit comprises an antibody or antigen binding fragment thereof that binds PSMA comprising the amino acid sequence of SEQ ID NOs: 84, 85, 86, 88, 89, 90, 92, 93, 94, 95, 96, 97, 98, 99, 100, 101, 102, 103, 268, 269, 282, 284, or 288.

In some embodiments, the kit comprises an antibody or antigen binding fragment thereof that binds PSMA comprising the amino acid sequence selected from the group consisting of (a) SEQ ID NO: 84 and SEQ ID NO: 85; (b) SEQ ID NO: 86 and SEQ ID NO: 85; (c) SEQ ID NO: 88 and SEQ ID NO: 89; (d) SEQ ID NO: 90 and SEQ ID NO: 89; (e) SEQ ID NO: 92 and SEQ ID NO: 93; f) SEQ ID NO: 94 and SEQ ID NO: 95; g) SEQ ID NO: 96 and SEQ ID NO: 97; h) SEQ ID NO: 98 and SEQ ID NO: 99; i) SEQ ID NO: 100 and SEQ ID NO: 101; j) SEQ ID NO: 102 and SEQ ID NO: 103; k) SEQ ID NO: 268 and SEQ ID NO: 269; l) SEQ ID NO: 284 and SEQ ID NO: 269; m) SEQ ID NO: 282 and n) SEQ ID NO: 288.

In In some embodiments, the kit comprises an antibody drug conjugate comprising an anti-PSMA antibody or antigen binding fragment thereof which comprises
a heavy chain variable region (VH) comprising a VH CDR1 having an amino acid sequence of SEQ ID NO:4, a VH CDR2 having an amino acid sequence of and SEQ ID NO:5 and a VH CDR3 having an amino acid sequence of SEQ ID NO:6; a light chain variable region (VL) comprising a VL CDR1 having an amino acid sequence of SEQ ID NO:7, a VL CDR2 having an amino acid sequence of and SEQ ID NO:8 and a VL CDR3 having an amino acid sequence of SEQ ID NO:9; and/or
a heavy chain variable region (VH) having at least 80%, at least 85%, at least 90%, at least 95%, or at least 98% sequence identity to the amino acid sequence of SEQ ID NO: 52, a light chain variable region (VL) having at least 80%, at least 85%, at least 90%, at least 95%, or at least 98% sequence identity to the amino acid sequence of SEQ ID NO: 53.

EXAMPLES

Example 1. Antigen Generation

Human prostate-specific membrane antigen (PSMA) is a type II transmembrane zinc metallopeptidase that has a unique three part structure: a 19 a.a. intracellular domain, a 24 a.a. transmembrane domain, and a 707 a.a. extracellular domain. It is known to overexpress in the epithelium of nearly all primary and metastatic prostate cancer cells versus normal cells and is thus an attractive target for targeted therapies such as ADCs and radio-conjugates.

To identify antibodies binding to this target, extracellular domains (ECD) of human PSMA and cyno PSMA were used as primary immunogen during antibody discovery. Human PSMA ECD was produced based on Uniprot Accession #Q04609 sequence. The ECD construct was designed with a 6X His-tag sequence (SEQ ID NO: 339) at the N-terminus (Protein AA ID PSMW39; SEQ ID NO: 1). The PSMA ECD from *Macaca fascicularis* was produced based on NCBI Accession #EHH56646.1, fused to an Avi tag and 6X His-tag (SEQ ID NO: 339) at the N-terminus (Protein AA ID PSMW1; SEQ ID NO: 2). The extracellular domain (ECD) of PSMA from *Mus musculus* was produced based on Uniprot Accession #O35409, fused to an Avi tag and 6X His-tag (SEQ ID NO: 339) at the N-terminus to facilitate purification (Protein AA ID PSMW29; SEQ ID NO: 3). The cynomolgus and murine ECD expression constructs were used to transiently transfect HEK293-6E cells using PEI MAX (transfection grade linear polyethylenimine hydrochloride, Polysciences). Briefly, transfected cells were incubated for six days at 37° C. with 5% $CO_2$ in a shake flask and harvested when the viability had dropped to 80%. The human ECD expression construct was used to stably transfect Expi-CHO using Expifectamine-CHO (ThermoFisher Scientific) according to the recommendations of the manufacturer. Briefly, stable transfectants were selected with G418 (Thermo Fisher Scientific; Cat #10131027). Monoclones expressing the highest levels of human PSMA ECD protein were identified by ELISA (R&D Systems; Cat #DY4234-05). High PSMW39-expressing monoclones were cultured in Dynamis media (Thermo Fisher Scientific; Cat #A2661501) supplemented with 5% Cell Boost 5 (Hyclone; Cat #SH30865.01) and incubated at 37° C., 125 rpm and 5% $CO_2$ until the cell viability dropped below 80%. On days 2, 4, 7, 9 and 11, 6 mL of 20% D-glucose (2 g/L final conc.) and 6 mL of 200 mM L-glutamine (2 mM final conc.) was added as feed to each of the flasks. For the purification of all recombinant PSMA proteins, cells were removed via centrifugation and His-tagged PSMA proteins were purified from the supernatant via immobilized metal affinity chromatography using His 60 Ni Superflow Resin (Clonetech, Cat #635662) followed by Superdex 200 preparative size exclusion chromatography (SEC) (GE Healthcare) and formulated into 1×DPBS, pH 7.2 containing 1 mM $CaCl_2$, 0.5 mM $MgCl_2$, and 0.5 mM $ZnCl_2$. The isolation of the homodimeric species was confirmed via analytical size exclusion chromatography. The amino acid sequences of the recombinant antigens are shown in Table 3.

TABLE 3

| Protein AA ID | Description | SEQ ID NO: | Amino Acid Sequence |
|---|---|---|---|
| PSMW39 | Human PSMA ECD (Lys44-Ala750), N-6xHis | 1 | HHHHHHKSSNEATNITPKHNMKAFLDELKAENIKKFLYNFTQIPHLAGTEQNFQLAKQIQSQWKEFGLDSVELAHYDVLLSYPNKTHPNYISIINEDGNEIFNTSLFEPPPPGYENVSDIVPPFSAFSPQGMPEGDLVYVNYARTEDFFKLERDMKINCSGKIVIARYGKVFRGNKVKNAQLAGAKGVILYSDPADYFAPGVKSYPDGWNLPGGGVQRGNILNLNGAGDPLTPGYPANEYAYRRGIAEAVGLPSIPVHPIGYYDAQKLLEKMGGSAPPDSSWRGSLKVPYNVGPGFTGNFSTQKVKMHIHSTNEVTRIYNVIGTLRGAVEPDRYVILGGHRDSWVFGGIDPQSGAAVVHEIVRSFGTLKKEGWRPRRTILFASWDAEEFGLLGSTEWAEENSRLLQERGVAYINADSSIEGNYTLRVDCTPLMYSLVHNLTKELKSPDEGFEGKSLYESWTKKSPSPEFSGMPRISKLGSGNDFEVFFQRLGIASGRARYTKNWETNKFSGYPLYHSVYETYELVEKFYDPMFKYHLTVAQVRGGMVFELANSIVLPFDCRDYAVVLRKYADKIYSISMKHPQEMKTYSVSFDSLFSAVKNFTEIASKFSERLQDFDKSNPIVLRMMNDQLMFLERAFIDPLGLPDRPFYRHVIYAPSSHNKYAGESFPGIYDALFDIESKVDPSKAWGEVKRQIYVAAFTVQAAAETLSEVA |

TABLE 3-continued

| Protein AA ID | Description | SEQ ID NO: | Amino Acid Sequence |
|---|---|---|---|
| PSMW1 | Avi-6xHis-GS-cyno PSMA ECD | 2 | GLNDIFEAQKIEWHEHHHHHHGSKSSSEATNITPKHNMKAFLDELKAENIKKFLHNFTQIPHLAGTEQNFQLAKQIQSQWKEFGLDSVELTHYDVLLSYPNKTHPNYISIINEDGNEIFNTSLFEPPPAGYENVSDIVPPFSAFSPQGMPEGDLVYVNYARTEDFFKLERDMKINCSGKIVIARYGKVFRGNKVKNAQLAGATGVILYSDPDDYFAPGVKSYPDGWNLPGGGVQRGNILNLNGAGDPLTPGYPANEYAYRRGMAEAVGLPSIPVHPIGYYDAQKLLEKMGGSASPDSSWRGSLKVPYNVGPGFTGNFSTQKVKMHIHSTSEVTRIYNVIGTLRGAVEPDRYVILGGHRDSWVFGGIDPQSGAAVVHEIVRSFGMLKKEGWRPRRTILFASWDAEEFGLLGSTEWAEENSRLLQERGVAYINADSSIEGNYTLRVDCTPLMYSLVYNLTKELESPDEGFEGKSLYESWTKKSPSPEFSGMPRISKLGSGNDFEVFFQRLGIASGRARYTKNWETNKFSSYPLYHSVYETYELVEKFYDPMFKYHLTVAQVRGGMVFELANSVVLPFDCRDYAVVLRKYADKIYNISMKHPQEMKTYSVSFDSLFSAVKNFTEIASKFSERLRDFDKSNPILLRMMNDQLMFLERAFIDPLGLPDRPFYRHVIYAPSSHNKYAGESFPGIYDALFDIESKVDPSQAWGEVKRQISIATFTVQAAAETLSEVA |
| PSMW29 | Avi-6xHis-GS-mouse PSMA (45-752) | 3 | GLNDIFEAQKIEWHEHHHHHHGSKPSNEATGNVSHSGMKKEFLHELKAENIKKFLYNFTRTPHLAGTQNNFELAKQIHDQWKEFGLDLVELSHYDVLLSYPNKTHPNYISIINEDGNEIFKTSLSEQPPPGYENISDVVPPYSAFSPQGTPEGDLVYVNYARTEDFFKLEREMKISCSGKIVIARYGKVFRGNMVKNAQLAGAKGMILYSDPADYFVPAVKSYPDGWNLPGGGVQRGNVLNLNGAGDPLTPGYPANEHAYRHELTNAVGLPSIPVHPIGYDDAQKLLEHMGGPAPPDSSWKGGLKVPYNVGPGFAGNFSTQKVKMHIHSYTKVTRIYNVIGTLKGALEPDRYVILGGHRDAWVFGGIDPQSGAAVVHEIVRSFGTLKKKGRRPRRTILFASWDAEEFGLLGSTEWAEEHSRLLQERGVAYINADSSIEGNYTLRVDCTPLMYSLVYNLTKELQSPDEGFEGKSLYDSWKEKSPSPEFIGMPRISKLGSGNDFEVFFQRLGIASGRARYTKNWKTNKVSSYPLYHSVYETYELVVKFYDPTFKYHLTVAQVRGAMVFELANSIVLPFDCQSYAVALKKYADTIYNISMKHPQEMKAYMISFDSLFSAVNNFTDVASKFNQRLQELDKSNPILLRIMNDQLMYLERAFIDPLGLPGRPFYRHIIYAPSSHNKYAGESFPGIYDALFDISSKVNASKAWNEVKRQISIATFTVQAAAETLREVA |

Example 2. Generation of Anti-PSMA Antibodies

Antibody generation using transgenic Ablexis® mice

Ablexis® kappa, lambda, and kappa/lambda hybrid mice were used for antibody discovery. Ablexis® mice generate antibodies having human variable domains linked to human CH1 and CL domains, chimeric human/mouse hinge regions, and mouse Fc regions. Antibodies produced by the Kappa Mouse lack sequence derived from mouse VH, DH and JH exons and mouse Vκ, Jκ and Cκ exons. The endogenous mouse Igλ. is active in the Kappa Mouse. The human Igκ chains comprise approximately 90-95% of the naïve repertoire and mouse Igλ. chains comprise approximately 5-10% of the naïve repertoire in this strain. Antibodies produced by the Lambda Mouse lack sequence derived from mouse VH, DH and JH exons and mouse Vλ, Jλ. and Cλ. exons. The endogenous mouse Igλ is active in the Lambda Mouse. The human Igλ, chains comprise approximately 40% of the naïve repertoire and mouse Igκ chains comprise approximately 60% of the naïve repertoire. The preparation and use of Ablexis®, and the genomic modifications carried by such mice, is described in WO11/123708.

For antibody discovery, Ablexis kappa/lambda hybrid mice were immunized with recombinant human PSMA antigen (PSMW39.002) and cynomolgus PSMA antigen (PSMW1.009) in combination with CL413 adjuvant (InvivoGen, VAC-C413-5). Briefly, mice were boosted on Days 0, 7, 14, 21, and 28 before being bled on Day 35 for serological analysis. Serology was performed on human PSMA (+) cells C4-2B (AG000002300) and a human PSMA knockout cell line (AG000002521). In total, 8 mice were selected for hybridoma fusion and finally boosted on Day 56 with PSMW39.002 or an equimolar mixture of PSMW39.002 and PSMW1.009. This preparation also included recombinant anti-mouse CD40 mAb (R&D Systems, MAB440) to stimulate B cell expansion. On Day 60, spleen and draining lymph nodes were harvested from these mice, pooled and homogenized into a single-cell suspension. Stable hybridomas were generated by PEG-mediated fusion of mouse myeloma cell line FO with the pooled mouse homogenate, followed by HAT selection.

Supernatants from these hybridomas were screened against PSMA (+) C4-2B cells by MSD. From this primary screen, 440 positive samples were identified and re-arrayed for confirmatory screening. Confirmatory screening was performed by ELISA as well as Fluorescence-activated cell sorting (FACS) to validate binding to PSMA protein and C4-2B cells, respectively. To ensure specificity, samples were also screened against an irrelevant negative control sample TfRW2. Based on the screening results, 96 samples were advanced past confirmatory screening from the 440 samples identified and submitted for V region recovery.

V Region Cloning

Total cellular RNA was prepared from $5 \times 10^6$ hybridoma cells using RNEASY Plus mini-kit (Qiagen) according to manufacturer protocol. cDNA was subsequently synthesized from total RNA using the SMARTER cDNA synthesis kit (Clontech, Mount View, CA) essentially according to manufacturer's instructions. Briefly, to facilitate first strand cDNA synthesis reaction, a modified oligo(dT) primer (SMART CDS primer IIA) was used to transcribe all mRNAs in conjunction with a reverse transcriptase (SMARTScribe RT) which also adds an oligonucleotide cap (Smarter II A) on the 3' end of the cDNA when it reaches the 5' end of mRNA. Subsequent amplification of the VH and VL fragments was performed using a 2-step PCR amplification using 5' primers targeting the Smarter IIA cap and 3' primers targeting consensus regions in CH1 or CL. Each 50 µl PCR reaction in the first step consisted of 20 µM of forward and reverse primer mixes, 25 µl of PRIMESTAR Max DNA polymerase premix, 2 µl of unpurified cDNA, and 21 µl of double-distilled $H_2O$. The PCR components were mixed on ice in thin-walled PCR tubes and transferred to a thermacycler preheated to 94° C. The cycling program consisted of the following steps: (i) 94° C. for 3 min; (ii) 35 cycles (94° C. for 30 Sec, 55° C. for 1 min, 68° C. for 1 min); (iii) 72° C. for 7 min. The PCR reaction fragments were then gel purified and subjected to another round of PCR (cycling conditions same as PCR #1) using VL and VH 2nd round primers that also contained an additional 15 bp region complementary to our in-house proprietary expression vectors for human light chain (Lonza-huIgk or Lonza-huIgk) and heavy chain (Lonza-huIgG1) constant regions. The subsequent PCR fragments were gel purified and VL and VH fragments subcloned in-frame in Lonza-huIgk/huIgλ and Lonza-huIgG1 vectors, respectively, using In-Fusion® HD Cloning kit (Takara Bio), according to manufacturer recommendations. The expression vectors were then purified using Qiaprep Miniprep Kit (Qiagen) and submitted to Genewiz for sanger sequencing, resulting in 126 unique VL and VH sequence pairs which were further narrowed down to 96 pairs based on an in-silico developability assessment risk analysis.

ExpiCHO Transfection and Purification

The 96 unique VH/VL pairs reformatted as huIgG1 were transiently produced using ExpiCHO-S™ system (ThermoFisher Scientific) according to manufacturer's recommendation. Briefly, ExpiCHO-S™ cells were maintained in suspension in ExpiCHO™ expression medium (ThermoFisher Scientific, Cat #A29100) in an orbital shaking incubator set at 37° C., 8% CO2 and 125 RPM. The cells were passaged and diluted prior to transfection to $6.0 \times 10^6$ cells/ml, maintaining cell viability at 95.0% or better. Transient transfections were done using the ExpiFectamine™ CHO transfection kit (ThermoFisher Scientific, Cat #A29131). For each ml of diluted cells to be transfected, 0.5 µg of encoding DNA (HC:LC=1:3) and 0.5 µg of pAdVAntage DNA (Promega, Cat #E1711) was used and diluted into OptiPRO™ SFM complexation medium (ThermoFisher Scientific, Cat #12309019). ExpiFectamine™ CHO reagent was used at a 1:4 ratio (v/v, DNA:reagent) and diluted into OptiPRO™. The diluted DNA and transfection reagent were combined for one minute, allowing DNA/lipid complex formation, and then added to the cells. After overnight incubation, ExpiCHO™ feed and ExpiFectamine™ CHO enhancers were added to the cells as per the manufacturer's Standard protocol. Cells were incubated with orbital shaking (125 rpm) at 37° C. for seven days post-transfection prior to harvesting the culture broth. The culture supernatant from the transiently transfected ExpiCHOS™ cells was clarified by centrifugation (30 min, 3000 rcf) followed by two sterile filtration steps, first through a 0.45 µm filter and then through a 0.2 µm filter (PES membrane, Corning; Corning, NY).

Purification of Anti-PSMA Antibodies

Antibodies were purified from the clarified supernatants using Mabselect SuRe Protein A columns equilibrated with 1×D-PBS, pH 7.2 prior. Unbound proteins were removed by washing extensively with 1×DPBS, pH 7.2. Bound protein was eluted with 0.1 M Na-acetate, pH 3.5. Peak fractions were neutralized with 2.5 M Tris pH 7.5 and pooled. The neutralized fraction pools were then dialyzed into 1×DPBS. The protein concentration for each elution pool was determined by measuring absorbance at OD280 nm and calculated using absorbance extinction coefficient based on the amino acid sequence.

Sequences of PSMA Antibodies

Sequences of representative PSMA antibodies are provided in Tables 4-19. Table 4 shows the Kabat HCDR1, HCDR2 and HCDR3 of selected anti-PSMA selected antibodies. Table 5 shows the Kabat LCDR1, LCDR2 and LCDR3 of the selected anti-PSMA antibodies. Table 6 shows the Chothia HCDR1, HCDR2 and HCDR3 of selected anti-PSMA antibodies. Table 7 shows the Chothia LCDR1, LCDR2 and LCDR3 of selected anti-PSMA antibodies. Table 8 shows the ABM HCDR1, HCDR2 and HCDR3 of selected anti-PSMA antibodies. Table 9 shows the ABM LCDR1, LCDR2 and LCDR3 of selected anti-PSMA antibodies. Table 10 shows the IMTG HCDR1, HCDR2 and HCDR3 of selected anti-PSMA antibodies. Table 11 shows the IMTG LCDR1, LCDR2 and LCDR3 of selected anti-PSMA antibodies. Table 12 shows the VH and VL amino acid sequences of selected anti-PSMA antibodies. Table 13 shows the VH nucleic acid sequences of selected anti-PSMA antibodies. Table 14 shows the VL nucleic acid sequences of selected anti-PSMA antibodies. Table 15 shows the HC amino acid sequences of selected anti-PSMA antibodies. Table 16 shows the LC amino acid sequences of selected anti-PSMA antibodies. Table 17 shows the HC nucleotide sequences of selected anti-PSMA antibodies. Table 18 shows the LC nucleotide sequences of selected anti-PSMA antibodies. Table 19 summarizes the SEQ ID NO: assigned to the selected anti-PSMA antibodies.

TABLE 4

HCDRs of selected anti-PSMA antibodies using Kabat delineation

| mAb | HCDR1 sequence | HCDR1 SEQ ID NO: | HCDR2 sequence | HCDR2 SEQ ID NO: | HCDR3 sequence | HCDR3 SEQ ID NO: |
|---|---|---|---|---|---|---|
| PSMB1154 | RYGMH | 4 | LISYDGSNRYYADSVKG | 5 | ERESSGWFEGYFDY | 6 |
| PSMB2945 | RYGMH | 4 | LISYDGSNRYYADSVKG | 5 | ERESSGWFEGYFDY | 6 |
| PSMB1183 | SYYWN | 10 | RIYSSGNTDYNPSLKS | 11 | GRGANVGLFDY | 12 |
| PSMB3003 | SYYWN | 10 | RIYSSGNTDYNPSLKS | 11 | GRGANVGLFDY | 12 |
| PSMB1157 | GYGMH | 16 | VISYDGSNRYYADSVKG | 17 | DGNWGSLDLYFDL | 18 |
| PSMB1156 | SYGMH | 22 | VISYDGSNKYYADSVKG | 23 | EHYDSSGYYHGYYGMDV | 24 |
| PSMB1088 | SYDMH | 28 | VISFDGSNKYYVDSVKG | 29 | TYYDILTGYSHYSYGMDV | 30 |
| PSMB1098 | TYGMH | 34 | FISYDGSNKYYADSVKG | 35 | RDNLRFLEWFMDV | 36 |
| PSMB1113 | IYSMN | 40 | SISSSSSYIFYADSVKG | 41 | SSYGADY | 42 |
| PSMB1195 | SYSLN | 46 | SISSSSSYISYADAVKG | 47 | DRGFLEDYYYYYGMDV | 48 |

TABLE 5

LCDRs of selected anti-PSMA antibodies using Kabat delineation

| mAb | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|
| PSMB1154 | GGNNIGSKSVH | 7 | DNSDRPS | 8 | QVWDSSSDHVV | 9 |
| PSMB2945 | GGNNIGSKSVH | 7 | DNSDRPS | 8 | QVWDSSSDHVV | 9 |
| PSMB1183 | TGSNSNIGANYDVH | 13 | GNINRPL | 14 | QSYDFSLSGSV | 15 |
| PSMB3003 | TGSNSNIGANYDVH | 13 | GNINRPL | 14 | QSYDFSLSGSV | 15 |
| PSMB1157 | TGSSSNIGADYDVH | 19 | VNNNRPS | 20 | QSYDNTLSGVV | 21 |
| PSMB1156 | SGSSSNIGSNYVY | 25 | SNNQRPS | 26 | AARDDSLGYV | 27 |
| PSMB1088 | RASQGISNYLA | 31 | ATSTLQS | 32 | QKYNSAPFT | 33 |
| PSMB1098 | RASQSVRSNLA | 37 | GASTRAT | 38 | HQYNDWPPYT | 39 |
| PSMB1113 | RASQDITNFLA | 43 | TASTLQS | 44 | QKYNSAPLT | 45 |
| PSMB1195 | RASQGISNWLA | 49 | VASSLQS | 50 | QQAYSFPLT | 51 |

TABLE 6

HCDRs of selected anti-PSMA antibodies using Chothia delineation

| mAb | HCDR1 sequence | HCDR1 SEQ ID NO: | HCDR2 sequence | HCDR2 SEQ ID NO: | HCDR3 sequence | HCDR3 SEQ ID NO: |
|---|---|---|---|---|---|---|
| PSMB1154 | GFTLSRY | 124 | SYDGSN | 125 | ERESSGWFEGYFDY | 6 |
| PSMB2945 | GFTLSRY | 124 | SYDGSN | 125 | ERESSGWFEGYFDY | 6 |
| PSMB1183 | GGSISSY | 130 | YSSGN | 131 | GRGANVGLFDY | 12 |
| PSMB3003 | GGSISSY | 130 | YSSGN | 131 | GRGANVGLFDY | 12 |
| PSMB1157 | VRTFSGY | 136 | SYDGSN | 125 | DGNWGSLDLYFDL | 18 |
| PSMB1156 | GFTFTSY | 142 | SYDGSN | 125 | EHYDSSGYYHGYYGMDV | 24 |
| PSMB1088 | GFTFSSY | 148 | SFDGSN | 149 | TYYDILTGYSHYSYGMDV | 30 |
| PSMB1098 | GFTFSTY | 154 | SYDGSN | 125 | RDNLRFLEWFMDV | 36 |
| PSMB1113 | GFTLSIY | 160 | SSSSSY | 161 | SSYGADY | 42 |
| PSMB1195 | GFTFSSY | 166 | SSSSSY | 167 | DRGFLEDYYYYGMDV | 48 |

TABLE 7

LCDRs of selected anti-PSMA antibodies using Chothia delineation

| mAb | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|
| PSMB1154 | GGNNIGSKSVH | 7 | DNSDRPS | 8 | QVWDSSSDHVV | 9 |
| PSMB2945 | GGNNIGSKSVH | 7 | DNSDRPS | 8 | QVWDSSSDHVV | 9 |
| PSMB1183 | TGSNSNIGANYDVH | 13 | GNINRPL | 14 | QSYDFSLSGSV | 15 |
| PSMB3003 | TGSNSNIGANYDVH | 13 | GNINRPL | 14 | QSYDFSLSGSV | 15 |
| PSMB1157 | TGSSSNIGADYDVH | 19 | VNNNRPS | 20 | QSYDNTLSGVV | 21 |
| PSMB1156 | SGSSSNIGSNYVY | 25 | SNNQRPS | 26 | AARDDSLSGYV | 27 |
| PSMB1088 | RASQGISNYLA | 31 | ATSTLQS | 32 | QKYNSAPFT | 33 |
| PSMB1098 | RASQSVRSNLA | 37 | GASTRAT | 38 | HQYNDWPPYT | 39 |
| PSMB1113 | RASQDITNFLA | 43 | TASTLQS | 44 | QKYNSAPLT | 45 |
| PSMB1195 | RASQGISNWLA | 49 | VASSLQS | 50 | QQAYSFPLT | 51 |

TABLE 8

HCDRs of selected anti-PSMA antibodies using ABM delineation

| mAb | HCDR1 sequence | HCDR1 SEQ ID NO: | HCDR2 sequence | HCDR2 SEQ ID NO: | HCDR3 sequence | HCDR3 SEQ ID NO: |
|---|---|---|---|---|---|---|
| PSMB1154 | GFTLSRYGMH | 172 | LISYDGSNRY | 173 | ERESSGWFEGYFDY | 6 |
| PSMB2945 | GFTLSRYGMH | 172 | LISYDGSNRY | 173 | ERESSGWFEGYFDY | 6 |
| PSMB1183 | GGSISSYYWN | 178 | RIYSSGNTD | 179 | GRGANVGLFDY | 12 |
| PSMB3003 | GGSISSYYWN | 178 | RIYSSGNTD | 179 | GRGANVGLFDY | 12 |
| PSMB1157 | VRTFSGYGMH | 184 | VISYDGSNRY | 185 | DGNWGSLDLYFDL | 18 |
| PSMB1156 | GFTFTSYGMH | 190 | VISYDGSNKY | 191 | EHYDSSGYYHGYYGMDV | 24 |
| PSMB1088 | GFTFSSYDMH | 196 | VISFDGSNKY | 197 | TYYDILTGYSHYSYGMDV | 30 |
| PSMB1098 | GFTFSTYGMH | 202 | FISYDGSNKY | 203 | RDNLRFLEWFMDV | 36 |

TABLE 8-continued

HCDRs of selected anti-PSMA antibodies using ABM delineation

| mAb | HCDR1 sequence | HCDR1 SEQ ID NO: | HCDR2 sequence | HCDR2 SEQ ID NO: | HCDR3 sequence | HCDR3 SEQ ID NO: |
|---|---|---|---|---|---|---|
| PSMB1113 | GFTLSIYSMN | 208 | SISSSSSYIF | 209 | SSYGADY | 42 |
| PSMB1195 | GFTFSSYSLN | 214 | SISSSSSYIS | 215 | DRGFLEDYYYYYGMDV | 48 |

TABLE 9

LCDRs of selected anti-PSMA antibodies using ABM delineation

| mAb | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|
| PSMB1154 | GGNNIGSKSVH | 7 | DNSDRPS | 8 | QVWDSSSDHVV | 9 |
| PSMB2945 | GGNNIGSKSVH | 7 | DNSDRPS | 8 | QVWDSSSDHVV | 9 |
| PSMB1183 | TGSNSNIGANYDVH | 13 | GNINRPL | 14 | QSYDFSLSGSV | 15 |
| PSMB3003 | TGSNSNIGANYDVH | 13 | GNINRPL | 14 | QSYDFSLSGSV | 15 |
| PSMB1157 | TGSSSNIGADYDVH | 19 | VNNNRPS | 20 | QSYDNTLSGVV | 21 |
| PSMB1156 | SGSSSNIGSNYVY | 25 | SNNQRPS | 26 | AARDDSLSGYV | 27 |
| PSMB1088 | RASQGISNYLA | 31 | ATSTLQS | 32 | QKYNSAPFT | 33 |
| PSMB1098 | RASQSVRSNLA | 37 | GASTRAT | 38 | HQYNDWPPYT | 39 |
| PSMB1113 | RASQDITNFLA | 43 | TASTLQS | 44 | QKYNSAPLT | 45 |
| PSMB1195 | RASQGISNWLA | 49 | VASSLQS | 50 | QQAYSF | 51 |

TABLE 10

HCDRs of selected anti-PSMA antibodies using IMTG delineation

| mAb | HCDR1 sequence | HCDR1 SEQ ID NO: | HCDR2 sequence | HCDR2 SEQ ID NO: | HCDR3 sequence | HCDR3 SEQ ID NO: |
|---|---|---|---|---|---|---|
| PSMB1154 | GFTLSRYG | 220 | ISYDGSNR | 221 | ARERESSGWFEGYFDY | 222 |
| PSMB2945 | GFTLSRYG | 220 | ISYDGSNR | 221 | ARERESSGWFEGYFDY | 222 |
| PSMB1183 | GGSISSYY | 226 | IYSSGNT | 227 | ARGRGANVGLFDY | 228 |
| PSMB3003 | GGSISSYY | 226 | IYSSGNT | 227 | ARGRGANVGLFDY | 228 |
| PSMB1157 | VRTFSGYG | 232 | ISYDGSNR | 233 | ARDGNWGSLDLYFDL | 234 |
| PSMB1156 | GFTFTSYG | 238 | ISYDGSNK | 239 | AREHYDSSGYYHGYYGMDV | 240 |
| PSMB1088 | GFTFSSYD | 244 | ISFDGSNK | 245 | ARTYYDILTGYSHYSYGMDV | 246 |
| PSMB1098 | GFTFSTYG | 250 | ISYDGSNK | 251 | AGRDNLRFLEWFMDV | 252 |
| PSMB1113 | GFTLSIYS | 256 | ISSSSSYI | 257 | ARSSYGADY | 258 |
| PSMB1195 | GFTFSSYS | 262 | ISSSSSYI | 263 | ARDRGFLEDYYYYYGMDV | 264 |

TABLE 11

LCDRs of selected anti-PSMA antibodies using IMTG delineation

| mAb | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|
| PSMB1154 | NIGSKS | 223 | DNS | NA | QVWDSSSDHVV | 9 |
| PSMB2945 | NIGSKS | 223 | DNS | NA | QVWDSSSDHVV | 9 |

TABLE 11-continued

LCDRs of selected anti-PSMA antibodies using IMTG delineation

| mAb | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|
| PSMB1183 | NSNIGANYD | 229 | GNI | NA | QSYDFSLSGSV | 15 |
| PSMB3003 | NSNIGANYD | 229 | GNI | NA | QSYDFSLSGSV | 15 |
| PSMB1157 | SSNIGADYD | 235 | VNN | NA | QSYDNTLSGVV | 21 |
| PSMB1156 | SSNIGSNY | 241 | SNN | NA | AARDDSLSGYV | 27 |
| PSMB1088 | QGISNY | 247 | ATS | NA | QKYNSAPFT | 33 |
| PSMB1098 | QSVRSN | 253 | GAS | NA | HQYNDWPPYT | 39 |
| PSMB1113 | QDITNF | 259 | TAS | NA | QKYNSAPLT | 45 |
| PSMB1195 | QGISNW | 265 | VAS | NA | QQAYSFPLT | 51 |

NA = Not Applicable.

TABLE 12

VH and VL amino acid sequence of selected anti-PSMA antibodies

| Antibody | VH name | VH amino acid sequence | VH SEQ ID NO: | VL name | VL amino acid sequence | VL SEQ ID NO: |
|---|---|---|---|---|---|---|
| PSMB1154 | VD000060663_VH | EVQLVESGGGEVQPGRSLRLTCAVSGFTLSRYGMHWVRQAPGKGLEWAALISYDGSNRYYADSVKGRFTISRDNSKNTVFLQMNSLRAEDTAVYYCARERESSGWFEGYFDYWGQGTTVTSS | 52 | VD000060661_VL | QLVLTQPPSVSVAPGQTARITCGGNNIGSKSVHWYQQKPGQAPVLVVYDNSDRPSGIPERFSGSNSGNTATLTISRVEVGDEADYYCQVWDSSSDHVVFGGGTKLTVL | 53 |
| PSMB2945 | VD000060663_VH | EVQLVESGGGEVQPGRSLRLTCAVSGFTLSRYGMHWVRQAPGKGLEWAALISYDGSNRYYADSVKGRFTISRDNSKNTVFLQMNSLRAEDTAVYYCARERESSGWFEGYFDYWGQGTTVTSS | 52 | VD000060661_VL | QLVLTQPPSVSVAPGQTARITCGGNNIGSKSVHWYQQKPGQAPVLVVYDNSDRPSGIPERFSGSNSGNTATLTISRVEVGDEADYYCQVWDSSSDHVVFGGGTKLTVL | 53 |
| PSMB1183 | VD000045910_VH | QVQLQESGPGLVKSSETLSLTCTVSGGSISSYYWNWIRQPAGKGLEWIGRIYSSGNTDYNPSLKSRVTMSVDTSKNQFSLKLISVTAADTAVYYCARGRGANVGLFDYWGQGTLVTVSS | 54 | VD000060769_VL | QSALTQPPSVSGAPGQRVTISCTGSNSNIGANYDVHWYQHLPGTAPKLLIYGNINRPLGVPDRFSGSRSGTSASLAITGLQAEDEADYYCQSYDFSLSGSVFGVGTKLTVL | 55 |
| PSMB3003 | VD000045910_VH | QVQLQESGPGLVKSSETLSLTCTVSGGSISSYYWNWIRQPAGKGLEWIGRIYSSGNTDYNPSLKSRVTMSVDTSKNQFSLKLISVTAADTAVYYCARGRGANVGLFDYWGQGTLVTVSS | 54 | VD000060769_VL | QSALTQPPSVSGAPGQRVTISCTGSNSNIGANYDVHWYQHLPGTAPKLLIYGNINRPLGVPDRFSGSRSGTSASLAITGLQAEDEADYYCQSYDFSLSGSVFGVGTKLTVL | 55 |

TABLE 12-continued

VH and VL amino acid sequence of selected anti-PSMA antibodies

| Antibody | VH name | VH amino acid sequence | VH SEQ ID NO: | VL name | VL amino acid sequence | VL SEQ ID NO: |
|---|---|---|---|---|---|---|
| PSMB1157 | VD0000 46232_VH | EVQLVESGGGVVQP GRSLRLSCAASVRTF SGYGMHWVRQVPG KGLEWVAVISYDGS NRYYADSVKGRFTI SRDNSKNTLYLQMN SLRTEDTAVYYCAR DGNWGSLDLYFDL WGRGTLVTVSS | 56 | VD0000 58301_VL | QSVLTQPPSVS GAPGQRVTISC TGSSSNIGADY DVHWYQQLPG TAPKLLIYVNN NRPSGVPDRFS GSRSGTSASLAI TGLQADDEAD YYCQSYDNTLS GVVFGGGTKLT VL | 57 |
| PSMB1156 | VD0000 46205_VH | EVQLVESGGGVVQP GRSLRLSCAASGFTF TSYGMHWVRQAPG KGLEWVAVISYDGS NKYYADSVKGRFTI SRDNSKNTLYLQMN SLRAEDTAVYYCAR EHYDSSGYYHGYY GMDVWGQGTTVTV SS | 58 | VD0000 60670_VL | QAVLTQPPSAS GTPGQRVTISCS GSSSNIGSNYV YWYQLLPGTAP KLLIYSNNQRPS GVPDRFSGSKS GTSASLAISGLR SEDEADYYCAA RDDSLSGYVFG TGTKLTVL | 59 |
| PSMB1088 | VD0000 60756_VH | EVQLVESGGGVVQP GRSLRLSCAASGFTF SSYDMHWVRQAPG KGLEWVTVISFDGS NKYYVDSVKGRFTI SRDNSKNTLYLQMN SLRAEDTAVYYCAR TYYDILTGYSHYSY GMDVWGQGTTVTV SS | 60 | VD0000 60755_VL | EIVMTQSPSSLS ASVGDRVTITC RASQGISNYLA WYQQKPGKVP KLLIYATSTLQS GVPSRFSGSGS GTDFILTISSLQP EDVANYYCQK YNSAPFTFGPG TKVEIK | 61 |
| PSMB1098 | VD0000 58433_VH | QVQLVESGGGVVQP GRSLRLSCAASGFTF STYGMHWVRQAPG KGLEWVAFISYDGS NKYYADSVKGRFTI SRDNSKHTLYLQMN SLRAEDTAVYYCAG RDNLRFLEWFMDV WGQGTTVTVSS | 62 | VD0000 60599_VL | EIVMTQSPATLS VSPGERATLSC RASQSVRSNLA WYQQKPGQAP RLLIYGASTRAT GIPARFSGSGSG TEFTLTISSLQSE DFAVYYCHQY NDWPPYTFGQG TKVEIK | 63 |
| PSMB1113 | VD0000 58464_VH | EVQLVESGGGLVKP GGSLRLSCAASGFTL SIYSMNWVRQAPGK GLEWVSSISSSSSYIF YADSVKGRFTISRD NAKNSLFLQMNSLR AEDTAVYYCARSSY GADYWGQGTLVTV SS | 64 | VD0000 60669_VL | EIVMTQSPSSLS ASVGDRVTITC RASQDITNFLA WYQQKPGKVP KLLIYTASTLQS GVPSRFSGSGS GTDPFTLTISSLQ PEDVATYYCQK YNSAPLTFGGG TKLEIK | 65 |
| PSMB1195 | VD0000 60752_VH | EVQLVESGGGLVKP GGSLRLSCAASGFTF SSYSLNWVRQAPGK GLEWVSSISSSSSYIS YADVKGRFTISRD NAKNSLYLQMNSLR AEDTAVYYCARDR GFLEDYYYYGMD VWGQGTTVTVSS | 66 | VD0000 60787_VL | DIVMTQSPSSVS ASVGDRVTITC RASQGISNWLA WYQQKPGKAP KLLIYVASSLQS GVPSRFSGSGS GTDFSLTISSLQ PEDFATYYCQQ AYSFPLTFGGG TKVEIK | 67 |

TABLE 13

VH nucleic acid sequence of selected anti-PSMA antibodies

| Antibody | VH name | VH nucleic acid sequence | VH SEQ ID NO: |
|---|---|---|---|
| PSMB1154 | VD00006066 3_VH | GAGGTGCAGCTGGTTGAATCTGGTGGCGGAGAAG TGCAGCCTGGCAGATCTCTGAGACTGACCTGTGC TGTGTCCGGCTTCACCCTGTCCAGATACGGAATG CACTGGGTCCGACAGGCCCCTGGCAAAGGATTGG AATGGGCCGCTCTGATCTCCTACGACGGCTCCAA TAGGTACTACGCCGACTCCGTGAAGGGCAGATTC ACCATCTCTCGGGACAACTCCAAGAACACCGTGT TTCTGCAGATGAACTCCCTGAGAGCCGAGGACAC CGCCGTGTACTACTGTGCCAGAGAGCGGGAATCC TCCGGCTGGTTCGAGGGCTACTTCGACTATTGGG GCCAGGGCACCACAGTGACCGTTTCTTCT | 68 |
| PSMB2945 | VD00006066 3_VH | GAGGTGCAGCTGGTTGAATCTGGTGGCGGAGAAG TGCAGCCTGGCAGATCTCTGAGACTGACCTGTGC TGTGTCCGGCTTCACCCTGTCCAGATACGGAATG CACTGGGTCCGACAGGCCCCTGGCAAAGGATTGG AATGGGCCGCTCTGATCTCCTACGACGGCTCCAA TAGGTACTACGCCGACTCCGTGAAGGGCAGATTC ACCATCTCTCGGGACAACTCCAAGAACACCGTGT TTCTGCAGATGAACTCCCTGAGAGCCGAGGACAC CGCCGTGTACTACTGTGCCAGAGAGCGGGAATCC TCCGGCTGGTTCGAGGGCTACTTCGACTATTGGG GCCAGGGCACCACAGTGACCGTTTCTTCT | 68 |
| PSMB1183 | VD00004591 0_VH | CAGGTGCAGCTGCAAGAGTCTGGACCTGGCCTGG TCAAGTCCTCCGAGACACTGTCTCTGACCTGCAC CGTGTCTGGCGGCTCCATCTCCTCCTACTACTGGA ACTGGATCAGACAGCCTGCCGGCAAAGGCCTGGA ATGGATCGGCAGAATCTACTCCTCCGGCAACACC GACTACAACCCCAGCCTGAAGTCCAGAGTGACCA TGTCCGTGGACACCTCCAAGAACCAGTTCTCCCT GAAGCTGATCTCCGTGACCGCCGCTGATACCGCC GTGTACTATTGTGCTAGAGGCAGAGGCGCCAACG TGGGCCTGTTTGATTATTGGGGCCAGGGCACCCT GGTCACCGTTTCTTCT | 70 |
| PSMB3003 | VD00004591 0_VH | CAGGTGCAGCTGCAAGAGTCTGGACCTGGCCTGG TCAAGTCCTCCGAGACACTGTCTCTGACCTGCAC CGTGTCTGGCGGCTCCATCTCCTCCTACTACTGGA ACTGGATCAGACAGCCTGCCGGCAAAGGCCTGGA ATGGATCGGCAGAATCTACTCCTCCGGCAACACC GACTACAACCCCAGCCTGAAGTCCAGAGTGACCA TGTCCGTGGACACCTCCAAGAACCAGTTCTCCCT GAAGCTGATCTCCGTGACCGCCGCTGATACCGCC GTGTACTATTGTGCTAGAGGCAGAGGCGCCAACG TGGGCCTGTTTGATTATTGGGGCCAGGGCACCCT GGTCACCGTTTCTTCT | 70 |
| PSMB1157 | VD00004623 2_VH | GAGGTGCAGCTGGTTGAATCTGGTGGCGGAGTGG TGCAGCCTGGCAGATCTCTGAGACTGTCTTGTGC CGCTTCCGTGCGACCTTCTCTGGCTACGGAATG CACTGGGTCCGACAGGTGCCAGGCAAAGGACTG GAATGGGTGGCCGTGATCTCCTACGATGGCTCCA ATCGGTACTACGCCGACTCCGTGAAGGGCAGATT CACCATCTCTCGGGACAACTCCAAGAACACCCTG TACCTGCAGATGAACTCCCTGCGGACCGAGGATA CCGCCGTGTACTACTGTGCCAGAGATGGCAACTG GGGCTCCCTGGACCTGTACTTCGATCTCTGGGGA CGGGGCACCCTGGTCACAGTCTCTTCT | 72 |
| PSMB1156 | VD00004620 5_VH | GAGGTGCAGCTGGTTGAATCTGGTGGCGGAGTGG TGCAGCCTGGCAGATCTCTGAGACTGTCTTGTGC CGCCTCCGGCTTCACCTTCACCAGCTACGGAATG CACTGGGTCCGACAGGCCCCTGGCAAAGGATTGG AATGGGTGGCCGTGATCTCCTACGACGGCTCCAA CAAGTACTACGCCGACTCCGTGAAGGGCAGATTC ACCATCTCTCGGGACAACTCCAAGAACACCCTGT ACCTGCAGATGAACTCCCTGAGAGCCGAGGACAC CGCCGTGTACTACTGTGCCAGAGAGCACTACGAC TCCTCCGGCTACTACCACGGCTACTATGGCATGG ATGTGTGGGGCCAGGGCACCACAGTGACAGTCTC TTCC | 74 |

TABLE 13-continued

VH nucleic acid sequence of selected anti-PSMA antibodies

| Antibody | VH name | VH nucleic acid sequence | VH SEQ ID NO: |
|---|---|---|---|
| PSMB1088 | VD000060756_VH | GAGGTGCAGCTGGTGGAGTCTGGGGGAGGCGTG GTCCAGCCTGGGAGGTCCCTGAGACTCTCCTGTG CAGCCTCTGGATTCACCTTCAGTAGTTATGACATG CACTGGGTCCGCCAGGCTCCAGGCAAGGGGCTGG AGTGGGTGACAGTTATATCATTTGATGGAAGTAA TAAATACTATGTAGACTCCGTGAAGGGCCGATTC ACCATCTCCAGAGACAATTCCAAGAATACGCTGT ATCTGCAAATGAACAGCCTGAGAGCTGAGGACAC GGCTGTGTATTACTGTGCGAGAACGTATTACGAT ATTTTGACTGGTTATTCCCACTACTCCTACGGTAT GGACGTCTGGGGCCAAGGGACCACGGTCACCGTC TCCTCA | 76 |
| PSMB1098 | VD000058433_VH | CAGGTGCAGCTGGTGGAGTCTGGGGGAGGCGTG GTCCAGCCTGGGAGGTCCCTGAGACTCTCCTGTG CAGCCTCTGGATTCACCTTCAGTACCTATGGCATG CACTGGGTCCGCCAGGCTCCAGGCAAGGGGCTGG AGTGGGTGGCATTTATATCATATGATGGAAGTAA TAAATACTATGCAGACTCCGTGAAGGGCCGATTC ACCATCTCCAGAGACAATTCCAAGCACACGCTAT ATCTGCAAATGAACAGCCTGAGAGCTGAGGACAC GGCTGTGTATTACTGTGCGGGGAGAGACAACCTA CGATTTTTGGAGTGGTTTATGGACGTCTGGGGCC AAGGGACCACGGTCACCGTCTCTTCA | 78 |
| PSMB1113 | VD000058464_VH | GAGGTGCAGCTGGTGGAGTCTGGGGGAGGCCTG GTCAAGCCGGGGGGGTCCCTGAGACTCTCCTGTG CAGCCTCTGGATTCACCCTCAGTATTTATAGCATG AACTGGGTCCGCCAGGCTCCAGGGAAGGGGCTG GAGTGGGTCTCATCCATTAGCAGTAGTAGTAGTT ACATATTCTACGCAGACTCAGTGAAGGGCCGATT CACCATCTCCAGAGACAACGCCAAGAACTCACTC TTTCTGCAAATGAACAGCCTGAGAGCCGAGGACA CGGCTGTGTATTACTGTGCGAGATCCTCCTACGGT GCGGACTACTGGGGCCAGGGAACCCTGGTCACCG TCTCTTCA | 80 |
| PSMB1195 | VD000060752_VH | GAGGTGCAGCTGGTGGAGTCTGGGGGAGGCCTG GTCAAGCCTGGGGGGTCCCTGAGACTCTCCTGTG CAGCCTCTGGATTCACCTTCAGCAGCTATAGCCT GAACTGGGTCCGCCAGGCTCCAGGGAAGGGGCT GGAGTGGGTCTCATCCATTAGTAGTAGTAGTAGT TACATATCCTACGCAGACGCAGTGAAGGGCCGAT TCACCATCTCCAGAGACAACGCCAAGAACTCACT GTATCTGCAAATGAACAGCCTGAGAGCCGAGGAC ACGGCTGTGTATTACTGTGCGAGAGATCGGGGAT TTTTGGAGGATTACTACTACTACTACGGTATGGA CGTCTGGGGCCAAGGGACCACGGTCACCGTCTCC TCA | 82 |

TABLE 14

VL nucleic acid sequence of selected anti-PSMA antibodies

| Antibody | VL name | VL nucleic acid sequence VL | SEQ ID NO: |
|---|---|---|---|
| PSMB1154 | VD000060661_VL | CAGCTGGTTCTGACCCAGCCTCCTTCTGTGTCTGTGGCTCC TGGCCAGACCGCCAGAATTACCTGTGGCGGCAACAACATC GGCTCCAAGTCCGTGCACTGGTATCAGCAGAAGCCTGGAC AGGCTCCTGTGCTGGTGGTGTACGACAACTCTGACCGGCC TTCTGGCATCCCTGAGAGATTCTCCGGCTCCAACAGCGGC AATACCGCCACACTGACCATCTCCAGAGTGGAAGTGGGCG ACGAGGCCGACTACTACTGCCAAGTGTGGGACTCCTCCTC CGATCATGTGGTGTTTGGCGGCGGAACAAAGCTGACAGTG CTG | 69 |

TABLE 14-continued

VL nucleic acid sequence of selected anti-PSMA antibodies

| Antibody | VL name | VL nucleic acid sequence VL | SEQ ID NO: |
|---|---|---|---|
| PSMB2945 | VD000 060661_VL | CAGCTGGTTCTGACCCAGCCTCCTTCTGTGTCTGTGGCTCC TGGCCAGACCGCCAGAATTACCTGTGGCGGCAACAACAT CGGCTCCAAGTCCGTGCACTGGTATCAGCAGAAGCCTGGA CAGGCTCCTGTGCTGGTGGTGTACGACAACTCTGACCGGC CTTCTGGCATCCCTGAGAGATTCTCCGGCTCCAACAGCGG CAATACCGCCACACTGACCATCTCCAGAGTGGAAGTGGGC GACGAGGCCGACTACTACTGCCAAGTGTGGGACTCCTCCT CCGATCATGTGGTGTTTGGCGGCGGAACAAAGCTGACAGT GCTG | 69 |
| PSMB1183 | VD000 060769_VL | CAGTCTGCTCTGACCCAGCCTCCTTCTGTGTCTGGCGCTCC TGGCCAGAGAGTGACCATCTCTTGTACCGGCTCCAACTCC AACATCGGCGCCAACTACGACGTGCACTGGTATCAGCATC TGCCCGGCACAGCTCCCAAGCTGCTGATCTACGGCAACAT CAACAGACCCCTGGGCGTGCCCGACCGGTTTTCTGGAAGC AGATCTGGCACCTCTGCCAGCCTGGCTATTACCGGACTGC AGGCTGAGGACGAGGCCGACTACTACTGCCAGTCCTACGA CTTCTCCCTGTCCGGCTCCGTGTTTGGCGTGGGCACAAAGC TGACAGTCCTG | 71 |
| PSMB3003 | VD000 060769_VL | CAGTCTGCTCTGACCCAGCCTCCTTCTGTGTCTGGCGCTCC TGGCCAGAGAGTGACCATCTCTTGTACCGGCTCCAACTCC AACATCGGCGCCAACTACGACGTGCACTGGTATCAGCATC TGCCCGGCACAGCTCCCAAGCTGCTGATCTACGGCAACAT CAACAGACCCCTGGGCGTGCCCGACCGGTTTTCTGGAAGC AGATCTGGCACCTCTGCCAGCCTGGCTATTACCGGACTGC AGGCTGAGGACGAGGCCGACTACTACTGCCAGTCCTACGA CTTCTCCCTGTCCGGCTCCGTGTTTGGCGTGGGCACAAAGC TGACAGTCCTG | 71 |
| PSMB1157 | VD000 058301_VL | CAGTCTGTGCTGACCCAGCCTCCTTCTGTGTCTGGCGCTCC TGGCCAGAGAGTGACCATCTCCTGTACCGGCTCCTCCTCT AACATCGGCGCTGACTACGACGTGCACTGGTATCAGCAGC TGCCTGGCACAGCTCCCAAACTGCTGATCTACGTGAACAA CAACCGGCCTTCTGGCGTGCCCGACAGATTCTCTGGAAGC AGATCTGGCACCTCTGCCAGCCTGGCTATTACCGGACTGC AGGCCGATGACGAGGCCGACTACTACTGCCAGTCCTACGA CAACACCCTGTCCGGCGTTGTGTTTGGCGGCGGAACAAAG CTGACAGTCCTG | 73 |
| PSMB1156 | VD000 060670_VL | CAGGCTGTTCTGACCCAGCCTCCTTCTGCTTCTGGCACCCC TGGACAGAGAGTGACCATCTCTTGCTCCGGCTCCTCCTCC AACATCGGCTCCAACTACGTGTACTGGTACCAGCTGCTGC CCGGCACCGCTCCTAAGCTGCTGATCTACTCCAACAACCA GCGGCCTTCTGGCGTGCCCGATAGATTCTCCGGCTCTAAG TCTGGCACCTCTGCCAGCCTGGCTATCTCCGGACTGAGAT CTGAGGACGAGGCCGACTACTACTGCGCCGCCAGAGATG ATTCCCTGTCCGGCTATGTGTTTGGCACCGGCACCAAGCT GACAGTGTTG | 75 |
| PSMB1088 | VD000 060755_VL | GAAATAGTGATGACGCAGTCTCCATCCTCCCTGTCTGCAT CTGTAGGAGACAGAGTCACCATCACTTGCCGGGCGAGTCA GGGCATTAGCAATTATTTAGCCTGGTATCAGCAGAAACCA GGGAAAGTTCCTAAGCTCCTGATCTATGCCACATCCACTTT GCAATCAGGGGTCCCATCTCGGTTCAGTGGCAGTGGATCT GGGACAGATTTCATTCTCACCATCAGCAGCCTGCAGCCTG AAGATGTTGCAAACTATTACTGTCAAAAGTATAACAGTGC CCCATTCACTTTCGGCCCTGGGACCAAGGTGGAGATCAAA | 77 |
| PSMB1098 | VD000 060599_VL | GAAATAGTGATGACGCAGTCTCCAGCCACCCTGTCTGTGT CTCCAGGGGAAAGAGCCACCCTCTCCTGCAGGGCCAGTCA GAGTGTAAGGAGCAACTTAGCCTGGTACCAGCAGAAACCT GGCCAGGCTCCCAGGCTCCTCATCTATGGTGCATCCACCA GGGCCACTGGTATCCCAGCCAGGTTCAGTGGCAGTGGGTC TGGGACAGAGTTCACTCTCACCATCAGCAGCCTGCAGTCT GAAGATTTTGCAGTTTATTACTGTCACCAGTATAATGACTG GCCTCCGTACACTTTTGGCCAAGGGACCAAGGTGGAAATC AAA | 79 |

TABLE 14-continued

VL nucleic acid sequence of selected anti-PSMA antibodies

| Antibody | VL name | VL nucleic acid sequence VL | SEQ ID NO: |
|---|---|---|---|
| PSMB1113 | VD000 060669_VL | GAAATAGTGATGACGCAGTCTCCATCCTCCCTGTCTGCAT CTGTAGGAGACAGAGTCACCATCACTTGCCGGGCGAGTCA GGACATTACCAATTTTTTAGCCTGGTATCAGCAGAAACCA GGGAAAGTTCCTAAACTCCTGATTTATACTGCATCCACTTT GCAATCAGGGGTCCCATCTCGGTTCAGTGGCAGTGGATCT GGGACAGATTTCACTCTCACCATCAGCAGCCTGCAGCCTG AAGATGTTGCGACTTATTACTGTCAAAAGTATAACAGTGC CCCACTCACTTTCGGCGGAGGGACCAAGCTGGAGATCAAA | 81 |
| PSMB1195 | VD000 060787_VL | GACATCGTGATGACCCAGTCTCCATCTTCCGTGTCTGCATC TGTAGGAGACAGAGTCACCATCACTTGTCGGGCGAGTCAA GGTATTAGCAACTGGTTAGCCTGGTATCAGCAGAAACCAG GGAAAGCCCCTAAGCTCCTGATCTATGTTGCATCCAGTTT GCAAAGTGGGGTTCCATCAAGGTTCAGCGGCAGTGGATCT GGGACAGATTTCTCTCTCACCATCAGCAGCCTGCAGCCTG AAGATTTTGCAACTTACTATTGTCAACAGGCTTACAGTTTC CCTCTCACTTTCGGCGGAGGGACCAAGGTGGAGATCAAA | 83 |

TABLE 15

HC amino acid sequence of selected anti-PSMA antibodies

| Antibody | HC PEPTIDE ID | HC PROTEIN SEQ ID NO: | HC AMINO ACID SEQUENCE |
|---|---|---|---|
| PSMB1154 | DCH0000 13726 | 84 | EVQLVESGGGEVQPGRSLRLTCAVSGFTLSRYGMHW VRQAPGKGLEWAALISYDGSNRYYADSVKGRFTISR DNSKNTVFLQMNSLRAEDTAVYYCARERESSGWFEG YFDYWGQGTTVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KKVEPKSCDKTHTCPPCPAPELLGGPSVFLFPPKPKDT LMISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSREEMT KNQVSLTCLVKGFYPSDIAVEWESNGQPENNYKTTPP VLDSDGSFFLYSKLTVDKSRWQQGNVFSCSVMHEAL HNHYTQKSLSLSPGK |
| PSMB2945 | DCH0000 18816 | 86 | EVQLVESGGGEVQPGRSLRLTCAVSGFTLSRYGMHW VRQAPGKGLEWAALISYDGSNRYYADSVKGRFTISR DNSKNTVFLQMNSLRAEDTAVYYCARERESSGWFEG YFDYWGQGTTVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KKVEPKSCDKTHTCPPCPAPEAAGGPSVFLFPPKPKD TLYITREPEVTCVVVSVSHEDPEVKFNWYVDGVEVH NAKTKPREEQYNSTYRVVSVLTVLHQDWLNGKEYK CKVSNKALPAPIEKTISKAKGQPREPQVYTLPPSREEM TKNQVSLTCLVKGFYPSDIAVEWESNGQPENNYKTTP PVLDSDGSFFLYSKLTVDKSRWQQGNVFSCSVMHEA LHNHYTQKSLSLSPGK |
| PSMB1183 | DCH0000 13720 | 88 | QVQLQESGPGLVKSSETLSLTCTVSGGSISSYYWNWI RQPAGKGLEWIGRIYSSGNTDYNPSLKSRVTMSVDTS KNQFSLKLISVTAADTAVYYCARGRGANVGLFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPK SCDKTHTCPPCPAPELLGGPSVFLFPPKPKDTLMISRT PEVTCVVVDVSHEDPEVKFNWYVDGVEVHNAKTKP REEQYNSTYRVVSVLTVLHQDWLNGKEYKCKVSNK ALPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYT QKSLSLSPGK |

TABLE 15-continued

HC amino acid sequence of selected anti-PSMA antibodies

| Antibody | HC PEPTIDE ID | HC PROTEIN SEQ ID NO: | HC AMINO ACID SEQUENCE |
|---|---|---|---|
| PSMB3003 | DCH0000 21551 | 90 | QVQLQESGPGLVKSSETLSLTCTVSGGSISSYYWNWI RQPAGKGLEWIGRIYSSGNTDYNPSLKSRVTMSVDTS KNQFSLKLISVTAADTAVYYCARGRGANVGLFDYW GQGTLVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPK SCDKTHTCPPCPAPEAAGGPSVFLFPPKPKDTLYITRE PEVTCVVVSVSHEDPEVKFNWYVDGVEVHNAKTKP REEQYNSTYRVVSVLTVLHQDWLNGKEYKCKVSNK ALPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYT QKSLSLSPGK |
| PSMB1157 | DCH0000 13724 | 92 | EVQLVESGGGVVQPGRSLRLSCAASVRTFSGYGMHW VRQVPGKGLEWVAVISYDGSNRYYADSVKGRFTISR DNSKNTLYLQMNSLRTEDTAVYYCARDGNWGSLDL YFDLWGRGTLVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KKVEPKSCDKTHTCPPCPAPELLGGPSVFLFPPKPKDT LMISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSREEMT KNQVSLTCLVKGFYPSDIAVEWESNGQPENNYKTTPP VLDSDGSFFLYSKLTVDKSRWQQGNVFSCSVMHEAL HNHYTQKSLSLSPGK |
| PSMB1156 | DCH0000 13725 | 94 | EVQLVESGGGVVQPGRSLRLSCAASGFTFTSYGMHW VRQAPGKGLEWVAVISYDGSNKYYADSVKGRFTISR DNSKNTLYLQMNSLRAEDTAVYYCAREHYDSSGYY HGYYGMDVWGQGTTVTVSSASTKGPSVFPLAPSSKS TSGGTAALGCLVKDYFPEPVTVSWNSGALTSGVHTF PAVLQSSGLYSLSSVVTVPSSSLGTQTYICNVNHKPSN TKVDKKVEPKSCDKTHTCPPCPAPELLGGPSVFLFPP KPKDTLMISRTPEVTCVVVDVSHEDPEVKFNWYVDG VEVHNAKTKPREEQYNSTYRVVSVLTVLHQDWLNG KEYKCKVSNKALPAPIEKTISKAKGQPREPQVYTLPPS REEMTKNQVSLTCLVKGFYPSDIAVEWESNGQPENN YKTTPPVLDSDGSFFLYSKLTVDKSRWQQGNVFSCSV MHEALHNHYTQKSLSLSPGK |
| PSMB1088 | DCH0000 17968 | 96 | EVQLVESGGGVVQPGRSLRLSCAASGFTFSSYDMHW VRQAPGKGLEWVTVISFDGSNKYYVDSVKGRFTISR DNSKNTLYLQMNSLRAEDTAVYYCARTYYDILTGYS HYSYGMDVWGQGTTVTVSSASTKGPSVFPLAPSSKS TSGGTAALGCLVKDYFPEPVTVSWNSGALTSGVHTF PAVLQSSGLYSLSSVVTVPSSSLGTQTYICNVNHKPSN TKVDKKVEPKSCDKTHTCPPCPAPELLGGPSVFLFPP KPKDTLMISRTPEVTCVVVDVSHEDPEVKFNWYVDG VEVHNAKTKPREEQYNSTYRVVSVLTVLHQDWLNG KEYKCKVSNKALPAPIEKTISKAKGQPREPQVYTLPPS REEMTKNQVSLTCLVKGFYPSDIAVEWESNGQPENN YKTTPPVLDSDGSFFLYSKLTVDKSRWQQGNVFSCSV MHEALHNHYTQKSLSLSPGK |
| PSMB1098 | DCH0000 19327 | 98 | QVQLVESGGGVVQPGRSLRLSCAASGFTFSTYGMHW VRQAPGKGLEWVAFISYDGSNKYYADSVKGRFTISR DNSKHTLYLQMNSLRAEDTAVYYCAGRDNLRFLEW FMDVWGQGTTVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KKVEPKSCDKTHTCPPCPAPELLGGPSVFLFPPKPKDT LMISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSREEMT KNQVSLTCLVKGFYPSDIAVEWESNGQPENNYKTTPP VLDSDGSFFLYSKLTVDKSRWQQGNVFSCSVMHEAL HNHYTQKSLSLSPGK |

TABLE 15-continued

HC amino acid sequence of selected anti-PSMA antibodies

| Antibody | HC PEPTIDE ID | HC PROTEIN SEQ ID NO: | HC AMINO ACID SEQUENCE |
|---|---|---|---|
| PSMB1113 | DCH0000 19326 | 100 | EVQLVESGGGLVKPGGSLRLSCAASGFTLSIYSMNW VRQAPGKGLEWVSSISSSSSYIFYADSVKGRFTISRDN AKNSLFLQMNSLRAEDTAVYYCARSSYGADYWGQG TLVTVSSASTKGPSVFPLAPSSKSTSGGTAALGCLVK DYFPEPVTVSWNSGALTSGVHTFPAVLQSSGLYSLSS VVTVPSSSLGTQTYICNVNHKPSNTKVDKKVEPKSCD KTHTCPPCPAPELLGGPSVFLFPPKPKDTLMISRTPEV TCVVVDVSHEDPEVKFNWYVDGVEVHNAKTKPREE QYNSTYRVVSVLTVLHQDWLNGKEYKCKVSNKALP APIEKTISKAKGQPREPQVYTLPPSREEMTKNQVSLTC LVKGFYPSDIAVEWESNGQPENNYKTTPPVLDSDGSF FLYSKLTVDKSRWQQGNVFSCSVMHEALHNHYTQK SLSLSPGK |
| PSMB1195 | DCH0000 17970 | 102 | EVQLVESGGGLVKPGGSLRLSCAASGFTFSSYSLNWV RQAPGKGLEWVSSISSSSSYISYADAVKGRFTISRDNA KNSLYLQMNSLRAEDTAVYYCARDRGFLEDYYYYY GMDVWGQGTTVTVSSASTKGPSVFPLAPSSKSTSGGT AALGCLVKDYFPEPVTVSWNSGALTSGVHTFPAVLQ SSGLYSLSSVVTVPSSSLGTQTYICNVNHKPSNTKVD KKVEPKSCDKTHTCPPCPAPELLGGPSVFLFPPKPKDT LMISRTPEVTCVVVDVSHEDPEVKFNWYVDGVEVHN AKTKPREEQYNSTYRVVSVLTVLHQDWLNGKEYKC KVSNKALPAPIEKTISKAKGQPREPQVYTLPPSREEMT KNQVSLTCLVKGFYPSDIAVEWESNGQPENNYKTTPP VLDSDGSFFLYSKLTVDKSRWQQGNVFSCSVMHEAL HNHYTQKSLSLSPGK |

TABLE 16

LC amino acid sequences of selected anti-PSMA antibodies.

| ANTIBODY | LC PEPTIDE ID | LC PROTEIN SEQ ID NO: | LC AMINO ACID SEQUENCE |
|---|---|---|---|
| PSMB1154 | DCH00001 0369 | 85 | QLVLTQPPSVSVAPGQTARITCGGNNIGSKSVHW YQQKPGQAPVLVVYDNSDRPSGIPERFSGSNSGN TATLTISRVEVGDEADYYCQVWDSSSDHVVFGG GTKLTVLGQPKAAPSVTLFPPSSEELQANKATLVC LISDFYPGAVTVAWKADSSPVKAGVETTTPSKQS NNKYAASSYLSLTPEQWKSHRSYSCQVTHEGSTV EKTVAPTECS |
| PSMB2945 | DCH00001 0369 | 85 | QLVLTQPPSVSVAPGQTARITCGGNNIGSKSVHW YQQKPGQAPVLVVYDNSDRPSGIPERFSGSNSGN TATLTISRVEVGDEADYYCQVWDSSSDHVVFGG GTKLTVLGQPKAAPSVTLFPPSSEELQANKATLVC LISDFYPGAVTVAWKADSSPVKAGVETTTPSKQS NNKYAASSYLSLTPEQWKSHRSYSCQVTHEGSTV EKTVAPTECS |
| PSMB1183 | DCH00001 0389 | 89 | QSALTQPPSVSGAPGQRVTISCTGSNSNIGANYDV HWYQHLPGTAPKLLIYGNINRPLGVPDRFSGSRSG TSASLAITGLQAEDEADYYCQSYDFSLSGSVFGVG TKLTVLGQPKAAPSVTLFPPSSEELQANKATLVCL ISDFYPGAVTVAWKADSSPVKAGVETTTPSKQSN NKYAASSYLSLTPEQWKSHRSYSCQVTHEGSTVE KTVAPTECS |
| PSMB3003 | DCH00001 0389 | 89 | QSALTQPPSVSGAPGQRVTISCTGSNSNIGANYDV HWYQHLPGTAPKLLIYGNINRPLGVPDRFSGSRSG TSASLAITGLQAEDEADYYCQSYDFSLSGSVFGVG TKLTVLGQPKAAPSVTLFPPSSEELQANKATLVCL ISDFYPGAVTVAWKADSSPVKAGVETTTPSKQSN NKYAASSYLSLTPEQWKSHRSYSCQVTHEGSTVE KTVAPTECS |

TABLE 16-continued

LC amino acid sequences of selected anti-PSMA antibodies.

| ANTIBODY | LC PEPTIDE ID | LC PROTEIN SEQ ID NO: | LC AMINO ACID SEQUENCE |
|---|---|---|---|
| PSMB1157 | DCH00001 0372 | 93 | QSVLTQPPSVSGAPGQRVTISCTGSSSNIGADYDV HWYQQLPGTAPKLLIYVNNNRPSGVPDRFSGSRS GTSASLAITGLQADDEADYYCQSYDNTLSGVVFG GGTKLTVLGQPKAAPSVTLFPPSSEELQANKATLV CLISDFYPGAVTVAWKADSSPVKAGVETTTPSKQ SNNKYAASSYLSLTPEQWKSHRSYSCQVTHEGST VEKTVAPTECS |
| PSMB1156 | DCH00001 0371 | 95 | QAVLTQPPSASGTPGQRVTISCSGSSSNIGSNYVY WYQLLPGTAPKLLIYSNNQRPSGVPDRFSGSKSGT SASLAISGLRSEDEADYYCAARDDSLSGYVFGTG TKLTVLGQPKAAPSVTLFPPSSEELQANKATLVCL ISDFYPGAVTVAWKADSSPVKAGVETTTPSKQSN NKYAASSYLSLTPEQWKSHRSYSCQVTHEGSTVE KTVAPTECS |
| PSMB1088 | DCH00001 0211 | 97 | EIVMTQSPSSLSASVGDRVTITCRASQGISNYLAW YQQKPGKVPKLLIYATSTLQSGVPSRFSGSGSGTD FILTISSLQPEDVANYYCQKYNSAPFTFGPGTKVEI KRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKS FNRGEC |
| PSMB1098 | DCH00001 0229 | 99 | EIVMTQSPATLSVSPGERATLSCRASQSVRSNLAW YQQKPGQAPRLLIYGASTRATGIPARFSGSGSGTE FTLTISSLQSEDFAVYYCHQYNDWPPYTFGQGTK VEIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVT KSFNRGEC |
| PSMB1113 | DCH00001 0258 | 101 | EIVMTQSPSSLSASVGDRVTITCRASQDITNFLAW YQQKPGKVPKLLIYTASTLQSGVPSRFSGSGSGTD FTLTISSLQPEDVATYYCQKYNSAPLTFGGGTKLE IKRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKS FNRGEC |
| PSMB1195 | DCH00001 0366 | 103 | DIVMTQSPSSVSASVGDRVTITCRASQGISNWLA WYQQKPGKAPKLLIYVASSLQSGVPSRFSGSGSG TDFSLTISSLQPEDFATYYCQQAYSFPLTFGGGTK VEIKRTVAAPSVFIFPPSDEQLKSGTASVVCLLNNF YPREAKVQWKVDNALQSGNSQESVTEQDSKDST YSLSSTLTLSKADYEKHKVYACEVTHQGLSSPVT KSFNRGEC |

TABLE 17

HC nucleotide sequences of selected anti-PSMA antibodies.

| Antibody | HC NUCLEOTIDE SEQ ID NO: | HC NUCLEIC ACID SEQUENCE |
|---|---|---|
| PSMB1154 | 104 | GAGGTGCAGCTGGTTGAATCTGGTGGCGGAGAAGTGCAGC CTGGCAGATCTCTGAGACTGACCTGTGCTGTGTCCGGCTTC ACCCTGTCCAGATACGGAATGCACTGGGTCCGACAGGCCC CTGGCAAAGGATTGGAATGGGCCGCTCTGATCTCCTACGAC GGCTCCAATAGGTACTACGCCGACTCCGTGAAGGGCAGAT TCACCATCTCTCGGGACAACTCCAAGAACACCGTGTTTCTG CAGATGAACTCCCTGAGAGCCGAGGACACCGCCGTGTACT ACTGTGCCAGAGAGCGGGAATCCTCCGGCTGGTTCGAGGG CTACTTCGACTATTGGGGCCAGGGCACCACAGTGACCGTTT CTTCTGCCTCCACCAAGGGCCCATCGGTCTTCCCCCTGGCA CCCTCCTCCAAGAGCACCTCTGGGGGCACAGCGGCCCTGG GCTGCCTGGTCAAGGACTACTTCCCCGAACCGGTGACGGTG TCGTGGAACTCAGGCGCCCTGACCAGCGGCGTGCACACCTT |

TABLE 17-continued

HC nucleotide sequences of selected anti-PSMA antibodies.

| Antibody | HC NUCLEOTIDE SEQ ID NO: | HC NUCLEIC ACID SEQUENCE |
|---|---|---|
| | | CCCGGCTGTCCTACAGTCCTCAGGACTCTACTCCCTCAGCA
GCGTGGTGACCGTGCCCTCCAGCAGCTTGGGCACCCAGACC
TACATCTGCAACGTGAATCACAAGCCCAGCAACACCAAGG
TGGACAAGAAAGTTGAGCCCAAATCTTGTGACAAAACTCA
CACATGCCCACCGTGCCCAGCACCTGAACTCCTGGGGGGA
CCGTCAGTCTTCCTCTTCCCCCCAAAACCCAAGGACACCCT
CATGATCTCCCGGACCCCTGAGGTCACATGCGTGGTGGTGG
ACGTGAGCCACGAAGACCCTGAGGTCAAGTTCAACTGGTA
CGTGGACGGCGTGGAGGTGCATAATGCCAAGACAAAGCCG
CGGGAGGAGCAGTACAACAGCACGTACCGTGTGGTCAGCG
TCCTCACCGTCCTGCACCAGGACTGGCTGAATGGCAAGGA
GTACAAGTGCAAGGTGTCCAACAAAGCCCTCCCAGCCCCC
ATCGAGAAAACCATCTCCAAAGCCAAAGGGCAGCCCCGAG
AACCACAGGTGTACACCCTGCCCCCATCCCGGGAGGAGAT
GACCAAGAACCAGGTCAGCCTGACCTGCCTGGTCAAAGGC
TTCTATCCCAGCGACATCGCCGTGGAGTGGGAGAGCAATG
GGCAGCCGGAGAACAACTACAAGACCACGCCTCCCGTGCT
GGACTCCGACGGCTCCTTCTTCCTCTACAGCAAGCTCACCG
TGGACAAGAGCAGATGGCAGCAGGGGAACGTCTTCTCATG
CTCCGTGATGCATGAGGCTCTGCACAACCACTACACGCAGA
AGTCTCTCTCCCTGTCTCCGGGAAAA |
| PSMB2945 | 106 | GAGGTGCAGCTGGTTGAATCTGGTGGCGGAGAAGTGCAGC
CTGGCAGATCTCTGAGACTGACCTGTGCTGTGTCCGGCTTC
ACCCTGTCCAGATACGGAATGCACTGGGTCCGACAGGCCC
CTGGCAAAGGATTGGAATGGGCCGCTCTGATCTCCTACGAC
GGCTCCAATAGGTACTACGCCGACTCCGTGAAGGGCAGAT
TCACCATCTCTCGGGACAACTCCAAGAACACCGTGTTTCTG
CAGATGAACTCCCTGAGAGCCGAGGACACCGCCGTGTACT
ACTGTGCCAGAGAGCGGGAATCCTCCGGCTGGTTCGAGGG
CTACTTCGACTATTGGGGCCAGGGCACCACAGTGACCGTTT
CTTCTGCCTCCACCAAGGGCCCATCGGTCTTCCCCCTGGCA
CCCTCCTCCAAGAGCACCTCTGGGGGCACAGCGGCCCTGG
GCTGCCTGGTCAAGGACTACTTCCCCGAACCGGTGACGGTG
TCGTGGAACTCAGGCGCCCTGACCAGCGGCGTGCACACCTT
CCCGGCTGTCCTACAGTCCTCAGGACTCTACTCCCTCAGCA
GCGTGGTGACCGTGCCCTCCAGCAGCTTGGGCACCCAGACC
TACATCTGCAACGTGAATCACAAGCCCAGCAACACCAAGG
TGGACAAGAAAGTTGAGCCCAAATCTTGTGACAAAACTCA
CACATGCCCACCGTGCCCAGCACCTGAAGCCGCGGGGGA
CCGTCAGTCTTCCTCTTCCCCCCAAAACCCAAGGACACCCT
CTACATCACCCGGGAGCCTGAGGTCACATGCGTGGTGGTG
AGCGTGAGCCACGAAGACCCTGAGGTCAAGTTCAACTGGT
ACGTGGACGGCGTGGAGGTGCATAATGCCAAGACAAAGCC
GCGGGAGGAGCAGTACAACAGCACGTACCGTGTGGTCAGC
GTCCTCACCGTCCTGCACCAGGACTGGCTGAATGGCAAGG
AGTACAAGTGCAAGGTGTCGAACAAAGCCCTCCCAGCCCC
CATCGAGAAAACCATCTCCAAAGCCAAAGGGCAGCCCCGA
GAACCACAGGTGTACACCCTGCCCCCATCCCGGGAGGAGA
TGACCAAGAACCAGGTCAGCCTGACCTGCCTGGTCAAAGG
CTTCTATCCCAGCGACATCGCCGTGGAGTGGGAGAGCAAT
GGGCAGCCGGAGAACAACTACAAGACCACGCCTCCCGTGC
TGGACTCCGACGGCTCCTTCTTCCTCTACAGCAAGCTCACC
GTGGACAAGAGCAGATGGCAGCAGGGGAACGTCTTCTCAT
GCTCCGTGATGCATGAGGCTCTGCACAACCACTACACGCAG
AAGTCTCTCCCTGTCTCCGGGAAAA |
| PSMB1183 | 108 | CAGGTGCAGCTGCAAGAGTCTGGACCTGGCCTGGTCAAGT
CCTCCGAGACACTGTCTCTGACCTGCACCGTGTCTGGCGGC
TCCATCTCCTCCTACTACTGGAACTGGATCAGACAGCCTGC
CGGCAAAGGCCTGGAATGGATCGGCAGAATCTACTCCTCC
GGCAACACCGACTACAACCCCAGCCTGAAGTCCAGAGTGA
CCATGTCCGTGGACACCTCCAAGAACCAGTTCTCCCTGAAG
CTGATCTCCGTGACCGCCGCTGATACCGCCGTGTACTATTG
TGCTAGAGGCAGAGGCGCCAACGTGGGCCTGTTTGATTATT
GGGGCCAGGGCACCCTGGTCACCGTTTCTTCTGCCTCCACC
AAGGGCCCATCGGTCTTCCCCCTGGCACCCTCCTCCAAGAG
CACCTCTGGGGGCACAGCGGCCCTGGGCTGCCTGGTCAAG
GACTACTTCCCCGAACCGGTGACGGTGTCGTGGAACTCAGG
CGCCCTGACCAGCGGCGTGCACACCTTCCCGGCTGTCCTAC
AGTCCTCAGGACTCTACTCCCTCAGCAGCGTGGTGACCGTG
CCCTCCAGCAGCTTGGGCACCCAGACCTACATCTGCAACGT
GAATCACAAGCCCAGCAACACCAAGGTGGACAAGAAAGTT
GAGCCCAAATCTTGTGACAAAACTCACACATGCCCACCGTG |

TABLE 17-continued

HC nucleotide sequences of selected anti-PSMA antibodies.

| Antibody | HC NUCLEOTIDE SEQ ID NO: | HC NUCLEIC ACID SEQUENCE |
|---|---|---|
| | | CCCAGCACCTGAACTCCTGGGGGACCGTCAGTCTTCCTCT<br>TCCCCCCAAAACCCAAGGACACCCTCATGATCTCCCGGACC<br>CCTGAGGTCACATGCGTGGTGGTGGACGTGAGCCACGAAG<br>ACCCTGAGGTCAAGTTCAACTGGTACGTGGACGGCGTGGA<br>GGTGCATAATGCCAAGACAAAGCCGCGGGAGGAGCAGTAC<br>AACAGCACGTACCGTGTGGTCAGCGTCCTCACCGTCCTGCA<br>CCAGGACTGGCTGAATGGCAAGGAGTACAAGTGCAAGGTG<br>TCCAACAAAGCCCTCCCAGCCCCCATCGAGAAAACCATCTC<br>CAAAGCCAAAGGGCAGCCCCGAGAACCACAGGTGTACACC<br>CTGCCCCCATCCCGGGAGGAGATGACCAAGAACCAGGTCA<br>GCCTGACCTGCCTGGTCAAAGGCTTCTATCCCAGCGACATC<br>GCCGTGGAGTGGGAGAGCAATGGGCAGCCGGAGAACAACT<br>ACAAGACCACGCCTCCCGTGCTGGACTCCGACGGCTCCTTC<br>TTCCTCTACAGCAAGCTCACCGTGGACAAGAGCAGATGGC<br>AGCAGGGGAACGTCTTCTCATGCTCCGTGATGCATGAGGCT<br>CTGCACAACCACTACACGCAGAAGTCTCTCTCCCTGTCTCC<br>GGGAAAA |
| PSMB3003 | 110 | CAGGTGCAGCTGCAAGAGTCTGGACCTGGCCTGGTCAAGT<br>CCTCCGAGACACTGTCTCTGACCTGCACCGTGTCTGGCGGC<br>TCCATCTCCTCCTACTACTGGAACTGGATCAGACAGCCTGC<br>CGGCAAAGGCCTGGAATGGATCGGCAGAATCTACTCCTCC<br>GGCAACACCGACTACAACCCCAGCCTGAAGTCCAGAGTGA<br>CCATGTCCGTGGACACCTCCAAGAACCAGTTCTCCCTGAAG<br>CTGATCTCCGTGACCGCCGCTGATACCGCCGTGTACTATTG<br>TGCTAGAGGCAGAGGCGCCAACGTGGGCCTGTTTGATTATT<br>GGGGCCAGGGCACCCTGGTCACCGTTTCTTCTGCCTCCACC<br>AAGGGCCCATCGGTCTTCCCCCTGGCACCCTCCTCCAAGAG<br>CACCTCTGGGGGCACAGCGGCCCTGGGCTGCCTGGTCAAG<br>GACTACTTCCCCGAACCGGTGACGGTGTCGTGGAACTCAGG<br>CGCCCTGACCAGCGGCGTGCACACCTTCCCGGCTGTCCTAC<br>AGTCCTCAGGACTCTACTCCCTCAGCAGCGTGGTGACCGTG<br>CCCTCCAGCAGCTTGGGCACCCAGACCTACATCTGCAACGT<br>GAATCACAAGCCCAGCAACACCAAGGTGGACAAGAAAGTT<br>GAGCCCAAATCTTGTGACAAAACTCACACATGCCCACCGTG<br>CCCAGCACCTGAAGCCGCCGGGGGACCGTCAGTCTTCCTCT<br>TCCCCCCAAAACCCAAGGACACCCTCTACATCACCCGGGA<br>GCCTGAGGTCACATGCGTGGTGGTGAGCGTGAGCCACGAA<br>GACCCTGAGGTCAAGTTCAACTGGTACGTGGACGGCGTGG<br>AGGTGCATAATGCCAAGACAAAGCCGCGGGAGGAGCAGTA<br>CAACAGCACGTACCGTGTGGTCAGCGTCCTCACCGTCCTGC<br>ACCAGGACTGGCTGAATGGCAAGGAGTACAAGTGCAAGGT<br>GTCGAACAAAGCCCTCCCAGCCCCCATCGAGAAAACCATC<br>TCCAAAGCCAAAGGGCAGCCCCGAGAACCACAGGTGTACA<br>CCCTGCCCCCATCCCGGGAGGAGATGACCAAGAACCAGGT<br>CAGCCTGACCTGCCTGGTCAAAGGCTTCTATCCCAGCGACA<br>TCGCCGTGGAGTGGGAGAGCAATGGGCAGCCGGAGAACAA<br>CTACAAGACCACGCCTCCCGTGCTGGACTCCGACGGCTCCT<br>TCTTCCTCTACAGCAAGCTCACCGTGGACAAGAGCAGATGG<br>CAGCAGGGGAACGTCTTCTCATGCTCCGTGATGCATGAGGC<br>TCTGCACAACCACTACACGCAGAAGTCTCTCTCCCTGTCTC<br>CGGGAAAA |
| PSMB1157 | 112 | GAGGTGCAGCTGGTTGAATCTGGTGGCGGAGTGGTGCAGC<br>CTGGCAGATCTCTGAGACTGTCTTGTGCCGCTTCCGTGCGG<br>ACCTTCTCTGGCTACGGAATGCACTGGGTCCGACAGGTGCC<br>AGGCAAAGGACTGGAATGGGTGGCCGTGATCTCCTACGAT<br>GGCTCCAATCGGTACTACGCCGACTCCGTGAAGGGCAGATT<br>CACCATCTCTCGGGACAACTCCAAGAACACCCTGTACCTGC<br>AGATGAACTCCCTGCGACCGAGGATACCGCCGTGTACTA<br>CTGTGCCAGAGATGGCAACTGGGGCTCCCTGGACCTGTACT<br>TCGATCTCTGGGGACGGGGCACCCTGGTCACAGTCTCTTCT<br>GCCTCCACCAAGGGCCCATCGGTCTTCCCCCTGGCACCCTC<br>CTCCAAGAGCACCTCTGGGGGCACAGCGGCCCTGGGCTGC<br>CTGGTCAAGGACTACTTCCCCGAACCGGTGACGGTGTCGTG<br>GAACTCAGGCGCCCTGACCAGCGGCGTGCACACCTTCCCG<br>GCTGTCCTACAGTCCTCAGGACTCTACTCCCTCAGCAGCGT<br>GGTGACCGTGCCCTCCAGCAGCTTGGGCACCCAGACCTACA<br>TCTGCAACGTGAATCACAAGCCCAGCAACACCAAGGTGGA<br>CAAGAAAGTTGAGCCCAAATCTTGTGACAAAACTCACACA<br>TGCCCACCGTGCCCAGCACCTGAACTCCTGGGGGACCGTC<br>AGTCTTCCTCTTCCCCCCAAAACCCAAGGACACCCTCATGA<br>TCTCCCGGACCCCTGAGGTCACATGCGTGGTGGTGGACGTG<br>AGCCACGAAGACCCTGAGGTCAAGTTCAACTGGTACGTGG |

TABLE 17-continued

HC nucleotide sequences of selected anti-PSMA antibodies.

| Antibody | HC NUCLEOTIDE SEQ ID NO: | HC NUCLEIC ACID SEQUENCE |
|---|---|---|
| | | ACGGCGTGGAGGTGCATAATGCCAAGACAAAGCCGCGGGA GGGAGCAGTACAACAGCACGTACCGTGTGGTCAGCGTCCTC ACCGTCCTGCACCAGGACTGGCTGAATGGCAAGGAGTACA AGTGCAAGGTGTCCAACAAAGCCCTCCCAGCCCCCATCGA GAAAACCATCTCCAAAGCCAAAGGGCAGCCCCGAGAACCA CAGGTGTACACCCTGCCCCCATCCCGGGAGGAGATGACCA AGAACCAGGTCAGCCTGACCTGCCTGGTCAAAGGCTTCTAT CCCAGCGACATCGCCGTGGAGTGGGAGAGCAATGGGCAGC CGGAGAACAACTACAAGACCACGCCTCCCGTGCTGGACTC CGACGGCTCCTTCTTCCTCTACAGCAAGCTCACCGTGGACA AGAGCAGATGGCAGCAGGGGAACGTCTTCTCATGCTCCGT GATGCATGAGGCTCTGCACAACCACTACACGCAGAAGTCT CTCTCCCTGTCTCCGGGAAAA |
| PSMB1156 | 114 | GAGGTGCAGCTGGTTGAATCTGGTGGCGGAGTGGTGCAGC CTGGCAGATCTCTGAGACTGTCTTGTGCCGCCTCCGGCTTC ACCTTCACCAGCTACGGAATGCACTGGGTCCGACAGGCCCC TGGCAAAGGATTGGAATGGGTGGCCGTGATCTCCTACGAC GGCTCCAACAAGTACTACGCCGACTCCGTGAAGGGCAGAT TCACCATCTCTCGGGACAACTCCAAGAACACCCTGTACCTG CAGATGAACTCCCTGAGAGCCGAGGACACCGCCGTGTACT ACTGTGCCAGAGAGCACTACGACTCCTCCGGCTACTACCAC GGCTACTATGGCATGGATGTGTGGGGCCAGGGCACCACAG TGACAGTCTCTTCCGCCTCCACCAAGGGCCCATCGGTCTTC CCCCTGGCACCCTCCTCCAAGAGCACCTCTGGGGGCACAGC GGCCCTGGGCTGCCTGGTCAAGGACTACTTCCCCGAACCGG TGACGGTGTCGTGGAACTCAGGCGCCCTGACCAGCGGCGT GCACACCTTCCCGGCTGTCCTACAGTCCTCAGGACTCTACT CCCTCAGCAGCGTGGTGACCGTGCCCTCCAGCAGCTTGGGC ACCCAGACCTACATCTGCAACGTGAATCACAAGCCCAGCA ACACCAAGGTGGACAAGAAAGTTGAGCCCAAATCTTGTGA CAAAACTCACACATGCCCACCGTGCCCAGCACCTGAACTCC TGGGGGGACCGTCAGTCTTCCTCTTCCCCCCAAAACCCAAG GACACCCTCATGATCTCCCGGACCCCTGAGGTCACATGCGT GGTGGTGGACGTGAGCCACGAAGACCCTGAGGTCAAGTTC AACTGGTACGTGGACGGCGTGGAGGTGCATAATGCCAAGA CAAAGCCGCGGGAGGAGCAGTACAACAGCACGTACCGTGT GGTCAGCGTCCTCACCGTCCTGCACCAGGACTGGCTGAATG GCAAGGAGTACAAGTGCAAGGTGTCCAACAAAGCCCTCCC AGCCCCCATCGAGAAAACCATCTCCAAAGCCAAAGGGCAG CCCCGAGAACCACAGGTGTACACCCTGCCCCCATCCCGGG AGGAGATGACCAAGAACCAGGTCAGCCTGACCTGCCTGGT CAAAGGCTTCTATCCCAGCGACATCGCCGTGGAGTGGGAG AGCAATGGGCAGCCGGAGAACAACTACAAGACCACGCCTC CCGTGCTGGACTCCGACGGCTCCTTCTTCCTCTACAGCAAG CTCACCGTGGACAAGAGCAGATGGCAGCAGGGGAACGTCT TCTCATGCTCCGTGATGCATGAGGCTCTGCACAACCACTAC ACGCAGAAGTCTCTCTCCCTGTCTCCGGGAAAA |
| PSMB1088 | 116 | GAGGTGCAGCTGGTGGAGTCTGGGGGAGGCGTGGTCCAGC CTGGGAGGTCCCTGAGACTCTCCTGTGCAGCCTCTGGATTC ACCTTCAGTAGTTATGACATGCACTGGGTCCGCCAGGCTCC AGGCAAGGGGCTGGAGTGGGTGACAGTTATATCATTTGAT GGAAGTAATAAATACTATGTAGACTCCGTGAAGGGCCGAT TCACCATCTCCAGAGACAATTCCAAGAATACGCTGTATCTG CAAATGAACAGCCTGAGAGCTGAGGACACGGCTGTGTATT ACTGTGCGAGAACGTATTACGATATTTTGACTGGTTATTCC CACTACTCCTACGGTATGGACGTCTGGGGCCAAGGGACCA CGGTCACCGTCTCCTCAGCCTCCACCAAGGGCCCATCGGTC TTCCCCCTGGCACCCTCCTCCAAGAGCACCTCTGGGGGCAC AGCGGCCCTGGGCTGCCTGGTCAAGGACTACTTCCCCGAAC CGGTGACGGTGTCGTGGAACTCAGGCGCCCTGACCAGCGG CGTGCACACCTTCCCGGCTGTCCTACAGTCCTCAGGACTCT ACTCCCTCAGCAGCGTGGTGACCGTGCCCTCCAGCAGCTTG GGCACCCAGACCTACATCTGCAACGTGAATCACAAGCCCA GCAACACCAAGGTGGACAAGAAAGTTGAGCCCAAATCTTG TGACAAAACTCACACATGCCCACCGTGCCCAGCACCTGAA CTCCTGGGGGGACCGTCAGTCTTCCTCTTCCCCCCAAAACC CAAGGACACCCTCATGATCTCCCGGACCCCTGAGGTCACAT GCGTGGTGGTGGACGTGAGCCACGAAGACCCTGAGGTCAA GTTCAACTGGTACGTGGACGGCGTGGAGGTGCATAATGCC AAGACAAAGCCGCGGGAGGAGCAGTACAACAGCACGTACC GTGTGGTCAGCGTCCTCACCGTCCTGCACCAGGACTGGCTG AATGGCAAGGAGTACAAGTGCAAGGTCTCCAACAAAGCCC |

TABLE 17-continued

HC nucleotide sequences of selected anti-PSMA antibodies.

| Antibody | HC NUCLEOTIDE SEQ ID NO: | HC NUCLEIC ACID SEQUENCE |
|---|---|---|
| | | TCCCAGCCCCCATCGAGAAAACCATCTCCAAAGCCAAAGG GCAGCCCCGAGAACCACAGGTGTACACCCTGCCCCCATCCC GGGAGGAGATGACCAAGAACCAGGTCAGCCTGACCTGCCT GGTCAAAGGCTTCTATCCCAGCGACATCGCCGTGGAGTGG GAGAGCAATGGGCAGCCGGAGAACAACTACAAGACCACGC CTCCCGTGCTGGACTCCGACGGCTCCTTCTTCCTCTACAGC AAGCTCACCGTGGACAAGAGCAGATGGCAGCAGGGGAACG TCTTCTCATGCTCCGTGATGCATGAGGCTCTGCACAACCAC TACACGCAGAAGAGCCTCTCCCTGTCTCCGGGTAAA |
| PSMB1098 | 118 | CAGGTGCAGCTGGTGGAGTCTGGGGGAGGCGTGGTCCAGC CTGGGAGGTCCCTGAGACTCTCCTGTGCAGCCTCTGGATTC ACCTTCAGTACCTATGGCATGCACTGGGTCCGCCAGGCTCC AGGCAAGGGGCTGGAGTGGGTGGCATTTATATCATATGAT GGAAGTAATAAATACTATGCAGACTCCGTGAAGGGCCGAT TCACCATCTCCAGAGACAATTCCAAGCACACGCTATATCTG CAAATGAACAGCCTGAGAGCTGAGGACACGGCTGTGTATT ACTGTGCGGGGAGAGACAACCTACGATTTTTGGAGTGGTTT ATGGACGTCTGGGGCCAAGGGACCACGGTCACCGTCTCTTC AGCCTCCACCAAGGGCCCATCGGTCTTCCCCCTGGCACCCT CCTCCAAGAGCACCTCTGGGGGCACAGCGGCCCTGGGCTG CCTGGTCAAGGACTACTTCCCCGAACCGGTGACGGTGTCGT GGAACTCAGGCGCCCTGACCAGCGGCGTGCACACCTTCCC GGCTGTCCTACAGTCCTCAGGACTCTACTCCCTCAGCAGCG TGGTGACCGTGCCCTCCAGCAGCTTGGGCACCCAGACCTAC ATCTGCAACGTGAATCACAAGCCCAGCAACACCAAGGTGG ACAAGAAAGTTGAGCCCAAATCTTGTGACAAAACTCACAC ATGCCCACCGTGCCCAGCACCTGAACTCCTGGGGGGACCGT CAGTCTTCCTCTTCCCCCCAAAACCCAAGGACACCCTCATG ATCTCCCGGACCCCTGAGGTCACATGCGTGGTGGTGGACGT GAGCCACGAAGACCCTGAGGTCAAGTTCAACTGGTACGTG GACGGCGTGGAGGTGCATAATGCCAAGACAAAGCCGCGGG AGGAGCAGTACAACAGCACGTACCGTGTGGTCAGCGTCCT CACCGTCCTGCACCAGGACTGGCTGAATGGCAAGGAGTAC AAGTGCAAGGTCTCCAACAAAGCCCTCCCAGCCCCCATCG AGAAAACCATCTCCAAAGCCAAAGGGCAGCCCCGAGAACC ACAGGTGTACACCCTGCCCCCATCCCGGGAGGAGATGACC AAGAACCAGGTCAGCCTGACCTGCCTGGTCAAAGGCTTCTA TCCCAGCGACATCGCCGTGGAGTGGGAGAGCAATGGGCAG CCGGAGAACAACTACAAGACCACGCCTCCCGTGCTGGACT CCGACGGCTCCTTCTTCCTCTACAGCAAGCTCACCGTGGAC AAGAGCAGATGGCAGCAGGGGAACGTCTTCTCATGCTCCG TGATGCATGAGGCTCTGCACAACCACTACACGCAGAAGAG CCTCTCCCTGTCTCCGGGTAAA |
| PSMB1113 | 120 | GAGGTGCAGCTGGTGGAGTCTGGGGGAGGCCTGGTCAAGC CGGGGGGGTCCCTGAGACTCTCCTGTGCAGCCTCTGGATTC ACCCTCAGTATTTATAGCATGAACTGGGTCCGCCAGGCTCC AGGGAAGGGGCTGGAGTGGGTCTCATCCATTAGCAGTAGT AGTAGTTACATATTCTACGCAGACTCAGTGAAGGGCCGATT CACCATCTCCAGAGACAACGCCAAGAACTCACTCTTTCTGC AAATGAACAGCCTGAGAGCCGAGGACACGGCTGTGTATTA CTGTGCGAGATCCTCCTACGGTGCGGACTACTGGGGCCAGG GAACCCTGGTCACCGTCTCTTCAGCCTCCACCAAGGGCCCA TCGGTCTTCCCCCTGGCACCCTCCTCCAAGAGCACCTCTGG GGGCACAGCGGCCCTGGGCTGCCTGGTCAAGGACTACTTCC CCGAACCGGTGACGGTGTCGTGGAACTCAGGCGCCCTGAC CAGCGGCGTGCACACCTTCCCGGCTGTCCTACAGTCCTCAG GACTCTACTCCCTCAGCAGCGTGGTGACCGTGCCCTCCAGC AGCTTGGGCACCCAGACCTACATCTGCAACGTGAATCACA AGCCCAGCAACACCAAGGTGGACAAGAAAGTTGAGCCCAA ATCTTGTGACAAAACTCACACATGCCCACCGTGCCCAGCAC CTGAACTCCTGGGGGGACCGTCAGTCTTCCTCTTCCCCCCA AAACCCAAGGACACCCTCATGATCTCCCGGACCCCTGAGGT CACATGCGTGGTGGTGGACGTGAGCCACGAAGACCCTGAG GTCAAGTTCAACTGGTACGTGGACGGCGTGGAGGTGCATA ATGCCAAGACAAAGCCGCGGGAGGAGCAGTACAACAGCAC GTACCGTGTGGTCAGCGTCCTCACCGTCCTGCACCAGGACT GGCTGAATGGCAAGGAGTACAAGTGCAAGGTCTCCAACAA AGCCCTCCCAGCCCCCATCGAGAAAACCATCTCCAAAGCC AAAGGGCAGCCCCGAGAACCACAGGTGTACACCCTGCCCC CATCCCGGGAGGAGATGACCAAGAACCAGGTCAGCCTGAC CTGCCTGGTCAAAGGCTTCTATCCCAGCGACATCGCCGTGG AGTGGGAGAGCAATGGGCAGCCGGAGAACAACTACAAGA |

TABLE 17-continued

HC nucleotide sequences of selected anti-PSMA antibodies.

| Antibody | HC NUCLEOTIDE SEQ ID NO: | HC NUCLEIC ACID SEQUENCE |
|---|---|---|
| | | CCACGCCTCCCGTGCTGGACTCCGACGGCTCCTTCTTCCTCT ACAGCAAGCTCACCGTGGACAAGAGCAGATGGCAGCAGGG GAACGTCTTCTCATGCTCCGTGATGCATGAGGCTCTGCACA ACCACTACACGCAGAAGAGCCTCTCCCTGTCTCCGGGTAAA |
| PSMB1195 | 122 | GAGGTGCAGCTGGTGGAGTCTGGGGGAGGCCTGGTCAAGC CTGGGGGGTCCCTGAGACTCTCCTGTGCAGCCTCTGGATTC ACCTTCAGCAGCTATAGCCTGAACTGGGTCCGCCAGGCTCC AGGGAAGGGGCTGGAGTGGGTCTCATCCATTAGTAGTAGT AGTAGTTACATATCCTACGCAGACGCAGTGAAGGGCCGAT TCACCATCTCCAGAGACAACGCCAAGAACTCACTGTATCTG CAAATGAACAGCCTGAGAGCCGAGGACACGGCTGTGTATT ACTGTGCGAGAGATCGGGGATTTTTGGAGGATTACTACTAC TACTACGGTATGGACGTCTGGGGCCAAGGGACCACGGTCA CCGTCTCCTCAGCCTCCACCAAGGGCCCATCGGTCTTCCCC CTGGCACCCTCCTCCAAGAGCACCTCTGGGGGCACAGCGG CCCTGGGCTGCCTGGTCAAGGACTACTTCCCCGAACCGGTG ACGGTGTCGTGGAACTCAGGCGCCCTGACCAGCGGCGTGC ACACCTTCCCGGCTGTCCTACAGTCCTCAGGACTCTACTCC CTCAGCAGCGTGGTGACCGTGCCCTCCAGCAGCTTGGGCAC CCAGACCTACATCTGCAACGTGAATCACAAGCCCAGCAAC ACCAAGGTGGACAAGAAAGTTGAGCCCAAATCTTGTGACA AAAACTCACACATGCCCACCGTGCCCAGCACCTGAACTCCTG GGGGGACCGTCAGTCTTCCTCTTCCCCCCAAAACCCAAGGA CACCCTCATGATCTCCCGGACCCCTGAGGTCACATGCGTGG TGGTGGACGTGAGCCACGAAGACCCTGAGGTCAAGTTCAA CTGGTACGTGGACGGCGTGGAGGTGCATAATGCCAAGACA AAGCCGCGGGAGGAGCAGTACAACAGCACGTACCGTGTGG TCAGCGTCCTCACCGTCCTGCACCAGGACTGGCTGAATGGC AAGGAGTACAAGTGCAAGGTCTCCAACAAAGCCCTCCCAG CCCCCATCGAGAAAACCATCTCCAAAGCCAAAGGGCAGCC CCGAGAACCACAGGTGTACACCCTGCCCCCATCCCGGGAG GAGATGACCAAGAACCAGGTCAGCCTGACCTGCCTGGTCA AAGGCTTCTATCCCAGCGACATCGCCGTGGAGTGGGAGAG CAATGGGCAGCCGGAGAACAACTACAAGACCACGCCTCCC GTGCTGGACTCCGACGGCTCCTTCTTCCTCTACAGCAAGCT CACCGTGGACAAGAGCAGATGGCAGCAGGGGAACGTCTTC TCATGCTCCGTGATGCATGAGGCTCTGCACAACCACTACAC GCAGAAGAGCCTCTCCCTGTCTCCGGGTAAA |

TABLE 18

LC nucleotide sequences of selected anti-PSMA antibodies.

| ANTIBODY | LC NUCLEOTIDE SEQ ID NO: | LC NUCLEIC ACID SEQUENCE |
|---|---|---|
| PSMB1154 | 105 | CAGCTGGTTCTGACCCAGCCTCCTTCTGTGTCTGTGGCTCCT GGCCAGACCGCCAGAATTACCTGTGGCGGCAACAACATCG GCTCCAAGTCCGTGCACTGGTATCAGCAGAAGCCTGGACA GGCTCCTGTGCTGGTGGTGTACGACAACTCTGACCGGCCTT CTGGCATCCCTGAGAGATTCTCCGGCTCCAACAGCGGCAAT ACCGCCACACTGACCATCTCCAGAGTGGAAGTGGGCGACG AGGCCGACTACTACTGCCAAGTGTGGGACTCCTCCTCCGAT CATGTGGTGTTTGGCGGCGGAACAAAGCTGACAGTGCTGG GTCAGCCCAAGGCTGCACCCAGTGTCACTCTGTTCCCGCCC TCCTCTGAGGAGCTTCAAGCCAACAAGGCCACACTGGTGTG TCTCATAAGTGACTTCTACCCGGGAGCCGTGACAGTGGCCT GGAAGGCCGATAGCAGCCCCGTCAAGGCGGGAGTCGAAAC CACCACACCCTCCAAACAAAGCAACAACAAGTACGCGGCC AGCAGCTATCTGAGCCTGACGCCTGAGCAGTGGAAGTCCC ACAGAAGCTACAGCTGCCAGGTCACGCATGAAGGGAGCAC CGTGGAGAAGACAGTGGCCCCTACAGAATGTTCA |
| PSMB2945 | 105 | CAGCTGGTTCTGACCCAGCCTCCTTCTGTGTCTGTGGCTCCT GGCCAGACCGCCAGAATTACCTGTGGCGGCAACAACATCG GCTCCAAGTCCGTGCACTGGTATCAGCAGAAGCCTGGACA GGCTCCTGTGCTGGTGGTGTACGACAACTCTGACCGGCCTT CTGGCATCCCTGAGAGATTCTCCGGCTCCAACAGCGGCAAT ACCGCCACACTGACCATCTCCAGAGTGGAAGTGGGCGACG |

TABLE 18-continued

LC nucleotide sequences of selected anti-PSMA antibodies.

| ANTIBODY | LC NUCLEOTIDE SEQ ID NO: | LC NUCLEIC ACID SEQUENCE |
|---|---|---|
| | | AGGCCGACTACTACTGCCAAGTGTGGGACTCCTCCTCCGAT<br>CATGTGGTGTTTGGCGGCGGAACAAAGCTGACAGTGCTGG<br>GTCAGCCCAAGGCTGCACCCAGTGTCACTCTGTTCCCGCCC<br>TCCTCTGAGGAGCTTCAAGCCAACAAGGCCACACTGGTGTG<br>TCTCATAAGTGACTTCTACCCGGGAGCCGTGACAGTGGCCT<br>GGAAGGCCGATAGCAGCCCCGTCAAGGCGGGAGTCGAAAC<br>CACCACACCCTCCAAACAAAGCAACAACAAGTACGCGGCC<br>AGCAGCTATCTGAGCCTGACGCCTGAGCAGTGGAAGTCCC<br>ACAGAAGCTACAGCTGCCAGGTCACGCATGAAGGGAGCAC<br>CGTGGAGAAGACAGTGGCCCCTACAGAATGTTCA |
| PSMB1183 | 109 | CAGTCTGCTCTGACCCAGCCTCCTTCTGTGTCTGGCGCTCCT<br>GGCCAGAGAGTGACCATCTCTTGTACCGGCTCCAACTCCAA<br>CATCGGCGCCAACTACGACGTGCACTGGTATCAGCATCTGC<br>CCGGCACAGCTCCCAAGCTGCTGATCTACGGCAACATCAAC<br>AGACCCCTGGGCGTGCCCGACCGGTTTTCTGGAAGCAGATC<br>TGGCACCTCTGCCAGCCTGGCTATTACCGGACTGCAGGCTG<br>AGGACGAGGCCGACTACTACTGCCAGTCCTACGACTTCTCC<br>CTGTCCGGCTCCGTGTTTGGCGTGGGCACAAAGCTGACAGT<br>CCTGGGTCAGCCCAAGGCTGCACCCAGTGTCACTCTGTTCC<br>CGCCCTCCTCTGAGGAGCTTCAAGCCAACAAGGCCACACTG<br>GTGTGTCTCATAAGTGACTTCTACCCGGGAGCCGTGACAGT<br>GGCCTGGAAGGCCGATAGCAGCCCCGTCAAGGCGGGAGTC<br>GAAACCACCACACCCTCCAAACAAAGCAACAACAAGTACG<br>CGGCCAGCAGCTATCTGAGCCTGACGCCTGAGCAGTGGAA<br>GTCCCACAGAAGCTACAGCTGCCAGGTCACGCATGAAGGG<br>AGCACCGTGGAGAAGACAGTGGCCCCTACAGAATGTTCA |
| PSMB3003 | 109 | CAGTCTGCTCTGACCCAGCCTCCTTCTGTGTCTGGCGCTCCT<br>GGCCAGAGAGTGACCATCTCTTGTACCGGCTCCAACTCCAA<br>CATCGGCGCCAACTACGACGTGCACTGGTATCAGCATCTGC<br>CCGGCACAGCTCCCAAGCTGCTGATCTACGGCAACATCAAC<br>AGACCCCTGGGCGTGCCCGACCGGTTTTCTGGAAGCAGATC<br>TGGCACCTCTGCCAGCCTGGCTATTACCGGACTGCAGGCTG<br>AGGACGAGGCCGACTACTACTGCCAGTCCTACGACTTCTCC<br>CTGTCCGGCTCCGTGTTTGGCGTGGGCACAAAGCTGACAGT<br>CCTGGGTCAGCCCAAGGCTGCACCCAGTGTCACTCTGTTCC<br>CGCCCTCCTCTGAGGAGCTTCAAGCCAACAAGGCCACACTG<br>GTGTGTCTCATAAGTGACTTCTACCCGGGAGCCGTGACAGT<br>GGCCTGGAAGGCCGATAGCAGCCCCGTCAAGGCGGGAGTC<br>GAAACCACCACACCCTCCAAACAAAGCAACAACAAGTACG<br>CGGCCAGCAGCTATCTGAGCCTGACGCCTGAGCAGTGGAA<br>GTCCCACAGAAGCTACAGCTGCCAGGTCACGCATGAAGGG<br>AGCACCGTGGAGAAGACAGTGGCCCCTACAGAATGTTCA |
| PSMB1157 | 113 | CAGTCTGTGCTGACCCAGCCTCCTTCTGTGTCTGGCGCTCCT<br>GGCCAGAGAGTGACCATCTCCTGTACCGGCTCCTCCTCTAA<br>CATCGGCGCTGACTACGACGTGCACTGGTATCAGCAGCTGC<br>CTGGCACAGCTCCCAAACTGCTGATCTACGTGAACAACAAC<br>CGGCCTTCTGGCGTGCCCGACAGATTCTCTGGAAGCAGATC<br>TGGCACCTCTGCCAGCCTGGCTATTACCGGACTGCAGGCCG<br>ATGACGAGGCCGACTACTACTGCCAGTCCTACGACAACAC<br>CCTGTCCGGCGTTGTGTTTGGCGGCGGAACAAAGCTGACAG<br>TCCTGGGTCAGCCCAAGGCTGCACCCAGTGTCACTCTGTTC<br>CCGCCCTCCTCTGAGGAGCTTCAAGCCAACAAGGCCACACT<br>GGTGTGTCTCATAAGTGACTTCTACCCGGGAGCCGTGACAG<br>TGGCCTGGAAGGCCGATAGCAGCCCCGTCAAGGCGGGAGT<br>GCGGCCAGCAGCTATCTGAGCCTGACGCCTGAGCAGTGGA<br>CGAAACCACCACACCCTCCAAACAAAGCAACAACAAGTAC<br>GCGGCCAGCAGCTATCTGAGCCTGACGCCTGAGCAGTGGA<br>AGTCCCACAGAAGCTACAGCTGCCAGGTCACGCATGAAGG<br>GAGCACCGTGGAGAAGACAGTGGCCCCTACAGAATGTTCA |
| PSMB1156 | 115 | CAGGCTGTTCTGACCCAGCCTCCTTCTGCTTCTGGCACCCCT<br>GGACAGAGAGTGACCATCTCTTGCTCCGGCTCCTCCTCCAA<br>CATCGGCTCCAACTACGTGTACTGGTACCAGCTGCTGCCCG<br>GCACCGCTCCTAAGCTGCTGATCTACTCCAACAACCAGCGG<br>CCTTCTGGCGTGCCCGATAGATTCTCCGGCTCTAAGTCTGG<br>CACCTCTGCCAGCCTGGCTATCTCCGGACTGAGATCTGAGG<br>ACGAGGCCGACTACTACTGCGCCGCCAGAGATGATTCCCTG<br>TCCGGCTATGTGTTTGGCACCGGCACCAAGCTGACAGTGTT<br>GGGTCAGCCCAAGGCTGCACCCAGTGTCACTCTGTTCCCGC<br>CCTCCTCTGAGGAGCTTCAAGCCAACAAGGCCACACTGGTG<br>TGTCTCATAAGTGACTTCTACCCGGGAGCCGTGACAGTGGC |

TABLE 18-continued

LC nucleotide sequences of selected anti-PSMA antibodies.

| ANTIBODY | LC NUCLEOTIDE SEQ ID NO: | LC NUCLEIC ACID SEQUENCE |
|---|---|---|
| | | CTGGAAGGCCGATAGCAGCCCCGTCAAGGCGGGAGTCGAA<br>ACCACCACACCCTCCAAACAAAGCAACAACAAGTACGCGG<br>CCAGCAGCTATCTGAGCCTGACGCCTGAGCAGTGGAAGTC<br>CCACAGAAGCTACAGCTGCCAGGTCACGCATGAAGGGAGC<br>ACCGTGGAGAAGACAGTGGCCCCTACAGAATGTTCA |
| PSMB1088 | 117 | GAAATAGTGATGACGCAGTCTCCATCCTCCCTGTCTGCATC<br>TGTAGGAGACAGAGTCACCATCACTTGCCGGGCGAGTCAG<br>GGCATTAGCAATTATTTAGCCTGGTATCAGCAGAAACCAGG<br>GAAAGTTCCTAAGCTCCTGATCTATGCCACATCCACTTTGC<br>AATCAGGGGTCCCATCTCGGTTCAGTGGCAGTGGATCTGGG<br>ACAGATTTCATTCTCACCATCAGCAGCCTGCAGCCTGAAGA<br>TGTTGCAAACTATTACTGTCAAAAGTATAACAGTGCCCCAT<br>TCACTTTCGGCCCTGGGACCAAGGTGGAGATCAAACGTAC<br>GGTGGCTGCACCATCTGTCTTCATCTTCCCGCCATCTGATG<br>AGCAGTTGAAATCTGGAACTGCCTCTGTTGTGTGCCTGCTG<br>AATAACTTCTATCCCAGAGAGGCCAAAGTACAGTGGAAGG<br>TGGATAACGCCCTCCAATCGGGTAACTCCCAGGAGAGTGTC<br>ACAGAGCAGGACAGCAAGGACAGCACCTACAGCCTCAGCA<br>GCACCCTGACGCTGAGCAAAGCAGACTACGAGAAACACAA<br>AGTCTACGCCTGCGAAGTCACCCATCAGGGCCTGAGCTCGC<br>CCGTCACAAAGAGCTTCAACAGGGGAGAGTGT |
| PSMB1098 | 119 | GAAATAGTGATGACGCAGTCTCCAGCCACCCTGTCTGTGTC<br>TCCAGGGGAAAGAGCCACCCTCTCCTGCAGGGCCAGTCAG<br>AGTGTAAGGAGCAACTTAGCCTGGTACCAGCAGAAACCTG<br>GCCAGGCTCCCAGGCTCCTCATCTATGGTGCATCCACCAGG<br>GCCACTGGTATCCCAGCCAGGTTCAGTGGCAGTGGGTCTGG<br>GACAGAGTTCACTCTCACCATCAGCAGCCTGCAGTCTGAAG<br>ATTTTGCAGTTTATTACTGTCACCAGTATAATGACTGGCCTC<br>CGTACACTTTTGGCCAAGGGACCAAGGTGGAAATCAAACG<br>TACGGTGGCTGCACCATCTGTCTTCATCTTCCCGCCATCTGA<br>TGAGCAGTTGAAATCTGAACTGCCTCTGTTGTGTGCCTGC<br>TGAATAACTTCTATCCCAGAGAGGCCAAAGTACAGTGGAA<br>GGTGGATAACGCCCTCCAATCGGGTAACTCCCAGGAGAGT<br>GTCACAGAGCAGGACAGCAAGGACAGCACCTACAGCCTCA<br>GCAGCACCCTGACGCTGAGCAAAGCAGACTACGAGAAACA<br>CAAAGTCTACGCCTGCGAAGTCACCCATCAGGGCCTGAGCT<br>CGCCCGTCACAAAGAGCTTCAACAGGGGAGAGTGT |
| PSMB1113 | 121 | GAAATAGTGATGACGCAGTCTCCATCCTCCCTGTCTGCATC<br>TGTAGGAGACAGAGTCACCATCACTTGCCGGGCGAGTCAG<br>GACATTACCAATTTTTTAGCCTGGTATCAGCAGAAACCAGG<br>GAAAGTTCCTAAACTCCTGATTTATACTGCATCCACTTTGC<br>AATCAGGGGTCCCATCTCGGTTCAGTGGCAGTGGATCTGGG<br>ACAGATTTCACTCTCACCATCAGCAGCCTGCAGCCTGAAGA<br>TGTTGCGACTTATTACTGTCAAAAGTATAACAGTGCCCCAC<br>TCACTTTCGGCGGAGGGACCAAGCTGGAGATCAAACGTAC<br>GGTGGCTGCACCATCTGTCTTCATCTTCCCGCCATCTGATG<br>AGCAGTTGAAATCTGGAACTGCCTCTGTTGTGTGCCTGCTG<br>AATAACTTCTATCCCAGAGAGGCCAAAGTACAGTGGAAGG<br>TGGATAACGCCCTCCAATCGGGTAACTCCCAGGAGAGTGTC<br>ACAGAGCAGGACAGCAAGGACAGCACCTACAGCCTCAGCA<br>GCACCCTGACGCTGAGCAAAGCAGACTACGAGAAACACAA<br>AGTCTACGCCTGCGAAGTCACCCATCAGGGCCTGAGCTCGC<br>CCGTCACAAAGAGCTTCAACAGGGGAGAGTGT |
| PSMB1195 | 123 | GACATCGTGATGACCCAGTCTCCATCTTCCGTGTCTGCATC<br>TGTAGGAGACAGAGTCACCATCACTTGTCGGGCGAGTCAA<br>GGTATTAGCAACTGGTTAGCCTGGTATCAGCAGAAACCAG<br>GGAAAGCCCCTAAGCTCCTGATCTATGTTGCATCCAGTTTG<br>CAAAGTGGGGTTCCATCAAGGTTCAGCGGCAGTGGATCTG<br>GGACAGATTTCTCTCTCACCATCAGCAGCCTGCAGCCTGAA<br>GATTTTGCAACTTACTATTGTCAACAGGCTTACAGTTTCCCT<br>CTCACTTTCGGCGGAGGGACCAAGGTGGAGATCAAACGTA<br>CGGTGGCTGCACCATCTGTCTTCATCTTCCCGCCATCTGATG<br>AGCAGTTGAAATCTGGAACTGCCTCTGTTGTGTGCCTGCTG<br>AATAACTTCTATCCCAGAGAGGCCAAAGTACAGTGGAAGG<br>TGGATAACGCCCTCCAATCGGGTAACTCCCAGGAGAGTGTC<br>ACAGAGCAGGACAGCAAGGACAGCACCTACAGCCTCAGCA<br>GCACCCTGACGCTGAGCAAAGCAGACTACGAGAAACACAA<br>AGTCTACGCCTGCGAAGTCACCCATCAGGGCCTGAGCTCGC<br>CCGTCACAAAGAGCTTCAACAGGGGAGAGTGT |

TABLE 19

Summary of anti-PSMA antibody SEQ ID NOs.

| Antibody | VH Amino Acid SEQ ID NO: | VL Amino Acid SEQ ID NO: | HC Amino Acid SEQ ID NO: | LC Amino Acid SEQ ID NO: | VH cDNA SEQ ID NO: | VL cDNA SEQ ID NO: | HC cDNA SEQ ID NO: | LC cDNA SEQ ID NO: |
|---|---|---|---|---|---|---|---|---|
| PSMB1154 | 52 | 53 | 84 | 85 | 68 | 69 | 104 | 105 |
| PSMB2945 | 52 | 53 | 86 | 85 | 68 | 69 | 106 | 105 |
| PSMB1183 | 54 | 55 | 88 | 89 | 70 | 71 | 108 | 109 |
| PSMB3003 | 54 | 55 | 90 | 89 | 70 | 71 | 110 | 109 |
| PSMB1157 | 56 | 57 | 92 | 93 | 72 | 73 | 112 | 113 |
| PSMB1156 | 58 | 59 | 94 | 95 | 74 | 75 | 114 | 115 |
| PSMB1088 | 60 | 61 | 96 | 97 | 76 | 77 | 116 | 117 |
| PSMB1098 | 62 | 63 | 98 | 99 | 78 | 79 | 118 | 119 |
| PSMB1113 | 64 | 65 | 100 | 101 | 80 | 81 | 120 | 121 |
| PSMB1195 | 66 | 67 | 102 | 103 | 82 | 83 | 122 | 123 |

Example 3. Characterization and Triage of Anti-PSMA Antibodies

Analytical Characterization of Anti-PSMA Antibodies

The protein concentration for the 96 purified mAb was determined by measuring the absorbance at 280 nm on a NANODROP1000 spectrophotometer or TRINEAN DROPSENSE96 multichannel spectrophotometer and calculated using the extinction coefficient based on the amino acid sequence.

SE HPLC of the purified antibodies was performed by running samples on a TOSOH TSKgel BioAssist G3SWxl column, in 0.2 M Na Phosphate pH 6.8 at 1 mL/min on a Waters Alliance HPLC for 20 min. The column effluent was monitored by absorbance at 280 nm. For a molecule to be considered a therapeutic lead, it is critical that it can be produced in substantial amounts with high purity and high yield. Typically, purification losses are higher, and yields are lower with aggregation-prone proteins. The initial monomer percentage is generally considered a good surrogate indicator of the manufacturability of a protein. Table 20 summarizes the SEC data for a subset of selected mAbs-majority of which had >90% monomers post protein A purification suggesting good manufacturability.

TABLE 20

| Antibody Name | SEC (% monomer post protein A) |
|---|---|
| PSMB1154 | 98.1 |
| PSMB1183 | 98.6 |
| PSMB1157 | 90.0 |
| PSMB1156 | 98.5 |
| PSMB1098 | 96.4 |
| PSMB1088 | 96.4 |
| PSMB1113 | 96.7 |
| PSMB1195 | 97.4 |

Anti-PSMA Antibodies Binding to PSMA Antigen

The binding affinity of purified anti-PSMA antibodies to the recombinant human ECD was determined by surface plasmon resonance (SPR) using a BIACORE 8K instrument. The antibodies were captured on a goat anti-Fc antibody-modified C1 chip and titrated with 3-fold serial dilutions of PSMA antigen spanning concentrations of 1 nM to 11.1 nM. The association and dissociation were monitored for 3 and 15 minutes, respectively, using a flow rate of 50 µL/min. Raw binding data was referenced by subtracting the analyte binding signals from blanks and analyzed using a 1:1 Langmuir binding model using the Biacore Insight evaluation software to obtain the kinetics which were used to calculate the binding affinity. The kinetic parameter of binding of selected antibodies are shown in Table 21. The anti-PSMA antibodies were found to bind human PSMA with picomolar to nanomolar affinities.

TABLE 21

| Antibody Name | Kon (1/Ms) | Koff (1/s) | SPR KD (M) |
|---|---|---|---|
| PSMB1154 | 1.74E+05 | 1.90E−04 | 1.09E−09 |
| PSMB1183 | 4.32E+05 | 4.01E−04 | 9.28E−10 |
| PSMB1157 | 1.94E+05 | 2.74E−04 | 1.42E−09 |
| PSMB1156 | 3.06E+05 | 1.68E−04 | 5.48E−10 |
| PSMB1098 | 5.27E+04 | 2.85E−05 | 5.40E−10 |
| PSMB1088 | 2.94E+04 | 2.85E−05 | 9.70E−10 |
| PSMB1113 | 5.73E+04 | 6.65E−05 | 1.16E−09 |
| PSMB1195 | 1.07E+04 | 1.01E−04 | 9.45E−09 |

FASCS Binding on C4-2B Cells

The affinity of the purified antibodies was also determined on C4-2B, a cell line with high PSMA levels. Briefly, C4-2B cells were washed once with 1×PBS and incubated with 3 mls/T150 flask of cell dissociation buffer until detached, the cells were collected and strained through a 100 uM sieve. Cells were resuspended at 0.5×10e6 cells/mL in staining buffer (BD #554657) and seeded at 25,000 cells/well in V bottom plate (Corning 3894). To each well, 50 µl of Ab 4-fold serially diluted in staining buffer from 120 nM (60 nM final) were added at 2 X final concentration. Control mAbs were added at 2 µg/ml, 1 µg/ml final (controls were: —secondary only and isotype control). All primary antibodies were incubated with the cells for 60 min at 4° C. After the primary incubation, 100 µl staining buffer were added to all wells and the cells were washed by pelleting by centrifugation at 300×g 5 min and buffer removed by flicking the plate. Then cells were similarly washed again with 200 µl staining buffer. 50 µl per well of goat anti human AF647 (Jackson 109-606-098) was then added at 2 µg/ml in staining buffer. After 30 minutes incubation at 4° C., the cells were washed as described above with 150 ul staining buffer, followed by a final wash with 200 ul running buffer (Running buffer is staining buffer plus 1 mM EDTA and 0.1% pluronic acid). Cells were resuspended in 30 ul/well running buffer with 1:1000 Sytox Blue viability stain (Invitrogen

S34857) and stored at 4° C. until read on the flow cytometer. Plates were read on an IntelliCyt IQue 3 instrument. Briefly, cells were gated on live cells, then populations were gated on singlets. Antibody binding was assessed by AF647 fluorescence at 647 nm. Data was analyzed in GeneData Screener with signal/background AF647 fluorescence plotted against antibody concentration. Curve fitting was done in a four-parameter fit to generate EC50 (qAC50, M) values shown in Table 22.

TABLE 22

| Antibody Name | FACS EC50 [M] |
|---|---|
| PSMB1154 | 3.06E−10 |
| PSMB1183 | 1.56E−10 |
| PSMB1157 | 3.81E−10 |
| PSMB1156 | 6.33E−10 |
| PSMB1098 | 2.46E−09 |
| PSMB1088 | 1.24E−08 |
| PSMB1113 | 2.52E−09 |
| PSMB1195 | 1.38E−08 |

Thermal Stability of Anti-PSMA Antibodies

The thermal stability (conformational stability) of the anti-PSMA antibodies was determined by nanoDSF method using a Prometheus instrument. Measurements were made by loading sample into 24 well capillary from a 384 well sample plate. Duplicate runs were performed. The thermal scans span from 20° C. to 95° C. at a rate of 1.0° C./minute. The data was processed to obtain integrated data and first derivation analysis for 330 nm, 350 nm, Ratio 330/350, and scatter data from which thermal transitions, onset of unfolding, Tm and Tagg were obtained.

"Tm" or "mid-point temperature" "is the temperature midpoint of a thermal unfolding curve. It refers to the temperature where 50% of the amino acid sequence is in its native conformation and the other 50% is denatured. A thermal unfolding curve is typically plotted as a function of temperature. Tm is used to measure protein stability. In general, a higher Tm is an indication of a more stable protein. The Tm can be readily determined using methods well known to those skilled in the art such as Circular Dichroism Spectroscopy, Differential Scanning calorimetry, Differential Scanning Fluorimetry (both intrinsic and extrinsic dye based), UV spectroscopy, FT-IR and Isothermal calorimetry (ITC).

"Tagg" refers to the temperature at which the protein starts to aggregate either through dimerization or oligomerization. The aggregation temperature detects the onset of aggregation, the temperature at which a protein will show a tendency to aggregate. Tagg can be determined by differential scanning calorimetry (DSC), Differential Scanning Fluorimetry (DSF) or by circular dichroism (CD). These techniques can detect small changes in the conformation of the protein and therefore detect the starting point of aggregation. Tagg values can be lower or higher than Tm. In cases where Tagg is lower than Tm, the protein either dimerizes and/or oligomerizes first and then starts unfolding later at higher temperatures than the Tagg. In cases where Tagg is higher than Tm, the protein starts to unfold first and then aggregates at a higher temperature than the Tm. Both events are commonly observed and depend on amino acid composition and protein conformation.

Thermal unfolding parameters, Tm or midpoint temperature of thermal unfolding and Tagg or aggregation temperature of selected anti-PSMA antibodies are shown in Table 23.

TABLE 23

| Antibody Name | Fab Tm (° C.) | Tagg (° C.) |
|---|---|---|
| PSMB1154 | 72.8 | 72.8 |
| PSMB1183 | 71.3 | 71.7 |
| PSMB1157 | 77.5 | 76.4 |
| PSMB1156 | 76.5 | 77.2 |
| PSMB1098 | 77.7 | 77.8 |
| PSMB1088 | 75.9 | 76.7 |
| PSMB1113 | 72.0 | 73.2 |
| PSMB1195 | 80.0 | 79.6 |

High Throughput Conjugation to MMAF mAbs were conjugated to a monomethyl auristatin F (MMAF) payload in a 96-well format to enable screening for optimal ADC candidates. 220 ug of each mAb (1 mg/mL in dPBS) was mixed with TCEP to a final concentration of 3 mM and incubated at 37° C. for 1 hr. Reduced mAbs were captured on protein A resin (Protein A HP Multitrap, GE) and washed 3× with 100 mM potassium phosphate containing 2 mM EDTA at pH 7.5 to remove TCEP.

A mixture of maleimide-PEG4-vcPAB-MMAF and N-ethyl maleimide (60:40 molar ratio, 100 uM total in 100 mM potassium phosphate containing 2 mM EDTA at pH 7.5) was prepared and the resin with bound mAb was resuspended in 300 uL of the maleimide mixture. Samples were rotated for 1 hr at RT followed by quenching with N—Ac-L-Cys (2.6 mM final). Resin was washed with dPBS and then bound mAbs were eluted with 100 mM sodium acetate pH 3.5 into 0.2-0.25 volumes of 1 M Tris pH 8.0 to neutralize. ADC concentrations and DAR (panel average of 4.0±0.5) of the eluted ADCs were determined by UV-Vis spectrophotometry at 248 and 280 nm based on previous reports (Hamblett, et. al., (2004) Clinical Cancer Research, 10, 7063-7070; Cruz and Kayser (2009) Cancers 11(6), 870)

Cytotoxicity Assessment on C4-2B Cells of Anti-PSMA Antibodies

C4-2b cells, a cell line with high PSMA expression, were cultured in RPMI1640 containing GlutaMAX, 25 mM HEPES and 10% fetal bovine serum (FBS) and then plated in white 96 well plates at 3000 cells per well (60 uL/well). Twenty four hours after plating, cells were treated with varying concentrations of the ADCs and then incubated at 37C, 5% CO2. Following 72h of treatment, cell viability was assessed by Cell Titer Glo (Promega), according to manufacturer's instructions. Relative luminescence units (RLU) were detected in an Envision plate reader (Molecular Devices) and then normalized to untreated controls. The concentration at which there was 50% toxicity was determined by fitting the values to a 3-point sigmoidal curve where the top was constrained to 100% and interpolating the X-value at Y=50%. Table 24 shows IC50 values for selected ADCs.

TABLE 24

| Antibody Name | Cytotox (IC50) C4-2B, DAR ~4.0 |
|---|---|
| PSMB1154 | 1.56E−11 |
| PSMB1183 | 1.60E−11 |
| PSMB1157 | 1.94E−11 |
| PSMB1156 | 2.60E−11 |
| PSMB1098 | 5.64E−11 |
| PSMB1088 | 6.70E−11 |
| PSMB1113 | 7.55E−11 |
| PSMB1195 | 1.66E−10 |

Example 4. Additional Characterization of Selected Anti-PSMA Antibodies

Based on the results summarized in Table 20-24 and in conjunction with an in-silico sequence analysis, 4 mAbs (PSMB1154, PSMB1183, PSMB1157 and PSMB1156) from diverse CDR families were selected for further pre-clinical evaluation and triaged using additional biophysical characterization assays such as HIC, CIC and HUVEC to assess hydrophobicity, self-interaction and non-specificity, respectively, as well as for cytotoxicity/internalization in cell lines with range of PSMA receptor densities.

Hydrophobic Interaction Chromatography (HIC)

To assess surface their hydrophobicity, the anti-PSMA antibodies were evaluated by HIC (hydrophobic interaction chromatography) method. In summary samples were diluted 1:5 in high salt buffer A and approximately 10 ugs of sample was injected on a TOSOH TSKgel Butyl-NPR column on an Agilent HPLC instrument. HIC was run under a linear Amonium-SO4 gradient from 1.1M-0M. UV280, and fluorescence (excitation at 280 nm and emission at 340 nm) signals were collected. The hydrophobicity propensity was evaluated as retention time relative to a control of known high hydrophobicity and reported as a hydrophobicity index (HI). Retention times and hydrophobicity index of selected anti-PSMA antibodies are shown in Table 25.

TABLE 25

Characterization of anti-PSMA antibodies by HIC.

| Antibody Name | Retention time (min) | HI |
|---|---|---|
| PSMB1183 | 3.576 | 0.69 |
| PSMB1157 | 4.361 | 0.84 |
| PSMB1156 | 3.348 | 0.64 |
| PSMB1154 | 2.338 | 0.45 |
| Low hydrophobicity control | 2.758 | 0.53 |
| high hydrophobicity control | 5.219 | 1.00 |

Cross Interaction Chromatography (CIC)

To assess IgG cross-interaction potential the anti-PSMA antibodies were evaluated by CIC (cross interaction chromatography) method. In summary, samples were diluted to 0.11 mg/mL in PBS and 15 uL of sample were injected on a Perfinity Custom IgG coupled column. HIC was run by eluting with PBS at 0.2 ml/min while monitoring A280, A214 and A254. The IgG cross-interaction propensity was evaluated as retention time relative to a control of known IgG cross-interaction. Retention times of selected anti-PSMA antibodies are shown in Table 26.

TABLE 26

Characterization of anti-PSMA antibodies by CIC

| Antibody Name | Retention time (min) |
|---|---|
| PSMB 1183 | 4.430 |
| PSMB1157 | 4.638 |
| PSMB 1156 | 4.565 |
| PSMB 1154 | 4.372 |
| Low CIC control | 4.598 |
| high CIC control | 5.321, 10.380 |

Serum Stability

To assess stability in serum, the anti-PSMA antibodies were labeled with AlexaFluor488 (AF488) and incubated (Conc: 1 mg/mL) for 1 week in human serum at 37° C. Following incubation aggregation and fragmentation were evaluated by SEC-FDS (Size exclusion chromatography with fluorescence detection) method. Briefly, the incubated samples were injected on a TOSOH TSKgel BioAssist G3000SWXL on an Agilent 1260 Infinity II HPLC. SEC-FDS was run by eluting with PBS at 1 mL/min while monitoring A280 and fluorescence (494 nm (emission) & 520 nm (excitation)). Results for selected anti-PSMA antibodies incubated at 37° C. for 7 days and controls at time zero are shown in Table 27.

TABLE 27

Serum stability testing of anti-PSMA antibodies by SEC-FDS

| | Fragmentation (%) | | Aggregation (%) | |
|---|---|---|---|---|
| Antibody Name | Time 0 | 37° C., 7 days | Time 0 | 37° C., 7 days |
| PSMB1154 | 0 | 0 | 0 | 0.6 |
| PSMB1157 | 0 | 0 | 0 | 0.6 |
| PSMB1183 | 0 | 0 | 0 | 0.2 |

ND: Not determined

Medium Scale Conjugation to DAR 4 for MMAF

Selected mAbs were conjugated to a monomethyl auristatin F (MMAF) payload to confirm results from initial screening. Briefly, 600 ug of each mAb (1.2 mg/mL in 1×dPBS) was adjusted to pH 7.5 by addition of 1M potassium phosphate containing 50 mM EDTA (1:10 volumes). pH adjusted mAb was mixed with TCEP to a final concentration of 0.6 mM and incubated at 37° C. for 1 hr. To quench the TCEP (Gololobov and Kasukhin (1991) Tetrahedron 48, 1353-1406; Kantner, et. al. (2017) *ACS Omega* 2, 5785-57) 5 mM 3-amino-propyl-azide was added to the reaction and incubated for 30 min at 37° C. A mixture of maleimide-PEG4-vcPAB-MMAF and N-ethyl maleimide (60:40 molar ratio, 108 uM total) was added to the reduced (TCEP neutralized) mAb and incubated for 1 hour at RT followed by quenching with N—Ac-L-Cys (2 mM final). ADCs were separated from reaction components and buffer exchanged into dPBS by diafiltration. ADC concentrations and DAR (panel average of 3.4±0.4) of the eluted ADCs were estimated by UV-Vis spectrophotometry at 248 and 280 nm based on previous reports of Hamblett et. al.[1], and Cruz and Kayser (Cruz and Kayser (2009) *Cancers* 11(6), 870). DAR was also calculated by liquid chromatography/mass spectroscopy. Deconvolution of the extracted charge state allowed for the identification and relative fraction (of total) for each light chain and heavy chain species present, as well as their respective degrees of labeling with either maleimide-PEG4-vcPAB-MMAF, N-ethyl maleimide, or (in the case of heavy chain) a combination of both. Total DAR (panel average of 3.4±0.5) for the ADC was calculated from the sum of light chain and heavy chain labeled only with maleimide-PEG4-vcPAB-MMAF. Size exclusion chromatography was carried out to determine percent monomeric fraction based on migration time relative to unlabeled mAbs.

Medium Scale Conjugation to DAR 8 with DX8951 (Camptothecinoid)

Selected mAbs were also conjugated via maleimide/thiol chemistry to an exatecan methansulfonate derived camptothecinoid DX8951, containing a Gly-Gly-Phe-Gly linker (SEQ ID NO: 340) to facilitate cleavage and release of the payload. Briefly, 350 ug of each mAb (1.1 mg/mL in dPBS) was adjusted to pH 8.0 by addition of 0.5M borate (1:10) and 0.5M EDTA. pH adjusted mAb was mixed with TCEP to a final concentration of 0.6 mM and incubated at 37° C. for 1 hr. To quench the TCEP (Gololobov and Kasukhin (1991) Tetrahedron 48, 1353-1406; Kantner, et. al. (2017) ACS Omega 2, 5785-57), 5 mM 3-amino-propyl-azide was added to the reaction and incubated for 30 min 37° C. MC-GGFG-DX8951 was added to the reduced mAb at 16-fold molar excess relative to mAb, and incubated for 1 hr at 37° C. ADCs were separated from reaction components and buffer exchanged into dPBS by diafiltration. Final molar concentration of ADC was determined by bicinchoninic acid assay, using unconjugated mAb as a standard. DAR was determined to be 8.0 for all ADCs by Liquid chromatography/mass spectroscopy as described in section 4.6. Size exclusion chromatography determined labeling to have minimal impact on aggregation, based on comparative analysis migration time relative to unlabeled mAbs.

In Vitro Cytotoxicity Assessment on C4-2B, 22RV1, and HUVECs Using MMAF and DX8951 as Payload In vitro cytotoxicity of selected ADCs was also assessed in a panel of cell lines expressing various levels of PSMA, and a human endothelial cell line HUVEC which was used as a surrogate for non-specific killing. Briefly, C4-2B cells, expressing high levels of PSMA, were cultured in RPMI1640 containing GlutaMAX, 25 mM HEPES and 10% fetal bovine serum (FBS) and then plated in white 96 well plates at 3000 cells per well. HUVEC cells, known to be PSMA negative, were plated at 8000 cells per well in Medium 200 containing low serum growth supplement (Gibco #S-003-10).

Twenty four hours after plating, cells were treated with varying concentrations of the ADCs and then set at 37C, 5% CO2. Following 72h of treatment, cell viability was assessed by Cell Titer Glo (Promega), according to manufacturer's instructions. Relative luminescence units (RLU) were detected in an Envision plate reader (Perkin Elmer) and then normalized to untreated controls. The concentration at which there was 50% toxicity was determined by fitting the values to a 3-point sigmoidal curve where the top was constrained to 100% and interpolating the X-value at Y=50%. IC50 values for selected mAbs are shown in Table 28 below. All selected mAbs showed very potent (low IC50 values) killing on C4-2B cells and also excellent selectivity (high IC50 value on HUVEC versus C4-2B).

TABLE 28

PSMA ADC potency is shown for a panel of PSMA mAbs conjugated to vcMMAF and treated on PSMA+ (C4-2B) or PSMA- (HUVEC) cells.

| mAb | DAR | C4-2B IC50 (nM) | HUVEC IC50 (nM) | Ratio of HUVEC/ C4-2B IC50 |
|---|---|---|---|---|
| PSMB1154 | 4 | 0.03 | 212 | 8450 |
| PSMB1157 | 3.6 | 0.03 | 400 | 14769 |
| PSMB1156 | 2.9 | 0.04 | 637 | 14859 |
| PSMB1183 | 3.6 | 0.03 | 389 | 13919 |

Cytotoxicity of PSMA ADCs conjugated to different payloads (MMAF or DX8951) were also evaluated in 22RV1 cells, a highly heterogeneous cell line expressing low levels of PSMA. 22RV1 cells were cultured in RPMI1640 containing GlutaMAX, 25 mM HEPES and 10% fetal bovine serum (FBS) and then plated in white 96 well plates at 5000 cells per well. Twenty-four hours after plating, cells were treated with varying concentrations of the ADCs and then set at 37C, 5% CO2. Following 6d of treatment, cell viability was assessed by Cell Titer Glo (Promega), according to manufacturer's instructions. Relative luminescence units (RLU) were detected in an Envision plate reader (Perkin Elmer) and then normalized to untreated controls. The concentration at which there was 25% or 50% toxicity was determined by fitting the values to a 3-point sigmoidal curve where the top was constrained to 100% and interpolating the X-value at Y=75 or 50%. (The concentration at which cells are 75% viable or 25% toxic is referred to as the IC25. The concentration at which cells are 50% viable is referred to as the IC50.) Relative potency of PSMA ADCs conjugated to MMAF or DX8951 are shown in Table 29 below. Note that cells treated with PSMA ADCs conjugated to MMAF did not reach 50% toxicity and therefore the IC25 is shown instead.

TABLE 29

Table shows relative potency for PSMA ADCs conjugated to either MMAF or DX8951 and treated on 22RV1 cells.

| | MMAF | | DX8951 | |
|---|---|---|---|---|
| mAb | DAR | IC25 (nM) | DAR | IC50 (nM) |
| PSMB1154 | 4 | 0.1 | 8 | 0.8 |
| PSMB1157 | 3.6 | 0.4 | 8 | 2.2 |
| PSMB1156 | 2.9 | 0.9 | 8 | 1.4 |
| PSMB1183 | 3.6 | N. D | 8 | 0.7 |
| Isotype control | 4.3 | >100 | 8 | 57.2 |

Example 5. Generation and Characterization of a Biparatopic Antibody Biparatopic Antibody Generation It is generally believed that approaches that can lead to higher ADC delivery or lysosomal processing may lead to better ADC efficacy and may also lower the receptor density threshold that's needed to see efficacy, thus increasing the size of patient population that could benefit by this therapy. We hypothesized that one way we could achieve that is by creating biparatopic antibodies that targets two different regions of the PSMA receptor. So, to test this hypothesis, by using VL and VH region of antibodies belonging to two different epitope bins, several biparatopic antibodies were created. Briefly, several scFvs were created by fusing VL and VH regions of antibodies from different epitope bins using a "GGSEGKSSGSGSESKSTGGS" linker (SEQ ID NO: 308). So, to create a bispecific, scFv from one bin were fused to an engineered Fc region containing the C220S (mutate unpaired cysteine to serine) and knob mutation (T366W); and the Fab region from another bin to an engineered Fc containing the hole mutation (T366S, L368A and Y407V). All numberings are based on EU system.

The sequence of selected biparatopic molecules is provided in Table 30. The genes corresponding to the bispecific antibodies were codon-optimized, synthesized and cloned into in-house proprietary plasmids using standard molecular biology techniques, and expressed and purified essentially according to procedures described in the following publication.

TABLE 30

HCDRs of anti-PSMA biparatopic antibodies using Kabat delineation

| mAb | Arm | HCDR1 sequence | HCDR1 SEQ ID NO: | HCDR2 sequence | HCDR2 SEQ ID NO: | HCDR3 sequence | HCDR3 SEQ ID NO: |
|---|---|---|---|---|---|---|---|
| PSMB2819 | Fab | RYGMH | 4 | LISYDGSNRYYADSVKG | 5 | ERESSGWFEGYFDY | 6 |
|  | scFv | SYYWS | 272 | RIYSSGSTNYNPSLKS | 273 | VGVWPGAFDI | 274 |
| PSMB3002 | Fab | RYGMH | 4 | LISYDGSNRYYADSVKG | 5 | ERESSGWFEGYFDY | 6 |
|  | scFv | SYYWS | 272 | RIYSSGSTNYNPSLKS | 273 | VGVWPGAFDI | 274 |

TABLE 31

LCDRs of anti-PSMA biparatopic antibodies using Kabat delineation

| mAb | Arm | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|---|
| PSMB2819 | Fab | GGNNIGKSVH | 7 | DNSDRPS | 8 | QVWDSSDHVV | 9 |
|  | scFv | SGSSSNIGSNTVN | 275 | SSNQRPS | 276 | AAWDDSLNGVV | 277 |
| PSMB3002 | Fab | GGNNIGKSVH | 7 | DNSDRPS | 8 | QVWDSSDHVV | 9 |
|  | scFv | SGSSSNIGSNTVN | 275 | SSNQRPS | 276 | AAWDDSLNGVV | 277 |

TABLE 32

HCDRs of anti-PSMA biparatopic antibodies using Chothia delineation

| mAb | Arm | HCDR1 sequence | HCDR1 SEQ ID NO: | HCDR2 sequence | HCDR2 SEQ ID NO: | HCDR3 sequence | HCDR3 SEQ ID NO: |
|---|---|---|---|---|---|---|---|
| PSMB2819 | Fab | GFTLSRY | 124 | SYDGSN | 125 | ERESSGWFEGYFDY | 6 |
|  | scFv | GGSIISY | 290 | YSSGS | 291 | VGVWPGAFDI | 274 |
| PSMB3002 | Fab | GFTLSRY | 124 | SYDGSN | 125 | ERESSGWFEGYFDY | 6 |
|  | scFv | GGSIISY | 290 | YSSGS | 291 | VGVWPGAFDI | 274 |

TABLE 33

LCDRs of anti-PSMA biparatopic antibodies using Chothia delineation

| mAb | Arm | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|---|
| PSMB281 | Fab | GGNNIGKSVH | 7 | DNSDRPS | 8 | QVWDSSDHVV | 9 |

TABLE 33-continued

LCDRs of anti-PSMA biparatopic antibodies using Chothia delineation

| mAb | Arm | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|---|
| 9 | scFv | SGSSSNIGSNTVN | 275 | SSNQRPS | 276 | AAWDDSLNGVV | 277 |
| PSMB300 | Fab | GGNNIGKSVH | 7 | DNSDRPS | 8 | QVWDSSSDHVV | 9 |
| 2 | scFv | SGSSSNIGSNTVN | 275 | SSNQRPS | 276 | AAWDDSLNGVV | 277 |

TABLE 34

HCDRs of anti-PSMA biparatopic antibodies using ABM delineation

| mAb | Arm | HCDR1 sequence | HCDR1 SEQ ID NO: | HCDR2 sequence | HCDR2 SEQ ID NO: | HCDR3 sequence | HCDR3 SEQ ID NO: |
|---|---|---|---|---|---|---|---|
| PSMB2819 | Fab | GFTLSRYGMH | 172 | LISYDGSNRY | 173 | ERESSGWFEGYFDY | 6 |
| | scFv | GGSIISYYWS | 296 | RIYSSGSTN | 297 | VGVWPGAFDI | 274 |
| PSMB3002 | Fab | GFTLSRYGMH | 172 | LISYDGSNRY | 173 | ERESSGWFEGYFDY | 6 |
| | scFv | GGSIISYYWS | 296 | RIYSSGSTN | 297 | VGVWPGAFDI | 274 |

TABLE 35

LCDRs of anti-PSMA biparatopic antibodies using ABM delineation

| mAb | Arm | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|---|
| PSMB2819 | Fab | GGNNIGKSVH | 7 | DNSDRPS | 8 | QVWDSSSDHVV | 9 |
| | scFv | SGSSSNIGSNTVN | 275 | SSNQRPS | 276 | AAWDDSLNGVV | 277 |
| PSMB3002 | Fab | GGNNIGKSVH | 7 | DNSDRPS | 8 | QVWDSSSDHVV | 9 |
| | scFv | SGSSSNIGSNTVN | 275 | SSNQRPS | 276 | AAWDDSLNGVV | 277 |

TABLE 36

HCDRs of anti-PSMA biparatopic antibodies using IMTG delineation

| mAb | Arm | HCDR1 sequence | HCDR1 SEQ ID NO: | HCDR2 sequence | HCDR2 SEQ ID NO: | HCDR3 sequence | HCDR3 SEQ ID NO: |
|---|---|---|---|---|---|---|---|
| PSMB2819 | Fab | GFTLSRYG | 220 | ISYDGSNR | 221 | ARERESSGWFEGYFDY | 222 |
| | scFv | GGSIISYY | 302 | IYSSGST | 303 | AKVGVWPGAFDI | 304 |
| PSMB3002 | Fab | GFTLSRYG | 220 | ISYDGSNR | 221 | ARERESSGWFEGYFDY | 222 |
| | scFv | GGSIISYY | 302 | IYSSGST | 303 | AKVGVWPGAFDI | 304 |

TABLE 37

LCDRs of anti-PSMA biparatopic antibodies using IMTG delineation

| mAb | Arm | LCDR1 sequence | LCDR1 SEQ ID NO: | LCDR2 sequence | LCDR2 SEQ ID NO: | LCDR3 sequence | LCDR3 SEQ ID NO: |
|---|---|---|---|---|---|---|---|
| PSMB2819 | Fab | NIGSKS | 223 | DNS | NA | QVWDSSSDHVV | 9 |
|  | scFv | SSNIGSNT | 305 | SSN | NA | AAWDDSLNGVV | 277 |
| PSMB3002 | Fab | NIGSKS | 223 | DNS | NA | QVWDSSSDHVV | 9 |
|  | scFv | SSNIGSNT | 305 | SSN | NA | AAWDDSLNGVV | 277 |

NA = Not applicable

TABLE 38

VH and VL amino acid and nucleic acid SEQ ID NOs of biparatopic anti-PSMA antibodies

| Antibody | Arm | VH name | VH amino acid SEQ ID NO: | VH Nucleic acid SEQ ID NO | VL name | VL amino acid SEQ ID NO: | VL nucleic acid SEQ ID NO: |
|---|---|---|---|---|---|---|---|
| PSMB2819 | Fab | VD000060663_VH | 52 | 134 | VD000060661_VL | 53 | 135 |
|  | scFv | VD000045978_VH | 278 | 280 | VD000045977_VL | 279 | 281 |
| PSMB3002 | Fab | VD000060663_VH | 52 | 134 | VD000060661_VL | 53 | 135 |
|  | scFv | VD000045978_VH | 278 | 280 | VD000045977_VL | 279 | 281 |

(PSMB2819 and PSMB3002 Fab VH amino acid sequence)
SEQ ID NO: 52
EVQLVESGGGEVQPGRSLRLTCAVSGFTLSRYGMHWVRQAPGKGLEWAA

LISYDGSNRYYADSVKGRFTISRDNSKNTVFLQMNSLRAEDTAVYYCAR

ERESSGWFEGYFDYWGQGTTVTVSS (PSMB2819 and PSMB3002 Fab VL amino acid sequence)
SEQ ID NO: 53
QLVLTQPPSVSVAPGQTARITCGGNNIGSKSVHWYQQKPGQAPVLVVYD

NSDRPSGIPERFSGSNSGNTATLTISRVEVGDEADYYCQVWDSSSDHVV

FGGGTKLTVL (PSMB2819 and PSMB3002 scFv VH amino acid sequence)
SEQ ID NO: 278
EVQLLESGPGLVKPSETLSLTCTVSGGSIISYYWSWIRQPAGKGLEWIG

RIYSSGSTNYNPSLKSRVTMSVDTSKNQFSLKLSSVTAADTAVYYCAKV

GVWPGAFDIWGQGTMVTVSS (PSMB2819 and PSMB3002 scFv VL amino acid sequence)
SEQ ID NO: 279
QSVLTQPPSASGTPGQRVTISCSGSSSNIGSNTVNWYQQLPGTAPKLLI

YSSNQRPSGVPDRFSGSKSGTSASLAISGLQSEDEADYYCAAWDSLNG

VVFGGGTKLTVL (PSMB2819 and PSMB3002 Fab VH nucleotide sequence)
SEQ ID NO: 134
GAGGTGCAATTGGTAGAGAGTGGCGGGGGAGAAGTCCAACCAGGCCGCA

GTCTCAGACTTACTTGTGCCGTCTCAGGCTTTACCCTCAGCCGTTACGG

TATGCACTGGGTTAGACAAGCTCCAGGGAAGGGACTTGAATGGGCCGCA

CTGATTTCCTATGATGGCTCCAACCGCTATTATGCCGACAGTGTGAAAG

GACGCTTCACAATTTCAAGGGATAATTCAAAGAATACAGTCTTTCTTCA

AATGAACTCTTTGCGAGCCGAGGATACAGCCGTTTATTACTGTGCACGG

GAAAGGGAGTCTAGTGGATGGTTTGAAGGGTATTTTGATTATTGGGGTC

AAGGGACCACAGTGACCGTAAGCTCA (PSMB2819 and PSMB3002 Fab VL nucleotide sequence)
SEQ ID NO: 135
CAGCTTGTCCTCACCCAGCCACCTAGCGTTAGTGTCGCCCCCGGTCAAA

CTGCTCGCATAACTTGTGGAGGCAACAACATTGGGAGCAAAAGCGTTCA

TTGGTACCAACAAAAACCAGGACAGGCCCCTGTTTTGGTAGTTTATGAC

AACTCTGATCGACCATCAGGGATTCCCGAGCGGTTTTCTGGTAGTAATT

CAGGGAATACTGCTACCCTGACTATCAGTCGCGTCGAAGTTGGCGACGA

AGCTGACTATTATTGTCAAGTCTGGGACAGCAGCAGCGACCATGTGGTT

TTTGGGGGAGGGACCAAACTTACCGTATTG (PSMB2819 and PSMB3002 scFv VH nucleotide sequence)
SEQ ID NO: 280
GAAGTTCAGCTGTTGGAATCTGGACCTGGCCTGGTCAAGCCTTCCGAGA

CACTGTCTCTGACCTGTACCGTGTCCGGCGGCTCCATCATCTCCTACTA

CTGGTCCTGGATCAGACAGCCTGCCGGCAAAGGACTGGAATGGATCGGC

AGAATCTACTCCTCCGGCAGCACCAACTACAACCCCAGCCTGAAGTCCC

GCGTGACCATGTCTGTGGACACCTCCAAGAACCAGTTCTCCCTGAAGCT

GTCCTCTGTGACCGCCGCTGATACCGCTGTGTACTACTGCGCTAAAGTC

GGAGTGTGGCCTGGCGCCTTTGATATCTGGGGACAGGGCACAATGGTCA

CCGTGTCCTCT (PSMB2819 and PSMB3002 scFv VL nucleotide sequence)
SEQ ID NO: 281
CAGTCCGTGCTGACCCAGCCTCCTTCTGCTTCTGGAACACCTGGCCAGA

GAGTGACCATCTCCTGCTCCGGCTCCTCCTCCAACATCGGCTCTAACAC

CGTGAACTGGTATCAGCAGCTGCCCGGCACAGCCCCTAAACTGCTGATC

TACTCTTCCAACCAGCGGCCTTCTGGCGTGCCCGATAGATTCTCTGGCT

CCAAGTCTGGCACCTCCGCTAGCCTGGCTATTTCTGGCCTGCAGTCTGA

GGACGAGGCCGATTACTACTGTGCCGCCTGGGATGATTCTCTGAACGGC

GTTGTGTTTGGCGGAGGCACCAAATTGACAGTTCTT (PSMB2819 and PSMB3002 Fab LC amino acid sequence)
SEQ ID NO: 269
QLVLTQPPSVSVAPGQTARITCGGNNIGSKSVHWYQQKPGQAPVLVVYD

NSDRPSGIPERFSGSNSGNTATLTISRVEVGDEADYYCQVWDSSSDHVV

FGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQ

VTHEGSTVEKTVAPTECS (PSMB2819 scFv HC amino acid sequence)
SEQ ID NO: 282
QSVLTQPPSASGTPGQRVTISCSGSSSNIGSNTVNWYQQLPGTAPKLLI

YSSNQRPSGVPDRFSGSKSGTSASLAISGLQSEDEADYYCAAWDDSLNG

VVFGGGTKLTVLGGSEGKSSGSGSESKSTGGSEVQLLESGPGLVKPSET

LSLTCTVSGGSIISYYWSWIRQPAGKGLEWIGRIYSSGSTNYNPSLKSR

VTMSVDTSKNQFSLKLSSVTAADTAVYYCAKVGVWPGAFDIWGQGTMVT

VSSEPKSSDKTHTCPPCPAPELLGGPSVFLFPPKPKDTLMISRTPEVTC

VVVDVSHEDPEVKFNWYVDGVEVHNAKTKPREEQYNSTYRVVSVLTVLH

QDWLNGKEYKCKVSNKALPAPIEKTISKAKGQPREPQVYTLPPSREEMT

KNQVSLWCLVKGFYPSDIAVEWESNGQPENNYKTTPPVLDSDGSFFLYS

KLTVDKSRWQQGNVFSCSVMHEALHNHYTQKSLSLSPGK

TABLE 39

HC and LC amino acid sequence and nucleic acid SEQ ID NOs of biparatopic

| Antibody | Arm | HC name | HC amino acid SEQ ID NO: | HC nucleic acid SEQ ID NO | LC name | LC amino acid SEQ ID NO: | LC nucleic acid SEQ ID NO: |
|---|---|---|---|---|---|---|---|
| PSMB2819 | Fab | DCH000015760 | 268 | 270 | DCH000010369 | 269 | 271 |
|  | scFv | DCH000014009 | 282 | 283 |  |  |  |
| PSMB3002 | Fab | DCH000021547 | 284 | 286 | DCH000010369 | 269 | 271 |
|  | scFv | DCH000021548 | 288 | 289 |  |  |  |

(PSMB2819 Fab HC amino acid sequence)
SEQ ID NO: 268
EVQLVESGGGEVQPGRSLRLTCAVSGFTLSRYGMHWVRQAPGKGLEWAA

LISYDGSNRYYADSVKGRFTISRDNSKNTVFLQMNSLRAEDTAVYYCAR

ERESSGWFEGYFDYWGQGTTVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSREEMTKNQVSLSCAVKGFYPSDIAVEWESNGQ

PENNYKTTPPVLDSDGSFFLVSKLTVDKSRWQQGNVFSCSVMHEALHNR

FTQKSLSLSPGK (PSMB3002 Fab HC amino acid sequence)
SEQ ID NO: 284
EVQLVESGGGEVQPGRSLRLTCAVSGFTLSRYGMHWVRQAPGKGLEWAA

LISYDGSNRYYADSVKGRFTISRDNSKNTVFLQMNSLRAEDTAVYYCAR

ERESSGWFEGYFDYWGQGTTVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPEAAGGPS

VFLFPPKPKDTLYITREPEVTCVVVSVSHEDPEVKFNWYVDGVEVHNAK

TKPREEQYNSTYRVVSVLTVLHQDWLNGKEYKCKVSNKALPAPIEKTIS

KAKGQPREPQVYTLPPSREEMTKNQVSLSCAVKGFYPSDIAVEWESNGQ

PENNYKTTPPVLDSDGSFFLVSKLTVDKSRWQQGNVFSCSVMHEALHNR

FTQKSLSLSPGK (PSMB3002 scFv HC amino acid sequence)
SEQ ID NO: 288
QSVLTQPPSASGTPGQRVTISCSGSSSNIGSNTVNWYQQLPGTAPKLLI
YSSNQRPSGVPDRFSGSKSGTSASLAISGLQSEDEADYYCAAWDDSLNG
VVFGGGTKLTVLGGSEGKSSGSGSESKSTGGSEVQLLESGPGLVKPSET
LSLTCTVSGGSIISYYWSWIRQPAGKGLEWIGRIYSSGSTNYNPSLKSR
VTMSVDTSKNQFSLKLSSVTAADTAVYYCAKVGVWPGAFDIWGQGTMVT
VSSEPKSSDKTHTCPPCPAPEAAGGPSVFLFPPKPKDTLYITREPEVTC
VVVSVSHEDPEVKFNWYVDGVEVHNAKTKPREEQYNSTYRVVSVLTVLH
QDWLNGKEYKCKVSNKALPAPIEKTISKAKGQPREPQVYTLPPSREEMT
KNQVSLWCLVKGFYPSDIAVEWESNGQPENNYKTTPPVLDSDGSFFLYS
KLTVDKSRWQQGNVFSCSVMHEALHNHYTQKSLSLSPGK (PSMB2819 Fab HC nucleic acid sequence)
SEQ ID NO: 270
GAGGTGCAATTGGTAGAGAGTGGCGGGGGAGAAGTCCAACCAGGCCGCA
GTCTCAGACTTACTTGTGCCGTCTCAGGCTTTACCCTCAGCCGTTACGG
TATGCACTGGGTTAGACAAGCTCCAGGGAAGGGACTTGAATGGGCCGCA
CTGATTTCCTATGATGGCTCCAACCGCTATTATGCCGACAGTGTGAAAG
GACGCTTCACAATTTCAAGGGATAATTCAAAGAATACAGTCTTTCTTCA
AATGAACTCTTTGCGAGCCGAGGATACAGCCGTTTATTACTGTGCACGG
GAAAGGGAGTCTAGTGGATGGTTTGAAGGGTATTTTGATTATTGGGGTC
AAGGGACCACAGTGACCGTAAGCTCAGCCTCCACCAAGGGCCCATCGGT
CTTCCCCCTGGCACCCTCCTCCAAGAGCACCTCTGGGGGCACAGCGGCC
CTGGGCTGCCTGGTCAAGGACTACTTCCCCGAACCGGTGACGGTGTCGT
GGAACTCAGGCGCCCTGACCAGCGGCGTGCACACCTTCCCGGCTGTCCT
ACAGTCCTCAGGACTCTACTCCCTCAGCAGCGTGGTGACCGTGCCCTCC
AGCAGCTTGGGCACCCAGACCTACATCTGCAACGTGAATCACAAGCCCA
GCAACACCAAGGTGGACAAGAAAGTTGAACCCAAATCCTGTGACAAAAC
CCATACTTGTCCCCCTTGCCCCGCCCCAGAGTTGCTTGGCGGACCTTCC
GTGTTTCTGTTCCCTCCAAAGCCCAAGGACACTCTTATGATAAGCCGAA
CACCAGAGGTCACATGCGTCGTCGTGGACGTAAGCCACGAGGATCCCGA
AGTAAAATTTAACTGGTACGTGGATGGGGTGGAAGTACATAATGCAAAA
ACTAAGCCCAGAGAGGAACAATATAATTCTACCTACCGAGTGGTATCCG
TCCTGACAGTGTTGCATCAGGACTGGTTGAATGGAAAGGAGTATAAGTG
CAAAGTGTCAAATAAGGCCCTGCCCGCTCCTATCGAGAAAACTATTTCC
AAAGCTAAGGGCCAGCCTCGCGAACCTCAGGTCTACACCCTGCCACCTT
CCAGAGAGGAGATGACCAAAAATCAAGTTTCATTGTCTTGTGCCGTAAA
AGGATTTTACCCCTCCGATATAGCTGTCGAGTGGGAGAGTAATGGTCAA
CCCGAGAATAATTACAAAACAACTCCACCCGTTCTCGATAGTGATGGGA
GCTTCTTTCTCGTTTCCAAATTGACTGTTGATAAATCTAGGTGGCAGCA
GGGCAATGTCTTTTCCTGCAGCGTGATGCACGAAGCCCTGCATAATCGC
TTTACTCAAAAAAGCCTTAGTCTGTCCCCAGGTAAG (PSMB2819 and PSMB3002 Fab LC nucleic acid sequence)
SEQ ID NO: 271
CAGCTTGTCCTCACCCAGCCACCTAGCGTTAGTGTCGCCCCCGGTCAAA
CTGCTCGCATAACTTGTGGAGGCAACAACATTGGGAGCAAAAGCGTTCA
TTGGTACCAACAAAAACCAGGACAGGCCCCTGTTTTGGTAGTTTATGAC
AACTCTGATCGACCATCAGGGATTCCCGAGCGGTTTTCTGGTAGTAATT
CAGGGAATACTGCTACCCTGACTATCAGTCGCGTCGAAGTTGGCGACGA
AGCTGACTATTATTGTCAAGTCTGGGACAGCAGCAGCGACCATGTGGTT
TTTGGGGGAGGGACCAAACTTACCGTATTGGGTCAGCCCAAGGCTGCAC
CCAGTGTCACTCTGTTCCCGCCCTCCTCTGAGGAGCTTCAAGCCAACAA
GGCCACACTGGTGTGTCTCATAAGTGACTTCTACCCGGGAGCCGTGACA
GTGGCCTGGAAGGCCGATAGCAGCCCCGTCAAGGCGGGAGTGGAGACCA
CCACACCCTCCAAACAAAGCAACAACAAGTACGCGGCCAGCAGCTATCT
GAGCCTGACGCCTGAGCAGTGGAAGTCCCACAGAAGCTACAGCTGCCAG
GTCACGCATGAAGGGAGCACCGTGGAGAAGACAGTGGCCCCTACAGAAT
GTTCA (PSMB2819 scFv HC nucleic acid sequence)
SEQ ID NO: 283
CAGTCCGTGCTGACCCAGCCTCCTTCTGCTTCTGGAACACCTGGCCAGA
GAGTGACCATCTCCTGCTCCGGCTCCTCCTCCAACATCGGCTCTAACAC
CGTGAACTGGTATCAGCAGCTGCCCGGCACAGCCCCTAAACTGCTGATC
TACTCTTCCAACCAGCGGCCTTCTGGCGTGCCCGATAGATTCTCTGGCT
CCAAGTCTGGCACCTCCGCTAGCCTGGCTATTTCTGGCCTGCAGTCTGA
GGACGAGGCCGATTACTACTGTGCCGCCTGGGATGATTCTCTGAACGGC
GTTGTGTTTGGCGGAGGCACCAAATTGACAGTTCTTGGCGGCTCCGAGG
GCAAGAGCAGCGGCAGCGGCAGCGAGAGCAAGAGCACCGGCGGCAGCGA
AGTTCAGCTGTTGGAATCTGGACCTGGCCTGGTCAAGCCTTCCGAGACA
CTGTCTCTGACCTGTACCGTGTCCGGCGGCTCCATCATCTCCTACTACT
GGTCCTGGATCAGACAGCCTGCCGGCAAAGGACTGGAATGGATCGGCAG
AATCTACTCCTCCGGCAGCACCAACTACAACCCCAGCCTGAAGTCCCGC
GTGACCATGTCTGTGGACACCTCCAAGAACCAGTTCTCCCTGAAGCTGT
CCTCTGTGACCGCCGCTGATACCGCTGTGTACTACTGCGCTAAAGTCGG
AGTGTGGCCTGGCGCCTTTGATATCTGGGGACAGGGCACAATGGTCACC
GTGTCCTCTGAGCCCAAATCTAGCGACAAAACTCACACATGTCCACCGT
GCCCAGCACCTGAACTGCTGGGGGGACCGTCAGTCTTCCTCTTCCCCCC
AAAACCCAAGGACACCCTCATGATCTCCCGGACCCCTGAGGTCACATGC
GTGGTGGTGGACGTGAGCCACGAAGACCCTGAGGTCAAGTTCAACTGGT
ACGTGGACGGCGTGGAGGTGCATAATGCCAAGACAAAGCCGCGGGAGGA
GCAGTACAACAGCACGTACCGTGTGGTCAGCGTCCTCACCGTCCTGCAC
CAGGACTGGCTGAATGGCAAGGAGTACAAGTGCAAGGTCTCCAACAAAG
CCCTCCCAGCCCCCATCGAGAAAACCATCTCCAAAGCCAAAGGGCAGCC
CCGAGAACCACAGGTGTACACCCTGCCCCCATCCCGGGAGGAGATGACC
AAGAACCAGGTCAGCCTGTGGTGCCTGGTCAAAGGCTTCTATCCCAGCG -continued
```
ACATCGCCGTGGAGTGGGAGAGCAATGGGCAGCCGGAGAACAACTACAA

GACCACGCCTCCCGTGCTGGACTCCGACGGCTCCTTCTTCCTCTACAGC

AAGCTCACCGTGGACAAGTCTAGATGGCAGCAGGGGAACGTCTTCTCAT

GCTCCGTGATGCATGAGGCTCTGCACAACCACTACACGCAGAAGAGCCT

CTCCCTGTCTCCGGGTAAA
```

(PSMB3002 Fab HC nucleic acid sequence)

SEQ ID NO: 286
```
GAGGTGCAATTGGTAGAGAGTGGCGGGGGAGAAGTCCAACCAGGCCGCA

GTCTCAGACTTACTTGTGCCGTCTCAGGCTTTACCCTCAGCCGTTACGG

TATGCACTGGGTTAGACAAGCTCCAGGGAAGGGACTTGAATGGGCCGCA

CTGATTTCCTATGATGGCTCCAACCGCTATTATGCCGACAGTGTGAAAG

GACGCTTCACAATTTCAAGGGATAATTCAAAGAATACAGTCTTTCTTCA

AATGAACTCTTTGCGAGCCGAGGATACAGCCGTTTATTACTGTGCACGG

GAAAGGGAGTCTAGTGGATGGTTTGAAGGGTATTTTGATTATTGGGGTC

AAGGGACCACAGTGACCGTAAGCTCAGCCTCCACCAAGGGCCCATCGGT

CTTCCCCCTGGCACCCTCCTCCAAGAGCACCTCTGGGGGCACAGCGGCC

CTGGGCTGCCTGGTCAAGGACTACTTCCCCGAACCGGTGACGGTGTCGT

GGAACTCAGGCGCCCTGACCAGCGGCGTGCACACCTTCCCGGCTGTCCT

ACAGTCCTCAGGACTCTACTCCCTCAGCAGCGTGGTGACCGTGCCCTCC

AGCAGCTTGGGCACCCAGACCTACATCTGCAACGTGAATCACAAGCCCA

GCAACACCAAGGTGGACAAGAAAGTTGAGCCCAAATCTTGTGACAAAAC

TCACACATGTCCACCGTGCCCAGCACCTGAAGCCGCCGGGGGACCGTCA

GTCTTCCTCTTCCCCCCAAAACCCAAGGACACCCTCTACATCACCCGGG

AGCCTGAGGTCACATGCGTGGTGGTGAGCGTGAGCCACGAAGACCCTGA

GGTCAAGTTCAACTGGTACGTGGACGGCGTGGAGGTGCATAATGCCAAG

ACAAAGCCGCGGGAGGAGCAGTACAACAGCACGTACCGTGTGGTCAGCG

TCCTCACCGTCCTGCACCAGGACTGGCTGAATGGCAAGGAGTACAAGTG

CAAGGTCTCCAACAAAGCCCTCCCAGCCCCCATCGAGAAAACCATCTCC

AAAGCCAAAGGGCAGCCCCGAGAACCACAGGTGTACACCCTGCCCCCAT

CCCGGGAGGAGATGACCAAGAACCAGGTCAGCCTGTCCTGCGCCGTCAA

AGGCTTCTATCCCAGCGACATCGCCGTGGAGTGGGAGAGCAATGGGCAG

CCGGAGAACAACTACAAGACCACGCCTCCCGTGCTGGACTCCGACGGCT

CCTTCTTCCTCGTGAGCAAGCTCACCGTGGACAAGTCTAGATGGCAGCA

GGGGAACGTCTTCTCATGCTCCGTGATGCATGAGGCTCTGCACAACCGG

TTCACGCAGAAGAGCCTCTCCCTGTCTCCGGGAAAA
```

(PSMB3002 scFv HC nucleic acid sequence)

SEQ ID NO: 289
```
CAGTCCGTGCTGACCCAGCCTCCTTCTGCTTCTGGAACACCTGGCCAGA

GAGTGACCATCTCCTGCTCCGGCTCCTCCTCCAACATCGGCTCTAACAC

CGTGAACTGGTATCAGCAGCTGCCCGGCACAGCCCCTAAACTGCTGATC

TACTCTTCCAACCAGCGGCCTTCTGGCGTGCCCGATAGATTCTCTGGCT

CCAAGTCTGGCACCTCCGCTAGCCTGGCTATTTCTGGCCTGCAGTCTGA
```

```
GGACGAGGCCGATTACTACTGTGCCGCCTGGGATGATTCTCTGAACGGC

GTTGTGTTTGGCGGAGGCACCAAATTGACAGTTCTTGGCGGCTCCGAGG

GCAAGAGCAGCGGCAGCGGCAGCGAGAGCAAGAGCACCGGCGGCAGCGA

AGTTCAGCTGTTGGAATCTGGACCTGGCCTGGTCAAGCCTTCCGAGACA

CTGTCTCTGACCTGTACCGTGTCCGGCGGCTCCATCATCTCCTACTACT

GGTCCTGGATCAGACAGCCTGCCGGCAAAGGACTGGAATGGATCGGCAG

AATCTACTCCTCCGGCAGCACCAACTACAACCCCAGCCTGAAGTCCCGC

GTGACCATGTCTGTGGACACCTCCAAGAACCAGTTCTCCCTGAAGCTGT

CCTCTGTGACCGCCGCTGATACCGCTGTGTACTACTGCGCTAAAGTCGG

AGTGTGGCCTGGCGCCTTTGATATCTGGGGACAGGGCACAATGGTCACC

GTGTCCTCTGAGCCCAAATCTAGCGACAAAACTCACACATGCCCACCGT

GCCCAGCACCTGAAGCCGCCGGGGGACCGTCAGTCTTCCTCTTCCCCCC

AAAACCCAAGGACACCCTCTACATCACCCGGGAGCCTGAGGTCACATGC

GTGGTGGTGAGCGTGAGCCACGAAGACCCTGAGGTCAAGTTCAACTGGT

ACGTGGACGGCGTGGAGGTGCATAATGCCAAGACAAAGCCGCGGGAGGA

GCAGTACAACAGCACGTACCGTGTGGTCAGCGTCCTCACCGTCCTGCAC

CAGGACTGGCTGAATGGCAAGGAGTACAAGTGCAAGGTGTCAACAAAG

CCCTCCCAGCCCCCATCGAGAAAACCATCTCCAAAGCCAAAGGGCAGCC

CCGAGAACCACAGGTGTACACCCTGCCCCCATCCCGGGAGGAGATGACC

AAGAACCAGGTCAGCCTGTGGTGCCTGGTCAAAGGCTTCTATCCCAGCG

ACATCGCCGTGGAGTGGGAGAGCAATGGGCAGCCGGAGAACAACTACAA

GACCACGCCTCCCGTGCTGGACTCCGACGGCTCCTTCTTCCTCTACAGC

AAGCTCACCGTGGACAAGAGCAGATGGCAGCAGGGGAACGTCTTCTCAT

GCTCCGTGATGCATGAGGCTCTGCACAACCACTACACGCAGAAGTCTCT

CTCCCTGTCTCCGGGAAAA
```

Example 6. HDX-MS Epitope Mapping of PSMW39 Against PSMB1154, PSMB1154-TOPA, and PSMB1183

HDX-MS behaviors of PSMW39 (a N-terminal 6-His tagged human PSMA as shown in Table 3 as SEQ ID NO: 1) were monitored (a) in the presence (b) in the absence of PSMB1154, PSMB1154-TOPA or PSMB1183 for 10 time points (15, 50, 150, 500, and 1,500 s at pH 6.4 and 23° C.; 15, 50, 150, 500, and 1,500 s at pH 8.4 and 23° C.). These time points correspond to the exchange times from 1.5 s to 15,000 s at pH 7.4 at 23° C. The residue numbers were converted from those of PSMW39 to those of Q04609 (full length human PSMA, SEQ ID NO:336).

The epitopes of PSMA (ΔG≤−1 kcal/mol) against PSMB1154 and PSMB1154-TOPA were virtually identical with residues 138-143 (IFNTSL; SEQ ID NO: 126), 271-276 (GYPANE; SEQ ID NO: 127), 279 (Y), 353-354 (TR), 377-383 (HRDSWVF; SEQ ID NO: 128) and 564-566 (KFY). The epitopes of PSMA (G≤−1 kcal/mol) against PSMB1183 were residues 188-191(LERD; SEQ ID NO: 132), 308-319 (KMGGSAPPDSSW; SEQ ID NO: 133), 327 (Y), and 353-354 (TR). The sequence coverage of PSMW39 was 98% (=693/713) when digested by pepsin-FPXII mixed bed column after quenched with 8 M urea, 1 M TCEP, pH 3.0.

SEQUENCE LISTING

```
Sequence total quantity: 340
SEQ ID NO: 1              moltype = AA  length = 713
FEATURE                   Location/Qualifiers
source                    1..713
                          mol_type = protein
                          organism = synthetic construct
SEQUENCE: 1
HHHHHHKSSN EATNITPKHN MKAFLDELKA ENIKKFLYNF TQIPHLAGTE QNFQLAKQIQ    60
SQWKEFGLDS VELAHYDVLL SYPNKTHPNY ISIINEDGNE IFNTSLFEPP PPGYENVSDI   120
VPPFSAFSPQ GMPEGDLVYV NYARTEDFFK LERDMKINCS GKIVIARYGK VFRGNKVKNA   180
QLAGAKGVIL YSDPADYFAP GVKSYPDGWN LPGGGVQRGN ILNLNGAGDP LTPGYPANEY   240
AYRRGIAEAV GLPSIPVHPI GYYDAQKLLE KMGGSAPPDS SWRGSLKPY NVGPGFTGNF    300
STQKVKMHIH STNEVTRIYN VIGTLRGAVE PDRYVILGGH RDSWVFGGID PQSGAAVVHE   360
IVRSFGTLKK EGWRPRRTIL FASWDAEEFG LLGSTEWAEE NSRLLQERGV AYINADSSIE   420
GNYTLRVDCT PLMYSLVHNL TKELKSPDEG FEGKSLYESW TKKSPSPEFS GMPRISKLGS   480
GNDFEVFFQR LGIASGRARY TKNWETNKFS GYPLYHSVYE TYELVEKFYD PMFKYHLTVA   540
QVRGGMVFEL ANSIVLPFDC RDYAVVLRKY ADKIYSISMK HPQEMKTYSV SFDSLFSAVK   600
NFTEIASKFS ERLQDFDKSN PIVLRMMNDQ LMFLERAFID PLGLPDRPFY RHVIYAPSSH   660
NKYAGESFPG IYDALFDIES KVDPSKAWGE VKRQIYVAAF TVQAAAETLS EVA          713

SEQ ID NO: 2              moltype = AA  length = 730
FEATURE                   Location/Qualifiers
source                    1..730
                          mol_type = protein
                          organism = synthetic construct
SEQUENCE: 2
GLNDIFEAQK IEWHEHHHHH HGSKSSSEAT NITPKHNMKA FLDELKAENI KKFLHNFTQI    60
PHLAGTEQNF QLAKQIQSQW KEFGLDSVEL THYDVLLSYP NKTHPNYISI INEDGNEIFN   120
TSLFEPPPAG YENVSDIVPP FSAFSPQGMP EGDLVYVNYA RTEDFFKLER DMKINCSGKI   180
VIARYGKVFR GNKVKNAQLA GATGVILYSD PDDYFAPGVK SYPDGWNLPG GGVQRGNILN   240
LNGAGDPLTP GYPANEYAYR RGMAEAVGLP SIPVHPIGYY DAQKLLEKMG GSASPDSSWR   300
GSLKVPYNVG PGFTGNFSTQ KVKMHIHSTS EVTRIYNVIG TLRGAVEPDR YVILGGHRDS   360
WVFGGIDPQS GAAVVHEIVR SFGMLKKEGW RPRRTILFAS WDAEEFGLLG STEWAEENSR   420
LLQERGVAYI NADSSIEGNY TLRVDCTPLM YSLVYNLTKE LESPDEGPEG KSLYESWTKK   480
SPSPEFSGMP RISKLGSGND FEVFFQRLGI ASGRARYTKN WETNKFSSYP LYHSVYETYE   540
LVEKFYDPMF KYHLTVAQVR GGMVFELANS VVLPFDCRDY AVVLRKYADK IYNISMKHPQ   600
EMKTYSVSFD SLFSAVKNFT EIASKFSERL RDFDKSNPIL LRMMNDQLMF LERAFIDPLG   660
LPDRPFYRHV IYAPSSHNKY AGESFPGIYD ALFDIESKVD PSQAWGEVKR QISIATFTVQ   720
AAAETLSEVA                                                         730

SEQ ID NO: 3              moltype = AA  length = 731
FEATURE                   Location/Qualifiers
source                    1..731
                          mol_type = protein
                          organism = synthetic construct
SEQUENCE: 3
GLNDIFEAQK IEWHEHHHHH HGSKPSNEAT GNVSHSGMKK EFLHELKAEN IKKFLYNFTR    60
TPHLAGTQNN FELAKQIHDQ WKEFGLDLVE LSHYDVLLSY PNKTHPNYIS IINEDGNEIF   120
KTSLSEQPPP GYENISDVVP PYSAFSPQGT PEGDLVYVNY ARTEDFFKLE REMKISCSGK   180
IVIARYGKVF RGNMVKNAQL AGAKGMILYS DPADYFVPAV KSYPDGWNLP GGGVQRGNVL   240
NLNGAGDPLT PGYPANEHAY RHELTNAVGL PSIPVHPIGY DDAQKLLEHM GGPAPPDSSW   300
KGGLKVPYNV GPGFAGNFST QKVKMHIHSY TKVTRIYNVI GTLKGALEPD RYVILGGHRD   360
AWVFGGIDPQ SGAAVVHEIV RSFGTLKKKG RRPRRTILFA SWDAEEFGLL GSTEWAEEHS   420
RLLQERGVAY INADSSIEGN YTLRVDCTPL MYSLVYNLTK ELQSPDEGFE GKSLYDSWKE   480
KSPSPEFIGM PRISKLGSGN DFEVFFQRLG IASGRARYTK NWKTNKVSSY PLYHSVYETY   540
ELVVKFYDPT FKYHLTVAQV RGAMVFELAN SIVLPFDCQS YAVALKKYAD TIYNISMKHP   600
QEMKAYMISF DSLFSAVNNF TDVASKFNQR LQELDKSNPI LLRIMNDQLM YLERAFIDPL   660
GLPGRPFYRH IIYAPSSHNK YAGESFPGIY DALFDISSKV NASKAWNEVK RQISIATFTV   720
QAAAETLREV A                                                       731

SEQ ID NO: 4              moltype = AA  length = 5
FEATURE                   Location/Qualifiers
source                    1..5
                          mol_type = protein
                          organism = synthetic construct
SEQUENCE: 4
RYGMH                                                                5

SEQ ID NO: 5              moltype = AA  length = 17
FEATURE                   Location/Qualifiers
source                    1..17
                          mol_type = protein
                          organism = synthetic construct
SEQUENCE: 5
LISYDGSNRY YADSVKG                                                  17

SEQ ID NO: 6              moltype = AA  length = 14
FEATURE                   Location/Qualifiers
```

```
source                  1..14
                        mol_type = protein
                        organism = synthetic construct
SEQUENCE: 6
ERESSGWFEG YFDY                                                                 14

SEQ ID NO: 7            moltype = AA   length = 11
FEATURE                 Location/Qualifiers
source                  1..11
                        mol_type = protein
                        organism = synthetic construct
SEQUENCE: 7
GGNNIGSKSV H                                                                    11

SEQ ID NO: 8            moltype = AA   length = 7
FEATURE                 Location/Qualifiers
source                  1..7
                        mol_type = protein
                        organism = synthetic construct
SEQUENCE: 8
DNSDRPS                                                                          7

SEQ ID NO: 9            moltype = AA   length = 11
FEATURE                 Location/Qualifiers
source                  1..11
                        mol_type = protein
                        organism = synthetic construct
SEQUENCE: 9
QVWDSSSDHV V                                                                    11

SEQ ID NO: 10           moltype = AA   length = 5
FEATURE                 Location/Qualifiers
source                  1..5
                        mol_type = protein
                        organism = synthetic construct
SEQUENCE: 10
SYYWN                                                                            5

SEQ ID NO: 11           moltype = AA   length = 16
FEATURE                 Location/Qualifiers
source                  1..16
                        mol_type = protein
                        organism = synthetic construct
SEQUENCE: 11
RIYSSGNTDY NPSLKS                                                               16

SEQ ID NO: 12           moltype = AA   length = 11
FEATURE                 Location/Qualifiers
source                  1..11
                        mol_type = protein
                        organism = synthetic construct
SEQUENCE: 12
GRGANVGLFD Y                                                                    11

SEQ ID NO: 13           moltype = AA   length = 14
FEATURE                 Location/Qualifiers
source                  1..14
                        mol_type = protein
                        organism = synthetic construct
SEQUENCE: 13
TGSNSNIGAN YDVH                                                                 14

SEQ ID NO: 14           moltype = AA   length = 7
FEATURE                 Location/Qualifiers
source                  1..7
                        mol_type = protein
                        organism = synthetic construct
SEQUENCE: 14
GNINRPL                                                                          7

SEQ ID NO: 15           moltype = AA   length = 11
FEATURE                 Location/Qualifiers
source                  1..11
                        mol_type = protein
                        organism = synthetic construct
SEQUENCE: 15
QSYDFSLSGS V                                                                    11

SEQ ID NO: 16           moltype = AA   length = 5
```

```
FEATURE                 Location/Qualifiers
source                  1..5
                        mol_type = protein
                        organism = synthetic construct
SEQUENCE: 16
GYGMH                                                                           5

SEQ ID NO: 17           moltype = AA  length = 17
FEATURE                 Location/Qualifiers
source                  1..17
                        mol_type = protein
                        organism = synthetic construct
SEQUENCE: 17
VISYDGSNRY YADSVKG                                                             17

SEQ ID NO: 18           moltype = AA  length = 13
FEATURE                 Location/Qualifiers
source                  1..13
                        mol_type = protein
                        organism = synthetic construct
SEQUENCE: 18
DGNWGSLDLY FDL                                                                 13

SEQ ID NO: 19           moltype = AA  length = 14
FEATURE                 Location/Qualifiers
source                  1..14
                        mol_type = protein
                        organism = synthetic construct
SEQUENCE: 19
TGSSSNIGAD YDVH                                                                14

SEQ ID NO: 20           moltype = AA  length = 7
FEATURE                 Location/Qualifiers
source                  1..7
                        mol_type = protein
                        organism = synthetic construct
SEQUENCE: 20
VNNNRPS                                                                         7

SEQ ID NO: 21           moltype = AA  length = 11
FEATURE                 Location/Qualifiers
source                  1..11
                        mol_type = protein
                        organism = synthetic construct
SEQUENCE: 21
QSYDNTLSGV V                                                                   11

SEQ ID NO: 22           moltype = AA  length = 5
FEATURE                 Location/Qualifiers
source                  1..5
                        mol_type = protein
                        organism = synthetic construct
SEQUENCE: 22
SYGMH                                                                           5

SEQ ID NO: 23           moltype = AA  length = 17
FEATURE                 Location/Qualifiers
source                  1..17
                        mol_type = protein
                        organism = synthetic construct
SEQUENCE: 23
VISYDGSNKY YADSVKG                                                             17

SEQ ID NO: 24           moltype = AA  length = 17
FEATURE                 Location/Qualifiers
source                  1..17
                        mol_type = protein
                        organism = synthetic construct
SEQUENCE: 24
EHYDSSGYYH GYYGMDV                                                             17

SEQ ID NO: 25           moltype = AA  length = 13
FEATURE                 Location/Qualifiers
source                  1..13
                        mol_type = protein
                        organism = synthetic construct
SEQUENCE: 25
SGSSSNIGSN YVY                                                                 13
```

-continued

```
SEQ ID NO: 26          moltype = AA   length = 7
FEATURE                Location/Qualifiers
source                 1..7
                       mol_type = protein
                       organism = synthetic construct
SEQUENCE: 26
SNNQRPS                                                                    7

SEQ ID NO: 27          moltype = AA   length = 11
FEATURE                Location/Qualifiers
source                 1..11
                       mol_type = protein
                       organism = synthetic construct
SEQUENCE: 27
AARDDSLSGY V                                                              11

SEQ ID NO: 28          moltype = AA   length = 5
FEATURE                Location/Qualifiers
source                 1..5
                       mol_type = protein
                       organism = synthetic construct
SEQUENCE: 28
SYDMH                                                                      5

SEQ ID NO: 29          moltype = AA   length = 17
FEATURE                Location/Qualifiers
source                 1..17
                       mol_type = protein
                       organism = synthetic construct
SEQUENCE: 29
VISFDGSNKY YVDSVKG                                                        17

SEQ ID NO: 30          moltype = AA   length = 18
FEATURE                Location/Qualifiers
source                 1..18
                       mol_type = protein
                       organism = synthetic construct
SEQUENCE: 30
TYYDILTGYS HYSYGMDV                                                       18

SEQ ID NO: 31          moltype = AA   length = 11
FEATURE                Location/Qualifiers
source                 1..11
                       mol_type = protein
                       organism = synthetic construct
SEQUENCE: 31
RASQGISNYL A                                                              11

SEQ ID NO: 32          moltype = AA   length = 7
FEATURE                Location/Qualifiers
source                 1..7
                       mol_type = protein
                       organism = synthetic construct
SEQUENCE: 32
ATSTLQS                                                                    7

SEQ ID NO: 33          moltype = AA   length = 9
FEATURE                Location/Qualifiers
source                 1..9
                       mol_type = protein
                       organism = synthetic construct
SEQUENCE: 33
QKYNSAPFT                                                                  9

SEQ ID NO: 34          moltype = AA   length = 5
FEATURE                Location/Qualifiers
source                 1..5
                       mol_type = protein
                       organism = synthetic construct
SEQUENCE: 34
TYGMH                                                                      5

SEQ ID NO: 35          moltype = AA   length = 17
FEATURE                Location/Qualifiers
source                 1..17
                       mol_type = protein
                       organism = synthetic construct
SEQUENCE: 35
FISYDGSNKY YADSVKG                                                        17
```

```
SEQ ID NO: 36           moltype = AA  length = 13
FEATURE                 Location/Qualifiers
source                  1..13
                        mol_type = protein
                        organism = synthetic construct SEQUENCE: 36
RDNLRFLEWF MDV                                                          13

SEQ ID NO: 37           moltype = AA  length = 11
FEATURE                 Location/Qualifiers
source                  1..11
                        mol_type = protein
                        organism = synthetic construct SEQUENCE: 37
RASQSVRSNL A                                                            11

SEQ ID NO: 38           moltype = AA  length = 7
FEATURE                 Location/Qualifiers
source                  1..7
                        mol_type = protein
                        organism = synthetic construct SEQUENCE: 38
GASTRAT                                                                 7

SEQ ID NO: 39           moltype = AA  length = 10
FEATURE                 Location/Qualifiers
source                  1..10
                        mol_type = protein
                        organism = synthetic construct SEQUENCE: 39
HQYNDWPPYT                                                              10

SEQ ID NO: 40           moltype = AA  length = 5
FEATURE                 Location/Qualifiers
source                  1..5
                        mol_type = protein
                        organism = synthetic construct SEQUENCE: 40
IYSMN                                                                   5

SEQ ID NO: 41           moltype = AA  length = 17
FEATURE                 Location/Qualifiers
source                  1..17
                        mol_type = protein
                        organism = synthetic construct SEQUENCE: 41
SISSSSSYIF YADSVKG                                                      17

SEQ ID NO: 42           moltype = AA  length = 7
FEATURE                 Location/Qualifiers
source                  1..7
                        mol_type = protein
                        organism = synthetic construct SEQUENCE: 42
SSYGADY                                                                 7

SEQ ID NO: 43           moltype = AA  length = 11
FEATURE                 Location/Qualifiers
source                  1..11
                        mol_type = protein
                        organism = synthetic construct SEQUENCE: 43
RASQDITNFL A                                                            11

SEQ ID NO: 44           moltype = AA  length = 7
FEATURE                 Location/Qualifiers
source                  1..7
                        mol_type = protein
                        organism = synthetic construct SEQUENCE: 44
TASTLQS                                                                 7

SEQ ID NO: 45           moltype = AA  length = 9
FEATURE                 Location/Qualifiers
source                  1..9
                        mol_type = protein
                        organism = synthetic construct

SEQUENCE: 45
```

```
QKYNSAPLT                                                                    9

SEQ ID NO: 46           moltype = AA  length = 5
FEATURE                 Location/Qualifiers
source                  1..5
                        mol_type = protein
                        organism = synthetic construct
SEQUENCE: 46
SYSLN                                                                        5

SEQ ID NO: 47           moltype = AA  length = 17
FEATURE                 Location/Qualifiers
source                  1..17
                        mol_type = protein
                        organism = synthetic construct
SEQUENCE: 47
SISSSSSYIS YADAVKG                                                          17

SEQ ID NO: 48           moltype = AA  length = 16
FEATURE                 Location/Qualifiers
source                  1..16
                        mol_type = protein
                        organism = synthetic construct
SEQUENCE: 48
DRGFLEDYYY YYGMDV                                                           16

SEQ ID NO: 49           moltype = AA  length = 11
FEATURE                 Location/Qualifiers
source                  1..11
                        mol_type = protein
                        organism = synthetic construct
SEQUENCE: 49
RASQGISNWL A                                                                11

SEQ ID NO: 50           moltype = AA  length = 7
FEATURE                 Location/Qualifiers
source                  1..7
                        mol_type = protein
                        organism = synthetic construct
SEQUENCE: 50
VASSLQS                                                                      7

SEQ ID NO: 51           moltype = AA  length = 9
FEATURE                 Location/Qualifiers
source                  1..9
                        mol_type = protein
                        organism = synthetic construct
SEQUENCE: 51
QQAYSFPLT                                                                    9

SEQ ID NO: 52           moltype = AA  length = 123
FEATURE                 Location/Qualifiers
source                  1..123
                        mol_type = protein
                        organism = synthetic construct
SEQUENCE: 52
EVQLVESGGG EVQPGRSLRL TCAVSGFTLS RYGMHWVRQA PGKGLEWAAL ISYDGSNRYY            60
ADSVKGRFTI SRDNSKNTVF LQMNSLRAED TAVYYCARER ESSGWFEGYF DYWGQGTTVT           120
VSS                                                                        123

SEQ ID NO: 53           moltype = AA  length = 108
FEATURE                 Location/Qualifiers
source                  1..108
                        mol_type = protein
                        organism = synthetic construct
SEQUENCE: 53
QLVLTQPPSV SVAPGQTARI TCGGNNIGSK SVHWYQQKPG QAPVLVVYDN SDRPSGIPER            60
FSGSNSGNTA TLTISRVEVG DEADYYCQVW DSSSDHVVFG GGTKLTVL                        108

SEQ ID NO: 54           moltype = AA  length = 119
FEATURE                 Location/Qualifiers
source                  1..119
                        mol_type = protein
                        organism = synthetic construct
SEQUENCE: 54
QVQLQESGPG LVKSSETLSL TCTVSGGSIS SYYWNWIRQP AGKGLEWIGR IYSSGNTDYN            60
PSLKSRVTMS VDTSKNQFSL KLISVTAADT AVYYCARGRG ANVGLFDYWG QGTLVTVSS            119

SEQ ID NO: 55           moltype = AA  length = 111
```

```
FEATURE                 Location/Qualifiers
source                  1..111
                        mol_type = protein
                        organism = synthetic construct
SEQUENCE: 55
QSALTQPPSV SGAPGQRVTI SCTGSNSNIG ANYDVHWYQH LPGTAPKLLI YGNINRPLGV   60
PDRFSGSRSG TSASLAITGL QAEDEADYYC QSYDFSLSGS VFGVGTKLTV L           111

SEQ ID NO: 56           moltype = AA  length = 122
FEATURE                 Location/Qualifiers
source                  1..122
                        mol_type = protein
                        organism = synthetic construct
SEQUENCE: 56
EVQLVESGGG VVQPGRSLRL SCAASVRTFS GYGMHWVRQV PGKGLEWVAV ISYDGSNRYY   60
ADSVKGRFTI SRDNSKNTLY LQMNSLRTED TAVYYCARDG NWGSLDLYFD LWGRGTLVTV   120
SS                                                                 122

SEQ ID NO: 57           moltype = AA  length = 111
FEATURE                 Location/Qualifiers
source                  1..111
                        mol_type = protein
                        organism = synthetic construct
SEQUENCE: 57
QSVLTQPPSV SGAPGQRVTI SCTGSSSNIG ADYDVHWYQQ LPGTAPKLLI YVNNNRPSGV   60
PDRFSGSRSG TSASLAITGL QADDEADYYC QSYDNTLSGV VFGGGTKLTV L           111

SEQ ID NO: 58           moltype = AA  length = 126
FEATURE                 Location/Qualifiers
source                  1..126
                        mol_type = protein
                        organism = synthetic construct
SEQUENCE: 58
EVQLVESGGG VVQPGRSLRL SCAASGFTFT SYGMHWVRQA PGKGLEWVAV ISYDGSNKYY   60
ADSVKGRFTI SRDNSKNTLY LQMNSLRAED TAVYYCAREH YDSSGYYHGY YGMDVWGQGT   120
TVTVSS                                                             126

SEQ ID NO: 59           moltype = AA  length = 110
FEATURE                 Location/Qualifiers
source                  1..110
                        mol_type = protein
                        organism = synthetic construct
SEQUENCE: 59
QAVLTQPPSA SGTPGQRVTI SCSGSSSNIG SNYVYWYQLL PGTAPKLLIY SNNQRPSGVP   60
DRFSGSKSGT SASLAISGLR SEDEADYYCA ARDDSLSGYV FGTGTKLTVL             110

SEQ ID NO: 60           moltype = AA  length = 127
FEATURE                 Location/Qualifiers
source                  1..127
                        mol_type = protein
                        organism = synthetic construct
SEQUENCE: 60
EVQLVESGGG VVQPGRSLRL SCAASGFTFS SYDMHWVRQA PGKGLEWVTV ISFDGSNKYY   60
VDSVKGRFTI SRDNSKNTLY LQMNSLRAED TAVYYCARTY YDILTGYSHY SYGMDVWGQG   120
TTVTVSS                                                            127

SEQ ID NO: 61           moltype = AA  length = 107
FEATURE                 Location/Qualifiers
source                  1..107
                        mol_type = protein
                        organism = synthetic construct
SEQUENCE: 61
EIVMTQSPSS LSASVGDRVT ITCRASQGIS NYLAWYQQKP GKVPKLLIYA TSTLQSGVPS   60
RFSGSGSGTD FILTISSLQP EDVANYYCQK YNSAPFTFGP GTKVEIK                107

SEQ ID NO: 62           moltype = AA  length = 122
FEATURE                 Location/Qualifiers
source                  1..122
                        mol_type = protein
                        organism = synthetic construct
SEQUENCE: 62
QVQLVESGGG VVQPGRSLRL SCAASGFTFS TYGMHWVRQA PGKGLEWVAF ISYDGSNKYY   60
ADSVKGRFTI SRDNSKHTLY LQMNSLRAED TAVYYCAGRD NLRFLEWFMD VWGQGTTVTV   120
SS                                                                 122

SEQ ID NO: 63           moltype = AA  length = 108
FEATURE                 Location/Qualifiers
source                  1..108
                        mol_type = protein
```

```
                          organism = synthetic construct
SEQUENCE: 63
EIVMTQSPAT LSVSPGERAT LSCRASQSVR SNLAWYQQKP GQAPRLLIYG ASTRATGIPA    60
RFSGSGSGTE FTLTISSLQS EDFAVYYCHQ YNDWPPYTFG QGTKVEIK                108

SEQ ID NO: 64           moltype = AA  length = 116
FEATURE                 Location/Qualifiers
source                  1..116
                        mol_type = protein
                        organism = synthetic construct
SEQUENCE: 64
EVQLVESGGG LVKPGGSLRL SCAASGFTLS IYSMNWVRQA PGKGLEWVSS ISSSSSYIFY    60
ADSVKGRFTI SRDNAKNSLF LQMNSLRAED TAVYYCARSS YGADYWGQGT LVTVSS       116

SEQ ID NO: 65           moltype = AA  length = 107
FEATURE                 Location/Qualifiers
source                  1..107
                        mol_type = protein
                        organism = synthetic construct
SEQUENCE: 65
EIVMTQSPSS LSASVGDRVT ITCRASQDIT NFLAWYQQKP GKVPKLLIYT ASTLQSGVPS    60
RFSGSGSGTD FTLTISSLQP EDVATYYCQK YNSAPLTFGG GTKLEIK                 107

SEQ ID NO: 66           moltype = AA  length = 125
FEATURE                 Location/Qualifiers
source                  1..125
                        mol_type = protein
                        organism = synthetic construct
SEQUENCE: 66
EVQLVESGGG LVKPGGSLRL SCAASGFTFS SYSLNWVRQA PGKGLEWVSS ISSSSSYISY    60
ADAVKGRFTI SRDNAKNSLY LQMNSLRAED TAVYYCARDR GFLEDYYYYY GMDVWGQGTT   120
VTVSS                                                               125

SEQ ID NO: 67           moltype = AA  length = 107
FEATURE                 Location/Qualifiers
source                  1..107
                        mol_type = protein
                        organism = synthetic construct
SEQUENCE: 67
DIVMTQSPSS VSASVGDRVT ITCRASQGIS NWLAWYQQKP GKAPKLLIYV ASSLQSGVPS    60
RFSGSGSGTD FSLTISSLQP EDFATYYCQQ AYSFPLTFGG GTKVEIK                 107

SEQ ID NO: 68           moltype = DNA  length = 369
FEATURE                 Location/Qualifiers
source                  1..369
                        mol_type = other DNA
                        organism = synthetic construct
SEQUENCE: 68
gaggtgcagc tggttgaatc tggtggcgga gaagtgcagc tggcagatc tctgagactg     60
acctgtgctg tgtccggctt caccctgtcc agatacggaa tgcactgggt ccgacaggcc   120
cctggcaaag gattggaatg ggccgctctg atctcctacg acggctccaa taggtactac   180
gccgactccg tgaagggcag attcaccatc tctcgggaca actccaagaa caccgtgttt   240
ctgcagatga actccctgag agccgaggac accgccgtgt actactgtgc cagagagcgg   300
gaatcctccg ctggttcgga gggctacttc gactattggg gccagggcac cacagtgacc   360
gtttcttct                                                           369

SEQ ID NO: 69           moltype = DNA  length = 324
FEATURE                 Location/Qualifiers
source                  1..324
                        mol_type = other DNA
                        organism = synthetic construct
SEQUENCE: 69
cagctggttc tgacccagcc tccttctgtg tctgtggctc ctggccagac cgccagaatt    60
acctgtggcg gcaacaacat cggctccaag tccgtgcact ggtatcagca gaagcctgga   120
caggctcctg tgctggtggt gtacgacaac tctgaccggc cttctggcat ccctgagaga   180
ttctccggct ccaacagcgg caataccgcc acactgacca tctccagagt ggaagtgggc   240
gacgaggcca actactactg ccaagtgtgg gactcctcct ccgatcatgt ggtgtttggc   300
ggcggaacaa agctgacagt gctg                                          324

SEQ ID NO: 70           moltype = DNA  length = 357
FEATURE                 Location/Qualifiers
source                  1..357
                        mol_type = other DNA
                        organism = synthetic construct
SEQUENCE: 70
caggtgcagc tgcaagagtc tggacctggc ctggtcaagt cctccagaga actgtctctg    60
acctgcaccg tgtctggcgg ctccatctcc tcctactact ggaactggat cagacagcct   120
gccggcaaag gcctggaatg gatcggcaga atctactcct ccggcaacac cgactacaac   180
cccagcctga agtccagagt gaccatgtcc gtggacacct ccaagaacca gttctccctg   240
```

```
aagctgatct ccgtgaccgc cgctgatacc gccgtgtact attgtgctag aggcagaggc   300
gccaacgtgg gcctgtttga ttattggggc cagggcaccc tggtcaccgt ttcttct     357

SEQ ID NO: 71           moltype = DNA   length = 333
FEATURE                 Location/Qualifiers
source                  1..333
                        mol_type = other DNA
                        organism = synthetic construct
SEQUENCE: 71
cagtctgctc tgacccagcc tccttctgtg tctggcgctc ctggccagag agtgaccatc   60
tcttgtaccg gctccaactc caacatcggc gccaactacg acgtgcactg gtatcagcat  120
ctgcccggca cagctcccaa gctgctgatc tacggcaaca tcaacagacc cctgggcgtg  180
cccgaccggt tttctggaag cagatctggc acctctgcca gcctggctat taccggactg  240
caggctgagg acgaggccga ctactactgc cagtcctacg acttctccct gtccggctcc  300
gtgtttggcg tgggcacaaa gctgacagtc ctg                               333

SEQ ID NO: 72           moltype = DNA   length = 366
FEATURE                 Location/Qualifiers
source                  1..366
                        mol_type = other DNA
                        organism = synthetic construct
SEQUENCE: 72
gaggtgcagc tggttgaatc tggtggcgga gtggtgcagc ctggcagatc tctgagactg   60
tcttgtgccg cttccgtgcg gaccttctct ggctacggaa tgcactgggt ccgacaggtg  120
ccaggcaaag gactggaatg ggtggccgtg atctcctacg atggctccaa tcggtactac  180
gccgactccg tgaagggcag attcaccatc tctcggacag acaaccgcc ttctggcgtg  240
ctgcagatga actccctgcg gaccgaggat accgccgtgt actactgtgc cagagatggc  300
aactggggct ccctggacct gtacttcgat ctctggggac ggggcaccct ggtcacagtc  360
tcttct                                                             366

SEQ ID NO: 73           moltype = DNA   length = 333
FEATURE                 Location/Qualifiers
source                  1..333
                        mol_type = other DNA
                        organism = synthetic construct
SEQUENCE: 73
cagtctgtgc tgacccagcc tccttctgtg tctggcgctc ctggccagag agtgaccatc   60
tcctgtaccg gctcctcctc taacatcggc gctgactacg acgtgcactg gtatcagcag  120
ctgcccggca cagctcccaa actgctgatc tacgtgaaca caaccggcc ttctggcgca  180
cccgacagat tctctggaag cagatctggc acctctgcca gcctggctat taccggactg  240
caggccgatg acgaggccga ctactactgc cagtcctacg acaacaccct gtccggcgtt  300
gtgtttggcg gcggaacaaa gctgacagtc ctg                               333

SEQ ID NO: 74           moltype = DNA   length = 378
FEATURE                 Location/Qualifiers
source                  1..378
                        mol_type = other DNA
                        organism = synthetic construct
SEQUENCE: 74
gaggtgcagc tggttgaatc tggtggcgga gtggtgcagc ctggcagatc tctgagactg   60
tcttgtgccg cctccggctt caccttcacc agctacggaa tgcactgggt ccgacaggcc  120
cctggcaaag gattggaatg ggtggccgtg atctcctacg acggctccaa caagtactac  180
gccgactccg tgaagggcag attcaccatc tctcggaca actccaagaa caccctgtac  240
ctgcagatga actccctgag agccgaggac accgccgtgt actactgtgc cagagagcac  300
tacgactcct ccggctacta ccacggctac tatggcatgg atgtgtgggg ccagggcacc  360
acagtgacag tctcttcc                                                378

SEQ ID NO: 75           moltype = DNA   length = 330
FEATURE                 Location/Qualifiers
source                  1..330
                        mol_type = other DNA
                        organism = synthetic construct
SEQUENCE: 75
caggctgttc tgacccagcc tccttctgct tctggcaccc ctggacagag agtgaccatc   60
tcttgctccg gctcctcctc caacatcggc tccaactacg tgtactgta ccagctgctg  120
cccggcaccc tcctaagct gctgatctac tccaacaacc agcggcctc tggcgtgccc  180
gatagattct ccgctctaa gtctggcacc tctgccagcc tggctatctc cggactgaga  240
tctgaggacg aggccgacta ctactgcgcc gccagagatg attccctgtc cggctatgtg  300
tttggcaccg gcaccaagct gacagtgttg                                   330

SEQ ID NO: 76           moltype = DNA   length = 381
FEATURE                 Location/Qualifiers
source                  1..381
                        mol_type = other DNA
                        organism = synthetic construct
SEQUENCE: 76
gaggtgcagc tggtggagtc tgggggaggc gtggtccagc ctggggagtc cctgagactc   60
tcctgtgcag cctctggatt caccttcagt agttatgaca tgcactgggt ccgccaggct  120
ccaggcaagg ggctggagtg ggtgacagtt atatcatttg atggaagtaa taaatactat  180
```

```
gtagactccg tgaagggccg attcaccatc tccagagaca attccaagaa tacgctgtat   240
ctgcaaatga acagcctgag agctgaggac acggctgtgt attactgtgc gagaacgtat   300
tacgatattt tgactggtta ttcccactac tcctacggta tggacgtctg gggccaaggg   360
accacggtca ccgtctcctc a                                             381

SEQ ID NO: 77          moltype = DNA   length = 321
FEATURE                Location/Qualifiers
source                 1..321
                       mol_type = other DNA
                       organism = synthetic construct
SEQUENCE: 77
gaaatagtga tgacgcagtc tccatcctcc ctgtctgcat ctgtaggaga cagagtcacc   60
atcacttgcc gggcgagtca gggcattagc aattatttag cctggtatca gcagaaacca   120
gggaaagttc ctaagctcct gatctatgcc acatccactt tgcaatcagg ggtcccatct   180
cggttcagtg gcagtggatc tgggacagat ttcattctca ccatcagcag cctgcagcct   240
gaagatgttg caaactatta ctgtcaaaag tataacagtg ccccattcac tttcggccct   300
gggaccaagg tggagatcaa a                                             321

SEQ ID NO: 78          moltype = DNA   length = 366
FEATURE                Location/Qualifiers
source                 1..366
                       mol_type = other DNA
                       organism = synthetic construct
SEQUENCE: 78
caggtgcagc tggtggagtc tgggggaggc gtggtccagc ctgggaggtc cctgagactc   60
tcctgtgcag cctctggatt cacccttcagt acctatggca tgcactgggt ccgccaggct   120
ccaggcaagg ggctggagtg ggtggcattt atatcatatg atggaagtaa taaatactat   180
gcagactccg tgaagggccg attcaccatc tccagagaca attccaagca cacgctatat   240
ctgcaaatga acagcctgag agctgaggac acggctgtgt attactgtgc ggggagagac   300
aacctacgat ttttggagtg gtttatggac gtctggggcc aagggaccac ggtcaccgtc   360
tcttca                                                              366

SEQ ID NO: 79          moltype = DNA   length = 324
FEATURE                Location/Qualifiers
source                 1..324
                       mol_type = other DNA
                       organism = synthetic construct
SEQUENCE: 79
gaaatagtga tgacgcagtc tccagccacc ctgtctgtgt ctccagggga aagagccacc   60
ctctcctgca gggccagtca gagtgtaagg agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcaccag tataatgact ggcctccgta cacttttggc   300
caagggacca aggtggaaat caaa                                          324

SEQ ID NO: 80          moltype = DNA   length = 348
FEATURE                Location/Qualifiers
source                 1..348
                       mol_type = other DNA
                       organism = synthetic construct
SEQUENCE: 80
gaggtgcagc tggtggagtc tgggggaggc ctggtcaagc cggggggtc cctgagactc   60
tcctgtgcag cctctggatt caccctcagt atttatagca tgaactgggt ccgccaggct   120
ccagggaagg ggctggagtg ggtctcatcc attagcagta gtagtagtta catattctac   180
gcagactcag tgaagggccg attcaccatc tccagagaca acgccaagaa ctcactcttt   240
ctgcaaatga acagcctgag agccgaggac acggctgtgt attactgtgc gagatcctcc   300
tacggtgcgg actactgggg ccagggaacc ctggtcaccg tctcttca                348

SEQ ID NO: 81          moltype = DNA   length = 321
FEATURE                Location/Qualifiers
source                 1..321
                       mol_type = other DNA
                       organism = synthetic construct
SEQUENCE: 81
gaaatagtga tgacgcagtc tccatcctcc ctgtctgcat ctgtaggaga cagagtcacc   60
atcacttgcc gggcgagtca ggacattacc aattttttag cctggtatca gcagaaacca   120
gggaaagttc ctaaactcct gatttatact gcatccactt tgcaatcagg ggtcccatct   180
cggttcagtg gcagtggatc tgggacagat ttcactctca ccatcagcag cctgcagcct   240
gaagatgttg cgacttatta ctgtcaaaag tataacagtg ccccactcac tttcggcgga   300
gggaccaagc tggagatcaa a                                             321

SEQ ID NO: 82          moltype = DNA   length = 375
FEATURE                Location/Qualifiers
source                 1..375
                       mol_type = other DNA
                       organism = synthetic construct
SEQUENCE: 82
gaggtgcagc tggtggagtc tgggggaggc ctggtcaagc ctggggggtc cctgagactc   60
tcctgtgcag cctctggatt caccttcagc agctatagca tgaactgggt ccgccaggct   120
```

```
ccagggaagg ggctggagtg gtctcatcc attagtagta gtagtagtta catatcctac   180
gcagacgcag tgaagggccg attcaccatc tccagagaca acgccaagaa ctcactgtat   240
ctgcaaatga acagcctgag agccgaggac acggctgtgt attactgtgc gagagatcgg   300
ggattttttgg aggattacta ctactactac ggtatgacg tctggggcca agggaccacg   360
gtcaccgtct cctca                                                    375

SEQ ID NO: 83           moltype = DNA   length = 321
FEATURE                 Location/Qualifiers
source                  1..321
                        mol_type = other DNA
                        organism = synthetic construct
SEQUENCE: 83
gacatcgtga tgacccagtc tccatcttcc gtgtctgcat ctgtaggaga cagagtcacc    60
atcacttgtc gggcgagtca aggtattagc aactggttag cctgtatca gcagaaacca   120
gggaaagccc ctaagctcct gatctatgtt gcatccagtt tgcaaagtgg ggttccatca   180
aggttcagcg gcagtggatc tgggacagat ttctctctca ccatcagcag cctgcagcct   240
gaagatttgg caacttacta ttgtcaacag gcttacagtt ccctctcac tttcggcgga   300
gggaccaagg tggagatcaa a                                             321

SEQ ID NO: 84           moltype = AA    length = 453
FEATURE                 Location/Qualifiers
source                  1..453
                        mol_type = protein
                        organism = synthetic construct
SEQUENCE: 84
EVQLVESGGG EVQPGRSLRL TCAVSGFTLS RYGMHWVRQA PGKGLEWAAL ISYDGSNRYY    60
ADSVKGRFTI SRDNSKNTVF LQMNSLRAED TAVYYCARER ESSGWFEGYF DYWGQGTTVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEL   240
LGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 85           moltype = AA    length = 214
FEATURE                 Location/Qualifiers
source                  1..214
                        mol_type = protein
                        organism = synthetic construct
SEQUENCE: 85
QLVLTQPPSV SVAPGQTARI TCGGNNIGSK SVHWYQQKPG QAPVLVVYDN SDRPSGIPER    60
FSGSNSGNTA TLTISRVEVG DEADYYCQVW DSSSDHVVFG GGTKLTVLGQ PKAAPSVTLF   120
PPSSEELQAN KATLVCLISD FYPGAVTVAW KADSSPVKAG VETTTPSKQS NNKYAASSYL   180
SLTPEQWKSH RSYSCQVTHE GSTVEKTVAP TECS                               214

SEQ ID NO: 86           moltype = AA    length = 453
FEATURE                 Location/Qualifiers
source                  1..453
                        mol_type = protein
                        organism = synthetic construct
SEQUENCE: 86
EVQLVESGGG EVQPGRSLRL TCAVSGFTLS RYGMHWVRQA PGKGLEWAAL ISYDGSNRYY    60
ADSVKGRFTI SRDNSKNTVF LQMNSLRAED TAVYYCARER ESSGWFEGYF DYWGQGTTVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV SVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
REEMTKNQVS LTCLVKGFYP SDIAVEWESN GQPENNYKTT PPVLDSDGSF FLYSKLTVDK   420
SRWQQGNVFS CSVMHEALHN HYTQKSLSLS PGK                                453

SEQ ID NO: 87           moltype = AA    length = 20
FEATURE                 Location/Qualifiers
source                  1..20
                        mol_type = protein
                        organism = synthetic construct
SEQUENCE: 87
GKPGSGKPGS GKPGSGKPGS                                                20

SEQ ID NO: 88           moltype = AA    length = 449
FEATURE                 Location/Qualifiers
source                  1..449
                        mol_type = protein
                        organism = synthetic construct
SEQUENCE: 88
QVQLQESGPG LVKSSETLSL TCTVSGGSIS SYYWNWIRQP AGKGLEWIGR IYSSGNTDYN    60
PSLKSRVTMS VDTSKNQFSL KLISVTAADT AVYYCARGRG ANVGLFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
```

```
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                     449

SEQ ID NO: 89              moltype = AA   length = 217
FEATURE                    Location/Qualifiers
source                     1..217
                           mol_type = protein
                           organism = synthetic construct
SEQUENCE: 89
QSALTQPPSV SGAPGQRVTI SCTGSNSNIG ANYDVHWYQH LPGTAPKLLI YGNINRPLGV     60
PDRFSGSRSG TSASLAITGL QAEDEADYYC QSYDFSLSGS VFGVGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                             217

SEQ ID NO: 90              moltype = AA   length = 449
FEATURE                    Location/Qualifiers
source                     1..449
                           mol_type = protein
                           organism = synthetic construct
SEQUENCE: 90
QVQLQESGPG LVKSSETLSL TCTVSGGSIS SYYWNWIRQP AGKGLEWIGR IYSSGNTDYN     60
PSLKSRVTMS VDTSKNQFSL KLISVTAADT AVYYCARGRG ANVGLFDYWG QGTLVTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPEAAGGP    240
SVFLFPPKPK DTLYITREPE VTCVVVSVSH EDPEVKFNWY VDGVEVHNAK TKPREEQYNS    300
TYRVVSVLTV LHQDWLNGKE YKCKVSNKAL PAPIEKTISK AKGQPREPQV YTLPPSREEM    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                     449

SEQ ID NO: 91              moltype = AA   length = 10
FEATURE                    Location/Qualifiers
source                     1..10
                           mol_type = protein
                           organism = synthetic construct
SEQUENCE: 91
APAPAPAPAP                                                           10

SEQ ID NO: 92              moltype = AA   length = 452
FEATURE                    Location/Qualifiers
source                     1..452
                           mol_type = protein
                           organism = synthetic construct
SEQUENCE: 92
EVQLVESGGG VVQPGRSLRL SCAASVRTFS GYGMHWVRQV PGKGLEWVAV ISYDGSNRYY     60
ADSVKGRFTI SRDNSKNTLY LQMNSLRTED TAVYYCARDG NWGSLDLYFD LWGRGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                 452

SEQ ID NO: 93              moltype = AA   length = 217
FEATURE                    Location/Qualifiers
source                     1..217
                           mol_type = protein
                           organism = synthetic construct
SEQUENCE: 93
QSVLTQPPSV SGAPGQRVTI SCTGSSSNIG ADYDVHWYQQ LPGTAPKLLI YVNNNRPSGV     60
PDRFSGSRSG TSASLAITGL QADDEADYYC QSYDNTLSGV VFGGGTKLTV LGQPKAAPSV    120
TLFPPSSEEL QANKATLVCL ISDFYPGAVT VAWKADSSPV KAGVETTTPS KQSNNKYAAS    180
SYLSLTPEQW KSHRSYSCQV THEGSTVEKT VAPTECS                             217

SEQ ID NO: 94              moltype = AA   length = 456
FEATURE                    Location/Qualifiers
source                     1..456
                           mol_type = protein
                           organism = synthetic construct
SEQUENCE: 94
EVQLVESGGG VVQPGRSLRL SCAASGFTFT SYGMHWVRQA PGKGLEWVAV ISYDGSNKYY     60
ADSVKGRFTI SRDNSKNTLY LQMNSLRAED TAVYYCAREH YDSSGYYHGY YGMDVWGQGT    120
TVTVSSASTK GPSVFPLAPS SKSTSGGTAA LGCLVKDYFP EPVTVSWNSG ALTSGVHTFP    180
AVLQSSGLYS LSSVVTVPSS SLGTQTYIC VNHKPSNTKV DKKVEPKSCD KTHTCPPCPA    240
PELLGGPSVF LFPPKPKDTL MISRTPEVTC VVVDVSHEDP EVKFNWYVDG VEVHNAKTKP    300
REEQYNSTYR VVSVLTVLHQ DWLNGKEYKC KVSNKALPAP IEKTISKAKG QPREPQVYTL    360
PPSREEMTKN QVSLTCLVKG FYPSDIAVEW ESNGQPENNY KTTPPVLDSD GSFFLYSKLT    420
VDKSRWQQGN VFSCSVMHEA LHNHYTQKSL SLSPGK                             456
```

```
SEQ ID NO: 95              moltype = AA   length = 216
FEATURE                    Location/Qualifiers
source                     1..216
                           mol_type = protein
                           organism = synthetic construct
SEQUENCE: 95
QAVLTQPPSA SGTPGQRVTI SCSGSSSNIG SNYVYWYQLL PGTAPKLLIY SNNQRPSGVP    60
DRFSGSKSGT SASLAISGLR SEDEADYYCA ARDDSLSGYV FGTGTKLTVL GQPKAAPSVT   120
LFPPSSEELQ ANKATLVCLI SDFYPGAVTV AWKADSSPVK AGVETTTPSK QSNNKYAASS   180
YLSLTPEQWK SHRSYSCQVT HEGSTVEKTV APTECS                             216

SEQ ID NO: 96              moltype = AA   length = 457
FEATURE                    Location/Qualifiers
source                     1..457
                           mol_type = protein
                           organism = synthetic construct
SEQUENCE: 96
EVQLVESGGG VVQPGRSLRL SCAASGFTFS SYDMHWVRQA PGKGLEWVTV ISFDGSNKYY    60
VDSVKGRFTI SRDNSKNTLY LQMNSLRAED TAVYYCARTY YDILTGYSHY SYGMDVWGQG   120
TTVTVSSAST KGPSVFPLAP SSKSTSGGTA ALGCLVKDYF PEPVTVSWNS GALTSGVHTF   180
PAVLQSSGLY SLSSVVTVPS SSLGTQTYIC NVNHKPSNTK VDKKVEPKSC DKTHTCPPCP   240
APELLGGPSV FLFPPKPKDT LMISRTPEVT CVVVDVSHED PEVKFNWYVD GVEVHNAKTK   300
PREEQYNSTY RVVSVLTVLH QDWLNGKEYK CKVSNKALPA PIEKTISKAK GQPREPQVYT   360
LPPSREEMTK NQVSLTCLVK GFYPSDIAVE WESNGQPENN YKTTPPVLDS DGSFFLYSKL   420
TVDKSRWQQG NVFSCSVMHE ALHNHYTQKS LSLSPGK                            457

SEQ ID NO: 97              moltype = AA   length = 214
FEATURE                    Location/Qualifiers
source                     1..214
                           mol_type = protein
                           organism = synthetic construct
SEQUENCE: 97
EIVMTQSPSS LSASVGDRVT ITCRASQGIS NYLAWYQQKP GKVPKLLIYA TSTLQSGVPS    60
RFSGSGSGTD FILTISSLQP EDVANYYCQK YNSAPFTFGP GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 98              moltype = AA   length = 452
FEATURE                    Location/Qualifiers
source                     1..452
                           mol_type = protein
                           organism = synthetic construct
SEQUENCE: 98
QVQLVESGGG VVQPGRSLRL SCAASGFTFS TYGMHWVRQA PGKGLEWVAF ISYDGSNKYY    60
ADSVKGRFTI SRDNSKHTLY LQMNSLRAED TAVYYCAGRD NLRFLEWFMD VWGQGTTVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 99              moltype = AA   length = 215
FEATURE                    Location/Qualifiers
source                     1..215
                           mol_type = protein
                           organism = synthetic construct
SEQUENCE: 99
EIVMTQSPAT LSVSPGERAT LSCRASQSVR SNLAWYQQKP GQAPRLLIYG ASTRATGIPA    60
RFSGSGSGTE FTLTISSLQS EDFAVYYCHQ YNDWPPYTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 100             moltype = AA   length = 446
FEATURE                    Location/Qualifiers
source                     1..446
                           mol_type = protein
                           organism = synthetic construct
SEQUENCE: 100
EVQLVESGGG LVKPGGSLRL SCAASGFTLS IYSMNWVRQA PGKGLEWVSS ISSSSSYIFY    60
ADSVKGRFTI SRDNAKNSLF LQMNSLRAED TAVYYCARSS YGADYWGQGT LVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSREEMTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                        446

SEQ ID NO: 101             moltype = AA   length = 214
```

```
FEATURE                 Location/Qualifiers
source                  1..214
                        mol_type = protein
                        organism = synthetic construct
SEQUENCE: 101
EIVMTQSPSS LSASVGDRVT ITCRASQDIT NFLAWYQQKP GKVPKLLIYT ASTLQSGVPS    60
RFSGSGSGTD FTLTISSLQP EDVATYYCQK YNSAPLTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 102          moltype = AA   length = 455
FEATURE                 Location/Qualifiers
source                  1..455
                        mol_type = protein
                        organism = synthetic construct
SEQUENCE: 102
EVQLVESGGG LVKPGGSLRL SCAASGFTFS SYSLNWVRQA PGKGLEWVSS ISSSSSYISY    60
ADAVKGRFTI SRDNAKNSLY LQMNSLRAED TAVYYCARDR GFLEDYYYYY GMDVWGQGTT   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KKVEPKSCDK THTCPPCPAP   240
ELLGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 103          moltype = AA   length = 214
FEATURE                 Location/Qualifiers
source                  1..214
                        mol_type = protein
                        organism = synthetic construct
SEQUENCE: 103
DIVMTQSPSS VSASVGDRVT ITCRASQGIS NWLAWYQQKP GKAPKLLIYV ASSLQSGVPS    60
RFSGSGSGTD FSLTISSLQP EDFATYYCQQ AYSFPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 104          moltype = DNA   length = 1359
FEATURE                 Location/Qualifiers
source                  1..1359
                        mol_type = other DNA
                        organism = synthetic construct
SEQUENCE: 104
gaggtgcagc tggttgaatc tggtggcgga gaagtgcagc tggcagatc tctgagactg     60
acctgtgctg tgtccggctt caccctgtcc agatacggaa tgcactgggt ccgacaggcc   120
cctggcaaag gattgaatg ggccgctctg atctcctacg acggctccaa taggtactac   180
gccgactccg tgaagggcag attcaccatc tctcgggaca actccaagaa caccgtgttt   240
ctgcaatga actccctgag agccgaggac accgccgtct actactgtgc cagagagcgg   300
gaatcctccg gctggttcga gggctacttc gactattggg gccagggcac acagtgacc   360
gtttcttctg cctccaccaa gggcccatcg gtcttccccc tggcaccctc ctccaagagc   420
acctctgggg gcacagcggc cctgggctgc ctggtcaagg actacttccc cgaaccggtg   480
acggtgtcgt ggaactcagg cgccctgacc agcggcgtgc acaccttccc ggctgtccta   540
cagtcctcag gactctactc cctcagcagc gtggtgaccg tgccctccag cagcttgggc   600
acccagacct acatctgcaa cgtgaatcac aagcccagca caccaaggt ggacaagaaa   660
gttgagccca aatcttgtga caaaactcac acatgcccac cgtgcccagc acctgaactc   720
ctgggggac cgtcagtctt cctcttcccc ccaaaaccc aaggacaccct catgatctcc   780
cggacccctg aggtcacatg cgtggtggtg gacgtgagcc acgaagaccc tgaggtcaag   840
ttcaactggt acgtggacgg cgtggaggtg cataatgcca agacaaagcc gcgggaggag   900
cagtacaaca gcacgtaccg tgtggtcagc gtcctcaccg tcctgcacca ggactggctg   960
aatggcaagg agtacaagtg caaggtctcc aacaaagcc tcccagcccc catcgagaaa  1020
accatctcca aagccaaagg gcagccccga gaaccacagg tgtacacct gcccccatcc  1080
cgggaggaga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcagatggc agcaggggaa cgtcttctca tgctccgtga tgcatgaggc tctgcacaac  1320
cactacacgc agaagtctct ctccctgtct ccgggaaaa                         1359

SEQ ID NO: 105          moltype = DNA   length = 642
FEATURE                 Location/Qualifiers
source                  1..642
                        mol_type = other DNA
                        organism = synthetic construct
SEQUENCE: 105
cagctggttc tgacccagcc tccttctgtg tctgtggctc tggccagac cgccagaatt    60
acctgtgccg gcaacaacat cggctccaag tccgtgcact ggtatcagca gaagcctgga   120
caggctcctg tgctggtggt gtacgacaac tctgaccggc cttctggcat ccctgagaga   180
ttctccggct ccaacagcgg caataccgcc acactgacca tctccagagt ggaagtgggc   240
gacgaggccg actactactg ccaagtgtgg gactcctcct ccgatcatgt ggtgtttggc   300
ggcggaacaa agctgacagt gctggtcag cccaaggctg cacccagtgt cactctgttc   360
ccgccctcct ctgaggagct tcaagccaac aaggccacac tggtgtgtct cataagtgac   420
```

```
ttctacccgg gagccgtgac agtggcctgg aaggccgata gcagcccgt caaggcggga    480
gtcgaaacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                       642

SEQ ID NO: 106          moltype = DNA   length = 1359
FEATURE                 Location/Qualifiers
source                  1..1359
                        mol_type = other DNA
                        organism = synthetic construct
SEQUENCE: 106
gaggtgcagc tggttgaatc tggtggcgga gaagtgcagc tggcagatc tctgagactg    60
acctgtgctg tgtccggctt caccctgtcc agatacggaa tgcactgggt ccgacaggcc   120
cctggcaaag gattggaatg ggccgctctg atctcctacg acggatccaa taggtactac   180
gccgactccg tgaagggcag attcaccatc tctcgggaca actccaagaa caccgtgttt   240
ctgcagatga actccctgag agccgaggac accgccgtgt actactgtgc cagagagcgg   300
gaatcctccg gctggttcga gggctacttc gactattggg gccagggcac cacagtgacc   360
gtttcttctg cctccaccaa gggcccatcg gtcttccccc tggcaccctc ctccaagagc   420
acctctgggg gcacagcggc cctgggctgc ctggtcaagg actacttccc cgaaccggtg   480
acggtgtcgt ggaactcagg cgccctgacc agcggcgtgc acaccttccc ggctgtccta   540
cagtcctcag gactctactc cctcagcagc gtggtgaccg tgccctccag cagcttgggc    600
acccagacct acatctgcaa cgtgaatcac aagcccagca acaccaaggt ggacaagaaa   660
gttgagccca atcttgtga caaaactcac acatgcccac cgtgcccagc acctgaagcc    720
gccgggggac cgtcagtctt cctcttcccc ccaaaaccca aggacaccct ctacatcacc   780
cgggagcctg aggtcacatg cgtggtggtg agcgtgagcc acgaagaccc tgaggtcaag   840
ttcaactggt acgtggacgg cgtggaggtg cataatgcca agacaaagcc gcgggaggag   900
cagtacaaca gcacgtaccg tgtggtcagc gtcctcaccg tcctgcacca ggactggctg   960
aatggcaagg agtacaagtg caaggtgtcg aacaaagccc tcccagcccc catcgagaaa  1020
accatctcca aagccaaagg gcagcccga gaaccacagg tgtacaccct gcccccatcc   1080
cgggagagga tgaccaagaa ccaggtcagc ctgacctgcc tggtcaaagg cttctatccc  1140
agcgacatcg ccgtggagtg ggagagcaat gggcagccgg agaacaacta caagaccacg  1200
cctcccgtgc tggactccga cggctccttc ttcctctaca gcaagctcac cgtggacaag  1260
agcagatggc agcaggggaa cgtcttctca tgctccgtga tgcatgaggc tctgcacaac  1320
cactacacgc agaagtctct ctccctgtct ccgggaaaa                          1359

SEQ ID NO: 107          moltype = AA    length = 4
FEATURE                 Location/Qualifiers
source                  1..4
                        mol_type = protein
                        organism = synthetic construct
SEQUENCE: 107
GSGS                                                                   4

SEQ ID NO: 108          moltype = DNA   length = 1347
FEATURE                 Location/Qualifiers
source                  1..1347
                        mol_type = other DNA
                        organism = synthetic construct
SEQUENCE: 108
caggtgcagc tgcaagagtc tggacctggc ctggtcaagt cctccgagac actgtctctg    60
acctgcaccg tgtctggcgg ctccatctcc tcctactact ggaactggat cagacagcct   120
gccggcaaag gcctggaatg gatcggcaga atctactcct ccggcaacac cgactacaac   180
cccagcctga gtccagagt gaccatgtcc gtggacacct ccaagaacca gttctccctg   240
aagctgatct ccgtgaccgc cgctgatacc gccgtgtact attgtgctag aggcagaggc   300
gccaacgtgg gcctgtttga ttattggggc cagggcaccc tggtcaccgt ttcttctgca   360
tccaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagaaagt tgagcccaaa   660
tcttgtgaca aaactcacac atgcccaccg tgcccagcac ctgaactcct gggggaccg    720
tcagtcttcc tcttcccccc aaaacccaag gacaccctca tgatctcccg gacccctgag   780
gtcacatgcg tggtggtgga cgtgagccac gaagaccctg aggtcaagtt caactggtac   840
gtggacggcg tggaggtgca taatgccaag acaaagccgc gggaggagca gtacaacagc   900
acgtaccgtg tggtcagcgt cctcaccgtc ctgcaccagg actggctgaa tggcaaggag   960
tacaagtgca aggtgtccaa caaagccctc ccagccccca tcgagaaaac catctccaaa  1020
gccaaagggc agcccgaga ccacaggtgt acaccctgcc ccatcccgg ggaggagatg   1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag cagatggcag  1260
caggggaacg tcttctcatg ctccgtgatg catgaggctc tgcacaacca ctacacgcag  1320
aagtctctct ccctgtctcc gggaaaa                                       1347

SEQ ID NO: 109          moltype = DNA   length = 651
FEATURE                 Location/Qualifiers
source                  1..651
                        mol_type = other DNA
                        organism = synthetic construct
SEQUENCE: 109
```

```
cagtctgctc tgacccagcc tccttctgtg tctggcgctc ctggccagag agtgaccatc   60
tcttgtaccg gctccaactc caacatcggc gccaactacg acgtgcactg gtatcagcat  120
ctgcccggca cagctcccaa gctgctgatc tacggcaaca tcaacagacc cctgggcgtg  180
cccgaccggt tttctggaag cagatctggc acctctgcca gctggctat taccggactg  240
caggctgagg acgaggccga ctactactgc cagtcctacg acttctccct gtccggctcc  300
gtgtttggcg tgggcacaaa gctgacagtc ctgggtcagc ccaaggctgc acccagtgtc  360
actctgttcc cgccctcctc tgaggagctt caagccaaca aggccacact ggtgtgtctc  420
ataagtgact tctacccggg agccgtgaca gtggcctgga aggccgatag cagcccgtc   480
aaggcgggag tcgaaaccac cacaccctcc aaacaaagca caacaagta cgcggccagc  540
agctatctga gcctgacgcc tgagcagtgg aagtcccaca gaagctacag ctgccaggtc  600
acgcatgaag ggagcaccgt ggagaagaca gtggccccta cagaatgttc a           651

SEQ ID NO: 110         moltype = DNA  length = 1347
FEATURE                Location/Qualifiers
source                 1..1347
                       mol_type = other DNA
                       organism = synthetic construct
SEQUENCE: 110
caggtgcagc tgcaagagtc tggacctggc ctggtcaagt cctccgagac actgtctctg   60
acctgcaccg tgtctggcgg ctccatctcc tcctactact ggaactggat cagacagcct  120
gccggcaaag gcctggaatg gatcggcaga atctactcct ccggcaacac cgactacaac  180
cccagcctga gtccagagt gaccatgtcc gtggacacct ccaagaacca gttctccctg  240
aagctgatct ccgtgaccgc cgctgatacc gccgtgtact attgtgctag aggcagaggc  300
gccaacgtgg gcctgtttga ttattgggc cagggcaccc tggtcaccgt ttcttctgcc  360
tccaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagaaagt tgagcccaaa  660
tcttgtgaca aaactcacac atgcccaccg tgcccagcac ctgaagccgc cggggggaccg  720
tcagtcttcc tcttcccccc aaaacccaag gacaccctct catcacccg ggagcctgag   780
gtcacatgcg tggtggtgag cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc cagccccca tcgagaaaac catctccaaa 1020
gccaaagggc agccccgaga accacaggtg tacaccctgc cccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag cagatggcag  1260
caggggaacg tcttctcatg ctccgtgatg catgaggctc tgcacaacca ctacacgcag  1320
aagtctctct ccctgtctcc gggaaaa                                      1347

SEQ ID NO: 111         moltype = AA   length = 20
FEATURE                Location/Qualifiers
source                 1..20
                       mol_type = protein
                       organism = synthetic construct
SEQUENCE: 111
APAPAPAPAP APAPAPAPAP                                                20

SEQ ID NO: 112         moltype = DNA  length = 1356
FEATURE                Location/Qualifiers
source                 1..1356
                       mol_type = other DNA
                       organism = synthetic construct
SEQUENCE: 112
gaggtgcagc tggttgaatc tggtggcgga gtggtgcagc ctggcagatc tctgagactg   60
tcttgtgccg cttccgtgcg gaccttctct ggctacggaa tgcactgggt ccgacaggtg  120
ccaggcaaag gactggaatg ggtggccgtg atctcctacg atggctccaa tcggtactac  180
gccgactccg tgaagggcag attcaccatc tctcgggaca actccaagaa caccctgtac  240
ctgcagatga actccctgcg gaccgaggat accgccgtgt actactgtgc cagagatggc  300
aactggggct ccctggacct gtacttcgat ctctggggac gggcaccct ggtcacagtc   360
tcttctgcct ccaccaaggg cccatcggtc ttccccctgg caccctcctc caagagcacc  420
tctgggggca cagcggccct gggctgcctg gtcaaggact acttccccga accggtgacg  480
gtgtcgtgga actcaggcgc cctgaccagc ggcgtgcaca ccttcccggc tgtcctacag  540
tcctcaggac tctactccct cagcagcgtg gtgaccgtgc cctccagcag cttgggcacc  600
cagacctaca tctgcaacgt gaatcacaag cccagcaaca ccaaggtgga caagaaagtt  660
gagcccaaat cttgtgacaa aactcacaca tgcccaccgt gcccagcacc tgaactcctg  720
gggggaccgt cagtcttcct cttccccca aaacccaagg acaccctcat gatctcccgg   780
acccctgagg tcacatgcgt ggtggtggac gtgagccacg aagaccctga ggtcaagttc  840
aactggtacg tggacggcgt ggaggtgcat aatgccaaga caaagccgcg ggaggagcag  900
tacaacagca cgtaccgtgt ggtcagcgtc ctcaccgtcc tgcaccagga ctggctgaat  960
ggcaaggagt acaagtgcaa ggtgtccaac aaagccctcc agcccccat cgagaaaacc  1020
atctccaaag ccaaagggca gccccgagaa ccacaggtgt acaccctgcc ccatcccgg   1080
gaggagatga ccaagaacca ggtcagcctg acctgcctgg tcaaaggctt ctatcccagc  1140
gacatcgccg tggagtggga gagcaatggg cagccggaga acaactacaa gaccacgcct  1200
cccgtgctga ctccgacgg ctccttcttc ctctacagca agctcaccgt ggacaagagc   1260
agatggcagc aggggaacgt cttctcatgc tccgtgatgc atgaggctct gcacaaccac  1320
tacacgcaga agtctctctc cctgtctccg ggaaaa                            1356
```

```
SEQ ID NO: 113           moltype = DNA  length = 651
FEATURE                  Location/Qualifiers
source                   1..651
                         mol_type = other DNA
                         organism = synthetic construct
SEQUENCE: 113
cagtctgtgc tgacccagcc tccttctgtg tctggcgctc ctggccagag agtgaccatc    60
tcctgtaccg gctcctcctc taacatcggc gctgactacg acgtgcactg gtatcagcag   120
ctgcctggca cagctcccaa actgctgatc tacgtgaaca caaaccggcc ttctggcgtg   180
cccgacagat tctctggaag cagatctggc acctctgcca gctggctgat taccggactg   240
caggccgatg acgaggccga ctactactgc cagtcctacg acaacaccct gtccggcgtt   300
gtgtttggcg gcggaacaaa gctgacagtc ctgggtcagc ccaaggctgc acccagtgtc   360
actctgttcc cgccctcctc tgaggagctt caagccaaca aggccacact ggtgtgtctc   420
ataagtgact tctacccggg agccgtgaca gtgcctggaa aggccgatag cagccccgtc   480
aaggcgggag tcgaaaccac cacaccctcc aaacaaagca caacaagta cgcggccagc   540
agctatctga gcctgacgcc tgagcagtgg aagtcccaca gaagctacag ctgccaggtc   600
acgcatgaag ggagcaccgt ggagaagaca gtggccccta cagaatgttc a            651

SEQ ID NO: 114           moltype = DNA  length = 1368
FEATURE                  Location/Qualifiers
source                   1..1368
                         mol_type = other DNA
                         organism = synthetic construct
SEQUENCE: 114
gaggtgcagc tggttgaatc tggtggcgga gtggtgcagc ctggcagatc tctgagactg    60
tcttgtgccg cctccggctt caccttcacc agctacggaa tgcactgggt ccgacaggcc   120
cctggcaaag gattgaatgg ggtggccgtg atctcctacg acggctccaa caagtactac   180
gccgactccg tgaagggcag attcaccatc tctcgggaca actccaagaa caccctgtac   240
ctgcagatga actccctgag agccgaggac accgccgtgt actactgtgc cagagagcac   300
tacgactcct ccggctacta ccacggctac tatggcatgg atgtgtgggg ccagggcacc   360
acagtgacag tctcttccgc ctccaccaag ggcccatcgg tcttccccct ggcaccctcc   420
tccaagagca cctctggggg cacagcggcc ctgggctgcc tggtcaagga ctacttcccc   480
gaaccggtga cggtgtcgtg gaactcaggc gccctgacca gcggcgtgca caccttcccg   540
gctgtcctac agtcctcagg actctactcc ctcagcagcg tggtgaccgt gccctccagc   600
agcttgggca cccagaccta catctgcaac gtgaatcaca agcccagcaa caccaaggtg   660
gacaagaaag ttgagcccaa atcttgtgac aaaactcaca catgcccacc gtgcccagca   720
cctgaactcc tggggggacc gtcagtcttc ctcttccccc caaaacccaa ggacaccctc   780
atgatctccc ggacccctga ggtcacatgc gtggtggtgg acgtgagcca cgaagaccct   840
gaggtcaagt tcaactggta cgtggacggc gtggaggtgc ataatgccaa gacaaagccg   900
cgggaggagc agtacaacag cacgtaccgt gtggtcagcg tcctcaccgt cctgcaccag   960
gactggctga atggcaagga gtacaagtgc aaggtgtcca acaaagccct cccagccccc  1020
atcgagaaaa ccatctccaa agccaaaggg cagccccgag aaccacaggt gtacaccctg  1080
cccccatccc gggaggagat gaccaagaac caggtcagcc tgacctgcct ggtcaaaggc  1140
ttctatccca gcgacatcgc cgtggagtgg gagagcaatg ggcagccgga gaacaactac  1200
aagaccacgc tcccgtgtct ggactccgac ggctccttct tcctctacag caagctcacc  1260
gtggacaaga gcaggtggca gcaggggaac gtcttctcat gctccgtgat gcatgaggct  1320
ctgcacaacc actacacgca gaagtctctc tccctgtctc cgggaaaa              1368

SEQ ID NO: 115           moltype = DNA  length = 648
FEATURE                  Location/Qualifiers
source                   1..648
                         mol_type = other DNA
                         organism = synthetic construct
SEQUENCE: 115
caggctgttc tgacccagcc tccttctgct tctggcaccc ctggacagag agtgaccatc    60
tcttgctccg gctcctcctc caacatcggc tccaactacg tgtactggta ccagctgctg   120
cccggcaccg ctcctaagct gctgatctac tccaacaacc agcggccttc tggcgtgccc   180
gatagattct ccggctctaa gtctggcacc tctgccacc tggctatctc cggactgaga   240
tctgaggacg aggccgacta ctactgcgcg gccagagatg attccctgtc cggctatgtg   300
tttggcaccg gcaccaagct gacagtgttg ggtcagccca ggctgcacc cagtgtcact   360
ctgttccgc cctcctctga ggagcttcaa gccaacaagg ccacactggt gtgtctcata   420
agtgacttct acccgggagc cgtgacagtg cctggaaagg ccgatagcag ccccgtcaag   480
gcgggagtcg aaaccaccac accctccaaa caaagcacaa caagtacgcg gccagcagc   540
tatctgagcc tgacgcctga gcagtggaag tcccacagaa gctacagctg ccaggtcacg   600
catgaaggga gcaccgtgga agacagtg cccctacag aatgttca                 648

SEQ ID NO: 116           moltype = DNA  length = 1371
FEATURE                  Location/Qualifiers
source                   1..1371
                         mol_type = other DNA
                         organism = synthetic construct
SEQUENCE: 116
gaggtgcagc tggtggagtc tgggggaggc gtggtccagc ctgggaggtc cctgagactc    60
tcctgtgcag cctctggatt caccttcagt agttatgaca tgcactgggt ccgccaggct   120
ccaggcaagg ggctggagtg ggtgacagtt atatcatttg atggaagtaa taaatactat   180
gtagactccg tgaagggccg attcaccatc tccagagaca attccaagaa tacgctgtat   240
ctgcaaatga acagcctgag agctgaggac acggctgtgt attactgtgc gagaacgtat   300
tacgatattt tgactggtta ttcccactac tcctacggta tggacgtctg gggccaaggg   360
```

```
accacggtca ccgtctcctc agcctccacc aagggcccat cggtcttccc cctggcaccc    420
tcctccaaga gcacctctgg gggcacagcg ccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga agttgagcc caaatcttgt gacaaaactc acacatgccc accgtgccca    720
gcacctgaac tcctggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggagga gatgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta cagcaagctc   1260
accgtggaca agagcagatg gcagcagggg aacgtcttct catgctccgt gatgcatgag   1320
gctctgcaca accactacac gcagaagagc ctctccctgt ctccgggtaa a            1371

SEQ ID NO: 117           moltype = DNA   length = 642
FEATURE                  Location/Qualifiers
source                   1..642
                         mol_type = other DNA
                         organism = synthetic construct
SEQUENCE: 117
gaaatagtga tgacgcagtc tccatcctcc ctgtctgcat ctgtaggaga cagagtcacc     60
atcacttgcc gggcgagtca gggcattagc aattatttag cctggtatca gcagaaacca    120
gggaaagttc ctaagctcct gatctatgcc acatccactt tgcaatcagg ggtcccatct    180
cggttcagtg gcagtggatc tgggacagat ttcattctca ccatcagcag cctgcagcct    240
gaagatgttg caaactatta ctgtcaaaag tataacagtg cccattcac tttcggccct    300
gggaccaagg tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

SEQ ID NO: 118           moltype = DNA   length = 1356
FEATURE                  Location/Qualifiers
source                   1..1356
                         mol_type = other DNA
                         organism = synthetic construct
SEQUENCE: 118
caggtgcagc tggtggagtc tgggggaggc gtggtccagc ctgggaggtc cctgagactc     60
tcctgtgcag cctctggatt cacccttcagt acctatggca tgcactgggt ccgccaggct    120
ccaggcaagg ggctggagtg ggtggcattt atatcatatg atggaagtaa taaatactat    180
gcagactccg tgaagggccg attcaccatc tccagagaca attccaagca cacgctatat    240
ctgcaaatga acagcctgag agctgaggac acggctgtgt attactgtgc gggagagac    300
aacctacgat ttttggagtg gtttatggac gtctgggggcc aagggaccac ggtcaccgtc    360
tcttcagcct ccaccaaggg cccatcggtc ttccccctgg cacccctcc caagagcacc    420
tctgggggca gcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagaaagtt    660
gagcccaaat cttgtgacaa aactcacaca tgcccaccgt gcccagcacc tgaactcctg    720
gggggaccgt cagtcttcct cttccccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagcccctc cagccccat cgagaaaacc   1020
atctccaaag ccaaagggca gccccgagaa ccacaggtgt acaccctgcc cccatcccgc   1080
gaggagatga ccaagaacca ggtcagcctg acctgcctgg tcaaaggctt ctatcccagc   1140
gacatcgccg tggagtggga gcaatgggc agccggaga acaactacaa gaccacgcct   1200
cccgtgctgg actccgacgg ctccttcttc ctctacagca agctcaccgt ggacaagagc   1260
agatggcagc aggggaacgt cttctcatgc tccgtgatgc atgaggctct gcacaaccac   1320
tacacgcaga agagcctctc cctgtctccg ggtaaa                             1356

SEQ ID NO: 119           moltype = DNA   length = 645
FEATURE                  Location/Qualifiers
source                   1..645
                         mol_type = other DNA
                         organism = synthetic construct
SEQUENCE: 119
gaaatagtga tgacgcagtc tccagccacc ctgtctgtgt ctccagggga aagagccacc     60
ctctcctgca gggccagtca gagtgtaagg agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcaccag tataatgact ggcctccgta cacttttggc    300
caagggacca aggtggaaat caaacgtacg gtggctgcac catctgtctt catcttcccg    360
ccatctgatg agcagttgaa atctggaact gcctctgttg tgtgcctgct gaataacttc    420
```

```
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645

SEQ ID NO: 120          moltype = DNA  length = 1338
FEATURE                 Location/Qualifiers
source                  1..1338
                        mol_type = other DNA
                        organism = synthetic construct
SEQUENCE: 120
gaggtgcagc tggtggagtc tgggggaggc ctggtcaagc cggggggtc cctgagactc     60
tcctgtgcag cctctggatt caccctcagt atttatagca tgaactgggt ccgccaggct    120
ccagggaagg ggctggagtg ggtctcatcc attagcagta gtagtagtta catattctac    180
gcagactcag tgaagggccg attcaccatc tccagagaca acgccaagaa ctcactcttt    240
ctgcaaatga acagcctgag agccgaggac acggctgtgt attactgtgc gagatcctcc    300
tacggtgcgg actactgggg ccagggaacc ctggtcaccg tctcttcagc ctccaccaag    360
ggcccatcgg tcttcccct ggcaccctcc tccaagagca cctctgggg cacagcggcc     420
ctgggctgcc tggtcaagga ctacttcccc gaaccggtga cggtgtcgtg gaactcaggc    480
gccctgacca gcggcgtgca ccttcccg gctgtcctac agtcctcagg actctactcc      540
ctcagcagcg tggtgaccgt gccctccagc agcttgggca cccagaccta catctgcaac    600
gtgaatcaca agcccagcaa caccaaggtg gacaagaaag ttgagcccaa atctttgtgac   660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg    1020
cagccccgag aaccacaggt gtacaccctg cccccatccc gggaggagat gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct cctctacag caagctcacc gtggacaaga gcagatggca gcaggggaac    1260
gtcttctcat gctccgtgat gcatgaggct ctgcacaacc actacacgca gaagagcctc    1320
tccctgtctc cgggtaaa                                                  1338

SEQ ID NO: 121          moltype = DNA  length = 642
FEATURE                 Location/Qualifiers
source                  1..642
                        mol_type = other DNA
                        organism = synthetic construct
SEQUENCE: 121
gaaatagtga tgacgcagtc tccatcctcc ctgtctgcat ctgtaggaga cagagtcacc     60
atcacttgcc gggcgagtca ggacattacc aattttttag cctggtatca gcagaaacca    120
gggaaagttc ctaaactcct gatttatact gcatccactt tgcaatcagg gtcccatctc    180
cggttcagtg gcagtggatc tgggacagat ttcactctca ccatcagcag cctgcagcct    240
gaagatgttg cgacttatta ctgtcaaaag tataacagtg ccccactcac tttcggcgga    300
gggaccaagc tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

SEQ ID NO: 122          moltype = DNA  length = 1365
FEATURE                 Location/Qualifiers
source                  1..1365
                        mol_type = other DNA
                        organism = synthetic construct
SEQUENCE: 122
gaggtgcagc tggtggagtc tgggggaggc ctggtcaagc ctggggggtc cctgagactc    60
tcctgtgcag cctctggatt caccttcagc agctatagcc tgaactgggt ccgccaggct    120
ccagggaagg ggctggagtg ggtctcatcc attagtagta gtagtagtta catatcctac    180
gcagacgcag tgaagggccg attcaccatc tccagagaca acgccaagaa ctcactgtat    240
ctgcaaatga acagcctgag agccgaggac acggctgtgt attactgtgc gagagtacag    300
ggatttttgg aggattacta ctactactac ggtatggacg tctggggcca agggaccacg    360
gtcaccgtct cctcagcctc caccaagggc ccatcggtct tccccctggc accctcctcc    420
aagagcacct ctgggggcac agcggccctg ggctgcctgg tcaaggacta cttcccccgaa   480
ccggtgacgg tgtcgtggaa ctcaggcgcc ctgaccagcg gcgtgcacac cttcccggct    540
gtcctacagt cctcaggact ctactccctc agcagcgtgg tgaccgtgcc ctccagcagc    600
ttgggcaccc agacctacat ctgcaacgtg aatcacaagc ccagcaacac caaggtggac    660
aagaaagttg agcccaaatc ttgtgacaaa actcacacat gcccaccgtg cccagcacct    720
gaactcctgg ggggaccgtc agtcttcctc ttccccccaa aacccaagga caccctcatg    780
atctcccgga cccctgaggt cacatgcgtg gtggtggacg tgagccacga agaccctgag    840
gtcaagttca actggtacgt ggacggcgtg gaggtgcata atgccaagac aaagccgcgg    900
gaggagcagt acaacagcac gtaccgtgtg gtcagcgtcc tcaccgtcct gcaccaggac    960
tggctgaatg gcaaggagta caagtgcaag gtctccaaca agcccctccc agcccccatc    1020
gagaaaacca tctccaaagc caagggcag ccccgagaac acaggtgta cacccctgccc    1080
catcccggga ggagatgac caagaaccag gtcagcctga cctgcctggt caaaggcttc    1140
tatcccagcg acatcgccgt ggagtgggag agcaatgggc agccgagaa caactacaag    1200
```

```
accacgcctc ccgtgctgga ctccgacggc tccttcttcc tctacagcaa gctcaccgtg   1260
gacaagagca gatggcagca ggggaacgtc ttctcatgct ccgtgatgca tgaggctctg   1320
cacaaccact acacgcagaa gagcctctcc ctgtctccgg gtaaa                   1365
```

SEQ ID NO: 123          moltype = DNA  length = 642
FEATURE                 Location/Qualifiers
source                  1..642
                        mol_type = other DNA
                        organism = synthetic construct
SEQUENCE: 123
```
gacatcgtga tgacccagtc tccatcttcc gtgtctgcat ctgtaggaga cagagtcacc   60
atcacttgtc gggcgagtca aggtattagc aactggttag cctggtatca gcagaaacca   120
gggaaagccc ctaagctcct gatctatgtt gcatccagtt tgcaaagtgg ggttccatca   180
aggttcagcg gcagtggatc tgggacagat ttctctctca ccatcagcag cctgcagcct   240
gaagattttg caacttacta ttgtcaacag gcttacagtt tccctctcac tttcggcgga   300
gggaccaagg tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                     642
```

SEQ ID NO: 124          moltype = AA  length = 7
FEATURE                 Location/Qualifiers
source                  1..7
                        mol_type = protein
                        organism = synthetic construct
SEQUENCE: 124
GFTLSRY                                                             7

SEQ ID NO: 125          moltype = AA  length = 6
FEATURE                 Location/Qualifiers
source                  1..6
                        mol_type = protein
                        organism = synthetic construct
SEQUENCE: 125
SYDGSN                                                              6

SEQ ID NO: 126          moltype = AA  length = 6
FEATURE                 Location/Qualifiers
source                  1..6
                        mol_type = protein
                        organism = Homo sapiens
SEQUENCE: 126
IFNTSL                                                              6

SEQ ID NO: 127          moltype = AA  length = 6
FEATURE                 Location/Qualifiers
source                  1..6
                        mol_type = protein
                        organism = Homo sapiens
SEQUENCE: 127
GYPANE                                                              6

SEQ ID NO: 128          moltype = AA  length = 7
FEATURE                 Location/Qualifiers
source                  1..7
                        mol_type = protein
                        organism = Homo sapiens
SEQUENCE: 128
HRDSWVF                                                             7

SEQ ID NO: 129          moltype =   length =
SEQUENCE: 129
000

SEQ ID NO: 130          moltype = AA  length = 7
FEATURE                 Location/Qualifiers
source                  1..7
                        mol_type = protein
                        organism = synthetic construct
SEQUENCE: 130
GGSISSY                                                             7

SEQ ID NO: 131          moltype = AA  length = 5
FEATURE                 Location/Qualifiers
source                  1..5
                        mol_type = protein
                        organism = synthetic construct

```
SEQUENCE: 131
YSSGN                                                                5

SEQ ID NO: 132          moltype = AA  length = 4
FEATURE                 Location/Qualifiers
source                  1..4
                        mol_type = protein
                        organism = Homo sapiens
SEQUENCE: 132
LERD                                                                 4

SEQ ID NO: 133          moltype = AA  length = 12
FEATURE                 Location/Qualifiers
source                  1..12
                        mol_type = protein
                        organism = Homo sapiens
SEQUENCE: 133
KMGGSAPPDS SW                                                       12

SEQ ID NO: 134          moltype = DNA  length = 369
FEATURE                 Location/Qualifiers
source                  1..369
                        mol_type = other DNA
                        organism = synthetic construct
SEQUENCE: 134
gaggtgcaat tggtagagag tggcggggga gaagtccaac caggccgcag tctcagactt     60
acttgtgccg tctcaggctt taccctcagc cgttacggta tgcactgggt tagacaagct    120
ccagggaagg gacttgaatg ggccgcactg atttcctatg atggctccaa ccgctattat    180
gccgacagtg tgaaaggacg cttcacaatt tcaaggaata attcaaagaa tacagtcttt    240
cttcaaatga actctttgcg agccgaggat acagccgttt attactgtgc acgggaaagg    300
gagtctagtg gatggtttga agggtatttt gattattggg gtcaagggac cacagtgacc    360
gtaagctca                                                            369

SEQ ID NO: 135          moltype = DNA  length = 324
FEATURE                 Location/Qualifiers
source                  1..324
                        mol_type = other DNA
                        organism = synthetic construct
SEQUENCE: 135
cagcttgtcc tcacccagcc acctagcgtt agtgtcgccc ccggtcaaac tgctcgcata     60
acttgtggag gcaacaacat tgggagcaaa agcgttcatt ggtaccaaca aaaaccagga    120
caggcccctg ttttggtagt ttatgacaac tctgatcgac catcaggat  tcccgagcgg    180
ttttctggta gtaattcagg gaatactgct accctgacta tcagtcgcgt cgaagttggc    240
gacgaagctg actattattg tcaagtctgg gacagcagca gcgaccatgt ggttttgggg    300
ggagggacca aacttaccgt attg                                           324

SEQ ID NO: 136          moltype = AA  length = 7
FEATURE                 Location/Qualifiers
source                  1..7
                        mol_type = protein
                        organism = synthetic construct
SEQUENCE: 136
VRTFSGY                                                              7

SEQ ID NO: 137          moltype =     length =
SEQUENCE: 137
000

SEQ ID NO: 138          moltype =     length =
SEQUENCE: 138
000

SEQ ID NO: 139          moltype =     length =
SEQUENCE: 139
000

SEQ ID NO: 140          moltype =     length =
SEQUENCE: 140
000

SEQ ID NO: 141          moltype =     length =
SEQUENCE: 141
000

SEQ ID NO: 142          moltype = AA  length = 7
FEATURE                 Location/Qualifiers
source                  1..7
                        mol_type = protein
                        organism = synthetic construct
```

```
SEQUENCE: 142
GFTFTSY                                                                  7

SEQ ID NO: 143          moltype =    length =
SEQUENCE: 143
000

SEQ ID NO: 144          moltype =    length =
SEQUENCE: 144
000

SEQ ID NO: 145          moltype =    length =
SEQUENCE: 145
000

SEQ ID NO: 146          moltype =    length =
SEQUENCE: 146
000

SEQ ID NO: 147          moltype =    length =
SEQUENCE: 147
000

SEQ ID NO: 148          moltype = AA   length = 7
FEATURE                 Location/Qualifiers
source                  1..7
                        mol_type = protein
                        organism = synthetic construct
SEQUENCE: 148
GFTFSSY                                                                  7

SEQ ID NO: 149          moltype = AA   length = 6
FEATURE                 Location/Qualifiers
source                  1..6
                        mol_type = protein
                        organism = synthetic construct
SEQUENCE: 149
SFDGSN                                                                   6

SEQ ID NO: 150          moltype =    length =
SEQUENCE: 150
000

SEQ ID NO: 151          moltype =    length =
SEQUENCE: 151
000

SEQ ID NO: 152          moltype =    length =
SEQUENCE: 152
000

SEQ ID NO: 153          moltype =    length =
SEQUENCE: 153
000

SEQ ID NO: 154          moltype = AA   length = 7
FEATURE                 Location/Qualifiers
source                  1..7
                        mol_type = protein
                        organism = synthetic construct
SEQUENCE: 154
GFTFSTY                                                                  7

SEQ ID NO: 155          moltype =    length =
SEQUENCE: 155
000

SEQ ID NO: 156          moltype =    length =
SEQUENCE: 156
000

SEQ ID NO: 157          moltype =    length =
SEQUENCE: 157
000

SEQ ID NO: 158          moltype =    length =
SEQUENCE: 158
000
```

| | | |
|---|---|---|
| SEQ ID NO: 159<br>SEQUENCE: 159<br>000 | moltype =   length = | |
| SEQ ID NO: 160<br>FEATURE<br>source | moltype = AA   length = 7<br>Location/Qualifiers<br>1..7<br>mol_type = protein<br>organism = synthetic construct | |
| SEQUENCE: 160<br>GFTLSIY | | 7 |
| SEQ ID NO: 161<br>FEATURE<br>source | moltype = AA   length = 6<br>Location/Qualifiers<br>1..6<br>mol_type = protein<br>organism = synthetic construct | |
| SEQUENCE: 161<br>SSSSSY | | 6 |
| SEQ ID NO: 162<br>SEQUENCE: 162<br>000 | moltype =   length = | |
| SEQ ID NO: 163<br>SEQUENCE: 163<br>000 | moltype =   length = | |
| SEQ ID NO: 164<br>SEQUENCE: 164<br>000 | moltype =   length = | |
| SEQ ID NO: 165<br>SEQUENCE: 165<br>000 | moltype =   length = | |
| SEQ ID NO: 166<br>FEATURE<br>source | moltype = AA   length = 7<br>Location/Qualifiers<br>1..7<br>mol_type = protein<br>organism = synthetic construct | |
| SEQUENCE: 166<br>GFTFSSY | | 7 |
| SEQ ID NO: 167<br>FEATURE<br>source | moltype = AA   length = 6<br>Location/Qualifiers<br>1..6<br>mol_type = protein<br>organism = synthetic construct | |
| SEQUENCE: 167<br>SSSSSY | | 6 |
| SEQ ID NO: 168<br>SEQUENCE: 168<br>000 | moltype =   length = | |
| SEQ ID NO: 169<br>SEQUENCE: 169<br>000 | moltype =   length = | |
| SEQ ID NO: 170<br>SEQUENCE: 170<br>000 | moltype =   length = | |
| SEQ ID NO: 171<br>SEQUENCE: 171<br>000 | moltype =   length = | |
| SEQ ID NO: 172<br>FEATURE<br>source | moltype = AA   length = 10<br>Location/Qualifiers<br>1..10<br>mol_type = protein<br>organism = synthetic construct | |
| SEQUENCE: 172<br>GFTLSRYGMH | | 10 |
| SEQ ID NO: 173<br>FEATURE<br>source | moltype = AA   length = 10<br>Location/Qualifiers<br>1..10 | |

```
                           mol_type = protein
                           organism = synthetic construct
SEQUENCE: 173
LISYDGSNRY                                                              10

SEQ ID NO: 174             moltype =    length =
SEQUENCE: 174
000

SEQ ID NO: 175             moltype =    length =
SEQUENCE: 175
000

SEQ ID NO: 176             moltype =    length =
SEQUENCE: 176
000

SEQ ID NO: 177             moltype =    length =
SEQUENCE: 177
000

SEQ ID NO: 178             moltype = AA   length = 10
FEATURE                    Location/Qualifiers
source                     1..10
                           mol_type = protein
                           organism = synthetic construct
SEQUENCE: 178
GGSISSYYWN                                                              10

SEQ ID NO: 179             moltype = AA   length = 9
FEATURE                    Location/Qualifiers
source                     1..9
                           mol_type = protein
                           organism = synthetic construct
SEQUENCE: 179
RIYSSGNTD                                                                9

SEQ ID NO: 180             moltype =    length =
SEQUENCE: 180
000

SEQ ID NO: 181             moltype =    length =
SEQUENCE: 181
000

SEQ ID NO: 182             moltype =    length =
SEQUENCE: 182
000

SEQ ID NO: 183             moltype =    length =
SEQUENCE: 183
000

SEQ ID NO: 184             moltype = AA   length = 10
FEATURE                    Location/Qualifiers
source                     1..10
                           mol_type = protein
                           organism = synthetic construct
SEQUENCE: 184
VRTFSGYGMH                                                              10

SEQ ID NO: 185             moltype = AA   length = 10
FEATURE                    Location/Qualifiers
source                     1..10
                           mol_type = protein
                           organism = synthetic construct
SEQUENCE: 185
VISYDGSNRY                                                              10

SEQ ID NO: 186             moltype =    length =
SEQUENCE: 186
000

SEQ ID NO: 187             moltype =    length =
SEQUENCE: 187
000

SEQ ID NO: 188             moltype =    length =
SEQUENCE: 188
```

```
SEQ ID NO: 189         moltype =    length =
SEQUENCE: 189
000

SEQ ID NO: 190         moltype = AA   length = 10
FEATURE                Location/Qualifiers
source                 1..10
                       mol_type = protein
                       organism = synthetic construct
SEQUENCE: 190
GFTFTSYGMH                                                          10

SEQ ID NO: 191         moltype = AA   length = 10
FEATURE                Location/Qualifiers
source                 1..10
                       mol_type = protein
                       organism = synthetic construct
SEQUENCE: 191
VISYDGSNKY                                                          10

SEQ ID NO: 192         moltype =    length =
SEQUENCE: 192
000

SEQ ID NO: 193         moltype =    length =
SEQUENCE: 193
000

SEQ ID NO: 194         moltype =    length =
SEQUENCE: 194
000

SEQ ID NO: 195         moltype =    length =
SEQUENCE: 195
000

SEQ ID NO: 196         moltype = AA   length = 10
FEATURE                Location/Qualifiers
source                 1..10
                       mol_type = protein
                       organism = synthetic construct
SEQUENCE: 196
GFTFSSYDMH                                                          10

SEQ ID NO: 197         moltype = AA   length = 10
FEATURE                Location/Qualifiers
source                 1..10
                       mol_type = protein
                       organism = synthetic construct
SEQUENCE: 197
VISFDGSNKY                                                          10

SEQ ID NO: 198         moltype =    length =
SEQUENCE: 198
000

SEQ ID NO: 199         moltype =    length =
SEQUENCE: 199
000

SEQ ID NO: 200         moltype =    length =
SEQUENCE: 200
000

SEQ ID NO: 201         moltype =    length =
SEQUENCE: 201
000

SEQ ID NO: 202         moltype = AA   length = 10
FEATURE                Location/Qualifiers
source                 1..10
                       mol_type = protein
                       organism = synthetic construct
SEQUENCE: 202
GFTFSTYGMH                                                          10

SEQ ID NO: 203         moltype = AA   length = 10
```

```
FEATURE              Location/Qualifiers
source               1..10
                     mol_type = protein
                     organism = synthetic construct
SEQUENCE: 203
FISYDGSNKY                                                                    10

SEQ ID NO: 204       moltype =    length =
SEQUENCE: 204
000

SEQ ID NO: 205       moltype =    length =
SEQUENCE: 205
000

SEQ ID NO: 206       moltype =    length =
SEQUENCE: 206
000

SEQ ID NO: 207       moltype =    length =
SEQUENCE: 207
000

SEQ ID NO: 208       moltype = AA  length = 10
FEATURE              Location/Qualifiers
source               1..10
                     mol_type = protein
                     organism = synthetic construct
SEQUENCE: 208
GFTLSIYSMN                                                                    10

SEQ ID NO: 209       moltype = AA  length = 10
FEATURE              Location/Qualifiers
source               1..10
                     mol_type = protein
                     organism = synthetic construct
SEQUENCE: 209
SISSSSSYIF                                                                    10

SEQ ID NO: 210       moltype =    length =
SEQUENCE: 210
000

SEQ ID NO: 211       moltype =    length =
SEQUENCE: 211
000

SEQ ID NO: 212       moltype =    length =
SEQUENCE: 212
000

SEQ ID NO: 213       moltype =    length =
SEQUENCE: 213
000

SEQ ID NO: 214       moltype = AA  length = 10
FEATURE              Location/Qualifiers
source               1..10
                     mol_type = protein
                     organism = synthetic construct
SEQUENCE: 214
GFTFSSYSLN                                                                    10

SEQ ID NO: 215       moltype = AA  length = 10
FEATURE              Location/Qualifiers
source               1..10
                     mol_type = protein
                     organism = synthetic construct
SEQUENCE: 215
SISSSSSYIS                                                                    10

SEQ ID NO: 216       moltype =    length =
SEQUENCE: 216
000

SEQ ID NO: 217       moltype =    length =
SEQUENCE: 217
000
```

```
SEQ ID NO: 218           moltype =    length =
SEQUENCE: 218
000

SEQ ID NO: 219           moltype =    length =
SEQUENCE: 219
000

SEQ ID NO: 220           moltype = AA  length = 8
FEATURE                  Location/Qualifiers
source                   1..8
                         mol_type = protein
                         organism = synthetic construct
SEQUENCE: 220
GFTLSRYG                                                                  8

SEQ ID NO: 221           moltype = AA  length = 8
FEATURE                  Location/Qualifiers
source                   1..8
                         mol_type = protein
                         organism = synthetic construct
SEQUENCE: 221
ISYDGSNR                                                                  8

SEQ ID NO: 222           moltype = AA  length = 16
FEATURE                  Location/Qualifiers
source                   1..16
                         mol_type = protein
                         organism = synthetic construct
SEQUENCE: 222
ARERESSGWF EGYFDY                                                        16

SEQ ID NO: 223           moltype = AA  length = 6
FEATURE                  Location/Qualifiers
source                   1..6
                         mol_type = protein
                         organism = synthetic construct
SEQUENCE: 223
NIGSKS                                                                    6

SEQ ID NO: 224           moltype =    length =
SEQUENCE: 224
000

SEQ ID NO: 225           moltype =    length =
SEQUENCE: 225
000

SEQ ID NO: 226           moltype = AA  length = 8
FEATURE                  Location/Qualifiers
source                   1..8
                         mol_type = protein
                         organism = synthetic construct
SEQUENCE: 226
GGSISSYY                                                                  8

SEQ ID NO: 227           moltype = AA  length = 7
FEATURE                  Location/Qualifiers
source                   1..7
                         mol_type = protein
                         organism = synthetic construct
SEQUENCE: 227
IYSSGNT                                                                   7

SEQ ID NO: 228           moltype = AA  length = 13
FEATURE                  Location/Qualifiers
source                   1..13
                         mol_type = protein
                         organism = synthetic construct
SEQUENCE: 228
ARGRGANVGL FDY                                                           13

SEQ ID NO: 229           moltype = AA  length = 9
FEATURE                  Location/Qualifiers
source                   1..9
                         mol_type = protein
                         organism = synthetic construct
SEQUENCE: 229
NSNIGANYD                                                                 9
```

```
SEQ ID NO: 230         moltype =    length =
SEQUENCE: 230
000

SEQ ID NO: 231         moltype =    length =
SEQUENCE: 231
000

SEQ ID NO: 232         moltype = AA  length = 8
FEATURE                Location/Qualifiers
source                 1..8
                       mol_type = protein
                       organism = synthetic construct
SEQUENCE: 232
VRTFSGYG                                                                 8

SEQ ID NO: 233         moltype = AA  length = 8
FEATURE                Location/Qualifiers
source                 1..8
                       mol_type = protein
                       organism = synthetic construct
SEQUENCE: 233
ISYDGSNR                                                                 8

SEQ ID NO: 234         moltype = AA  length = 15
FEATURE                Location/Qualifiers
source                 1..15
                       mol_type = protein
                       organism = synthetic construct
SEQUENCE: 234
ARDGNWGSLD LYFDL                                                        15

SEQ ID NO: 235         moltype = AA  length = 9
FEATURE                Location/Qualifiers
source                 1..9
                       mol_type = protein
                       organism = synthetic construct
SEQUENCE: 235
SSNIGADYD                                                                9

SEQ ID NO: 236         moltype =    length =
SEQUENCE: 236
000

SEQ ID NO: 237         moltype =    length =
SEQUENCE: 237
000

SEQ ID NO: 238         moltype = AA  length = 8
FEATURE                Location/Qualifiers
source                 1..8
                       mol_type = protein
                       organism = synthetic construct
SEQUENCE: 238
GFTFTSYG                                                                 8

SEQ ID NO: 239         moltype = AA  length = 8
FEATURE                Location/Qualifiers
source                 1..8
                       mol_type = protein
                       organism = synthetic construct
SEQUENCE: 239
ISYDGSNK                                                                 8

SEQ ID NO: 240         moltype = AA  length = 19
FEATURE                Location/Qualifiers
source                 1..19
                       mol_type = protein
                       organism = synthetic construct
SEQUENCE: 240
AREHYDSSGY YHGYYGMDV                                                    19

SEQ ID NO: 241         moltype = AA  length = 8
FEATURE                Location/Qualifiers
source                 1..8
                       mol_type = protein
                       organism = synthetic construct
SEQUENCE: 241
```

```
SSNIGSNY                                                                                   8

SEQ ID NO: 242         moltype =    length =
SEQUENCE: 242
000

SEQ ID NO: 243         moltype =    length =
SEQUENCE: 243
000

SEQ ID NO: 244         moltype = AA   length = 8
FEATURE                Location/Qualifiers
source                 1..8
                       mol_type = protein
                       organism = synthetic construct
SEQUENCE: 244
GFTFSSYD                                                                                   8

SEQ ID NO: 245         moltype = AA   length = 8
FEATURE                Location/Qualifiers
source                 1..8
                       mol_type = protein
                       organism = synthetic construct
SEQUENCE: 245
ISFDGSNK                                                                                   8

SEQ ID NO: 246         moltype = AA   length = 20
FEATURE                Location/Qualifiers
source                 1..20
                       mol_type = protein
                       organism = synthetic construct
SEQUENCE: 246
ARTYYDILTG YSHYSYGMDV                                                                     20

SEQ ID NO: 247         moltype = AA   length = 6
FEATURE                Location/Qualifiers
source                 1..6
                       mol_type = protein
                       organism = synthetic construct
SEQUENCE: 247
QGISNY                                                                                     6

SEQ ID NO: 248         moltype =    length =
SEQUENCE: 248
000

SEQ ID NO: 249         moltype =    length =
SEQUENCE: 249
000

SEQ ID NO: 250         moltype = AA   length = 8
FEATURE                Location/Qualifiers
source                 1..8
                       mol_type = protein
                       organism = synthetic construct
SEQUENCE: 250
GFTFSTYG                                                                                   8

SEQ ID NO: 251         moltype = AA   length = 8
FEATURE                Location/Qualifiers
source                 1..8
                       mol_type = protein
                       organism = synthetic construct
SEQUENCE: 251
ISYDGSNK                                                                                   8

SEQ ID NO: 252         moltype = AA   length = 15
FEATURE                Location/Qualifiers
source                 1..15
                       mol_type = protein
                       organism = synthetic construct
SEQUENCE: 252
AGRDNLRFLE WFMDV                                                                          15

SEQ ID NO: 253         moltype = AA   length = 6
FEATURE                Location/Qualifiers
source                 1..6
                       mol_type = protein
                       organism = synthetic construct
```

```
SEQUENCE: 253
QSVRSN                                                                          6

SEQ ID NO: 254         moltype =    length =
SEQUENCE: 254
000

SEQ ID NO: 255         moltype =    length =
SEQUENCE: 255
000

SEQ ID NO: 256         moltype = AA   length = 8
FEATURE                Location/Qualifiers
source                 1..8
                       mol_type = protein
                       organism = synthetic construct
SEQUENCE: 256
GFTLSIYS                                                                        8

SEQ ID NO: 257         moltype = AA   length = 8
FEATURE                Location/Qualifiers
source                 1..8
                       mol_type = protein
                       organism = synthetic construct
SEQUENCE: 257
ISSSSSYI                                                                        8

SEQ ID NO: 258         moltype = AA   length = 9
FEATURE                Location/Qualifiers
source                 1..9
                       mol_type = protein
                       organism = synthetic construct
SEQUENCE: 258
ARSSYGADY                                                                       9

SEQ ID NO: 259         moltype = AA   length = 6
FEATURE                Location/Qualifiers
source                 1..6
                       mol_type = protein
                       organism = synthetic construct
SEQUENCE: 259
QDITNF                                                                          6

SEQ ID NO: 260         moltype =    length =
SEQUENCE: 260
000

SEQ ID NO: 261         moltype =    length =
SEQUENCE: 261
000

SEQ ID NO: 262         moltype = AA   length = 8
FEATURE                Location/Qualifiers
source                 1..8
                       mol_type = protein
                       organism = synthetic construct
SEQUENCE: 262
GFTFSSYS                                                                        8

SEQ ID NO: 263         moltype = AA   length = 8
FEATURE                Location/Qualifiers
source                 1..8
                       mol_type = protein
                       organism = synthetic construct
SEQUENCE: 263
ISSSSSYI                                                                        8

SEQ ID NO: 264         moltype = AA   length = 18
FEATURE                Location/Qualifiers
source                 1..18
                       mol_type = protein
                       organism = synthetic construct
SEQUENCE: 264
ARDRGFLEDY YYYYGMDV                                                            18

SEQ ID NO: 265         moltype = AA   length = 6
FEATURE                Location/Qualifiers
source                 1..6
                       mol_type = protein
```

```
                        organism = synthetic construct
SEQUENCE: 265
QGISNW                                                                      6

SEQ ID NO: 266          moltype =    length =
SEQUENCE: 266
000

SEQ ID NO: 267          moltype =    length =
SEQUENCE: 267
000

SEQ ID NO: 268          moltype = AA   length = 453
FEATURE                 Location/Qualifiers
source                  1..453
                        mol_type = protein
                        organism = synthetic construct
SEQUENCE: 268
EVQLVESGGG EVQPGRSLRL TCAVSGFTLS RYGMHWVRQA PGKGLEWAAL ISYDGSNRYY            60
ADSVKGRFTI SRDNSKNTVF LQMNSLRAED TAVYYCARER ESSGWFEGYF DYWGQGTTVT           120
VSSASTKGPS VFPLAPSSKS TSGGTAALGC LVKDYFPEPV TVSWNSGALT SGVHTFPAVL           180
QSSGLYSLSS VVTVPSSSLG TQTYICNVNH KPSNTKVDKK VEPKSCDKTH TCPPCPAPEL           240
LGGPSVFLFP PKPKDTLMIS RTPEVTCVVV DVSHEDPEVK FNWYVDGVEV HNAKTKPREE           300
QYNSTYRVVS VLTVLHQDWL NGKEYKCKVS NKALPAPIEK TISKAKGQPR EPQVYTLPPS           360
REEMTKNQVS LSCAVKGFYP SDIAVEWESN GQPENNYKTT PPVLDSDGSF FLVSKLTVDK           420
SRWQQGNVFS CSVMHEALHN RFTQKSLSLS PGK                                       453

SEQ ID NO: 269          moltype = AA   length = 214
FEATURE                 Location/Qualifiers
source                  1..214
                        mol_type = protein
                        organism = synthetic construct
SEQUENCE: 269
QLVLTQPPSV SVAPGQTARI TCGGNNIGSK SVHWYQQKPG QAPVLVVYDN SDRPSGIPER            60
FSGSNSGNTA TLTISRVEVG DEADYYCQVW DSSSDHVVFG GGTKLTVLGQ PKAAPSVTLF           120
PPSSEELQAN KATLVCLISD FYPGAVTVAW KADSSPVKAG VETTTPSKQS NNKYAASSYL           180
SLTPEQWKSH RSYSCQVTHE GSTVEKTVAP TECS                                      214

SEQ ID NO: 270          moltype = DNA   length = 1359
FEATURE                 Location/Qualifiers
source                  1..1359
                        mol_type = other DNA
                        organism = synthetic construct
SEQUENCE: 270
gaggtgcaat tggtagagag tggcggggga gaagtccaac caggccgcag tctcagactt            60
acttgtgccg tctcaggctt taccctcagc cgttacggta tgcactgggt tagacaagct           120
ccagggaagg gacttgaatg ggccgcactg atttcctatg atggctccaa ccgctattat           180
gccgacagtg tgaaaggacg cttcacaatt tcaaggata attcaaagaa tacagtctttt           240
cttcaaatga actctttgcg agccgaggat acagccgttt attactgtgc acgggaaagg           300
gagtctagtg gatggtttga agggtatttt gattattggg gtcaagggac cacagtgacc           360
gtaagctcag cctccaccaa gggcccatcg gtcttccccc tggcaccctc ctccaagagc           420
acctctgggg gcacagcggc cctgggctgc ctggtcaagg actacttccc gaaccggtg            480
acggtgtcgt ggaactcagg cgccctgacc agcggcgtgc acaccttccc ggctgtccta           540
cagtcctcag gactctactc cctcagcagc gtggtgaccg tgccctccag cagcttgggc           600
acccagacct acatctgcaa cgtgaatcac aagcccagca acaccaaggt ggacaagaaa           660
gttgaaccca aatcctgtga caaaacccat acttgtcccc cttgccccgc cccagagttg           720
cttggcggac cttccgtgtt tctgttccct ccaaagccca aggacactct tatgataagc           780
cgaacaccag aggtcacatg cgtcgtcgtg gacgtaagcc acgaggatcc cgaagtaaaa           840
tttaactggt acgtggatgg ggtggaagta cataatgcaa aaactaagcc cagagaggaa           900
caatataatt ctaccaccg agtggtatcc gtcctgacag tgttgcatca ggactggttg            960
aatgaaaagg agtataagtg caaagtgtca ataaggccc tgcccgctcc tatcgagaaa          1020
actatttcca agctaaggg ccagcctcgc gaacctcagg tctacaccct gccaccttcc           1080
agagaggaga tgaccaaaaa tcaagtttca ttgtcttgtg ccgtaaaagg attttacccc           1140
tccgatatag ctgtcgagtg ggagataat ggtcaaccg agaataatta caaaacaact            1200
ccacccgttc tcgatagtga tgggagcttc tttctcgttt ccaaattgac tgttgataaa           1260
tctaggtggc agcagggcaa tgtcttttcc tgcagcgtga tgcacgaagc cctgcataat           1320
cgctttactc aaaaaagcct tagtctgtcc ccaggtaag                                 1359

SEQ ID NO: 271          moltype = DNA   length = 642
FEATURE                 Location/Qualifiers
source                  1..642
                        mol_type = other DNA
                        organism = synthetic construct
SEQUENCE: 271
cagcttgtcc tcacccagcc acctagcgtt agtgtcgccc ccggtcaaac tgctcgcata            60
acttgtggag gcaacaacat tgggagcaaa agcgttcatt ggtaccaaca aaaaccagga           120
caggcccctg ttttggtagt ttatgacaac tctgatcgac catcagggat tcccgagcgg           180
ttttctggta gtaattcagg gaatactgct accctgacta tcagtcgcgt cgaagttggc           240
gacgaagctg actattattg tcaagtctgg gacagcagca gcgaccatgt ggttttggg            300
```

```
ggagggacca aacttaccgt attgggtcag cccaaggctg cacccagtgt cactctgttc    360
ccgcccctcct ctgaggagct tcaagccaac aaggccacac tggtgtgtct cataagtgac   420
ttctacccgg gagccgtgac agtggcctgg aaggccgata gcagccccgt caaggcggga    480
gtggagacca ccacaccctc caaacaaagc aacaacaagt acgcggccag cagctatctg    540
agcctgacgc tgagcagtg gaagtcccac agaagctaca gctgccaggt cacgcatgaa     600
gggagcaccg tggagaagac agtggcccct acagaatgtt ca                       642
```

```
SEQ ID NO: 272          moltype = AA   length = 5
FEATURE                 Location/Qualifiers
source                  1..5
                        mol_type = protein
                        organism = synthetic construct
SEQUENCE: 272
SYYWS                                                                 5

SEQ ID NO: 273          moltype = AA   length = 16
FEATURE                 Location/Qualifiers
source                  1..16
                        mol_type = protein
                        organism = synthetic construct
SEQUENCE: 273
RIYSSGSTNY NPSLKS                                                    16

SEQ ID NO: 274          moltype = AA   length = 10
FEATURE                 Location/Qualifiers
source                  1..10
                        mol_type = protein
                        organism = synthetic construct
SEQUENCE: 274
VGVWPGAFDI                                                           10

SEQ ID NO: 275          moltype = AA   length = 13
FEATURE                 Location/Qualifiers
source                  1..13
                        mol_type = protein
                        organism = synthetic construct
SEQUENCE: 275
SGSSSNIGSN TVN                                                       13

SEQ ID NO: 276          moltype = AA   length = 7
FEATURE                 Location/Qualifiers
source                  1..7
                        mol_type = protein
                        organism = synthetic construct
SEQUENCE: 276
SSNQRPS                                                               7

SEQ ID NO: 277          moltype = AA   length = 11
FEATURE                 Location/Qualifiers
source                  1..11
                        mol_type = protein
                        organism = synthetic construct
SEQUENCE: 277
AAWDDSLNGV V                                                         11

SEQ ID NO: 278          moltype = AA   length = 118
FEATURE                 Location/Qualifiers
source                  1..118
                        mol_type = protein
                        organism = synthetic construct
SEQUENCE: 278
EVQLLESGPG LVKPSETLSL TCTVSGGSII SYYWSWIRQP AGKGLEWIGR IYSSGSTNYN    60
PSLKSRVTMS VDTSKNQFSL KLSSVTAADT AVYYCAKVGV WPGAFDIWGQ GTMVTVSS     118

SEQ ID NO: 279          moltype = AA   length = 110
FEATURE                 Location/Qualifiers
source                  1..110
                        mol_type = protein
                        organism = synthetic construct
SEQUENCE: 279
QSVLTQPPSA SGTPGQRVTI SCSGSSSNIG SNTVNWYQQL PGTAPKLLIY SSNQRPSGVP    60
DRFSGSKSGT SASLAISGLQ SEDEADYYCA AWDDSLNGVV FGGGTKLTVL              110

SEQ ID NO: 280          moltype = DNA   length = 354
FEATURE                 Location/Qualifiers
source                  1..354
                        mol_type = other DNA
                        organism = synthetic construct
SEQUENCE: 280
```

```
gaagttcagc tgttggaatc tggacctggc ctggtcaagc cttccgagac actgtctctg   60
acctgtaccg tgtccggcgg ctccatcatc tcctactact ggtcctggat cagacagcct  120
gccggcaaag gactggaatg gatcggcaga atctactcct ccgcagcac caactacaac   180
cccagcctga gtcccgcgt gaccatgtct gtggacacct ccaagaacca gttctccctg  240
aagctgtcct ctgtgaccgc cgctgatacc gctgtgtact actgcgctaa agtcggagtg  300
tggcctggcg cctttgatat ctggggacag ggcacaatgg tcaccgtgtc ctct        354

SEQ ID NO: 281           moltype = DNA  length = 330
FEATURE                  Location/Qualifiers
source                   1..330
                         mol_type = other DNA
                         organism = synthetic construct
SEQUENCE: 281
cagtccgtgc tgacccagcc tccttctgct tctggaacac ctggccagag agtgaccatc   60
tcctgctccg gctcctcctc caacatcggc tctaacaccg tgaactggta tcagcagctg  120
cccggcacag cccctaaact gctgatctac tcttccaacc agcggccttc tggcgtgccc  180
gatagattct ctggctccaa gtctggcacc tccgctagcc tggctatttc tggcctgcag  240
tctgaggacg aggccgatta ctactgtgcc gcctgggatg attctctgaa cggcgttgtg  300
tttggcggag gcaccaaatt gacagttctt                                    330

SEQ ID NO: 282           moltype = AA  length = 480
FEATURE                  Location/Qualifiers
source                   1..480
                         mol_type = protein
                         organism = synthetic construct
SEQUENCE: 282
QSVLTQPPSA SGTPGQRVTI SCSGSSSNIG SNTVNWYQQL PGTAPKLLIY SSNQRPSGVP   60
DRFSGSKSGT SASLAISGLQ SEDEADYYCA AWDDSLNGVV FGGGTKLTVL GGSEGKSSGS  120
GSESKSTGGS EVQLLESGPG LVKPSETLSL TCTVSGGSII SYYWSWIRQP AGKGLEWIGR  180
IYSSGSTNYN PSLKSRVTMS VDTSKNQFSL KLSSVTAADT AVYYCAKVGV WPGAFDIWGQ  240
GTMVTVSSEP KSSDKTHTCP PCPAPELLGG PSVFLFPPKP KDTLMISRTP EVTCVVVDVS  300
HEDPEVKFNW YVDGVEVHNA KTKPREEQYN STYRVVSVLT VLHQDWLNGK EYKCKVSNKA  360
LPAPIEKTIS KAKGQPREPQ VYTLPPSREE MTKNQVSLWC LVKGFYPSDI AVEWESNGQP  420
ENNYKTTPPV LDSDGSFFLY SKLTVDKSRW QQGNVFSCSV MHEALHNHYT QKSLSLSPGK  480

SEQ ID NO: 283           moltype = DNA  length = 1440
FEATURE                  Location/Qualifiers
source                   1..1440
                         mol_type = other DNA
                         organism = synthetic construct
SEQUENCE: 283
cagtccgtgc tgacccagcc tccttctgct tctggaacac ctggccagag agtgaccatc   60
tcctgctccg gctcctcctc caacatcggc tctaacaccg tgaactggta tcagcagctg  120
cccggcacag cccctaaact gctgatctac tcttccaacc agcggccttc tggcgtgccc  180
gatagattct ctggctccaa gtctggcacc tccgctagcc tggctatttc tggcctgcag  240
tctgaggacg aggccgatta ctactgtgcc gcctgggatg attctctgaa cggcgttgtg  300
tttggcggag gcaccaaatt gacagttctt ggcggctccg agggcaagag cagcggcagc  360
ggcagcgaga gcaagagcac cggcggcagc gaagttcagc tgttggaatc tggacctggc  420
ctggtcaagc cttccgagac actgtctctg acctgtaccg tgtccggcgg ctccatcatc  480
tcctactact ggtcctggat cagacagcct gccggcaaag gactggaatg gatcggcaga  540
atctactcct ccggcagcac caactacaac cccagcctga gtcccgcgt gaccatgtct  600
gtggacacct ccaagaacca gttctccctg aagctgtcct ctgtgaccgc cgctgatacc  660
gctgtgtact actgcgctaa agtcggagtg tggcctggcg cctttgatat ctggggacag  720
ggcacaatgg tcaccgtgtc ctctgagccc aaatctagcg acaaaactca cacatgtcca  780
ccgtgcccag cacctgaactg ctggggggga ccgtcagtct tcctcttccc cccaaaaccc  840
aaggacaccc tcatgatctc ccggacccct gaggtcacat gcgtggtggt ggacgtgagc  900
cacgaagacc ctgaggtcaa gttcaactgg tacgtggacg gcgtggaggt gcataatgcc  960
aagacaaagc cgcgggagga gcagtacaac agcacgtacc gtgtggtcag cgtcctcacc 1020
gtcctgcacc aggactggct gaatggcaag gagtacaagt gcaaggtctc caacaaagcc 1080
ctcccagccc ccatcgagaa aaccatctcc aaagccaaag gcagccccg agaaccacag 1140
gtgtacaccc tgcccccatc ccgggaggag atgaccaaga accaggtcag cctgtggtgc 1200
ctggtcaaag gcttctatcc cagcgacatc gccgtggagt gggagagcaa tgggcagccg 1260
gagaacaact acaagaccac gcctcccgtg ctggactccg acggctcctt cttcctctac 1320
agcaagctca ccgtggacaa gtctagatgg cagcagggga acgtcttctc atgctccgtg 1380
atgcatgagg ctctgcacaa ccactacacg cagaagagcc tctccctgtc tccgggtaaa 1440

SEQ ID NO: 284           moltype = AA  length = 453
FEATURE                  Location/Qualifiers
source                   1..453
                         mol_type = protein
                         organism = synthetic construct
SEQUENCE: 284
EVQLVESGGG EVQPGRSLRL TCAVSGFTLS RYGMHWVRQA PGKGLEWAAL ISYDGSNRYY   60
ADSVKGRFTI SRDNSKNTVF LQMNSLRAED TAVYYCARER ESSGWFEGYF DYWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV SVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
REEMTKNQVS LSCAVKGFYP SDIAVEWESN GQPENNYKTT PPVLDSDGSF FLVSKLTVDK  420
```

```
SRWQQGNVFS CSVMHEALHN RFTQKSLSLS PGK                              453

SEQ ID NO: 285          moltype = AA  length = 32
FEATURE                 Location/Qualifiers
source                  1..32
                        mol_type = protein
                        organism = synthetic construct
SEQUENCE: 285
AEAAAKEAAA KEAAAAKEAA AAKEAAAAKA AA                               32

SEQ ID NO: 286          moltype = DNA  length = 1359
FEATURE                 Location/Qualifiers
source                  1..1359
                        mol_type = other DNA
                        organism = synthetic construct
SEQUENCE: 286
gaggtgcaat tggtagagag tggcggggga gaagtccaac caggccgcag tctcagactt   60
acttgtgccg tctcaggctt taccctcagc cgttacggta tgcactgggt tagacaagct  120
ccagggaagg gacttgaatg ggccgcactg atttcctatg atggctccaa ccgctattat  180
gccgacagtg tgaaaggacg cttcacaatt tcaaggata attcaaagaa tacagtcttt   240
cttcaaatga actctttgcg agccgaggat acagccgttt attactgtgc acgggaaagg  300
gagtcctagtg gatggtttga agggtatttt gattattggg gtcaagggac cacagtgacc  360
gtaagctcag cctccaccaa gggcccatcg gtcttcccc tggcaccctc ctccaagagc   420
acctctgggg gcacagcggc cctgggctgc ctggtcaagg actacttccc cgaaccggtg  480
acggtgtcgt ggaactcagg cgccctgacc agcggcgtgc acaccttccc ggctgtccta  540
cagtcctcag gactctactc cctcagcagc gtggtgaccg tgccctccag cagcttgggc  600
acccagacct acatctgcaa cgtgaatcac aagcccagca caccaaggt ggacaagaaa   660
gttgagccca aatcttgtga caaaactcac acatgtccac cgtgcccagc acctgaagcc  720
gccggggac cgtcagtctt cctcttcccc ccaaaaccca aggacaccct ctacatcacc   780
cgggacgctg aggtcacatg cgtggtggtg gacgtgagcc acgaagaccc tgaggtcaag  840
ttcaactggt acgtggacgg cgtggaggtg cataatgcca agacaaagcc gcggaggag   900
cagtacaaca gcacgtaccg tgtggtcagc gtcctcaccg tcctgcacca ggactggctg   960
aatggcaagg agtacaagtg caaggtctcc aacaaagccc tcccagcccc catcgagaaa  1020
accatctcca aagccaaagg gcagccccga gaaccacagg tgtacaccct gccccatcc   1080
cgggaggaga tgaccaagaa ccaggtcagc ctgtcctgcg ccgtcaaagg cttctatccc  1140
agcgacatcg ccgtggagtg ggagagcaat gggcagccgg agaacaacta caagaccacg  1200
cctcccgtgc tggactccga cggctccttc ttcctcgtga gcaagctcac cgtggacaag  1260
tctagatggc agcaggggaa cgtcttctca tgctccgtga tgcatgaggc tctgcacaac  1320
cggttcacgc agaagagcct ctccctgtct ccgggaaaa                         1359

SEQ ID NO: 287          moltype = AA  length = 16
FEATURE                 Location/Qualifiers
source                  1..16
                        mol_type = protein
                        organism = synthetic construct
SEQUENCE: 287
GTEGKSSGSG SESKST                                                 16

SEQ ID NO: 288          moltype = AA  length = 480
FEATURE                 Location/Qualifiers
source                  1..480
                        mol_type = protein
                        organism = synthetic construct
SEQUENCE: 288
QSVLTQPPSA SGTPGQRVTI SCSGSSSNIG SNTVNWYQQL PGTAPKLLIY SSNQRPSGVP   60
DRFSGSKSGT SASLAISGLQ SEDEADYYCA AWDDSLNGVV FGGGTKLTVL GGSEGKSSGS  120
GSESKSTGGS EVQLLESGPG LVKPSETLSL TCTVSGGSII SYYWSWIRQP AGKGLEWIGR  180
IYSSGSTNYN PSLKSRVTMS VDTSKNQFSL KLSSVTAADT AVYYCAKVGV WPGAFDIWGQ  240
GTMVTVSSEP KSSDKTHTCP PCPAPEAAGG PSVFLFPPKP KDTLYITREP EVTCVVVSVS  300
HEDPEVKFNW YVDGVEVHNA KTKPREEQYN STYRVVSVLT VLHQDWLNGK EYKCKVSNKA  360
LPAPIEKTIS KAKGQPREPQ VYTLPPSREE MTKNQVSLWC LVKGFYPSDI AVEWESNGQP  420
ENNYKTTPPV LDSDGSFFLY SKLTVDKSRW QQGNVFSCSV MHEALHNHYT QKSLSLSPGK  480

SEQ ID NO: 289          moltype = DNA  length = 1440
FEATURE                 Location/Qualifiers
source                  1..1440
                        mol_type = other DNA
                        organism = synthetic construct
SEQUENCE: 289
cagtccgtgc tgacccagcc tccttctgct tctggaacac ctggccagag agtgaccatc   60
tcctgctccg gctcctcctc caacatcggc tctaacaccg tgaactggta tcagcagctg  120
cccggcacac cccctaaact gctgatctac tcttccaacc agcggcctttc tggcgtgccc  180
gatagattct ctggctccaa gtctggcacc tccgctagct ggctatttc tggcctgcag  240
tctgaggacg aggccgatta ctactgtgcc gcctgggatg attctctgaa cggcgttgtg  300
tttggcggag gcaccaaatt gacagttctt ggcggctccg agggcaagag cagcggcagc  360
ggcagcgaga gcaagagcac cggcggcagc gaagttcagc tgttggaatc tggacctggc  420
ctggtcaagc cttccgagac actgtctctg acctgtaccg tgtccggcgg ctccatcatc  480
tcctactact ggtcctggat cagacagcct gccggcaaag actgaatg gatcggcaga  540
atctactcct ccggcagcac caactacaac cccagcctga gtcccgcgt gaccatgtct  600
```

```
gtggacacct ccaagaacca gttctccctg aagctgtcct ctgtgaccgc cgctgatacc    660
gctgtgtact actgcgctaa agtcggagtc tggcctggcg cctttgatat ctggggacag    720
ggcacaatgg tcaccgtgtc ctctgagccc aaatctagcg acaaaactca cacatgccca    780
ccgtgcccag cacctgaagc cgccggggga ccgtcagtct tcctcttccc cccaaaaccc    840
aaggacaccc tctacatcac ccgggagcct gaggtcacat gcgtggtggt gagcgtgagc    900
cacgaagacc ctgaggtcaa gttcaactgg tacgtggacg gcgtggaggt gcataatgcc    960
aagacaaagc cgcggggagga gcagtacaac agcacgtacc gtgtggtcag cgtcctcacc   1020
gtcctgcacc aggactggct gaatggcaag gagtacaagt gcaaggtgtc gaacaaagcc   1080
ctcccagccc ccatcgagaa aaccatctcc aaagccaaag ggcagccccg agaaccacag   1140
gtgtacaccc tgcccccatc ccgggaggag atgaccaaga accaggtcag cctgtggtgc   1200
ctggtcaaag gcttctatcc cagcgacatc gccgtggagt gggagagcaa tgggcagccg   1260
gagaacaact acaagaccac gcctcccgtg ctggactccg acggctcctt cttcctctac   1320
agcaagctca ccgtggacaa gagcagatgg cagcagggga acgtcttctc atgctccgtg   1380
atgcatgagg ctctgcacaa ccactacacg cagaagtctc tctccctgtc tccgggaaaa   1440
```

SEQ ID NO: 290      moltype = AA    length = 7
FEATURE                 Location/Qualifiers
source                  1..7
                         mol_type = protein
                         organism = synthetic construct
SEQUENCE: 290
GGSIISY                                                           7

SEQ ID NO: 291      moltype = AA    length = 5
FEATURE                 Location/Qualifiers
source                  1..5
                         mol_type = protein
                         organism = synthetic construct
SEQUENCE: 291
YSSGS                                                             5

SEQ ID NO: 292      moltype =    length =
SEQUENCE: 292
000

SEQ ID NO: 293      moltype =    length =
SEQUENCE: 293
000

SEQ ID NO: 294      moltype =    length =
SEQUENCE: 294
000

SEQ ID NO: 295      moltype =    length =
SEQUENCE: 295
000

SEQ ID NO: 296      moltype = AA    length = 10
FEATURE                 Location/Qualifiers
source                  1..10
                         mol_type = protein
                         organism = synthetic construct
SEQUENCE: 296
GGSIISYYWS                                              10

SEQ ID NO: 297      moltype = AA    length = 9
FEATURE                 Location/Qualifiers
source                  1..9
                         mol_type = protein
                         organism = synthetic construct
SEQUENCE: 297
RIYSSGSTN                                                9

SEQ ID NO: 298      moltype =    length =
SEQUENCE: 298
000

SEQ ID NO: 299      moltype =    length =
SEQUENCE: 299
000

SEQ ID NO: 300      moltype =    length =
SEQUENCE: 300
000

SEQ ID NO: 301      moltype =    length =
SEQUENCE: 301
000

-continued

```
SEQ ID NO: 302          moltype = AA   length = 8
FEATURE                 Location/Qualifiers
source                  1..8
                        mol_type = protein
                        organism = synthetic construct
SEQUENCE: 302
GGSIISYY                                                                  8

SEQ ID NO: 303          moltype = AA   length = 7
FEATURE                 Location/Qualifiers
source                  1..7
                        mol_type = protein
                        organism = synthetic construct
SEQUENCE: 303
IYSSGST                                                                   7

SEQ ID NO: 304          moltype = AA   length = 12
FEATURE                 Location/Qualifiers
source                  1..12
                        mol_type = protein
                        organism = synthetic construct
SEQUENCE: 304
AKVGVWPGAF DI                                                            12

SEQ ID NO: 305          moltype = AA   length = 8
FEATURE                 Location/Qualifiers
source                  1..8
                        mol_type = protein
                        organism = synthetic construct
SEQUENCE: 305
SSNIGSNT                                                                  8

SEQ ID NO: 306          moltype =     length =
SEQUENCE: 306
000

SEQ ID NO: 307          moltype =     length =
SEQUENCE: 307
000

SEQ ID NO: 308          moltype = AA   length = 20
FEATURE                 Location/Qualifiers
source                  1..20
                        mol_type = protein
                        organism = synthetic construct
SEQUENCE: 308
GGSEGKSSGS GSESKSTGGS                                                    20

SEQ ID NO: 309          moltype = AA   length = 8
FEATURE                 Location/Qualifiers
source                  1..8
                        mol_type = protein
                        organism = synthetic construct
SEQUENCE: 309
GGGSGGGS                                                                  8

SEQ ID NO: 310          moltype = AA   length = 12
FEATURE                 Location/Qualifiers
source                  1..12
                        mol_type = protein
                        organism = synthetic construct
SEQUENCE: 310
GGGSGGGSGG GS                                                            12

SEQ ID NO: 311          moltype = AA   length = 16
FEATURE                 Location/Qualifiers
source                  1..16
                        mol_type = protein
                        organism = synthetic construct
SEQUENCE: 311
GGGSGGGSGG GSGGGS                                                        16

SEQ ID NO: 312          moltype = AA   length = 20
FEATURE                 Location/Qualifiers
source                  1..20
                        mol_type = protein
                        organism = synthetic construct
SEQUENCE: 312
GGGSGGGSGG GSGGGSGGGS                                                    20
```

```
SEQ ID NO: 313           moltype = AA   length = 15
FEATURE                  Location/Qualifiers
source                   1..15
                         mol_type = protein
                         organism = synthetic construct
SEQUENCE: 313
GGGGSGGGGS GGGGS                                                         15

SEQ ID NO: 314           moltype = AA   length = 20
FEATURE                  Location/Qualifiers
source                   1..20
                         mol_type = protein
                         organism = synthetic construct
SEQUENCE: 314
GGGGSGGGGS GGGGSGGGGS                                                    20

SEQ ID NO: 315           moltype = AA   length = 25
FEATURE                  Location/Qualifiers
source                   1..25
                         mol_type = protein
                         organism = synthetic construct
SEQUENCE: 315
GGGGSGGGGS GGGGSGGGGS GGGGS                                              25

SEQ ID NO: 316           moltype = AA   length = 18
FEATURE                  Location/Qualifiers
source                   1..18
                         mol_type = protein
                         organism = synthetic construct
SEQUENCE: 316
GSTSGSGKPG SGEGSTKG                                                      18

SEQ ID NO: 317           moltype = AA   length = 14
FEATURE                  Location/Qualifiers
source                   1..14
                         mol_type = protein
                         organism = synthetic construct
SEQUENCE: 317
IRPRAIGGSK PRVA                                                          14

SEQ ID NO: 318           moltype = AA   length = 15
FEATURE                  Location/Qualifiers
source                   1..15
                         mol_type = protein
                         organism = synthetic construct
SEQUENCE: 318
GKGGSGKGGS GKGGS                                                         15

SEQ ID NO: 319           moltype = AA   length = 15
FEATURE                  Location/Qualifiers
source                   1..15
                         mol_type = protein
                         organism = synthetic construct
SEQUENCE: 319
GGKGSGGKGS GGKGS                                                         15

SEQ ID NO: 320           moltype = AA   length = 15
FEATURE                  Location/Qualifiers
source                   1..15
                         mol_type = protein
                         organism = synthetic construct
SEQUENCE: 320
GGGKSGGGKS GGGKS                                                         15

SEQ ID NO: 321           moltype = AA   length = 15
FEATURE                  Location/Qualifiers
source                   1..15
                         mol_type = protein
                         organism = synthetic construct
SEQUENCE: 321
GKGKSGKGKS GKGKS                                                         15

SEQ ID NO: 322           moltype = AA   length = 15
FEATURE                  Location/Qualifiers
source                   1..15
                         mol_type = protein
                         organism = synthetic construct
SEQUENCE: 322
```

```
GGGKSGGKGS GKGGS                                                                15

SEQ ID NO: 323          moltype = AA  length = 15
FEATURE                 Location/Qualifiers
source                  1..15
                        mol_type = protein
                        organism = synthetic construct
SEQUENCE: 323
GKPGSGKPGS GKPGS                                                                15

SEQ ID NO: 324          moltype = AA  length = 20
FEATURE                 Location/Qualifiers
source                  1..20
                        mol_type = protein
                        organism = synthetic construct
SEQUENCE: 324
GKPGSGKPGS GKPGSGKPGS                                                           20

SEQ ID NO: 325          moltype = AA  length = 20
FEATURE                 Location/Qualifiers
source                  1..20
                        mol_type = protein
                        organism = synthetic construct
SEQUENCE: 325
GKGKSGKGKS GKGKSGKGKS                                                           20

SEQ ID NO: 326          moltype = AA  length = 14
FEATURE                 Location/Qualifiers
source                  1..14
                        mol_type = protein
                        organism = synthetic construct
SEQUENCE: 326
STAGDTHLGG EDFD                                                                 14

SEQ ID NO: 327          moltype = AA  length = 15
FEATURE                 Location/Qualifiers
source                  1..15
                        mol_type = protein
                        organism = synthetic construct
SEQUENCE: 327
GEGGSGEGGS GEGGS                                                                15

SEQ ID NO: 328          moltype = AA  length = 15
FEATURE                 Location/Qualifiers
source                  1..15
                        mol_type = protein
                        organism = synthetic construct
SEQUENCE: 328
GGEGSGGEGS GGEGS                                                                15

SEQ ID NO: 329          moltype = AA  length = 15
FEATURE                 Location/Qualifiers
source                  1..15
                        mol_type = protein
                        organism = synthetic construct
SEQUENCE: 329
GEGESGEGES GEGES                                                                15

SEQ ID NO: 330          moltype = AA  length = 15
FEATURE                 Location/Qualifiers
source                  1..15
                        mol_type = protein
                        organism = synthetic construct
SEQUENCE: 330
GGGESGGEGS GEGGS                                                                15

SEQ ID NO: 331          moltype = AA  length = 20
FEATURE                 Location/Qualifiers
source                  1..20
                        mol_type = protein
                        organism = synthetic construct
SEQUENCE: 331
GEGESGEGES GEGESGEGES                                                           20

SEQ ID NO: 332          moltype = AA  length = 18
FEATURE                 Location/Qualifiers
source                  1..18
                        mol_type = protein
                        organism = synthetic construct
```

```
SEQUENCE: 332
GSTSGSGKPG SGEGSTKG                                                18

SEQ ID NO: 333           moltype = AA   length = 19
FEATURE                  Location/Qualifiers
source                   1..19
                         mol_type = protein
                         organism = synthetic construct
SEQUENCE: 333
PRGASKSGSA SQTGSAPGS                                               19

SEQ ID NO: 334           moltype = AA   length = 19
FEATURE                  Location/Qualifiers
source                   1..19
                         mol_type = protein
                         organism = synthetic construct
SEQUENCE: 334
GTAAAGAGAA GGAAAGAAG                                               19

SEQ ID NO: 335           moltype = AA   length = 19
FEATURE                  Location/Qualifiers
source                   1..19
                         mol_type = protein
                         organism = synthetic construct
SEQUENCE: 335
GTSGSSGSGS GGSGSGGGG                                               19

SEQ ID NO: 336           moltype = AA   length = 750
FEATURE                  Location/Qualifiers
source                   1..750
                         mol_type = protein
                         organism = Homo sapiens
SEQUENCE: 336
MWNLLHETDS AVATARRPRW LCAGALVLAG GFFLLGFLFG WFIKSSNEAT NITPKHNMKA  60
FLDELKAENI KKFLYNFTQI PHLAGTEQNF QLAKQIQSQW KEFGLDSVEL AHYDVLLSYP 120
NKTHPNYISI INEDGNEIFN TSLFEPPPPG YENVSDIVPP FSAFSPQGMP EGDLVYVNYA 180
RTEDFFKLER DMKINCSGKI VIARYGKVFR GNKVKNAQLA GAKGVILYSD PADYFAPGVK 240
SYPDGWNLPG GGVQRGNILN LNGAGDPLTP GYPANEYAYR RGIAEAVGLP SIPVHPIGYY 300
DAQKLLEKMG GSAPPDSSWR GSLKVPYNVG PGFTGNFSTQ KVKMHIHSTN EVTRIYNVIG 360
TLRGAVEPDR YVILGGHRDS WVFGGIDPQS GAAVVHEIVR SFGTLKKEGW RPRRTILFAS 420
WDAEEFGLLG STEWAEENSR LLQERGVAYI NADSSIEGNY TLRVDCTPLM YSLVHNLTKE 480
LKSPDEGFEG KSLYESWTKK SPSPEFSGMP RISKLGSGND FEVFFQRLGI ASGRARYTKN 540
WETNKFSGYP LYHSVYETYE LVEKFYDPMF KYHLTVAQVR GGMVFELANS IVLPFDCRDY 600
AVVLRKYADK IYSISMKHPQ EMKTYSVSFD SLFSAVKNFT EIASKFSERL QDFDKSNPIV 660
LRMMNDQLMF LERAFIDPLG LPDRPFYRHV IYAPSSHNKY AGESFPGIYD ALFDIESKVD 720
PSKAWGEVKR QIYVAAFTVQ AAAETLSEVA                                  750

SEQ ID NO: 337           moltype = AA   length = 5
FEATURE                  Location/Qualifiers
source                   1..5
                         mol_type = protein
                         organism = synthetic construct
SEQUENCE: 337
GGGGS                                                              5

SEQ ID NO: 338           moltype = AA   length = 4
FEATURE                  Location/Qualifiers
source                   1..4
                         mol_type = protein
                         organism = synthetic construct
SEQUENCE: 338
GGGC                                                               4

SEQ ID NO: 339           moltype = AA   length = 6
FEATURE                  Location/Qualifiers
source                   1..6
                         mol_type = protein
                         organism = synthetic construct
SEQUENCE: 339
HHHHHH                                                             6

SEQ ID NO: 340           moltype = AA   length = 4
FEATURE                  Location/Qualifiers
source                   1..4
                         mol_type = protein
                         organism = synthetic construct
SEQUENCE: 340
GGFG                                                               4
```

The invention claimed is:

1. An isolated antibody or an antigen binding fragment thereof that binds prostate specific membrane antigen (PSMA), the antibody or antigen binding fragment thereof comprising a heavy chain complementarity determining region 1 (HCDR1) comprising the amino acid sequence of RYGMH (SEQ ID NO: 4), a HCDR2 comprising the amino acid sequence of LISYDGSNRYYADSVKG (SEQ ID NO: 5), and a HCDR3 comprising the amino acid sequence of ERESSGWFEGYFDY (SEQ ID NO: 6), and a light chain complementarity determining region 1 (LCDR1) comprising the amino acid sequence of GGNNIGSKSVH (SEQ ID NO: 7), a LCDR2 comprising the amino acid sequence of DNSDRPS (SEQ ID NO: 8), and a LCDR3 comprising the amino acid sequence of QVWDSSSDHVV (SEQ ID NO: 9).

2. The isolated antibody or antigen binding fragment thereof of claim 1, comprising a heavy chain comprising the amino acid sequence of SEQ ID NO: 84 and a light chain comprising the amino acid sequence of SEQ ID NO: 85.

3. The isolated antibody or antigen binding fragment thereof of claim 1, wherein the antibody or the antigen binding fragment thereof is an IgG1, an IgG2, an IgG3, or an IgG4 isotype.

4. The isolated antibody or antigen binding fragment thereof of claim 3, wherein the antibody or antigen binding fragment thereof is an IgG1 isotype.

5. The isolated antibody or antigen binding fragment thereof of claim 1, further comprising an Ig constant region, wherein the Ig constant region comprises at least one mutation that results in reduced binding of the antibody or antigen binding fragment thereof to a Fcγ receptor (FcγR).

6. The isolated antibody or antigen binding fragment thereof of claim 5, wherein the at least one mutation that results in reduced binding of the antibody or antigen binding fragment thereof to the FcγR is selected from F234A/L235A, L234A/L235A, L234A/L235A/D265S, V234A/G237A/P238S/H268A/V309L/A330S/P331S, S228P/F234A/L235A, N297A, V234A/G237A, K214T/E233P/L234V/L235A/G236-deleted/A327G/P331A/D365E/L358M, H268Q/V309L/A330S/P331S, S267E/L328F, L234F/L235E/D265A, L234A/L235A/G237A/P238S/H268A/A330S/P331S, S228P/F234A/L235A/G237A/P238S, and S228P/F234A/L235A/G236-deleted/G237A/P238S, wherein residue numbering is according to the EU index.

7. The isolated antibody or antigen binding fragment thereof of claim 6, wherein the at least one mutation that results in reduced binding of the antibody or antigen binding fragment thereof to the FcγR is L234A/L235A/D265S.

8. The isolated antibody or antigen binding fragment thereof of claim 1, further comprising an Ig constant region, wherein the Ig constant region comprises at least one mutation that modulates a half-life of the antibody or antigen binding fragment thereof.

9. The isolated antibody or antigen binding fragment thereof of claim 8, wherein the at least one mutation that modulates the half-life of the antibody or antigen binding fragment thereof is selected from H435A, P257I/N434H, D376V/N434H, M252Y/S254T/T256E, M252Y/S254T/T256E/H433K/N434F, T308P/N434A, and H435R, wherein residue numbering is according to the EU index.

10. The isolated antibody or antigen binding fragment thereof of claim 9, wherein the at least one mutation that modulates the half-life of the antibody or antigen binding fragment thereof is M252Y/S254T/T256E.

11. A pharmaceutical composition comprising the isolated antibody or antigen binding fragment thereof of claim 1, and a pharmaceutically acceptable carrier.

12. A kit comprising the isolated antibody or antigen binding fragment thereof of claim 1.

13. An antibody drug conjugate comprising the antibody or antigen binding fragment thereof of claim 1.

14. A pharmaceutical composition comprising the antibody drug conjugate of claim 13, and a pharmaceutically acceptable carrier.

15. An isolated antibody or antigen binding fragment thereof that binds prostate specific membrane antigen (PSMA), the antibody or antigen binding fragment thereof comprising a heavy chain variable region (VH) comprising the amino acid sequence of SEQ ID NO: 52 and a light chain variable region (VL) comprising the amino acid sequence of SEQ ID NO: 53.

16. The isolated antibody or antigen binding fragment thereof of claim 15, wherein the antibody or the antigen binding fragment thereof is an IgG1, an IgG2, an IgG3, or an IgG4 isotype.

17. The isolated antibody or antigen binding fragment thereof of claim 16, wherein the antibody or antigen binding fragment thereof is an IgG1 isotype.

18. The isolated antibody or antigen binding fragment thereof of claim 15, further comprising an Ig constant region, wherein the Ig constant region comprises at least one mutation that results in reduced binding of the antibody or antigen binding fragment thereof to a Fcγ receptor (FcγR).

19. The isolated antibody or antigen binding fragment thereof of claim 18, wherein the at least one mutation that results in reduced binding of the antibody or antigen binding fragment thereof to the FcγR is selected from F234A/L235A, L234A/L235A, L234A/L235A/D265S, V234A/G237A/P238S/H268A/V309L/A330S/P331S, S228P/F234A/L235A, N297A, V234A/G237A, K214T/E233P/L234V/L235A/G236-deleted/A327G/P331A/D365E/L358M, H268Q/V309L/A330S/P331S, S267E/L328F, L234F/L235E/D265A, L234A/L235A/G237A/P238S/H268A/A330S/P331S, S228P/F234A/L235A/G237A/P238S, and S228P/F234A/L235A/G236-deleted/G237A/P238S, wherein residue numbering is according to the EU index.

20. The isolated antibody or antigen binding fragment thereof of claim 19, wherein the at least one mutation that results in reduced binding of the antibody or antigen binding fragment thereof to the FcγR is L234A/L235A/D265S.

21. The isolated antibody or antigen binding fragment thereof of claim 15, further comprising an Ig constant region, wherein the Ig constant region comprises at least one mutation that modulates a half-life of the antibody or the antigen binding fragment thereof.

22. The isolated antibody or antigen binding fragment thereof of claim 21, wherein the at least one mutation that modulates the half-life of the antibody or antigen binding fragment thereof is selected from H435A, P257I/N434H, D376V/N434H, M252Y/S254T/T256E, M252Y/S254T/T256E/H433K/N434F, T308P/N434A, and H435R, wherein residue numbering is according to the EU index.

23. The isolated antibody or antigen binding fragment thereof of claim 22, wherein the at least one mutation that modulates the half-life of the antibody or antigen binding fragment thereof is M252Y/S254T/T256E.

24. A pharmaceutical composition comprising the isolated antibody or antigen binding fragment thereof of claim 15, and a pharmaceutically acceptable carrier.

25. A kit comprising the isolated antibody or antigen binding fragment thereof of claim 15.

26. An antibody drug conjugate comprising the antibody or antigen binding fragment thereof of claim 15.

27. A pharmaceutical composition comprising the antibody drug conjugate of claim 26, and a pharmaceutically acceptable carrier.

* * * * *